US012162863B2

(12) United States Patent
Dobrzanska et al.

(10) Patent No.: US 12,162,863 B2
(45) Date of Patent: Dec. 10, 2024

(54) MODULATORS OF STIMULATOR OF INTERFERON GENES (STING)

(71) Applicant: RYVU THERAPEUTICS S.A., Cracow (PL)

(72) Inventors: Monika Patrycja Dobrzanska, Dobroszyce (PL); Magdalena Izabela Zawadzka, Gdansk (PL); Adam Radzimierski, Kutno (PL); Grzegorz Witold Topolnicki, Piekary Slaskie (PL); Grzegorz Wojciech Cwiertnia, Kamesznica (PL); Tushar Ravindra Mahajan, Cracow (PL); Charles-Henry Fabritius, Cracow (PL); Stefan Chmielewski, Slubice (PL); Karolina Maria Gluza, Wroclaw (PL); Jose Alvarez, Piedras Blancas (ES); Maciej Krzysztof Rogacki, Cracow (PL); Magdalena Mroczkowska, Wizna (PL)

(73) Assignee: RYVU THERAPEUTICS S.A., Cracow (PL)

( * ) Notice: Subject to any disclaimer, the term of this patent is extended or adjusted under 35 U.S.C. 154(b) by 803 days.

(21) Appl. No.: 17/251,291

(22) PCT Filed: Jun. 12, 2019

(86) PCT No.: PCT/EP2019/065404
§ 371 (c)(1),
(2) Date: Dec. 11, 2020

(87) PCT Pub. No.: WO2019/238786
PCT Pub. Date: Dec. 19, 2019

(65) Prior Publication Data
US 2022/0402898 A1 Dec. 22, 2022

(30) Foreign Application Priority Data

Jun. 12, 2018 (EP) .................................... 18460033

(51) Int. Cl.
*C07D 405/14* (2006.01)
*A61K 39/39* (2006.01)
*C07D 401/14* (2006.01)
*C07D 471/04* (2006.01)
*C07D 473/00* (2006.01)
*C07D 473/30* (2006.01)
*C07D 473/34* (2006.01)
*C07D 487/04* (2006.01)

(52) U.S. Cl.
CPC ............ *C07D 405/14* (2013.01); *A61K 39/39* (2013.01); *C07D 401/14* (2013.01); *C07D 471/04* (2013.01); *C07D 473/00* (2013.01); *C07D 473/30* (2013.01); *C07D 473/34* (2013.01); *C07D 487/04* (2013.01)

(58) Field of Classification Search
CPC .................................................... C07D 405/14
See application file for complete search history.

(56) References Cited

U.S. PATENT DOCUMENTS

| 3,410,851 | A | * | 11/1968 | Stauffer | ............... | C07D 311/30 |
|---|---|---|---|---|---|---|
| | | | | | | 546/256 |
| 2008/0139558 | A1 | | 6/2008 | Smith et al. | | |
| 2011/0212946 | A1 | | 9/2011 | Barrow et al. | | |
| 2022/0251082 | A1 | | 8/2022 | Zawadzka et al. | | |
| 2023/0055741 | A1 | | 2/2023 | Zawadzka et al. | | |
| 2023/0076506 | A1 | | 3/2023 | Zawadzka et al. | | |

FOREIGN PATENT DOCUMENTS

| GB | 2563642 A | 12/2018 |
|---|---|---|
| WO | WO-2004042083 A2 | 5/2004 |
| WO | WO-2007128568 A1 | 11/2007 |
| WO | WO-2019023635 A1 | 1/2019 |
| WO | WO-2019182886 A1 | 9/2019 |

OTHER PUBLICATIONS

Database Registry [online], Chemical Abstracts Service, Database Accession No. 1011381-60-4, Columbus, Ohio, United States (Apr. 1, 2008), 11 pages, accessed Aug. 7, 2018.*
Database Registry [online], Chemical Abstracts Service, Database Accession No. 1244927-19-2, Columbus, Ohio, United States (Oct. 3, 2010), 3 pages, accessed Aug. 7, 2018.*
Misra et al., Synthesis of 2-phenyl benzimidazole derivatives and their Schiff bases as possible antimicrobial agents, Rasayan J. Chem., vol. 3 Issue: 1, pp. 51-54, 2010.*
STN document No. 70:77793 (1969).*
2010.*
1969.*
Aguirre, S., et al., "DENV Inhibits Type I IFN Production in Infected Cells by Cleaving Human STING," PLoS Pathogens 8(10):e1002934, Public Library of Science, United States (2012).
Chen, X., et al., "SARS Coronavirus Papain-like Protease Inhibits the Type I Interferon Signaling Pathway Through Interaction With the STING-TRAF3-TBK1 Complex," Protein Cell 5(5):369-381, Springer, Germany (2014).
Cirulli, E.T., et al., "Exome Sequencing in Amyotrophic Lateral Sclerosis Identifies Risk Genes and Pathways," Science 347(6229):1436-1441, Author manuscript, American Association for the Advancement of Science, United States (2015).
Collins, A.C., et al., "Cyclic GMP-AMP Synthase Is an Innate Immune DNA Sensor for *Mycobacterium tuberculosis*," Cell Host & Microbe 17(6):820-828, Cell Press, United States (2015).

(Continued)

*Primary Examiner* — Svetlana M Ivanova
(74) *Attorney, Agent, or Firm* — Sterne, Kessler, Goldstein & Fox P.L.L.C.

(57) ABSTRACT

The present invention relates to compounds of formula (I) and salts, stereoisomers, tautomers or N-oxides thereof that are useful as modulators of STING (Stimulator of Interferon Genes). The present invention further relates to the compounds of formula (I) for use as a medicament and to a pharmaceutical composition comprising said compounds.

11 Claims, No Drawings

(56) References Cited

OTHER PUBLICATIONS

Corrales, L and Gajewski, T.F., "Molecular Pathways: Targeting the Stimulator of Interferon Genes (STING) in the Immunotherapy of Cancer," Clinical Cancer Research 21(21):4774-4779, American Association of Cancer Research, United States (2015).

Corrales, L., at al., "Extremely potent immunotherapeutic activity of a STING agonist in the B16 melanoma model in vivo," Journal for ImmunoTherapy of Cancer 1 (Suppl 1): O15, BioMed Central, United Kingdom (2013).

Corrales, L., et al., "Direct Activation of STING in the Tumor Microenvironment Leads to Potent and Systemic Tumor Regression and Immunity," Cell Reports 11(7):1018-1030, Cell Press, United States (2015).

Crow, Y.J., et al., "Mutations in the Gene Encoding the 3'-5' DNA Exonuclease TREX1 Cause Aicardi-Goutières Syndrome at the AGS1 Locus," Nature Genetics 38(8):917-920, Nature, United States (2006).

Database Registry [online], Chemical Abstracts Service, Database Accession No. 1011381-60-4, Columbus, Ohio, United States (Apr. 1, 2008), 11 pages, assessed Aug. 7, 2018.

Database Registry [online], Chemical Abstracts Service, Database Accession No. 1244927-19-2, Columbus, Ohio, United States (Oct. 3, 2010), 3 pages, assessed Aug. 7, 2018.

Ding, Q., et al., "Hepatitis C Virus NS4B Blocks the Interaction of STING and TBK1 to Evade Host Innate Immunity," Journal of Hepatology 59(1):52-58, Elsevier, Netherlands (2013).

Dubensky, T.W., et al., "Rationale, Progress and Development of Vaccines Utilizing STING-Activating Cyclic Dinucleotide Adjuvants," Therapeutic Advances in Vaccines, 1(4):131-143, Sage Publications, London (2013).

Freischmidt, A., et al., "Haploinsufficiency of TBK1 Causes Familial ALS and Fronto-temporal Dementia," Nature Neuroscience 18(5):631-636, Nature Publishing Group, United States (2015).

Fu, J., et al., "STING Agonist Formulated Cancer Vaccines Can Cure Established Tumors Resistant to PD-1 Blockade," Science Translational Medicine 7(283):283ra52, Author manuscript, American Association for the Advancement of Science, United States (2015).

Gao, D., et al., "Cyclic GMP-AMP Synthase Is an Innate Immune Sensor of HIV and Other Retroviruses," Science 341(6148):903-906, Author manuscript, American Association for the Advancement of Science, United States (2013).

Gao, P., et al., "Cyclic [G(2',5')pA(3',5')p] is the Metazoan Second Messenger Produced by DNA-activated Cyclic GMP-AMP Synthase," Cell 153(5):1094-1107, Elsevier, Inc., United States (2013).

Herzner, A., et al., "Sequence-specific Activation of the DNA Sensor cGAS by Y-form DNA Structures as Found in Primary HIV-1 cDNA, " Nature Immunology 16(10):1025-1033, Author manuscript, Nature America Inc., United States (2015).

Holm, C.K., et al., "Influenza A Virus Targets a cGAS-independent STING Pathway That Controls Enveloped RNA Viruses," Nature Communications 7:10680, Nature Publishing Group, England (2016).

Huber, J.P., et al., "Cutting Edge: Type I IFN Reverses Human Th2 Commitment and Stability by Suppressing GATA3," Journal of Immunology 185(2):813-817, American Association of Immunologists, United States (2010).

International Search Report and Written Opinion for Application No. PCT/EP2019/065404, European Patent Office, Rijswijk, Netherlands, mailed on Oct. 31, 2019, 8 pages.

Ishikawa, H and Barber, G.N., "STING Is an Endoplasmic Reticulum Adaptor That Facilitates Innate Immune Signaling," Nature 455(7213):674-678, Author manuscript, Nature Publishing Group, England (2008).

Ishikawa, H., et al., "STING Regulates Intracellular DNA-mediated, Type I Interferon-dependent Innate Immunity," Nature 461(7265):788-792, Author manuscript, Nature Publishing Group, England (2009).

Jin, L., et al., "MPYS is Required for IFN Response Factor 3 Activation and Type I IFN Production in the Response of Cultured Phagocytes to Bacterial Second Messengers Cyclic-di-AMP and Cyclic-di-GMP," Journal of Immunology 187(5):2595-2601, American Association of Immunologists, United States (2011).

Lau et al., DNA tumor virus oncogenes antagonize the cGAS-STING DNA-sensing pathway, Science 350(6260):568-571, America Association for the Advancement of Science, United States (2015).

Lemos, H., et al., "Activation of the STING Adaptor Attenuates Experimental Autoimmune Encephalitis," Journal of Immunology 192(12):5571-5578, American Association of Immunologists, United States (2014).

Liu, Y., et al., "RIG-I-Mediated STING Upregulation Restricts Herpes Simplex Virus 1 Infection," Journal of Virology 90(20):9406-9419, American Society for Microbiology, United States (2016).

Ma, Z and Damania, B., "The cGAS-STING Defense Pathway and Its Counteraction by Viruses," Cell Host & Microbe 19(2):150-158, Elsevier, Inc., United States (2016).

Ma, Z., et al., "Modulation of the cGAS-STING DNA Sensing Pathway by Gammaherpesviruses," Proceedings of the National Academy of Sciences of the United States of America 112(31):E4306-E4315, National Academy of Sciences, United States (2015).

McNab, F., et al., "Type I Interferons in Infectious Disease," Nature Reviews Immunology 15(2):87-103, Macmillan Publishers Ltd., England (2015).

Moisan, J., et al., "TLR7 Ligand Prevents Allergen-induced Airway Hyperresponsiveness and Eosinophilia in Allergic Asthma by a MYD88-dependent and MK2-independent Pathway," American Journal of Physiology—Lung Cellular and Molecular Physiology 290(5):L987-L995, American Physiological Society, United States (2006).

Nitta, S., et al., "Hepatitis C Virus NS4B protein targets STING and Abrogates RIG-I-mediated Type I Interferon-dependent Innate Immunity," Hepatology 57(1):46-58, The American Association for the Study of Liver Diseases, United States (2013).

Persing, D.H., et al., "Taking Toll: Lipid A Mimetics as Adjuvants and Immunomodulators," Trends in Microbiology 10(10 Suppl):S32-S37, Elsevier Science Ltd., England (2002).

Prantner, D., et al., "Stimulator of IFN Gene Is Critical for Induction of IFN-ß During *Chlamydia muridarum* Infection," Journal of Immunology 184(5):2551-2560, American Association of Immunologists, United States (2010).

Rakoff-Nahoum, S., et al., "Recognition of Commensal Microflora by Toll-like Receptors is Required for Intestinal Homeostasis," Cell 118(2):229-241, Cell Press, United States (2004).

Sharma, S., et al., "Innate Immune Recognition of an AT-rich Stem-loop DNA Motif in the *Plasmodium falciparum* Genome," Immunity 35(2):194-207, Elsevier Inc., United States (2011).

Stetson, D.B., et al., "Trex1 Prevents Cell-intrinsic Initiation of Autoimmunity," Cell 134(4):587-598, Cell Press, United States (2008).

Storek K.M., et al., "cGAS and Ifi204 Cooperate to Produce Type I IFNs in Response to *Francisella* Infection," Journal of Immunology 194(7):3236-3245, American Association of Immunologists, United States (2015).

Sun, L., et al., "Coronavirus Papain-like Proteases Negatively Regulate Antiviral Innate Immune Response Through Disruption of STING-mediated Signaling," Plos One 7(2):e30802, Public Library of Science, United States (2012).

Sun, L., et al., "Cyclic GMP-AMP Synthase Is a Cytosolic DNA Sensor That Activates the Type I Interferon Pathway," Science 339(6121):786-791, Author manuscript, American Association for the Advancement of Science, United States (2013).

Todorov, A.R., et al., "Tautomeric Switching and Metal-cation Sensing of Ligand-equipped 4-hydroxy-/4-oxo-1,4-dihydroquinolines," Eur. J. Chem. 18(23):7269-7277, Wiley-VCH, Germany (2012).

Wassermann, R., et al., "*Mycobacterium tuberculosis* Differentially Activates cGAS- and Inflammasome-Dependent Intracellular Immune Responses through ESX-1," Cell Host & Microbe 17(6):799-810, Cell Press, United States (2015).

Watson, R.O., et al., "The Cytosolic Sensor cGAS Detects *Mycobacterium tuberculosis* DNA to Induce Type I Interferons and Activate Autophagy," Cell Host & Microbe 17(6):811-819, Cell Press, United States (2015).

(56) References Cited

OTHER PUBLICATIONS

Woo, S.-R., et al., "The STING Pathway and the T Cell-inflamed Tumor Microenvironment," Trends in Immunology 36(4):250-256, Author manuscript, Elsevier Science Ltd., England (2015).

Wu, J.-J., et al., "Inhibition of cGAS DNA Sensing by a Herpesvirus Virion Protein," Cell Host & Microbe 18(3):333-344, Cell Press, United States (2015).

Zhang, B., et al., "Molecular Design, Synthesis and Biological Research of Novel Pyridyl Acridones as Potent DNA-binding and Apoptosis-inducing Agents," European Journal of Medicinal Chemistry 93:214-226, Elsevier Masson SAS, France (2015).

Zitvogel, L., et al., "Type I Interferons in Anticancer Immunity," Nature Reviews Immunology 15(7):405-414, Macmillan Publishers Ltd., England (2015).

Beck, A., et al., "Strategies and challenges for the next generation of antibody-drug conjugates," Nature Reviews Drug Discovery 16(5):315-337, Springer Nature, Germany (2017).

Mousavizadeh, A., et al., "Cell targeting peptides as smart ligands for targeting of therapeutic or diagnostic agents: a systematic review," Colloids Surfaces B. 158:507-517, Elsevier, Netherlands (2017).

Orava, E.W., et al., "Delivering cargoes into cancer cells using DNA aptamers targeting internalized surface portals," Biochimica Biophys. Acta 1798:2190-2200, Elsevier, Netherlands (2010).

Pedley, R.B., et al., "The potential for enhanced tumour localisation by poly(ethylene glycol) modification of anti-CEA antibody," Br. J. Cancer 70:1126-1130, Macmillan Press Ltd, Great Britain (1994).

Polakis, P., "Antibody Drug Conjugates for Cancer Therapy," Pharmacol. Revs. 68(1):3-19, American Society for Pharmacology and Experimental Therapeutics, United States (2016).

Turner, A., et al., "Comparative biodistributions of indium-111-labelled macrocycle chimeric B72.3 antibody conjugates in tumour-bearing mice," Br. J. Cancer 70:35-41, Macmillan Press Ltd, Great Britain (1994).

Office Action mailed Sep. 30, 2024, in U.S. Appl. No. 17/618,007, Zawadzka M., et al., § 371(c) date Dec. 10, 2021, 31 pages.

* cited by examiner

MODULATORS OF STIMULATOR OF INTERFERON GENES (STING)

FIELD OF THE INVENTION

The present invention relates to compounds of formula (I) and salts, stereoisomers, tautomers or N-oxides thereof that are useful as modulators of STING (Stimulator of Interferon Genes). The present invention further relates to the compounds of formula (I) for use as a medicament and to a pharmaceutical composition comprising said compounds.

BACKGROUND OF THE INVENTION

The cellular innate immune system is essential for recognizing pathogen infection and for establishing effective host defense. The adaptor protein STING (Stimulator of Interferon Genes), also known as TMEM 173, MPYS, MITA and ERIS, has been identified as a central signaling molecule in the innate immune response to cytosolic nucleic acids (H. Ishikawa, G. N. Barber, Nature, 2008, vol. 455, pp. 674-678). STING inter alia induces type I interferon (IFN) production when cells are infected with intracellular pathogens, such as viruses, mycobacteria and intracellular parasites.

Activation of STING promotes IRF3 and NFkB-dependent signaling leading in consequence to production of proinflammatory cytokines and interferons, including type I and type III interferons and TNF α of particular importance in cancer immunotherapy. STING is responsible for sensing of cytoplasmic nucleic acids and their derivatives called cyclic dinucleotides (CDN), both of pathogen or host origin (e.g. double stranded DNA from bacteria or viruses and cytoplasmic self-DNA).

Endogenous STING direct agonist 2',3'-cGAMP (2',3'-cyclic guanosine monophosphate-adenosine monophosphate) is produced in mammalian cells by enzyme cGAS (cyclic GMP-AMP synthase, MB21D1 or C6orf150) (P. Gao et al., Cell, 2013, 153, pp. 1094-1107, Wu et al. Science, 2013, 339, pp. 786-791) and has proven activity in modulating STING-dependent pathway, together with its derivatives (L. Corrales at al., J Immunother Cancer, 2013, 1(Suppl 1): 015, L. Corrales at al., Cell Rep., 2015, May 19; 11(7), pp. 1018-30, S-R. Woo at al., Trends Immunol., 2015, 36 (4), 250, J. Fu at al., Sci. Trans. Med., Vol. 7, Issue 283, pp. 283ra52).

Recent evidence supports findings that once STING is activated by CDN within tumor microenvironment, preferably in tumor-resident dendritic cells, it promotes type I IFN and TNF α release which results in immunity-mediated anti-tumor response. STING-dependent activation of antigen-presenting cells (APC) efficiently drives highly specific T-cell priming against neoantigens (L. Corrales and T F. Gajewski, Clin Cancer Res, 2015, 21 (21), pp. 4774-9). STING activation not only provides generation of tumor-specific killer T cells which directly eradicate tumors, but also results in vaccine-like long-lasting immunity protecting from cancer recurrence.

Thus, synthetic STING agonist are of special interest as potential anticancer agents. The activation or inhibition of type I interferon production is an important strategy for the treatment or prevention of human diseases including viral infections and autoimmune disease. It has been found that compounds activating or inhibiting type I interferon production may be useful not only in infectious disease innate immunity, but also in cancer (L. Zitvogel et al., Nature Reviews Immunology, 2015, vol. 15(7), pp. 405-414), allergic diseases (J. Moisan et al., Am. J. Physiol. Lung Cell Mol. Physiol., 2006, vol. 290, L987-995), neurodegenerative diseases such as amyotrophic lateral sclerosis and multiple sclerosis (H. Lemos et al., J. Immunol, 2014, vol. 192(12), pp. 5571-8; E. Cirulli et al., Science, 2015, vol. 347(6229), pp. 1436-41; A. Freischmidt et al., Nat. Neurosci., vol. 18(5), 631-6), other inflammatory conditions such as irritable bowel disease (S. Rakoff-Nahoum, Cell, 2004, 23, 118(2), pp. 229-41), and as vaccine adjuvants (Persing et al., Trends Microbiol. 2002, 10(10 Suppl), S32-7; Dubensky et al, Therapeutic Advances in Vaccines, published online Sep. 5, 2013).

STING is essential for antimicrobial host defense, including protection against a range of DNA and RNA viruses and bacteria (reviewed in Barber et al., Nat. Rev. Immunol., 2015, vol. 15(2), pp. 87-103, Ma and Damania, Cell Host & Microbe, 2016, vol. 19(2), pp. 150-158). Herpesviridae, Flaviviridae, Coronaviridae, Papillomaviridae, Adenoviridae, Hepadnaviridae, ortho- and paramyxoviridae and rhabdoviridae have evolved mechanisms to inhibit STING mediated Type I interferon production and evade host immune control (Holm et al., Nat Comm., 2016, vol. 7, p. 10680; Ma et al., PNAS 2015, vol. 112(31) E4306-E4315; Wu et al., Cell Host Microbe, 2015, vol. 18(3), pp. 333-44; Liu et al., J Virol, 2016, vol. 90(20), pp. 9406-19; Chen et al., Protein Cell 2014, vol. 5(5), pp. 369-81; Lau et al., Science, 2013, vol. 350(6260), pp. 568-71; Ding et al., J Hepatol, 2013, vol. 59(1), pp. 52-8; Nitta et al., Hepatology, 2013, vol. 57(1), pp. 46-58; Sun et al., PloS One, 2012, vol. 7(2), e30802; Aguirre et al., PloS Pathog, 2012, vol. 8(10), e1002934; Ishikawa et al., Nature, 2009, vol. 461(7265), pp. 788-92). Thus, small molecule activation of STING is considered to be beneficial for treatment of these infectious diseases.

In contrast, increased and prolonged type I IFN production is associated with a variety of chronic infections, including Mycobacteria (Collins et al., Cell Host Microbe, 2015, vol. 17(6), pp. 820-8); Wassermann et al., Cell Host Microbe, 2015, vol. 17(6), pp. 799-810; Watson et al., Cell Host Microbe, 2015, vol. 17(6), pp. 811-9), Franciscella (Storek et al., J Immunol., 2015, vol. 194(7), pp. 3236-45; Jin et al., J Immunol., 2011, vol. 187(5), pp. 2595-601), *Chlamydia* (Prantner et al., J Immunol, 2010, vol. 184(5), pp. 2551-60), *Plasmodium* (Sharma et al., Immunity, 2011, vol. 35(2), pp. 194-207), and HIV (Herzner et al., Nat Immunol, 2015, vol. 16(10), pp. 1025-33; Gao et al., Science, 2013, vol. 341(6148), pp. 903-6). Similarly, excess type I interferon production is found among patients with complex forms of autoimmune disease. Genetic evidence in humans and support from studies in animal models support the hypothesis that inhibition of STING results in reduced type I interferon that drives autoimmune disease (Y. J. Crow et al., Nat. Genet., 2006, vol. 38(8), pp. 38917-920, D. B. Stetson et al., Cell, 2008, pp. 134587-598). Therefore, inhibitors of STING provide a treatment to patients with chronic type I interferon and proinflammatory cytokine production associated with infections or complex autoimmune diseases. Allergic diseases are associated with a Th2-biased immune-response to allergens. Th2 responses are associated with raised levels of IgE, which, via its effects on mast cells, promotes a hypersensitivity to allergens, resulting in the symptoms seen, for example, in allergic rhinitis and asthma. In healthy individuals the immune-response to allergens is more balanced with a mixed Th2/Th1 and regulatory T cell response. Induction of Type 1 interferons have been shown to result in reduction of Th2-type cytokines in the local environment and promote Th1/Treg responses. In this context, induction of type 1 interferons by, for example, activation of STING, may offer benefit in treatment of allergic diseases such as asthma and allergic rhinitis (J. P. Huber et al., J Immunol, 2010, vol. 185, pp. 813-817).

In view of the above, compounds modulating STING are useful for treating one or more diseases selected from the group consisting of inflammatory, allergic, and autoimmune diseases, infectious diseases, cancer, pre-cancerous syndromes, and/or as immunogenic composition or vaccine adjuvants. Of particular relevance is the immunotherapy of cancer and viral infections, in particular prostate cancer, renal carcinoma, melanoma, pancreatic cancer, cervical cancer, ovarian cancer, colon cancer, head and neck cancer, lung cancer, fibrosarcoma, breast cancer and hepatitis B. Furthermore, activation of local immune response to the lesions is considered to be preferably an intratumoral therapeutic approach.

Accordingly, there is a need for compounds modulating the activity of STING, and accordingly, provide a therapeutic impact in the treatment of diseases, in which the modulation of STING is beneficial.

OBJECTS AND SUMMARY OF THE INVENTION

It is therefore an object of the present invention to provide compounds, which modulate STING, in particular compounds, which act as STING agonists, thereby activating STING.

It is another object of the present invention to provide compounds, which are suitable for use as a medicament. It is another object of the present invention to provide compounds, which are suitable for use in the treatment of one or more diseases, which are linked to STING modulation. It is yet another object to provide compounds, which are suitable for use in the treatment of one or more diseases selected from the group consisting of inflammatory diseases, allergic diseases, autoimmune diseases, infectious diseases, cancer, and pre-cancerous syndromes. In particular, it is an object to provide compounds, which are suitable for the treatment of cancer, in particular prostate cancer, lung cancer, and/or melanoma. It is yet another object to provide compounds, which are suitable for use in immunogenic compositions are as vaccine adjuvants.

The above objects can be achieved by the compounds of formula (I) as defined herein as well as pharmaceutical compositions comprising the same, and by the medical uses thereof.

The inventors of the present invention inter alia surprisingly found that the compounds of formula (I) as defined herein modulate STING, in particular act as STING agonists. Accordingly, the compounds of formula (I) can be used as a medicament, in particular for the treatment of one or more diseases selected from the group consisting of inflammatory diseases, allergic diseases, autoimmune diseases, infectious diseases, cancer, and pre-cancerous syndromes. In particular, the compounds of formula (I) are suitable for the treatment of cancer, in particular prostate cancer, lung cancer, and/or melanoma. Further the compounds of formula (I) are suitable for use in immunogenic compositions are as vaccine adjuvants.

In a first aspect, the present invention therefore relates to a compound of formula (I)

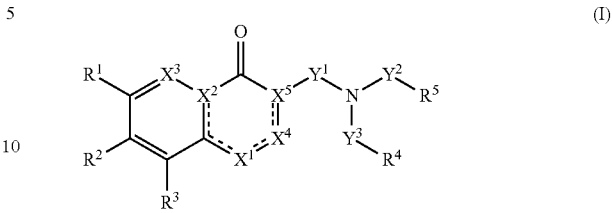

or a salt, stereoisomer, tautomer, or N-oxide thereof, wherein the dashed lines in the 6-membered ring that contains the =O substituent denote the presence of one or two additional bonds, so that one or two double bonds are formed, wherein, in case of two double bonds, between each double bond a single bond must be present;

and wherein $X^1$ is O, S, S(=O), S(=O)$_2$, N, or NR$^N$;

$X^2$ is C, CH, or N;

$X^3$ is CR$^A$, or N;

$X^4$ is CR$^A$, CR$^A$R$^B$, N, or NR$^N$;

$X^5$ is C, CH, or N;

$Y^1$ is S(=O)$_2$, or C$_1$-C$_2$-alkylene, which is unsubstituted or substituted with one or more, same or different substituents R$^Z$;

$Y^2$ is absent, S(=O)$_2$, S(=O)$_2$—C$_1$-C$_4$-alkylene, S(=O)$_2$-arylene, or C$_1$-C$_4$-alkylene, wherein the carbon atoms are in each case unsubstituted or substituted with one or more, same or different substituents R$^Z$;

$Y^3$ is absent, S(=O)$_2$, or C$_1$-alkylene, which is unsubstituted or substituted with one or more, same or different substituents R$^Z$;

$R^1$, $R^2$ and $R^3$ are independently H, OH, CN, halogen, C$_1$-C$_4$-alkyl, C$_1$-C$_4$-alkoxy, aryloxy, benzyloxy, C(=O)R$^E$, NR$^F$C(=O)R$^E$, or 5- or 6-membered saturated, partially or fully unsaturated, or aromatic carbocyclyl, carbocyclyl-C$_1$-C$_2$-alkyl, heterocyclyl, or heterocyclyl-C$_1$-C$_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents R$^X$;

or $R^1$ and $R^2$ or $R^2$ and $R^3$ together with the carbon atoms to which they are bonded form a 5- or 6-membered saturated, partially or fully unsaturated, or aromatic carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents R$^X$;

$R^4$ is a 5- or 6-membered aromatic carbocyclic or heterocyclic ring, or a 9- or 10-membered aromatic carbobycyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^X$;

$R^5$ is a 5- or 6-membered saturated, partially or fully unsaturated, or aromatic carbocyclic or heterocyclic ring, or a 9- or 10-membered saturated, partially or fully unsaturated, or aromatic carbobycyclic or heterobicyclic ring, wherein the heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^Y$;

and wherein $R^N$ is H, $C_1$-$C_6$-alkyl or 3- to 6-membered carbocyclyl or heterocyclyl, wherein the aforementioned heterocyclic ring comprises one or more, same or different heteroatoms selected from O, N or S, wherein said N-atoms are independently oxidized or non-oxidized;

$R^A$ is H, halogen, CN, OH, $C_1$-$C_3$-alkyl, $C_1$-$C_3$-alkoxy, or 3- to 6-membered saturated, partially or fully unsaturated, or aromatic carbocyclyl, or heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^B$ is H, halogen, CN, OH, $C_1$-$C_3$-alkyl, or $C_1$-$C_3$-alkoxy; or $R^A$ and $R^B$ together with the carbon atom to which they are bonded form a 3- to 5-membered saturated, partially or fully unsaturated, or aromatic carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^C$ and $R^D$ are independently H, or $C_1$-$C_2$-alkyl; or $R^C$ and $R^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^E$ is H, $C_1$-$C_2$-alkyl, phenyl, benzyl, $OR^G$, or $NR^HR^I$;

$R^F$ is H, $C_1$-$C_2$-alkyl, $C_3$-$C_6$-cycloalkyl, phenyl, or benzyl;

$R^G$ is H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized; or $R^H$ and $R^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^X$ is halogen, CN, $C_1$-$C_2$-alkyl, or $C_1$-$C_2$-alkoxy;

$R^Y$ is halogen, CN, OH, $C_1$-$C_2$-alkyl, $C_3$-$C_6$-cycloalkyl, $C_1$-$C_2$-alkoxy, $NR^CR^D$, $S(=O)_2NR^CR^D$, $C(=O)R^E$, or 5- or 6-membered saturated, partially or fully unsaturated, or aromatic carbocyclyl, carbocyclyl-$C_1$-$C_2$-alkyl, heterocyclyl, and heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$; or two $R^Y$ form =O;

$R^Z$ is halogen, CN, $C_1$-$C_3$-alkyl, or $C_3$-$C_6$-cycloalkyl; or two $R^Z$ together with the atom to which they are bonded form a 3- to 5-membered saturated carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In a preferred embodiment, the present invention relates to a compound of formula (I)

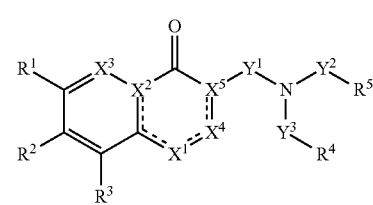

(I)

or a salt, stereoisomer, tautomer, or N-oxide thereof, wherein the dashed lines in the 6-membered ring that contains the =O substituent denote the presence of one or two additional bonds, so that one or two double bonds are formed, wherein, in case of two double bonds, between each double bond a single bond must be present;

and wherein $X^1$ is O, S, S(=O), $S(=O)_2$, N, or $NR^N$;

$X^2$ is C, CH, or N;

$X^3$ is $CR^A$, or N;

$X^4$ is $CR^A$, $CR^AR^B$, N, or $NR^N$;

$X^5$ is C, CH, or N;

$Y^1$ is $S(=O)_2$, or $C_1$-$C_2$-alkylene, which is unsubstituted or substituted with one or more, same or different substituents $R^Z$;

$Y^2$ is absent, or $C_3$- or $C_4$-alkylene, wherein the carbon atoms are in each case unsubstituted or substituted with one or more, same or different substituents $R^Z$;

$Y^3$ is absent, $S(=O)_2$, or $C_1$-alkylene, which is unsubstituted or substituted with one or more, same or different substituents $R^Z$;

$R^1$, $R^2$ and $R^3$ are independently H, OH, CN, halogen, $C_1$-$C_4$-alkyl, $C_1$-$C_4$-alkoxy, aryloxy, benzyloxy, C(=O)$R^E$, $NR^FC(=O)R^E$, or 5- or 6-membered saturated, partially or fully unsaturated, or aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$; or $R^1$ and $R^2$ or $R^2$ and $R^3$ together with the carbon atoms to which they are bonded form a 5- or 6-membered saturated, partially or fully unsaturated, or aromatic carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^X$;

$R^4$ is pyridinyl, wherein each substitutable carbon or heteroatom in the aforementioned pyridinyl ring is independently unsubstituted or substituted with one or more, same or different substituents $R^X$;

$R^5$ is a 5- or 6-membered saturated, partially or fully unsaturated, or aromatic carbocyclic or heterocyclic ring, or a 9- or 10-membered saturated, partially or fully unsaturated, or aromatic carbobycyclic or heterobicyclic ring, wherein the heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^Y$;

and wherein $R^N$ is H, $C_1$-$C_6$-alkyl or 3- to 6-membered carbocyclyl or heterocyclyl, wherein the aforementioned heterocyclic ring comprises one or more, same or different heteroatoms selected from O, N or S, wherein said N-atoms are independently oxidized or non-oxidized;

$R^A$ is H, halogen, CN, OH, $C_1$-$C_3$-alkyl, $C_1$-$C_3$-alkoxy, or 3- to 6-membered saturated, partially or fully unsaturated, or aromatic carbocyclyl, or heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^B$ is H, halogen, CN, OH, $C_1$-$C_3$-alkyl, or $C_1$-$C_3$-alkoxy; or $R^A$ and $R^B$ together with the carbon atom to which they are bonded form a 3- to 5-membered saturated, partially or fully unsaturated, or aromatic carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^C$ and $R^D$ are independently H, or $C_1$-$C_2$-alkyl; or $R^C$ and $R^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^E$ is H, $C_1$-$C_2$-alkyl, phenyl, benzyl, $OR^G$, or $NR^HR^I$;

$R^F$ is H, $C_1$-$C_2$-alkyl, $C_3$-$C_6$-cycloalkyl, phenyl, or benzyl;

$R^G$ is H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized; or $R^H$ and $R^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^X$ is halogen, CN, $C_1$-$C_2$-alkyl, or $C_1$-$C_2$-alkoxy;

$R^Y$ is halogen, CN, OH, $C_1$-$C_2$-alkyl, $C_3$-$C_6$-cycloalkyl, $C_1$-$C_2$-alkoxy, $NR^CR^D$, $S(=O)_2NR^CR^D$, $C(=O)R^E$, or 5- or 6-membered saturated, partially or fully unsaturated, or aromatic carbocyclyl, carbocyclyl-$C_1$-$C_2$-alkyl, heterocyclyl, and heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$; or two $R^Y$ form =O;

$R^Z$ is halogen, CN, $C_1$-$C_3$-alkyl, or $C_3$-$C_6$-cycloalkyl; or two $R^Z$ together with the atom to which they are bonded form a 3- to 5-membered saturated carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In a preferred embodiment, the compound of formula (I) is not:

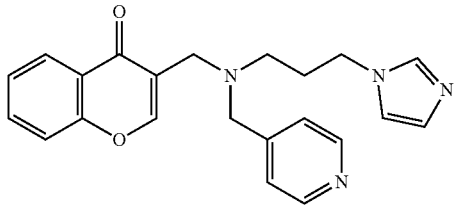 [SMILES: O=c1c(CN(CCCn2ccnc2)Cc2ccncc2)coc2ccccc12]

In another preferred embodiment, the compound is a compound according to formula (Ia*):

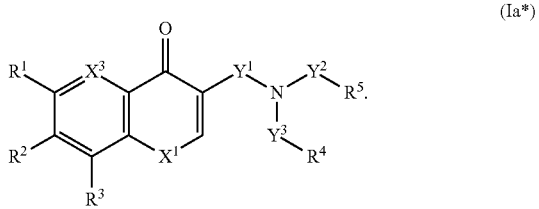

In another preferred embodiment,
$X^1$ is O; and
$X^3$ is CH.

In another preferred embodiment,
$Y^1$ is $C_1$-alkylene, which is unsubstituted or substituted with one or more, same or different substituents $R^Z$.

In another preferred embodiment,
$Y^2$ is absent, or $C_1$-$C_4$-alkylene, preferably $C_2$- or $C_3$-alkylene, wherein the carbon atoms are in each case unsubstituted or substituted with one or more, same or different substituents $R^Z$.

In another preferred embodiment,
$Y^2$ is absent, or $C_3$- or $C_4$-alkylene, preferably $C_3$-alkylene, wherein the carbon atoms are in each case unsubstituted or substituted with one or more, same or different substituents $R^Z$.

In another preferred embodiment,
$Y^3$ is $C_1$-alkylene, which is unsubstituted or substituted with one or more, same or different substituents $R^Z$.

In another preferred embodiment,
$R^1$ is H or halogen, preferably H or F.

In another preferred embodiment,
$R^2$ and $R^3$ are independently H, halogen, CN, OH, $C_1$-$C_2$-alkyl, $C_1$-$C_2$-alkoxy, benzyloxy, or 6-membered saturated heterocyclyl, wherein the aforementioned heterocyclic ring comprises one or more nitrogen atoms, wherein said N-atoms are independently oxidized or non-oxidized, and wherein each substitutable carbon or heteroatom in the aforementioned groups is independently unsubstituted or substituted with one or more, same or different substituents $R^X$;
or
$R^2$ and $R^3$ together with the carbon atoms to which they are bonded form 6-membered aromatic carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^X$.

In another preferred embodiment,
$R^4$ is pyridinyl, wherein each substitutable carbon or heteroatom in the cyclic ring is independently unsubstituted or substituted with one or more, same or different substituents $R^X$.

In another preferred embodiment,
$R^5$ is a 5- or 6-membered saturated, partially or fully unsaturated, or aromatic heterocyclic ring, or a 9- or 10-membered saturated, partially or fully unsaturated, or aromatic heterobicyclic ring, wherein the heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^Y$.

In another preferred embodiment, the compound of formula (I) is a compound selected from the group consisting of:

3-({[3-(1H-imidazol-1-yl)propyl](pyridin-4-ylmethyl)amino}methyl)-7,8-dimethyl-4H-chromen-4-one;
3-({[3-(1H-imidazol-1-yl)propyl](pyridin-4-ylmethyl)amino}methyl)-4H-benzo[h]chromen-4-one;
3-({[3-(1H-imidazol-1-yl)propyl](pyridin-4-ylmethyl)amino}methyl)-7-methoxy-4H-chromen-4-one;
7-bromo-3-({[3-(1H-imidazol-1-yl)propyl](pyridin-4ylmethyl)amino}methyl)-4H-chromen-4-one;
3-({[3-(1H-imidazol-1-yl)propyl](pyridin-4-ylmethyl)amino}methyl)-7-(4-methylpiperazin-1-yl)-4H-chromen-4-one;
7-(benzyloxy)-3-({[3-(1H-imidazol-1-yl)propyl](pyridin-4-ylmethyl)amino}methyl)-4H-chromen-4-one;
3-({[3-(1H-1,3-benzodiazol-1-yl)propyl](pyridin-4-ylmethyl)amino}methyl)-4H-chromen-4-one;
3-({[3-(pyridin-3-yl)propyl][(pyridin-4-yl)methyl]amino}methyl)-4H-chromen-4-one;
3-({[3-(1H-imidazol-1-yl)propyl](pyridin-4-ylmethyl)amino}methyl)-4H,7H,8H,9H,10H-cyclohexa[h]chromen-4-one;
3-({[(pyridin-4-yl)methyl][3-(pyridin-4-yl)propyl]amino}methyl)-4H-chromen-4-one;
3-({[3-(pyridin-3-yl)propyl](pyridin-4-ylmethyl)amino}methyl)-4H-benzo[h]chromen-4-one;
6-fluoro-3-({[3-(1H-imidazol-1-yl)propyl][(pyridin-4-yl)methyl]amino}methyl)-4H-chromen-4-one;
3-({[3-(1H-imidazol-1-yl)propyl][(2-methoxypyridin-4-yl)methyl]amino}methyl)-4H-benzo[h]chromen-4-one;
6-fluoro-3-({[3-(1H-imidazol-1-yl)propyl][(pyridin-4-yl)methyl]amino}methyl)-4H benzo[h]chromen-4-one;
7-bromo-3-({[3-(1H-imidazol-1-yl)propyl][(pyridin-4-yl)methyl]amino}methyl)-2-methyl-4H chromen-4-one;
6-fluoro-3-({[3-(1H-imidazol-1-yl)propyl][(pyridin-4-yl)methyl]amino}methyl)-7-(4-methylpiperazin-1-yl)-4H-chromen-4-one;
3-({[3-(1H-1,3-benzodiazol-1-yl)propyl][(pyridin-4-yl)methyl]amino}methyl)-4H-benzo[h]chromen-4-one;
3-({[3-(1H-imidazol-1-yl)propyl][(2-methoxypyridin-4-yl)methyl]amino}methyl)-7,8-dimethyl-4H chromen-4-one;
9-methoxy-3-({[3-(pyridin-3-yl)propyl][(pyridin-4-yl)methyl]amino}methyl)-4H-benzo[h]chromen-4-one;
3-({[3-(1H-1,3-benzodiazol-1-yl)propyl][(2-methoxypyridin-4-yl)methyl]amino}methyl)-4H-benzo[h]chromen-4-one;

6-fluoro-3-({[3-(pyridin-3-yl)propyl][(pyridin-4-yl)methyl]amino}methyl)-4H-benzo[h]chromen-4-one;
2,7,8-trimethyl-3-({[3-(pyridin-3-yl)propyl][(pyridin-4-yl)methyl]amino}methyl)-4H-chromen-4-one;
6-fluoro-7-(4-methylpiperazin-1-yl)-3-({[3-(pyridin-3-yl)propyl](pyridin-4-ylmethyl)amino}methyl)-4H-chromen-4-one;
3-({[3-(1H-1,3-benzodiazol-1-yl)propyl][(pyridin-4-yl)methyl]amino}methyl)-9-methoxy-4H benzo[h]chromen-4-one;
7-bromo-6-fluoro-2-methyl-3-({[3-(pyridin-3-yl)propyl][(pyridin-4-yl)methyl]amino}methyl)-4H chromen-4-one;
7-bromo-2-methyl-3-({[3-(pyridin-3-yl)propyl](pyridin-4-ylmethyl)amino}methyl)-4H-chromen-4-one;
6-fluoro-2-methyl-7-(4-methylpiperazin-1-yl)-3-({[3-(pyridin-3-yl)propyl][(pyridin-4-yl)methyl]amino}methyl)-4H-chromen-4-one;
3-{[(3-{1H-imidazo[4,5-b]pyridin-1-yl}propyl)(pyridin-4-ylmethyl)amino]methyl}-4H benzo[h]chromen-4-one;
6-fluoro-2-methyl-7-(piperazin-1-yl)-3-({[3-(pyridin-3-yl)propyl][(pyridin-4-yl)methyl]amino}methyl)-4H-chromen-4-one;
6-fluoro-2-methyl-7-(morpholin-4-yl)-3-({[3-(pyridin-3-yl)propyl][(pyridin-4-yl)methyl]amino}methyl)-4H-chromen-4-one;
3-({[4-(1H-1,3-benzodiazol-1-yl)butan-2-yl](pyridin-4-ylmethyl)amino}methyl)-4H-benzo[h]chromen-4-one;
7-bromo-6-fluoro-2-methyl-3-({[3-(9H-purin-9-yl)propyl][(pyridin-4-yl)methyl]amino}methyl)-4H chromen-4-one;
6-fluoro-3-({[(2-methoxypyridin-4-yl)methyl][3-(pyridin-3-yl)propyl]amino}methyl)-2-methyl-7-(morpholin-4-yl)-4H-chromen-4-one;
7-bromo-6-fluoro-3-({[(2-methoxypyridin-4-yl)methyl][3-(9H-purin-9-yl)propyl]amino}methyl)-2-methyl-4H-chromen-4-one;
6-fluoro-2-methyl-7-(4-methylpiperazin-1-yl)-3-({[3-(9H-purin-9-yl)propyl][(pyridin-4-yl)methyl]amino}methyl)-4H-chromen-4-one;
3-({[3-(1H-1,3-benzodiazol-1-yl)propyl][(2-methoxypyridin-4-yl)methyl]amino}methyl)-1-methyl-1,4-dihydroquinolin-4-one;
3-({[(2-methoxypyridin-4-yl)methyl][4-(pyridin-3-yl)butan-2-yl]amino}methyl)-4H benzo[h]chromen-4-one;
3-({[(2-methoxypyridin-4-yl)methyl][3-(9H-purin-9-yl)propyl]amino}methyl)-1-methyl-1,4-dihydroquinolin-4-one;
3-({[(2-methoxypyridin-4-yl)methyl][4-(pyridin-3-yl)butan-2-yl]amino}methyl)-1-methyl-1,4-dihydroquinolin-4-one;
3-({[3-(1H-1,3-benzodiazol-1-yl)propyl][(2-methylpyridin-4-yl)methyl]amino}methyl)-1-methyl-1,4-dihydroquinolin-4-one;
and
1-methyl-3-({[(2-methylpyridin-4-yl)methyl][3-(pyridin-3-yl)propyl]amino}methyl)-1,4-dihydroquinolin-4-one.

In a further aspect, the present invention relates to pharmaceutical composition comprising a pharmaceutically effective amount of the compound of formula (I) as defined herein, and optionally a pharmaceutically acceptable carrier, diluent or excipient.

In yet another aspect, the present invention relates to a compound of formula (I) as defined herein or a pharmaceutical composition comprising the same as defined herein for use in medicine. In particular, the present invention relates to a compound of formula (I) as defined herein or a pharmaceutical composition comprising the same as defined herein for use in modulating STING, in particular activating STING.

In yet another aspect, the present invention relates to a compound of formula (I) as defined herein or a pharmaceutical composition comprising the same as defined herein for use in a method of treating a disease, in which the modulation of STING, in particular the activation of STING, is beneficial.

In one embodiment, the compound of the present invention or a pharmaceutical composition comprising the same is for use in the treatment of a disease selected from the group consisting of cancer, pre-cancerous syndromes, and infectious diseases; or for use in an immunogenic composition or as vaccine adjuvant.

In another embodiment, the compound of the present invention or a pharmaceutical composition comprising the same is for use in the treatment of a disease selected from the group consisting of inflammatory diseases, allergic diseases, and autoimmune diseases.

In further aspects, the present invention relates to methods of treatment comprising the administration of a compound of formula (I) as defined herein or a pharmaceutical composition comprising the same as defined herein to a human or animal body.

DETAILED DESCRIPTION

In the following, preferred embodiments of the substituents in the above formula (I) are described in further detail. It is to be understood that each preferred embodiment is relevant on its own as well as in combination with other preferred embodiments. Furthermore, it is to be understood that the preferences in each case also apply to the salts, stereoisomers, tautomers, and N-oxides of the compounds of the invention.

As indicated above, in the compound of formula (I)

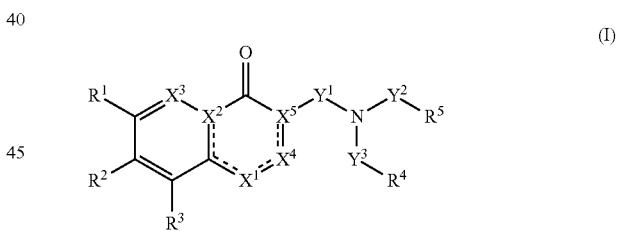

(I)

the dashed lines in the 6-membered ring that contains the =O substituent denote the presence of one or two additional bonds, so that a double bond is formed, wherein, in case of two double bonds, between each double bond a single bond must be present. In principal, the compound of formula (I) may therefore be a compound of formula (Ia), (Ib), (Ic), (Id), or (Ie) as shown below:

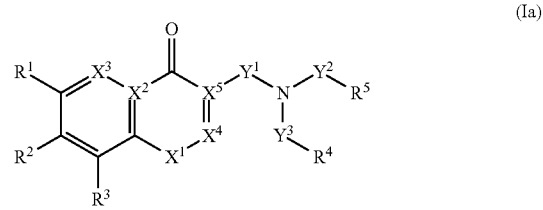

(Ia)

-continued

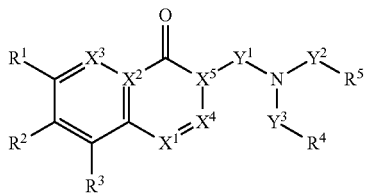
(Ib)

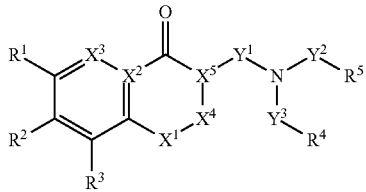
(Ic)

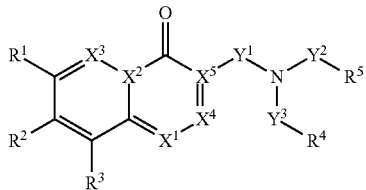
(Id)

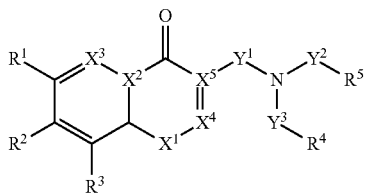
(Ie)

It is to be understood that the substituent meanings for $X^1$, $X^2$, $X^3$, $X^4$, and $X^5$ are in each case selected such that suitable valences of the atoms are realized. In connection with compounds of formula (Ia), this means that preferably $X^1$ is O, S, S(=O), S(=O)$_2$, or $NR^N$;
$X^2$ is C;
$X^3$ is $CR^A$, or N;
$X^4$ is $CR^A$, or N;
$X^5$ is C.

In connection with compounds of formula (Ib), this means that preferably $X^1$ is N;
$X^2$ is C;
$X^3$ is $CR^A$, or N;
$X^4$ is $CR^A$, or N;
$X^5$ is CH, or N.

In connection with compounds of formula (Ic), this means that preferably $X^1$ is O, S, S(=O), S(=O)$_2$, or $NR^N$;
$X^2$ is C;
$X^3$ is $CR^A$, or N;
$X^4$ is $CR^A R^B$, or $NR^N$;
$X^5$ is CH, or N.

In connection with compounds of formula (Id), this means that preferably $X^1$ is N;
$X^2$ is CH, or N;
$X^3$ is $CR^A$, or N;
$X^4$ is $CR^A$, or N;
$X^5$ is C.

In connection with compounds of formula (Ie), this means that preferably $X^1$ is O, S, S(=O), S(=O)$_2$, or $NR^N$;
$X^2$ is CH, or N;
$X^3$ is $CR^A$, or N;
$X^4$ is $CR^A$, or N;
$X^5$ is C.

It is to be understood that in each case $R^A$ is independently selected from the group of substituents as defined above in the context of formula (I). Further, it is to be understood that $R^B$ and $R^N$ as well as the remaining substituents of the compounds of formula (Ia), (Ib), (Ic), (Id), and (Ie) are as defined in formula (I) above. Further preferences regarding these substituents are provided further below.

In a preferred embodiment, the compound of formula (I) is a compound of formula (Ia), (Ib), or (Ic), i.e. a compound, wherein the 6-membered ring that is fused to the 6-membered ring that contains the =O substituent is aromatic. Thus, the compound of formula (I) is preferably a compound of the following formula (I')

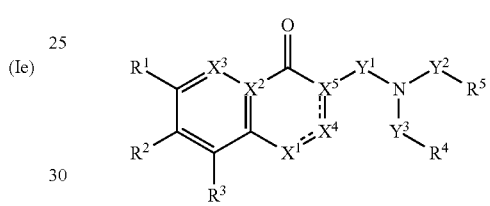
(I')

wherein the dashed lines in the 6-membered ring that contains the =O substituent denote the presence or absence of one additional bond, so that one further double bond in the ring may be present. In connection with the compounds of formula (I'), the following substituent meanings are preferred for $X^1$, $X^2$, $X^3$, $X^4$, and $X^5$:

$X^1$ is O, S, S(=O), S(=O)$_2$, N, or $NR^N$;
$X^2$ is C;
$X^3$ is $CR^A$, or N;
$X^4$ is $CR^A$, $CR^A R^B$, N or $NR^N$;
$X^5$ is C, CH, or N.

In a more preferred embodiment, the compound of formula (I) is a compound of formula (Ia)

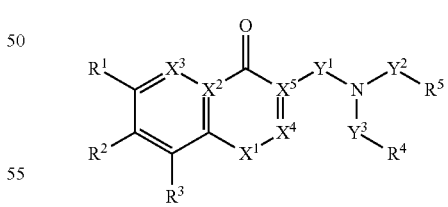
(Ia)

wherein $X^1$ is O, S, S(=O), S(=O)$_2$, or $NR^N$;
$X^2$ is C;
$X^3$ is $CR^A$, or N;
$X^4$ is $CR^A$, or N;
$X^5$ is C.

In this connection, the following combinations of meanings for $X^1$, $X^2$, $X^3$, $X^4$, and $X^5$ according to embodiments A-1 to A-20 according to Table A are preferred.

TABLE A

| No. | X$^1$ | X$^2$ | X$^3$ | X$^4$ | X$^5$ |
|---|---|---|---|---|---|
| A-1 | O | C | CR$^A$ | CR$^A$ | C |
| A-2 | O | C | N | CR$^A$ | C |
| A-3 | O | C | CR$^A$ | N | C |
| A-4 | O | C | N | N | C |
| A-5 | S | C | CR$^A$ | CR$^A$ | C |
| A-6 | S | C | N | CR$^A$ | C |
| A-7 | S | C | CR$^A$ | N | C |
| A-8 | S | C | N | N | C |
| A-9 | S(=O) | C | CR$^A$ | CR$^A$ | C |
| A-10 | S(=O) | C | N | CR$^A$ | C |
| A-11 | S(=O) | C | CR$^A$ | N | C |
| A-12 | S(=O) | C | N | N | C |
| A-13 | S(=O)$_2$ | C | CR$^A$ | CR$^A$ | C |
| A-14 | S(=O)$_2$ | C | N | CR$^A$ | C |
| A-15 | S(=O)$_2$ | C | CR$^A$ | N | C |
| A-16 | S(=O)$_2$ | C | N | N | C |
| A-17 | NR$^N$ | C | CR$^A$ | CR$^A$ | C |
| A-18 | NR$^N$ | C | N | CR$^A$ | C |
| A-19 | NR$^N$ | C | CR$^A$ | N | C |
| A-20 | NR$^N$ | C | N | N | C |

In an even more preferred embodiment, the compound of formula (I) is a compound of formula (Ia)

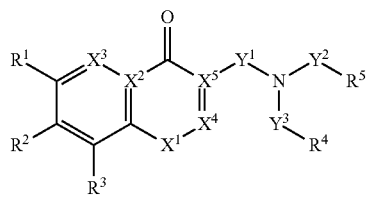

(Ia)

wherein
X$^1$, X$^2$, X$^3$, X$^4$, and X$^5$ are selected according to any one of embodiments A-1, A-2, A-5, A-6, A-9, A-10, A-13, A-14, A-17, or A-18, preferably according to any one of embodiments A-1, A-5, A-9, A-13, or A-17, in particular according to embodiment A-1. It is to be understood that for X$^3$ being CR$^A$ and for X$^4$ being CR$^A$, R$^A$ is in each case independently selected, so that the CR$^A$ groups may be identical or different from each other. In particular,
R$^A$ is H, halogen, ON, OH, C$_1$-C$_3$-alkyl, C$_1$-C$_3$-alkoxy, or 3- to 6-membered saturated, partially or fully unsaturated, or aromatic carbocyclyl, or heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents R$^X$;
and preferably
R$^A$ is H, C$_1$-C$_3$-alkyl, or 3- to 6-membered saturated, partially or fully unsaturated, or aromatic carbocyclyl, or heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents R$^X$.
In one particularly preferred embodiment X$^3$ is CH, and X$^4$ is CR$^A$, wherein R$^A$ is as defined above. In another particularly preferred embodiment X$^3$ is CR$^A$, or N, wherein R$^A$ is as defined above, and X$^4$ is CH. Such compounds may be represented by the following general formula (Ia*)

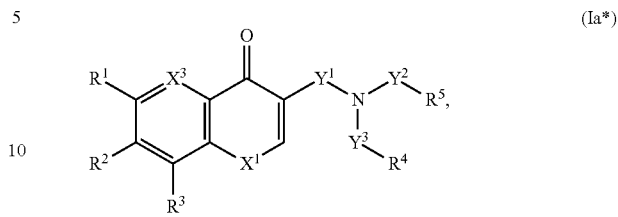

(Ia*)

wherein
X$^1$ is O, S, S(=O), S(=O)$_2$, or NR$^N$;
X$^3$ is CR$^A$, or N;
and the remaining substituents are as defined in formula (I) above.
In a preferred embodiment,
X$^1$ is O; and
X$^3$ is CH.
In connection with the compounds of formula (I), as well as in connection the compounds of formula (Ia), (Ib), (Ic), (Id), or (Ie), and in connection with the compounds of formula (I'), especially in connection with the compounds of formula (Ia) including embodiments A-1 to A-20, preferably embodiments A-1, A-2, A-5, A-6, A-9, A-10, A-13, A-14, A-17, or A-18, more preferably embodiments A-1, A-5, A-9, A-13, or A-17, most preferably embodiment A-1, and in particular in connection with the compounds of (Ia*), it is preferred that the compound is not:

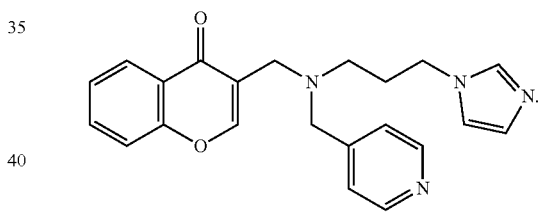

In connection with the compounds of formula (I), as well as in connection the compounds of formula (Ia), (Ib), (Ic), (Id), or (Ie), and in connection with the compounds of formula (I'), especially in connection with the compounds of formula (Ia) including embodiments A-1 to A-20, preferably embodiments A-1, A-2, A-5, A-6, A-9, A-10, A-13, A-14, A-17, or A-18, more preferably embodiments A-1, A-5, A-9, A-13, or A-17, most preferably embodiment A-1, and in particular in connection with the compounds of (Ia*), the following preferred embodiments regarding the remaining substituents Y$^1$, Y$^2$, and Y$^3$ are relevant.
As indicate above, in connection with the compounds of the present invention,
Y$^1$ is S(=O)$_2$, C$_1$-C$_2$-alkylene, which is unsubstituted or substituted with one or more, same or different substituents R$^Z$.
In one preferred embodiment, Y$^1$ is S(=O)$_2$. In another preferred embodiment, Y$^1$ is C$_1$-C$_2$-alkylene, which is unsubstituted or substituted with one or more, same or different substituents R$^Z$, wherein R$^Z$ is as defined above in connection with the compounds of formula (I), and wherein preferably
R$^Z$ is halogen, or C$_1$-C$_3$-alkyl; or two R$^Z$ together with the atom to which they are bonded form a 3- to 5-membered saturated carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In a more preferred embodiment, $Y^1$ is $C_1$-alkylene, which is unsubstituted or substituted with one or more, same or different substituents $R^Z$. In one particularly preferred embodiment, $Y^1$ is unsubstituted $C_1$-alkylene. In another particularly preferred embodiment $Y^1$ is $C_1$-alkylene, which is substituted with one or more, same or different substituents $R^Z$, wherein $R^Z$ is as defined above in connection with the compounds of formula (I), and wherein preferably $R^Z$ is halogen, or $C_1$-$C_3$-alkyl; or two $R^Z$ together with the atom to which they are bonded form a 3- to 5-membered saturated carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

If two $R^z$ groups together with the atom to which they are bonded form a 3- to 5-membered saturated carbocyclic or heterocyclic ring, this ring is preferably any one of the following rings:

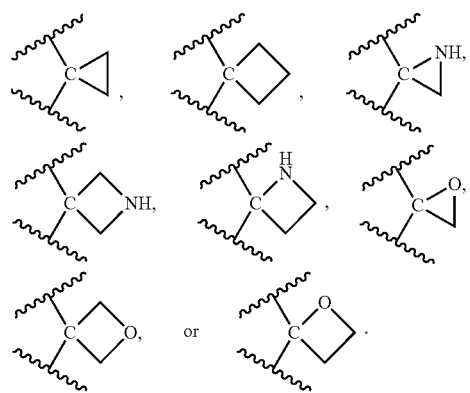

Further, in connection with the compounds of the present invention $Y^2$ is absent, $S(=O)_2$, $S(=O)_2$—$C_1$-$C_4$-alkylene, $S(=O)_2$-arylene or $C_1$-$C_4$-alkylene, wherein the carbon atoms are in each case unsubstituted or substituted with one or more, same or different substituents $R^Z$.

In one preferred embodiment, $Y^2$ is absent. In another preferred embodiment, $Y^2$ is $S(=O)_2$. In yet another preferred embodiment, $Y^2$ is $S(=O)_2$—$C_1$-$C_4$-alkylene, wherein the carbon atoms are in each case unsubstituted or substituted with one or more, same or different substituents $R^Z$. In yet another preferred embodiment, $Y^2$ is $S(=O)_2$-arylene, wherein the carbon atoms are in each case unsubstituted or substituted with one or more, same or different substituents $R^Z$. In yet another preferred embodiment, $Y^2$ is $C_1$-$C_4$-alkylene, wherein the carbon atoms are in each case unsubstituted or substituted with one or more, same or different substituents $R^Z$, wherein in each case $R^Z$ is as defined above in connection with the compounds of formula (I), and wherein preferably $R^Z$ is halogen, or $C_1$-$C_3$-alkyl; or two $R^Z$ together with the atom to which they are bonded form a 3- to 5-membered saturated carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In a more preferred embodiment, $Y^2$ is absent, or $C_1$-$C_4$-alkylene, preferably $C_2$- or $C_3$-alkylene, wherein the carbon atoms are in each case unsubstituted or substituted with one or more, same or different substituents $R^Z$. In one particularly preferred embodiment, $Y^2$ is absent. In another particularly preferred embodiment $Y^2$ is unsubstituted $C_2$- or $C_3$-alkylene, especially unsubstituted $C_3$-alkylene. In yet another particularly preferred embodiment $Y^2$ is $C_2$- or $C_3$-alkylene, especially $C_3$-alkylene, wherein the carbon atoms are in each case substituted with one or more, same or different substituents $R^Z$, wherein in each case $R^Z$ is as defined above in connection with the compounds of formula (I), and wherein preferably $R^Z$ is halogen, or $C_1$-$C_3$-alkyl; or two $R^Z$ together with the atom to which they are bonded form a 3- to 5-membered saturated carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In yet another more preferred embodiment, $Y^2$ is absent, or $C_3$- or $C_4$-alkylene, wherein the carbon atoms are in each case unsubstituted or substituted with one or more, same or different substituents $R^Z$. In one particularly preferred embodiment, $Y^2$ is absent. In another particularly preferred embodiment $Y^2$ is unsubstituted $C_3$- or $C_4$-alkylene, especially unsubstituted $C_3$-alkylene. In yet another particularly preferred embodiment $Y^2$ is $C_3$- or $C_4$-alkylene, especially $C_3$-alkylene, wherein the carbon atoms are in each case substituted with one or more, same or different substituents $R^Z$, wherein in each case $R^Z$ is as defined above in connection with the compounds of formula (I), and wherein preferably $R^Z$ is halogen, or $C_1$-$C_3$-alkyl; or two $R^Z$ together with the atom to which they are bonded form a 3- to 5-membered saturated carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

If two $R^z$ groups together with the atom to which they are bonded form a 3- to 5-membered saturated carbocyclic or heterocyclic ring, this ring is preferably any one of the following rings:

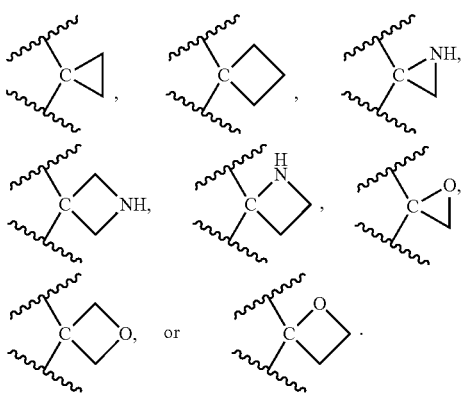

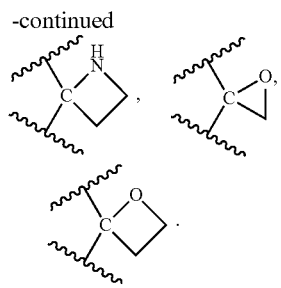

Further, in connection with the compounds of the present invention $Y^3$ is absent, $S(=O)_2$, or $C_1$-alkylene, which is unsubstituted or substituted with one or more, same or different substituents $R^Z$.

In one preferred embodiment, $Y^3$ is absent. In another preferred embodiment, $Y^3$ is $S(=O)_2$. In yet another preferred embodiment, $Y^3$ is $C_1$-alkylene, wherein the carbon atoms are in each case unsubstituted or substituted with one or more, same or different substituents $R^Z$, wherein in each case $R^Z$ is as defined above in connection with the compounds of formula (I), and wherein preferably $R^Z$ is halogen, or $C_1$-$C_3$-alkyl; or two $R^Z$ together with the atom to which they are bonded form a 3- to 5-membered saturated carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In a more preferred embodiment, $Y^3$ is $C_1$-alkylene, which is unsubstituted or substituted with one or more, same or different substituents $R^Z$. In one particularly preferred embodiment, $Y^3$ is unsubstituted $C_1$-alkylene. In another particularly preferred embodiment $Y^3$ is $C_1$-alkylene, which is substituted with one or more, same or different substituents $R^Z$, wherein $R^Z$ is as defined above in connection with the compounds of formula (I), and wherein preferably $R^Z$ is halogen, or $C_1$-$C_3$-alkyl; or two $R^Z$ together with the atom to which they are bonded form a 3- to 5-membered saturated carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

If two $R^Z$ groups together with the atom to which they are bonded form a 3- to 5-membered saturated carbocyclic or heterocyclic ring, this ring is preferably any one of the following rings:

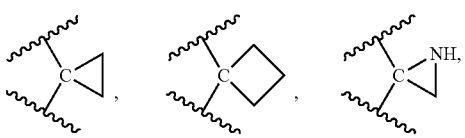

Thus, the following combinations of meanings for $Y^1$, $Y^2$, and $Y^3$ according to embodiments B-1 to B-5 according to Table B are preferred in connection with the compounds of formula (I), as well as in connection the compounds of formula (Ia), (Ib), (Ic), (Id), or (Ie), and in connection with the compounds of formula (I'), especially in connection with the compounds of formula (Ia) including embodiments A-1 to A-20, preferably embodiments A-1, A-2, A-5, A-6, A-9, A-10, A13, A-14, A-17, or A-18, more preferably embodiments A-1, A-5, A-9, A-13, or A-17, most preferably embodiment A-1, and in particular in connection with the compounds of (Ia*).

TABLE B

| No. | $Y^1$ | $Y^2$ | $Y^3$ |
|---|---|---|---|
| B-1 | $CH_2$ | absent | $CH_2$ |
| B-2 | $CH_2$ | $CH_2$ | $CH_2$ |
| B-3 | $CH_2$ | $CH_2CH_2$ | $CH_2$ |
| B-4 | $CH_2$ | $CH_2CH_2CH_2$ | $CH_2$ |
| B-5 | $CH_2$ | $CH_2CH_2CH_2CH_2$ | $CH_2$ |

Particularly preferably, $Y^1$, $Y^2$, and $Y^3$ are selected in accordance with embodiment B-4.

In view of the above, in connection with the compound of formula (Ia), the following combinations of embodiments according to table C are preferred.

TABLE C

| Combination no. | Embodiment no. | Embodiment no. |
|---|---|---|
| C-1 | A-1 | B-1 |
| C-2 | A-2 | B-1 |
| C-3 | A-3 | B-1 |
| C-4 | A-4 | B-1 |
| C-5 | A-5 | B-1 |
| C-6 | A-6 | B-1 |
| C-7 | A-7 | B-1 |
| C-8 | A-8 | B-1 |
| C-9 | A-9 | B-1 |
| C-10 | A-10 | B-1 |
| C-11 | A-11 | B-1 |
| C-12 | A-12 | B-1 |
| C-13 | A-13 | B-1 |
| C-14 | A-14 | B-1 |
| C-15 | A-15 | B-1 |
| C-16 | A-16 | B-1 |
| C-17 | A-17 | B-1 |
| C-18 | A-18 | B-1 |
| C-19 | A-19 | B-1 |
| C-20 | A-20 | B-1 |
| C-21 | A-1 | B-2 |
| C-22 | A-2 | B-2 |
| C-23 | A-3 | B-2 |
| C-24 | A-4 | B-2 |
| C-25 | A-5 | B-2 |
| C-26 | A-6 | B-2 |
| C-27 | A-7 | B-2 |
| C-28 | A-8 | B-2 |

TABLE C-continued

| Combination no. | Embodiment no. | Embodiment no. |
|---|---|---|
| C-29 | A-9 | B-2 |
| C-30 | A-10 | B-2 |
| C-31 | A-11 | B-2 |
| C-32 | A-12 | B-2 |
| C-33 | A-13 | B-2 |
| C-34 | A-14 | B-2 |
| C-35 | A-15 | B-2 |
| C-36 | A-16 | B-2 |
| C-37 | A-17 | B-2 |
| C-38 | A-18 | B-2 |
| C-39 | A-19 | B-2 |
| C-40 | A-20 | B-2 |
| C-41 | A-1 | B-3 |
| C-42 | A-2 | B-3 |
| C-43 | A-3 | B-3 |
| C-44 | A-4 | B-3 |
| C-45 | A-5 | B-3 |
| C-46 | A-6 | B-3 |
| C-47 | A-7 | B-3 |
| C-48 | A-8 | B-3 |
| C-49 | A-9 | B-3 |
| C-50 | A-10 | B-3 |
| C-51 | A-11 | B-3 |
| C-52 | A-12 | B-3 |
| C-53 | A-13 | B-3 |
| C-54 | A-14 | B-3 |
| C-55 | A-15 | B-3 |
| C-56 | A-16 | B-3 |
| C-57 | A-17 | B-3 |
| C-58 | A-18 | B-3 |
| C-59 | A-19 | B-3 |
| C-60 | A-20 | B-3 |
| C-61 | A-1 | B-4 |
| C-62 | A-2 | B-4 |
| C-63 | A-3 | B-4 |
| C-64 | A-4 | B-4 |
| C-65 | A-5 | B-4 |
| C-66 | A-6 | B-4 |
| C-67 | A-7 | B-4 |
| C-68 | A-8 | B-4 |
| C-69 | A-9 | B-4 |
| C-70 | A-10 | B-4 |
| C-71 | A-11 | B-4 |
| C-72 | A-12 | B-4 |
| C-73 | A-13 | B-4 |
| C-74 | A-14 | B-4 |
| C-75 | A-15 | B-4 |
| C-76 | A-16 | B-4 |
| C-77 | A-17 | B-4 |
| C-78 | A-18 | B-4 |
| C-79 | A-19 | B-4 |
| C-80 | A-20 | B-4 |
| C-81 | A-1 | B-5 |
| C-82 | A-2 | B-5 |
| C-83 | A-3 | B-5 |
| C-84 | A-4 | B-5 |
| C-85 | A-5 | B-5 |
| C-86 | A-6 | B-5 |
| C-87 | A-7 | B-5 |
| C-88 | A-8 | B-5 |
| C-89 | A-9 | B-5 |
| C-90 | A-10 | B-5 |
| C-91 | A-11 | B-5 |
| C-92 | A-12 | B-5 |
| C-93 | A-13 | B-5 |
| C-94 | A-14 | B-5 |
| C-95 | A-15 | B-5 |
| C-96 | A-16 | B-5 |
| C-97 | A-17 | B-5 |
| C-98 | A-18 | B-5 |
| C-99 | A-19 | B-5 |
| C-100 | A-20 | B-5 |

Of particular relevance in this regard are embodiment combinations C-61 to C-80, preferably 0-61, C-62, C-6S, C-66, C-69, C-70, C-73, C-74, C-77, and C-88, more preferably C-61, C-6S, 0-69, C-73, and C-77, most preferably C-61.

In connection with the compounds of formula (I), as well as in connection the compounds of formula (Ia), (Ib), (Ic), (Id), or (Ie), and in connection with the compounds of formula (I'), especially in connection with the compounds of formula (Ia) including embodiments A-1 to A-20, preferably embodiments A-1, A-2, A-5, A-6, A-9, A-10, A-13, A-14, A-17, or A-18, more preferably embodiments A-1, A-5, A-9, A-13, or A-17, most preferably embodiment A-1, as well as embodiment combinations C-1 to C-100, preferably embodiment combinations C-61 to C-80, more preferably embodiment combinations C-61, C-62, C-65, C-66, C-69, C-70, C-73, C-74, C-77, or C-88, even more preferably embodiment combinations C-61, C-65, C-69, C-73, or C-77, most preferably embodiment combination C-61, and in particular in connection with the compounds of (Ia*), the following preferred embodiments regarding the remaining substituents $R^1$, $R^2$, $R^3$, $R^4$, and $R^5$ are relevant.

As indicate above, in connection with the compounds of the present invention, $R^1$ is H, OH, CN, halogen, $C_1$-$C_4$-alkyl, $C_1$-$C_4$-alkoxy, aryloxy, benzyloxy, $C(=O)R^E$, $NR^FC(=O)R^E$, or 5- or 6-membered saturated, partially or fully unsaturated, or aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or $R^1$ and $R^2$ together with the carbons atom to which they are bonded form a 5- or 6-membered saturated, partially or fully unsaturated, or aromatic carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^X$.

In a preferred embodiment, $R^1$ is H or halogen.

In a more preferred embodiment, $R^1$ is H or F.

In one particularly preferred embodiment, $R^1$ is H.

In another particularly preferred embodiment, $R^1$ is F.

Further, in connection with the compounds of the present invention, $R^2$ and $R^3$ are independently H, OH, CN, halogen, $C_1$-$C_4$-alkyl, $C_1$-$C_4$-alkoxy, aryloxy, benzyloxy, $C(=O)R^E$, $NR^FC(=O)R^E$, or 5- or 6-membered saturated, partially or fully unsaturated, or aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

or

R² and R³ together with the carbon atoms to which they are bonded form a 5- or 6-membered saturated, partially or fully unsaturated, or aromatic carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^X$.

In a preferred embodiment,

R² and R³ are independently H, halogen, CN, OH, $C_1$-$C_2$-alkyl, $C_1$-$C_2$-alkoxy, benzyloxy, or 6-membered saturated heterocyclyl, wherein the aforementioned heterocyclic ring comprises one or more nitrogen atoms, wherein said N-atoms are independently oxidized or non-oxidized, and wherein each substitutable carbon or heteroatom in the aforementioned groups is independently unsubstituted or substituted with one or more, same or different substituents $R^X$;

or

R² and R³ together with the carbon atoms to which they are bonded form 6-membered aromatic carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^X$.

In one more preferred embodiment,

R² is H, halogen, CN, OH, $C_1$-$C_2$-alkyl, $C_1$-$C_2$-alkoxy, benzyloxy, or 6-membered saturated heterocyclyl, wherein the aforementioned heterocyclic ring comprises one or more nitrogen atoms, wherein said N-atoms are independently oxidized or non-oxidized, and wherein each substitutable carbon or heteroatom in the aforementioned groups is independently unsubstituted or substituted with one or more, same or different substituents $R^X$; and R³ is H, or $C_1$-$C_2$-alkyl.

In another more preferred embodiment,

R² and R³ together with the carbon atoms to which they are bonded form 6-membered aromatic carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^X$.

In one particularly preferred embodiment,

R² is H.

In another particularly preferred embodiment,

R² is $CH_3$.

In yet another particularly preferred embodiment,

R² is OH.

In yet another particularly preferred embodiment,

R² is $OCH_3$.

In yet another particularly preferred embodiment,

R² is Br.

In yet another particularly preferred embodiment,

R² is F.

In yet another particularly preferred embodiment,

R² is CN.

In yet another particularly preferred embodiment, R² is

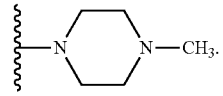

(R²-1)

In yet another particularly preferred embodiment, R² is benzyloxy (R²-2).

In yet another particularly preferred embodiment, R² is p-fluoropheny (R²-3).

In yet another particularly preferred embodiment, R² is p-methoxyphenyl (R²-4).

In one particularly preferred embodiment, R³ is H.

In another particularly preferred embodiment, R³ is $CH_3$.

In one particularly preferred embodiment, R² and R³ together with the carbon atoms to which they are bonded form a fused benzo ring.

In one particularly preferred embodiment, R² and R³ together with the carbon atoms to which they are bonded form a fused cyclohexane ring.

Further, in connection with the compounds of the present invention,

R⁴ is a 5- or 6-membered aromatic carbocyclic or heterocyclic ring, or a 9- or 10-membered aromatic carbobycyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^X$.

Preferably, the term "aromatic" in connection with the carbobycyclic or heterobicyclic ring means that both rings of the bicyclic moiety are aromatic, so that 8 π electrons are present.

In a preferred embodiment,

R⁴ is a 6-membered aromatic heterocyclic ring, wherein the heterocyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^X$.

Preferably, the 6-membered aromatic heterocyclic ring is a nitrogen-containing heterocyclic ring comprising one or more nitrogen atoms as heteroatoms.

In a more preferred embodiment,

R⁴ is pyridinyl, wherein each substitutable carbon or heteroatom in the cyclic ring is independently unsubstituted or substituted with one or more, same or different substituents $R^X$.

Preferred $R^X$ groups in this connection include halogen, $C_1$-$C_2$-alkyl, and $C_1$-$C_2$-alkoxy, in particular F, $CH_3$, and $OCH_3$.

In an even more preferred embodiment, R⁴ is unsubstituted pyridinyl, wherein the nitrogen atom of the pyridinyl group is in para position to the $Y^3$-group, i.e. R⁴ is the following group:

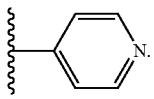
(R⁴-1)

Further, in connection with the compounds of the present invention, $R^5$ is a 5- or 6-membered saturated, partially or fully unsaturated, or aromatic carbocyclic or heterocyclic ring, or a 9- or 10-membered saturated, partially or fully unsaturated, or aromatic carbobycyclic or heterobicyclic ring, wherein the heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^Y$.

In a preferred embodiment, $R^5$ is a 5- or 6-membered saturated, partially or fully unsaturated, or aromatic heterocyclic ring, or a 9- or 10-membered saturated, partially or fully unsaturated, or aromatic heterobicyclic ring, wherein the heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^Y$.

In a more preferred embodiment, $R^5$ is a 5- or 6-membered aromatic heterocyclic ring, or 9- or 10-membered aromatic heterobicyclic ring, wherein the heterocyclic or heterobicyclic ring comprises one, two, or three nitrogen atoms, wherein said N-atom may be oxidized or non-oxidized, and wherein each substitutable carbon or heteroatom in the aforementioned cyclic rings is independently unsubstituted or substituted with one or more, same or different substituents $R^Y$.

Preferably, the 5- or 6-membered aromatic heterocyclic ring, or 9- or 10-membered aromatic heterobicyclic ring, comprise one or more nitrogen atoms as heteroatoms.

In an even more preferred embodiment, $R^5$ is any one of the following groups:

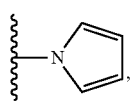
(R⁵-1)

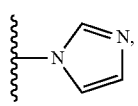
(R⁵-2)

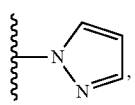
(R⁵-3)

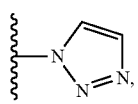
(R⁵-4)

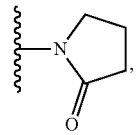
(R⁵-5)

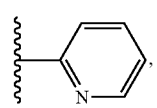
(R⁵-6)

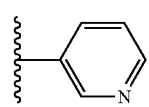
(R⁵-7)

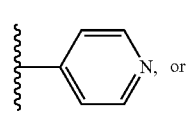
(R⁵-8)

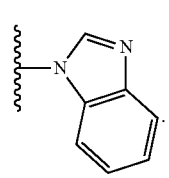
(R⁵-9)

In one particularly preferred embodiment,
$R^5$ is $R^5$-1.
In another particularly preferred embodiment,
$R^5$ is $R^5$-2.
In yet another particularly preferred embodiment,
$R^5$ is $R^5$-3.
In yet another particularly preferred embodiment,
$R^5$ is $R^5$-4.
In yet another particularly preferred embodiment,
$R^5$ is $R^5$-5.
In yet another particularly preferred embodiment,
$R^5$ is $R^5$-6.
In yet another particularly preferred embodiment,
$R^5$ is $R^5$-7.
In yet another particularly preferred embodiment,
$R^5$ is $R^5$-8.
In yet another particularly preferred embodiment,
$R^5$ is $R^5$-9.

In view of the above, the present invention relates in certain particularly preferred embodiments to compounds of formula (Ia), wherein $X^1$, $X^2$, $X^3$, $X^4$, and $X^5$ are selected according to embodiment A-1, i.e. compounds of the following formula (Ia-A-1):

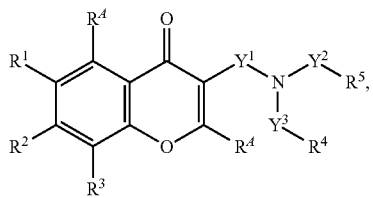
(Ia-A-1)

wherein the remaining substituents are defined as in connection with formula (I), and wherein preferably, the meanings of $R^1$, $R^2$, $R^3$, $R^4$, and $R^5$ and $Y^1$, $Y^2$, and $Y^3$ correspond to the preferred embodiments defined above. Preferred compounds of formula (Ia-A-1) are compounds, wherein both $R^4$ substituents are H, i.e. compounds of formula (Ia*) as defined above, wherein $X^1$ is O and $X^3$ is CH.

In other particularly preferred embodiments, the present invention relates to compounds of formula (Ia), wherein $Y^1$, $Y^2$, and $Y^3$ are selected according to embodiment B-4, i.e. compounds of the following formula (Ia-B-4):

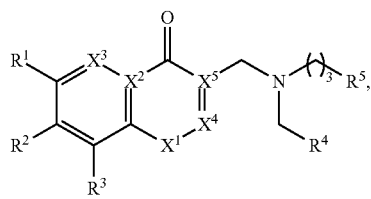
(Ia-B-4)

wherein the remaining substituents are defined as in connection with formula (I), and wherein preferably, the meanings of $X^1$, $X^2$, $X^3$, $X^4$, and $X^5$ as well as $R^1$, $R^2$, $R^3$, $R^4$, and $R^5$ correspond to the preferred embodiments defined above.

In other especially preferred embodiments, the present invention relates to compounds of formula (Ia), wherein $X^1$, $X^2$, $X^3$, $X^4$, and $X^5$ as well as $Y^1$, $Y^2$, and $Y^3$ are selected according to embodiment combination C-61, i.e. compounds of the following formula (Ia-C-61).

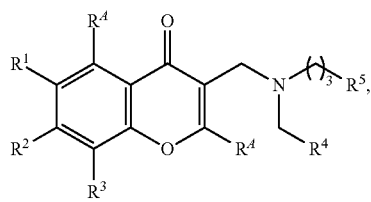
(Ia-C-61)

wherein the remaining substituents are defined as in connection with formula (I), and wherein preferably, the meanings of $R^1$, $R^2$, $R^3$, $R^4$, and $R^5$ correspond to the preferred embodiments defined above.

In connection with the compounds of formula Ia-C-61, it is particularly preferred that $R^4$ is in both positions H. Such compounds correspond to compounds of formula (Ia-C-61-$R^4$-H).

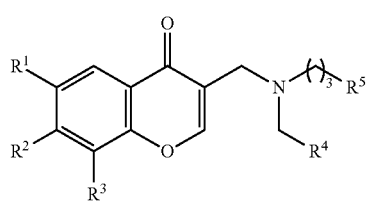
(Ia-C-61-$R^4$-H)

Particularly preferred compounds of the invention are compounds of formula (Ia-C-61-$R^4$-H), wherein
$R^1$ is H, or F;
$R^2$ is H, $CH_3$, OH, $OCH_3$, Br, F, CN,

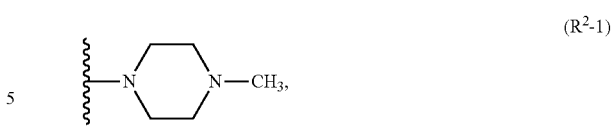
(R²-1)

benzyloxy (R²-2), p-fluorophenyl (R²-3), or p-methoxyphenyl (R²-4);
$R^3$ is H, or $CH_3$; or
$R^2$ and $R^3$ together with the carbon atoms to which they are bonded form a fused benzo ring, or a fused cyclohexane ring;
$R^4$

(R⁴-1)

and
$R^5$ is any one of the following groups:

(R⁵-1)

(R⁵-2)

(R⁵-3)

(R⁵-4)

(R⁵-5)

(R⁵-6)

(R⁵-7)

(R⁵-8)

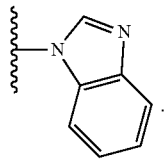
(R⁵-9)

Thus, particularly preferred compounds of the invention are compounds of formula (Ia-C-61-R⁴-H) as compiled in the tables below.

Table 1
Compounds of the formula (Ia-C-61-R⁴-H), in which $R^2$ is H, $R^3$ is H, $R^4$ is $R^4$-1, and $R^1$ and $R^5$ correspond in each case to one row of Table D Table 2
Compounds of the formula (Ia-C-61-R⁴-H), in which $R^2$ is $CH_3$, $R^3$ is H, $R^4$ is $R^4$-1, and $R^1$ and $R^5$ correspond in each case to one row of Table D Table 3
Compounds of the formula (Ia-C-61-R⁴-H), in which $R^2$ is OH, $R^3$ is H, $R^4$ is $R^4$-1, and $R^1$ and $R^5$ correspond in each case to one row of Table D Table 4
Compounds of the formula (Ia-C-61-R⁴-H), in which $R^2$ is $OCH_3$, $R^3$ is H, $R^4$ is $R^4$-1, and $R^1$ and $R^5$ correspond in each case to one row of Table D Table 5
Compounds of the formula (Ia-C-61-R⁴-H), in which $R^2$ is Br, $R^3$ is H, $R^4$ is $R^4$-1, and $R^1$ and $R^5$ correspond in each case to one row of Table D Table 6
Compounds of the formula (Ia-C-61-R⁴-H), in which $R^2$ is F, $R^3$ is H, $R^4$ is $R^4$-1, and $R^1$ and $R^5$ correspond in each case to one row of Table D Table 7
Compounds of the formula (Ia-C-61-R⁴-H), in which $R^2$ is CN, $R^3$ is H, $R^4$ is $R^4$-1, and $R^1$ and $R^5$ correspond in each case to one row of Table D Table 8
Compounds of the formula (Ia-C-61-R⁴-H), in which $R^2$ is $R^2$-1, $R^3$ is H, $R^4$ is $R^4$-1, and $R^1$ and $R^5$ correspond in each case to one row of Table D Table 9
Compounds of the formula (Ia-C-61-R⁴-H), in which $R^2$ is $R^2$-2, $R^3$ is H, $R^4$ is $R^4$-1, and $R^1$ and $R^5$ correspond in each case to one row of Table D Table 10
Compounds of the formula (Ia-C-61-R⁴-H), in which $R^2$ is $R^2$-3, $R^3$ is H, $R^4$ is $R^4$-1, and $R^1$ and $R^5$ correspond in each case to one row of Table D Table 11
Compounds of the formula (Ia-C-61-R⁴-H), in which $R^2$ is H, $R^3$ is $CH_3$, $R^4$ is $R^4$-1, and $R^1$ and $R^5$ correspond in each case to one row of Table D Table 12
Compounds of the formula (Ia-C-61-R⁴-H), in which $R^2$ is $CH_3$, $R^3$ is $CH_3$, $R^4$ is $R^4$-1, and $R^1$ and $R^5$ correspond in each case to one row of Table D Table 13
Compounds of the formula (Ia-C-61-R⁴-H), in which $R^2$ is OH, $R^3$ is $CH_3$, $R^4$ is $R^4$-1, and $R^1$ and $R^5$ correspond in each case to one row of Table D Table 14
Compounds of the formula (Ia-C-61-R⁴-H), in which $R^2$ is $OCH_3$, $R^3$ is $CH_3$, $R^4$ is $R^4$-1, and $R^1$ and $R^5$ correspond in each case to one row of Table D Table 15
Compounds of the formula (Ia-C-61-R⁴-H), in which $R^2$ is Br, $R^3$ is $CH_3$, $R^4$ is $R^4$-1, and $R^1$ and $R^5$ correspond in each case to one row of Table D Table 16
Compounds of the formula (Ia-C-61-R⁴-H), in which $R^2$ is F, $R^3$ is $CH_3$, $R^4$ is $R^4$-1, and $R^1$ and $R^5$ correspond in each case to one row of Table D Table 17
Compounds of the formula (Ia-C-61-R⁴-H), in which $R^2$ is CN, $R^3$ is $CH_3$, $R^4$ is $R^4$-1, and $R^1$ and $R^5$ correspond in each case to one row of Table D Table 18
Compounds of the formula (Ia-C-61-R⁴-H), in which $R^2$ is $R^2$-1, $R^3$ is $CH_3$, $R^4$ is $R^4$-1, and $R^1$ and $R^5$ correspond in each case to one row of Table D Table 19
Compounds of the formula (Ia-C-61-R⁴-H), in which $R^2$ is $R^2$-2, $R^3$ is $CH_3$, $R^4$ is $R^4$-1, and $R^1$ and $R^5$ correspond in each case to one row of Table D Table 20
Compounds of the formula (Ia-C-61-R⁴-H), in which $R^2$ is $R^2$-3, $R^3$ is $CH_3$, $R^4$ is $R^4$-1, and $R^1$ and $R^5$ correspond in each case to one row of Table D Table 21
Compounds of the formula (Ia-C-61-R⁴-H), in which $R^2$ and $R^3$ together with the carbon atoms to which they are bonded form a fused benzo ring, $R^4$ is $R^4$-1, and $R^1$ and $R^5$ correspond in each case to one row of Table D Table 22
Compounds of the formula (Ia-C-61-R⁴-H), in which $R^2$ and $R^3$ together with the carbon atoms to which they are bonded form a fused cyclohexane ring, $R^4$ is $R^4$-1, and $R^1$ and $R^5$ correspond in each case to one row of Table D

TABLE D

| No. | $R^1$ | $R^5$ |
| --- | --- | --- |
| D-1 | H | $R^5$-1 |
| D-2 | H | $R^5$-2 |
| D-3 | H | $R^5$-3 |
| D-4 | H | $R^5$-4 |
| D-5 | H | $R^5$-5 |
| D-6 | H | $R^5$-6 |
| D-7 | H | $R^5$-7 |
| D-8 | H | $R^5$-8 |
| D-9 | H | $R^5$-9 |
| D-10 | F | $R^5$-1 |
| D-11 | F | $R^5$-2 |
| D-12 | F | $R^5$-3 |
| D-13 | F | $R^5$-4 |
| D-14 | F | $R^5$-5 |
| D-15 | F | $R^5$-6 |
| D-16 | F | $R^5$-7 |
| D-17 | F | $R^5$-8 |
| D-18 | F | $R^5$-9 |

It has been found that the compounds as defined in the above tables are particularly advantageous as STING agonists, and may therefore particularly advantageously be used in the pharmaceutical compositions of the present invention as well as the medical uses as defined herein. Therefore, the compound of formula (I) of the invention is preferably a compound according to any one of tables 1 to 22, and the present invention preferably relates to pharmaceutical compositions comprising the same and to medical uses thereof.

However, it is preferred that the compound is not a compound in accordance with table 1+table D-2. Thus, the compound of formula (I) is preferably not:

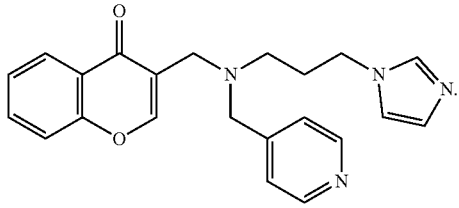 [SMILES: O=c1c(CN(CCCn2ccnc2)Cc2ccncc2)coc2ccccc12]

In particularly preferred embodiments, the compound of formula (I) is a compound selected from the group consisting of:
3-({[4-(1H-imidazol-1-yl)butyl](pyridin-4-ylmethyl)amino}methyl)-4H-chromen-4-one;
3-({[(pyridin-4-yl)methyl][3-(1H-pyrrol-1-yl)propyl]amino}methyl)-4H-chromen-4-one;
3-({[3-(1H-pyrazol-1-yl)propyl](pyridin-4-ylmethyl)amino}methyl)-4H-chromen-4-one;
3-{[(pyridin-4-ylmethyl)[3-(1H-1,2,3-triazol-1-yl)propyl]amino]methyl}-4H-chromen-4-one;
3-({[3-(1H-imidazol-1-yl)propyl](pyridin-4-ylmethyl)amino}methyl)-7,8-dimethyl-4H-chromen-4-one;
3-({[3-(pyridin-2-yl)propyl][(pyridin-4-yl)methyl]amino}methyl)-4H-chromen-4-one;
3-({[3-(1H-imidazol-1-yl)propyl](pyridin-4-ylmethyl)amino}methyl)-4H-benzo[h]chromen-4-one;
1-(3-{[(4-oxo-4H-chromen-3-yl)methyl](pyridin-4-ylmethyl)amino}propyl)pyrrolidin-2-one;
3-({[3-(1H-imidazol-1-yl)propyl](pyridin-4-ylmethyl)amino}methyl)-7-methoxy-4H-chromen-4-one;
7-bromo-3-({[3-(1H-imidazol-1-yl)propyl](pyridin-4ylmethyl)amino}methyl)-4H-chromen-4-one;
7-fluoro-3-({[3-(1H-imidazol-1-yl)propyl](pyridin-4-ylmethyl)amino}methyl)-4H-chromen-4-one;
3-({[3-(1H-imidazol-1-yl)propyl](pyridin-4-ylmethyl)amino}methyl)-7-(4-methylpiperazin-1-yl)-4H-chromen-4-one;
7-(benzyloxy)-3-({[3-(1H-imidazol-1-yl)propyl](pyridin-4-ylmethyl)amino}methyl)-4H-chromen-4-one;
7,8-dimethyl-3-{[(pyridin-4-ylmethyl)[3-(1H-1,2,3-triazol-1-yl)propyl]amino]methyl}-4H-chromen-4-one;
7,8-dimethyl-3-{[(pyridin-4-ylmethyl)[3-(1H-pyrrol-1-yl)propyl]amino]methyl}-4H-chromen-4-one;
7-hydroxy-3-({[3-(1H-imidazol-1-yl)propyl](pyridin-4-ylmethyl)amino}methyl)-4H-chromen-4-one;
3-({[3-(1H-1,3-benzodiazol-1-yl)propyl](pyridin-4-ylmethyl)amino}methyl)-4H-chromen-4-one;
3-({[3-(1H-imidazol-1-yl)propyl][(2-methoxypyridin-4-yl)methyl]amino}methyl)-4H-chromen-4-one;
3-({[3-(pyridin-3-yl)propyl][(pyridin-4-yl)methyl]amino}methyl)-4H-chromen-4-one;
3-({[3-(1H-imidazol-1-yl)propyl](pyridin-4-ylmethyl)amino}methyl)-4H,7H,8H,9H,10H-cyclohexa[h]chromen-4-one;
3-({[(pyridin-4-yl)methyl][3-(pyridin-4-yl)propyl]amino}methyl)-4H-chromen-4-one;
7-bromo-3-{[(pyridin-4-ylmethyl)[3-(1H-1,2,3-triazol-1-yl)propyl]amino]methyl}-4H-chromen-4-one;
7-(4-fluorophenyl)-3-({[3-(1H-imidazol-1-yl)propyl](pyridin-4-ylmethyl)amino}methyl)-4H-chromen-4-one;
3-({[3-(1H-imidazol-1-yl)propyl][(pyridin-4-yl)methyl]amino}methyl)-4-oxo-4H-chromene-7-carbonitrile;
3-({[3-(1H-imidazol-1-yl)propyl][(2-methylpyridin-4-yl)methyl]amino}methyl)-4H-chromen-4-one;
3-({[(2-fluoropyridin-4-yl)methyl][3-(1H-imidazol-1-yl)propyl]amino}methyl)-7,8-dimethyl-4H-chromen-4-one;
7-hydroxy-3-({[3-(1H-imidazol-1-yl)propyl][(2-methoxypyridin-4-yl)methyl]amino}methyl)-4H-chromen-4-one;
3-({[3-(pyridin-3-yl)propyl](pyridin-4-ylmethyl)amino}methyl)-4H-benzo[h]chromen-4-one;
6-fluoro-3-({[3-(1H-imidazol-1-yl)propyl][(pyridin-4-yl)methyl]amino}methyl)-4H-chromen-4-one;
3-({[3-(1H-imidazol-1-yl)propyl][(2-methoxypyridin-4-yl)methyl]amino}methyl)-4H-benzo[h]chromen-4-one;
3-({[3-(1H-imidazol-1-yl)propyl][(pyridin-4-yl)methyl]amino}methyl)-1-methyl-1,4-dihydroquinolin-4-one;
3-({[3-(1H-imidazol-1-yl)propyl](pyridin-4-ylmethyl)amino}methyl)-7-(4-methoxyphenyl)-4H-chromen-4-one; and
3-({[3-(1H-imidazol-1-yl)propyl](pyridin-4-ylmethyl)amino}methyl)-4H-chromen-4-one.

Even more preferably, the compound of formula (I) is a compound selected from the group consisting of:
3-({[3-(1H-imidazol-1-yl)propyl](pyridin-4-ylmethyl)amino}methyl)-7,8-dimethyl-4H-chromen-4-one;
3-({[3-(1H-imidazol-1-yl)propyl](pyridin-4-ylmethyl)amino}methyl)-4H-benzo[h]chromen-4-one;
3-({[3-(1H-imidazol-1-yl)propyl](pyridin-4-ylmethyl)amino}methyl)-7-methoxy-4H-chromen-4-one;
7-bromo-3-({[3-(1H-imidazol-1-yl)propyl](pyridin-4ylmethyl)amino}methyl)-4H-chromen-4-one;
3-({[3-(1H-imidazol-1-yl)propyl](pyridin-4-ylmethyl)amino}methyl)-7-(4-methylpiperazin-1-yl)-4H-chromen-4-one;
7-(benzyloxy)-3-({[3-(1H-imidazol-1-yl)propyl](pyridin-4-ylmethyl)amino}methyl)-4H-chromen-4-one;
3-({[3-(1H-1,3-benzodiazol-1-yl)propyl](pyridin-4-ylmethyl)amino}methyl)-4H-chromen-4-one;
3-({[3-(pyridin-3-yl)propyl][(pyridin-4-yl)methyl]amino}methyl)-4H-chromen-4-one;
3-({[3-(1H-imidazol-1-yl)propyl](pyridin-4-ylmethyl)amino}methyl)-4H,7H,8H,9H,10H-cyclohexa[h]chromen-4-one;
3-({[(pyridin-4-yl)methyl][3-(pyridin-4-yl)propyl]amino}methyl)-4H-chromen-4-one;
3-({[3-(pyridin-3-yl)propyl](pyridin-4-ylmethyl)amino}methyl)-4H-benzo[h]chromen-4-one;
6-fluoro-3-({[3-(1H-imidazol-1-yl)propyl][(pyridin-4-yl)methyl]amino}methyl)-4H-chromen-4-one;
3-({[3-(1H-imidazol-1-yl)propyl][(2-methoxypyridin-4-yl)methyl]amino}methyl)-4H-benzo[h]chromen-4-one;
6-fluoro-3-({[3-(1H-imidazol-1-yl)propyl][(pyridin-4-yl)methyl]amino}methyl)-4H benzo[h]chromen-4-one;
7-bromo-3-({[3-(1H-imidazol-1-yl)propyl][(pyridin-4-yl)methyl]amino}methyl)-2-methyl-4H chromen-4-one;
6-fluoro-3-({[3-(1H-imidazol-1-yl)propyl][(pyridin-4-yl)methyl]amino}methyl)-7-(4-methylpiperazin-1-yl)-4H-chromen-4-one;
3-({[3-(1H-1,3-benzodiazol-1-yl)propyl][(pyridin-4-yl)methyl]amino}methyl)-4H-benzo[h]chromen-4-one;
3-({[3-(1H-imidazol-1-yl)propyl][(2-methoxypyridin-4-yl)methyl]amino}methyl)-7,8-dimethyl-4H chromen-4-one;
9-methoxy-3-({[3-(pyridin-3-yl)propyl][(pyridin-4-yl)methyl]amino}methyl)-4H-benzo[h]chromen-4-one;
3-({[3-(1H-1,3-benzodiazol-1-yl)propyl][(2-methoxypyridin-4-yl)methyl]amino}methyl)-4H-benzo[h]chromen-4-one;

6-fluoro-3-({[3-(pyridin-3-yl)propyl][(pyridin-4-yl)methyl]amino}methyl)-4H-benzo[h]chromen-4-one;

2,7,8-trimethyl-3-({[3-(pyridin-3-yl)propyl][(pyridin-4-yl)methyl]amino}methyl)-4H-chromen-4-one;

6-fluoro-7-(4-methylpiperazin-1-yl)-3-({[3-(pyridin-3-yl)propyl](pyridin-4-ylmethyl)amino}methyl)-4H-chromen-4-one;

3-({[3-(1H-1,3-benzodiazol-1-yl)propyl][(pyridin-4-yl)methyl]amino}methyl)-9-methoxy-4H benzo[h]chromen-4-one;

7-bromo-6-fluoro-2-methyl-3-({[3-(pyridin-3-yl)propyl][(pyridin-4-yl)methyl]amino}methyl)-4H-chromen-4-one;

7-bromo-2-methyl-3-({[3-(pyridin-3-yl)propyl](pyridin-4-ylmethyl)amino}methyl)-4H-chromen-4-one;

6-fluoro-2-methyl-7-(4-methylpiperazin-1-yl)-3-({[3-(pyridin-3-yl)propyl][(pyridin-4-yl)methyl]amino}methyl)-4H-chromen-4-one;

3-{[(3-{1H-imidazo[4,5-b]pyridin-1-yl}propyl)(pyridin-4-ylmethyl)amino]methyl}-4H benzo[h]chromen-4-one;

6-fluoro-2-methyl-7-(piperazin-1-yl)-3-({[3-(pyridin-3-yl)propyl][(pyridin-4-yl)methyl]amino}methyl)-4H-chromen-4-one;

6-fluoro-2-methyl-7-(morpholin-4-yl)-3-({[3-(pyridin-3-yl)propyl][(pyridin-4-yl)methyl]amino}methyl)-4H-chromen-4-one;

3-({[4-(1H-1,3-benzodiazol-1-yl)butan-2-yl](pyridin-4-ylmethyl)amino}methyl)-4H-benzo[h]chromen-4-one;

7-bromo-6-fluoro-2-methyl-3-({[3-(9H-purin-9-yl)propyl][(pyridin-4-yl)methyl]amino}methyl)-4H chromen-4-one;

6-fluoro-3-({[(2-methoxypyridin-4-yl)methyl][3-(pyridin-3-yl)propyl]amino}methyl)-2-methyl-7-(morpholin-4-yl)-4H-chromen-4-one;

7-bromo-6-fluoro-3-({[(2-methoxypyridin-4-yl)methyl][3-(9H-purin-9-yl)propyl]amino}methyl)-2-methyl-4H-chromen-4-one;

6-fluoro-2-methyl-7-(4-methylpiperazin-1-yl)-3-({[3-(9H-purin-9-yl)propyl][(pyridin-4-yl)methyl]amino}methyl)-4H-chromen-4-one;

3-({[3-(1H-1,3-benzodiazol-1-yl)propyl][(2-methoxypyridin-4-yl)methyl]amino}methyl)-1-methyl-1,4-dihydroquinolin-4-one;

3-({[(2-methoxypyridin-4-yl)methyl][4-(pyridin-3-yl)butan-2-yl]amino}methyl)-4H benzo[h]chromen-4-one;

3-({[(2-methoxypyridin-4-yl)methyl][3-(9H-purin-9-yl)propyl]amino}methyl)-1-methyl-1,4-dihydroquinolin-4-one;

3-({[(2-methoxypyridin-4-yl)methyl][4-(pyridin-3-yl)butan-2-yl]amino}methyl)-1-methyl-1,4-dihydroquinolin-4-one;

3-({[3-(1H-1,3-benzodiazol-1-yl)propyl][(2-methylpyridin-4-yl)methyl]amino}methyl)-1-methyl-1,4-dihydroquinolin-4-one;

and 1-methyl-3-({[(2-methylpyridin-4-yl)methyl][3-(pyridin-3-yl)propyl]amino}methyl)-1,4-dihydroquinolin-4-one.

Definitions

The term "compound(s) of the present invention" is to be understood as equivalent to the term "compound(s) according to the invention", and also covers a salt, stereoisomer, tautomer or N-oxide thereof.

The compounds according to the invention may be amorphous or may exist in one or more different crystalline states (polymorphs), which may have different macroscopic properties such as stability or show different biological properties such as activities. The present invention relates to amorphous and crystalline forms of compounds of formula (I), mixtures of different crystalline states of the compounds of formula (I), as well as amorphous or crystalline salts thereof.

Salts of the compounds according to the invention are preferably pharmaceutically acceptable salts, such as those containing counterions present in drug products listed in the US FDA Orange Book database. They can be formed in a customary manner, e.g., by reacting the compound with an acid of the anion in question, if the compounds according to the invention have a basic functionality, or by reacting acidic compounds according to the invention with a suitable base.

Suitable cationic counterions are in particular the ions of the alkali metals, preferably lithium, sodium and potassium, of the alkaline earth metals, preferably calcium, magnesium and barium, and of the transition metals, preferably manganese, copper, silver, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore the cations of 1,4-piperazine, meglumine, benzathine and lysine.

Suitable anionic counterions are in particular chloride, bromide, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate, furthermore lactate, gluconate, and the anions of poly acids such as succinate, oxalate, maleate, fumarate, malate, tartrate and citrate, furthermore sulfonate anions such as besylate (benzenesulfonate), tosylate (p-toluenesulfonate), napsylate (naphthalene-2-sulfonate), mesylate (methanesulfonate), esylate (ethanesulfonate), and ethanedisulfonate. They can be formed by reacting compounds according to the invention that have a basic functionality with an acid of the corresponding anion.

Depending on the substitution pattern, the compounds according to the invention may have one or more centres of chirality, including axial chirality. The invention provides both, pure enantiomers or pure diastereomers, of the compounds according to the invention, and their mixtures, including racemic mixtures. Suitable compounds according to the invention also include all possible geometrical stereoisomers (cis/trans isomers or E/Z isomers) and mixtures thereof. E/Z-isomers may be present with respect to, e.g., an alkene, carbon-nitrogen double-bond or amide group.

Tautomers may be formed, if a substituent is present at the compound of formula (I), which allows for the formation of tautomers such as keto-enol tautomers, imine-enamine tautomers, amide-imidic acid tautomers or the like. Furthermore, the core structure comprising the 6-membered ring that contains the =O substituent principally allows for keto-enol-tautomerization.

The term "N-oxide" includes any compound of the present invention which has at least one tertiary nitrogen atom that is oxidized to a N-oxide moiety.

The term "substituted", as used herein, means that a hydrogen atom bonded to a designated atom is replaced with a specified substituent, provided that the substitution results in a stable or chemically feasible compound. Unless otherwise indicated, a substituted atom may have one or more substituents and each substituent is independently selected.

The term "substitutable", when used in reference to a designated atom, means that attached to the atom is a hydrogen, which can be replaced with a suitable substituent.

When it is referred to certain atoms or moieties being substituted with "one or more" substituents, the term "one or more" is intended to cover at least one substituent, e.g. 1 to 10 substituents, preferably 1, 2, 3, 4, or 5 substituents, more preferably 1, 2, or 3 substituents, most preferably 1, or 2 substituents. When neither the term "unsubstituted" nor "substituted" is explicitly mentioned concerning a moiety, said moiety is to be considered as unsubstituted.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine, or bromine.

The term "alkyl" as used herein denotes in each case a straight-chain or branched alkyl group having usually from 1 to 6 carbon atoms, preferably 1 to 5 or 1 to 4 carbon atoms, more preferably 1 to 3 or 1 or 2 carbon atoms. Examples of an alkyl group are methyl, ethyl, n-propyl, isopropyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "haloalkyl" as used herein denotes in each case a straight-chain or branched alkyl group having usually from 1 to 6 carbon atoms, frequently 1 to 5 or 1 to 4 carbon atoms, preferably 1 to 3 or 1 or 2 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_3$-haloalkyl or $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkenyl" as used herein denotes in each case an unsaturated hydrocarbon group having usually 2 to 6, preferably 2 to 4 carbon atoms comprising at least one carbon-carbon double bond in any position, e.g. vinyl (ethenyl), allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like. If geometric isomers are possible with regard to the double bond, the present invention relates to both, the E- and Z-isomers. Preferred alkenyl groups according to the invention are terminal alkenyl groups. The bonding of vinyl is exemplified below:

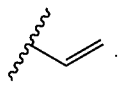

The term "haloalkenyl" as used herein refers to an alkenyl group as defined above, wherein the hydrogen atoms are partially or totally replaced with halogen atoms.

The term "alkynyl" as used herein denotes in each case an unsaturated hydrocarbon group having usually 2 to 6, preferably 2 to 5 or 2 to 4 carbon atoms, more preferably 2 to 3 carbon atoms, comprising at least one carbon-carbon triple bond in any position, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "haloalkynyl" as used herein refers to an alkynyl group as defined above, wherein the hydrogen atoms are partially or totally replaced with halogen atoms.

The term "alkoxy" as used herein denotes in each case a straight-chain or branched alkyl group which is bonded via an oxygen atom and has usually from 1 to 6 carbon atoms, preferably 1 to 2 carbon atoms, more preferably 1 carbon atom. Examples of an alkoxy group are methoxy, ethoxy, n-propoxy, iso-propoxy, n-butyloxy, 2-butyloxy, iso-butyloxy, tert.-butyloxy, and the like.

The term "haloalkoxy" as used herein denotes in each case a straight-chain or branched alkoxy group having from 1 to 6 carbon atoms, preferably 1 to 2 carbon atoms, more preferably 1 carbon atom, wherein the hydrogen atoms of this group are partially or totally replaced with halogen atoms, in particular fluorine atoms. Preferred haloalkoxy moieties include $C_1$-haloalkoxy, in particular $C_1$-fluoroalkoxy, such as trifluoromethoxy and the like.

The term "cycloalkyl" as used herein denotes in each case a monocyclic cycloaliphatic radical having usually from 3 to 10 or from 3 to 6 carbon atoms, such as cyclopropyl, cyclobutyl, cyclopentyl, cyclohexyl, cycloheptyl, cyclooctyl, cyclononyl and cyclodecyl or cyclopropyl, cyclobutyl, cyclopentyl and cyclohexyl.

The term "carbocyclic" or "carbocyclyl" includes, unless otherwise indicated, in general a 3- to 9-membered, preferably a 4- to 8-membered or a 3- to 6-membered or a 5- to 7-membered, more preferably a 5- or 6-membered monocyclic ring comprising 3 to 9, preferably 4 to 8 or 3 to 6 or 5 to 7, more preferably 5 or 6 carbon atoms. The carbocycle may be saturated, partially or fully unsaturated, or aromatic, wherein saturated means that only single bonds are present, and partially or fully unsaturated means that one or more double bonds may be present in suitable positions, while the Hückel rule for aromaticity is not fulfilled, whereas aromatic means that the Hückel (4n+2) rule is fulfilled. The term "carbocylce" or "carbocyclyl", unless otherwise indicated, may therefore cover inter alia cycloalkyl, cycloalkenyl, as well as phenyl. Preferably, the term "carbocycle" covers cycloalkyl and cycloalkenyl groups, for example cyclopropane, cyclobutane, cyclopentane and cyclohexane rings.

The term "carbobicyclic" or "carbobicyclyl" includes in general 6 to 14-membered, preferably 7- to 12-membered or 8- to 10-membered, more preferably 9- or 10-membered bicyclic rings comprising 6 to 14, preferably 7 to 12 or 8 to 10, more preferably 9 or 10 carbon atoms. The carbobicycle may be saturated, partially or fully unsaturated, or aromatic, wherein saturated means that only single bonds are present, and partially or fully unsaturated means that one or more double bonds may be present in suitable positions, while the Hückel rule for aromaticity is not fulfilled, whereas aromatic means that the Hückel (4n+2) rule is fulfilled. Preferably, the term "aromatic" in connection with the carbobicyclic ring means that both rings of the bicylic moiety are aromatic, so that, e.g., 8 π electrons are present in case of a 10-membered aromatic carbobicyclic ring. The term "carbobicylce" or "carbobicyclyl", unless otherwise indicated, may therefore cover inter alia bicycloalkyl, bicycloalkenyl, as well as bicyclic aromatic groups, for example bicyclohexane (decalin), bicycloheptane (such as norbornane), bicyclooctane (such as bicyclo[2.2.2]octane, bicyclo[3.2.1]octane or bicyclo[4.2.0]octane), bicyclononane (such as bicyclo[3.3.1]nonane or bicyclo[4.3.0]nonane), bicyclodecane (such as bicyclo[3.3.3]undecane), norbornene, naphthalene and the like. Preferably, the carbobicycle is a fused carbobicycle, which is preferably aromatic, for example naphthalene.

The term "heterocyclic" or "heterocyclyl" includes, unless otherwise indicated, in general a 3- to 9-membered, preferably a 4- to 8-membered or 5- to 7-membered, more preferably 5- or 6-membered, in particular 6-membered monocyclic ring. The heterocycle may be saturated, partially or fully unsaturated, or aromatic, wherein saturated means that only single bonds are present, and partially or fully unsaturated means that one or more double bonds may be present in suitable positions, while the Hückel rule for aromaticity is not fulfilled, whereas aromatic means that the Hückel (4n+2) rule is fulfilled. The heterocycle typically comprises one or more, e.g. 1, 2, 3, or 4, preferably 1, 2, or 3 heteroatoms selected from N, O and S as ring members, where S-atoms as ring members may be present as S, SO or SO$_2$. The remaining ring members are carbon atoms. In a preferred embodiment, the heterocycle is an aromatic heterocycle, preferably a 5- or 6-membered aromatic heterocycle comprising one or more, e.g. 1, 2, 3, or 4, preferably 1, 2, or 3 heteroatoms selected from N, O and S as ring members, where S-atoms as ring members may be present as S, SO or SO$_2$. Examples of aromatic heterocycles are provided below in connection with the definition of "hetaryl". "Hetaryls" or "heteroaryls" are covered by the term "heterocycles". The saturated or partially or fully unsaturated heterocycles usually comprise 1, 2, 3, 4 or 5, preferably 1, 2 or 3 heteroatoms selected from N, O and S as ring members, where S-atoms as ring members may be present as S, SO or SO$_2$. The skilled person is aware that S, SO or SO$_2$ is to be understood as follows:

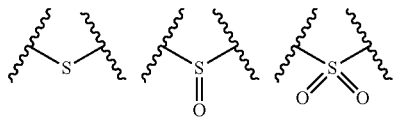

Further, a skilled person is aware that resonance structures of the oxidized forms may be possible. Saturated heterocycles include, unless otherwise indicated, in general 3- to 9-membered, preferably 4- to 8-membered or 5- to 7-membered, more preferably 5- or 6-membered monocyclic rings comprising 3 to 9, preferably 4 to 8 or 5 to 7, more preferably 5 or 6 atoms comprising at least one heteroatom, such as pyrrolidine, tetrahydrothiophene, tetrahydrofuran, piperidine, tetrahydropyran, dioxane, morpholine or piperazine.

The term "heterobicyclic" or "heterobicyclyl" includes, unless otherwise indicated, in general 6 to 14-membered, preferably 7- to 12-membered or 8- to 10-membered, more preferably 9- or 10-membered bicyclic rings. The heterobicycle may be saturated, partially or fully unsaturated, or aromatic, wherein saturated means that only single bonds are present, and partially or fully unsaturated means that one or more double bonds may be present in suitable positions, while the Hückel rule for aromaticity is not fulfilled, whereas aromatic means that the Hückel (4n+2) rule is fulfilled. In principal, for being "aromatic", it is sufficient if one of the two rings of the bicyclic moieties is aromatic, while the other is non-aromatic. However, it is preferred in connection with the term "aromatic" that both rings of the bicylic moiety are aromatic, so that, e.g., 8 π electrons are present in case of a 9- or 10-membered aromatic heterobicyclic ring. The heterobicycle typically comprises one or more, e.g. 1, 2, 3, or 4, preferably 1, 2, or 3 heteroatoms selected from N, O and S as ring members, where S-atoms as ring members may be present as S, SO or SO$_2$. The remaining ring members are carbon atoms. Examples of heterobicycles include benzofuranyl, benzothienyl, indolyl, indazolyl, benzimidazolyl, benzoxathiazolyl, benzoxadiazolyl, benzothiadiazolyl, benzoxazinyl, quinolinyl, isoquinolinyl, purinyl, 1,8-naphthyridyl, pteridyl, pyrido[3,2-d]pyrimidyl, pyridoimidazolyl, triethylenediamine or quinuclidine and the like. Preferred heterobicycles according to the invention are aromatic heterobicycles such as benzodiazole, benzothiazole, quinoline, and iso-quinoline.

The term "hetaryl" or "heteroaryl" or "aromatic heterocycle" or "aromatic heterocyclic ring" includes monocyclic 5- or 6-membered aromatic heterocycles comprising as ring members 1, 2, 3 or 4 heteroatoms selected from N, O and S, where S-atoms as ring members may be present as S, SO or SO$_2$. Examples of 5- or 6-membered aromatic heterocycles include pyridyl (also referred to as pyridinyl), i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl. Unless otherwise indicated, the term "hetaryl" further covers "aromatic heterobicycles" as defined above.

The term "aryl" or "aromatic carbocycle" preferably includes 6-membered aromatic carbocyclic rings based on carbon atoms as ring members. A preferred example is phenyl. Unless otherwise indicated, the term "aryl" further covers "aromatic carbobicycles" as defined above.

As used herein, the terms "carbocyclylalkyl" and "heteroocyclylalkyl" as well as the terms "arylalkyl", "cycloalkylalkyl", "hetarylalkyl", and the like refer to the corresponding groups, which are bonded to the remainder of the molecule via an alkyl, preferably via a $C_1$-$C_2$-alkyl group. Preferred examples include benzyl (i.e. phenylmethyl), cyclohexylmethyl, pyridinylmethyl, and piperidinomethyl.

As used herein, the terms "aryloxy" and "benzyloxy" refer to the corresponding groups, which are bonded to the remainder of the molecule via an oxygen atom. Preferred examples include phenyloxy and phenylmethyloxy (i.e. benzyloxy).

As used herein, the term "alkylene" refers to a linking straight-chain or branched alkylene group having usually from 1 to 4 carbon atoms, e.g. 1, 2, 3, or 4 carbon atoms. The alkylene group bridges a certain group to the remainder of the molecule. Preferred alkylene groups include methylene ($CH_2$), ethylene ($CH_2CH_2$), propylene ($CH_2CH_2CH_2$) and the like. A skilled person understands that, if it is referred, e.g., to $CH_2$ that the carbon atom being tetravalent has two valences left for forming a bridge (—CH$_2$—). Similarly, when it is referred, e.g., to CH$_2$CH$_2$, each carbon atom has one valence left for forming a bridge (—CH$_2$CH$_2$—). Furthermore, when is it referred, e.g., to CH$_2$CH$_2$CH$_2$, each terminal carbon atom has one valence left for forming a bridge (—CH$_2$CH$_2$CH$_2$—).

As used herein, the term "S(=O)$_2$—C$_1$-C$_4$-alkylene" refers to a linking group comprising an alkylene group as defined above, which is bonded to an S(=O)$_2$ group. The S(=O)$_2$—C$_1$-C$_4$-alkylene group bridges a certain group to the remainder of the molecule, wherein one linking bond is formed by the S(=O)$_2$ group, while the other linking bond is formed by the terminal carbon atom of the alkylene group (—S(=O)$_2$—C$_1$-C$_4$-alkylene-).

As used herein, the term "arylene" refers to a linking aryl group usually having 6 carbon atoms forming a ring, of which two carbon atoms have a free valence, so that the aryl group can bridge a certain group to the remainder of the molecule.

As used herein, the term "S(=O)$_2$-arylene" refers to a linking group comprising an arylene group as defined above, which is bonded via one carbon atom having a free valence to an S(=O)$_2$ group. The S(=O)$_2$-arylene group bridges a certain group to the remainder of the molecule, wherein one linking bond is formed by the S(=O)$_2$ group, while the other linking bond is formed by the carbon atom of the arylene group, which has a free valence (—S(=O)$_2$-arylene-).

As used in the specification and the claims, the singular forms of "a" and "an" also include the corresponding plurals unless the context clearly dictates otherwise. The same applies for plural forms used herein, which also include the singular forms unless the context clearly dictates otherwise.

The terms "about" and "approximately" in the context of the present invention denotes an interval of accuracy that a person skilled in the art will understand to still ensure the technical effect of the feature in question. The term typically indicates a deviation from the indicated numerical value of ±10% and preferably ±5%.

It needs to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to encompass a group which preferably consists of these embodiments only.

The term "pharmaceutically acceptable excipient" as used herein refers to compounds commonly comprised in pharmaceutical compositions, which are known to the skilled person. Examples of suitable excipients are exemplary listed below. Typically, a pharmaceutically acceptable excipient can be defined as being pharmaceutically inactive.

The term "treatment" is to be understood as also including the option of "prophylaxis". Thus, whenever reference is made herein to a "treatment" or "treating", this is to be understood as "treatment and/or prophylaxis" or "treating and/or preventing".

Description of pharmaceutical compositions according to the present invention

A pharmaceutical composition according to the present invention may be formulated for oral, buccal, nasal, rectal, topical, transdermal or parenteral application. Preferred nonparenteral routes include mucosal (e.g., oral, vaginal, nasal, cervical, etc.) routes, of which the oral application may be preferred. Preferred parenteral routes include but, are not limited to, one or more of subcutaneous, intravenous, intramuscular, intraarterial, intradermal, intrathecal and epidural administrations. Preferably administration is by subcutaneous, intra-tumoral or peri-tumoral routes. Particularly preferred is intratumoral administration. The compound according to formula (I) should be applied in pharmaceutically effective amounts, for example in the amounts as set out herein below.

A pharmaceutical composition of the present invention may also be designated as formulation or dosage form. A compound of formula (I) may also be designated in the following as (pharmaceutically) active agent or active compound.

Pharmaceutical compositions may be solid or liquid dosage forms or may have an intermediate, e.g. gel-like character depending inter alia on the route of administration.

In general, the inventive dosage forms can comprise various pharmaceutically acceptable excipients which will be selected depending on which functionality is to be achieved for the dosage form. A "pharmaceutically acceptable excipient" in the meaning of the present invention can be any substance used for the preparation of pharmaceutical dosage forms, including coating materials, film-forming materials, fillers, disintegrating agents, release-modifying materials, carrier materials, diluents, binding agents and other adjuvants. Typical pharmaceutically acceptable excipients include substances like sucrose, mannitol, sorbitol, starch and starch derivatives, lactose, and lubricating agents such as magnesium stearate, disintegrants and buffering agents.

The term "carrier" denotes pharmaceutically acceptable organic or inorganic carrier substances with which the active ingredient is combined to facilitate the application. Suitable pharmaceutically acceptable carriers include, for instance, water, aqueous salt solutions, alcohols, oils, preferably vegetable oils, propylene glycol, polyoxyethelene sorbitans, polyethylene-polypropylene block co-polymers such as poloxamer 188 or poloxamer 407, polyethylene glycols such as polyethylene glycol 200, 300, 400, 600, etc., gelatin, lactose, amylose, magnesium stearate, surfactants, perfume oil, fatty acid monoglycerides, diglycerides and triglycerides, polyoxyethylated medium or long chain fatty acids such as ricinoleic acid, and polyoxyethylated fatty acid mono-, di, and triglycerides such as capric or caprilic acids, petroethral fatty acid esters, hydroxymethyl celluloses such as hydroxymethyl, hydroxyethyl, hydroxypropyl, hydroxypropyl acetate succinate, polyvinylpyrrolidone, crosspovidone and the like. Preferably, the compounds of the present invention are administered in a pharmaceutical composition comprising of lipids, interbilayer crosslinked multilamellar vesicles, biodegradeable poly(D,L-lactic-co-glycolic acid) [PLGA]-based or poly anhydride-based nanoparticles or microparticles, nanoporous particle-supported lipid bilayers and as a conjugate with an antibody.

The pharmaceutical compositions can be sterile and, if desired, mixed with auxiliary agents, like lubricants, preservatives, stabilizers, wetting agents, emulsifiers, salts for influencing osmotic pressure, buffers, colorings, flavoring and/or aromatic substances and the like which do not deleteriously react with the active compound. It is to be understood that the term "carrier" also covers an antibody that delivers the compound of formula (I).

If liquid dosage forms are considered for the present invention, these can include pharmaceutically acceptable emulsions, solutions, suspensions and syrups containing inert diluents commonly used in the art such as water. These dosage forms may contain e.g. microcrystalline cellulose for imparting bulk, alginic acid or sodium alginate as a suspending agent, methylcellulose as a viscosity enhancer and sweeteners/flavoring agents.

For parenteral application, particularly suitable vehicles consist of solutions, preferably oily or aqueous solutions, as well as suspensions, emulsions, or implants. Pharmaceutical formulations for parenteral administration are particularly preferred and include aqueous solutions of the compounds of formula (I) in water-soluble form. Additionally, suspensions of the compounds of formula (I) may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran.

Particularly preferred dosage forms are injectable preparations of a compound of formula (I). Thus, sterile injectable aqueous or oleaginous suspensions can for example be formulated according to the known art using suitable dispersing agents, wetting agents and/or suspending agents. A sterile injectable preparation can also be a sterile injectable solution or suspension in a non-toxic parenterally acceptable diluent or solvent. Among the acceptable vehicles and solvents that can be used are water and isotonic sodium chloride solution. Sterile oils are also conventionally used as solvent or suspending medium. Preferred applications for injectable preparations comprising the compounds of the present invention are intravenous, intratumoral and peritumoral administration.

Suppositories for rectal administration of a compound of formula (I) can be prepared by e.g. mixing the compound with a suitable non-irritating excipient such as cocoa butter, synthetic triglycerides and polyethylene glycols which are solid at room temperature but liquid at rectal temperature such that they will melt in the rectum and release the compound according to formula (I) from said suppositories.

For administration by inhalation, the compounds according to the present invention may be conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Oral dosage forms may be liquid or solid and include e.g. tablets, troches, pills, capsules, powders, effervescent formulations, dragees and granules. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. The oral dosage forms may be formulated to ensure an immediate release of the compound of formula (I) or a sustained release of the compound of formula (I).

A solid dosage form may comprise a film coating. For example, the inventive dosage form may be in the form of a so-called film tablet. A capsule of the invention may be a two-piece hard gelatin capsule, a two-piece hydroxypropylmethylcellulose capsule, a two-piece capsule made of vegetable or plant-based cellulose or a two-piece capsule made of polysaccharide.

The dosage form according to the invention may be formulated for topical application. Suitable pharmaceutical application forms for such an application may be a topical nasal spray, sublingual administration forms and controlled and/or sustained release skin patches. For buccal administration, the compositions may take the form of tablets or lozenges formulated in conventional manner.

The compositions may conveniently be presented in unit dosage forms and may be prepared by any of the methods well known in the art of pharmacy. The methods can include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

As regards human patients, the compound of formula (I) may be administered to a patient in an amount of about 0.001 mg to about 5000 mg per day, preferably of about 0.01 mg to about 1000 mg per day, more preferably of about 0.05 mg to about 250 mg per day, which is the effective amount. The phrase "effective amount" means an amount of compound that, when administered to a mammal in need of such treatment, is sufficient to treat or prevent a particular disease or condition.

Furthermore, the pharmaceutical composition may also contain the compound of formula (I) as a prodrug such as an ester or amide thereof. A prodrug is any compound which is converted under physiological conditions or by solvolysis to any of the compounds of the invention. A prodrug may be inactive prior to administration but may be converted to an active compound of the invention in vivo.

Indications, for which the compounds of the present invention may be used

The compounds according to the present invention are suitable for use in medicine. In particular, the compounds according to the present invention are suitable for use in the treatment of a disease selected from the group consisting of inflammatory diseases, allergic diseases, autoimmune diseases, infectious diseases, cancer, and pre-cancerous syndromes. Further, the compounds of formula (I) are suitable for use in immunogenic compositions and as vaccine adjuvants.

In one embodiment, the compound of the present invention or a pharmaceutical composition comprising the same is for use in the treatment of a disease selected from the group consisting of cancer, pre-cancerous syndromes, and infectious diseases; or for use in an immunogenic composition or as vaccine adjuvant.

In another embodiment, the compound of the present invention or a pharmaceutical composition comprising the same is for use in the treatment of a disease selected from the group consisting of inflammatory diseases, allergic diseases, and autoimmune diseases.

In one preferred embodiment, the compound of the present invention or a pharmaceutical composition comprising the same is for use in the treatment of a disease selected from the group consisting of cancer or pre-cancerous syndromes.

In another preferred embodiment, the compound of the present invention or a pharmaceutical composition comprising the same is for use in the treatment of a disease selected from the group consisting of infectious diseases or for use in an immunogenic composition or as vaccine adjuvant.

In another preferred embodiment, the compound of the present invention or a pharmaceutical composition comprising the same is for use in the treatment of inflammatory diseases, allergic diseases, infectious diseases.

Of particular relevance in connection with the present invention is the treatment of cancer. Preferably, said cancer is selected from the group consisting of breast cancer, inflammatory breast cancer, ductal carcinoma, lobular carcinoma, colon cancer, pancreatic cancer, insulinomas, adenocarcinoma, ductal adenocarcinoma, adenosquamous carcinoma, acinar cell carcinoma, glucagonoma, skin cancer, melanoma, metastatic melanoma, lung cancer, small cell lung cancer, non-small cell lung cancer, squamous cell carcinoma, adenocarcinoma, large cell carcinoma, brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocyte leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), neuroendocrine cancers and testicular cancer.

More preferably, said cancer is selected from prostate cancer, renal carcinoma, melanoma, pancreatic cancer, cervical cancer, ovarian cancer, colon cancer, head and neck cancer, lung cancer, fibrosarcoma and breast cancer.

Preferably, said autoimmune disease is selected from the group consisting of systemic lupus erythematosis, Addison's disease, autoimmune polyglandular disease (also known as autoimmune polyglandular syndrome), glomerulonephritis, rheumatoid arthritis scleroderma, chronic thyroiditis, Graves' disease, autoimmune gastritis, diabetes, autoimmune hemolytic anemia, glomerulonephritis, rheumatoid arthritis autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, asthma, bronchitis, acute pancreatitis, chronic pancreatitis and allergies of various types.

It is to be understood that in connection with the medical uses of the invention it can be preferred that the compounds according to the present invention are administered in combination with antibodies, radiotherapy, surgical therapy, immunotherapy, chemotherapy, toxin therapy, gene therapy, or any other therapy known to those of ordinary skill in the art for treatment of a particular disease. This is particularly relevant in connection with the treatment of cancer Preferably, the compounds of the present invention are administered in combination with antibodies. Preferred antibodies include anti-PD-1, anti-PD-L1, anti-CTLA-4, anti-IDO, anti-KIR, anti-TIM-3, anti-Vista, anti-TIGIT, anti-BTLA and anti-LAG3 antibody. Non-limiting examples are BMS936559, MPDL3280A and MED14736 or avelumab (anti-PD-L1 antibodies), MK-3475, pembrolizumab or pidilizumab (anti-PD-1 antibodies) as well as ipilimumab (anti-CTLA-4 antibodies). Preferably, the compounds of the present invention are administered in a pharmaceutical composition comprising one or more of adjuvants, inactivated or attenuated bacteria (e.g., inactivated or attenuated *Listeria monocytogenes*), modulators of innate immune activation, preferably agonists of Toll-like Receptors (TLRs, preferably TLR7 or TLR9 agonists, e.g. SM360320, AZD8848), (NOD)-like receptors (NLRs, preferably NOD2 agonist), retinoic acid inducible gene-based (RIG)-l-like receptors (RLRs), C-type lectin receptors (CLRs), or pathogen-associated molecular patterns ("PAMPs"), cytokines (not limiting examples e.g. IL-2, IL-12, IL-6), interferons (including, but not limited to IFN alpha, IFN beta, IFN gamma, IFN lambda) or chemotherapeutic agents. The medical use may further compromise administering at least one HBV vaccine, a nucleoside HBV inhibitor or any combination thereof (e.g. RECOMBIVAX HB, ENGERIX-B, GENEVAC-B).

Combination therapy may be achieved by use of a single pharmaceutical composition that includes both agents, or by administering two distinct compositions at the same time, wherein one composition includes a compound of the present invention, and the other includes the second agent(s).

The two therapies may be given in either order and may precede or follow the other treatment by intervals ranging from minutes to weeks. In embodiments where the other agents are applied separately, one would generally ensure that a significant period of time did not expire between the time of each delivery, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In some embodiments, the compound of the present invention is administered prior to administration of the distinct cancer treatment. In other embodiments, the distinct cancer treatment is administered prior to administration of the compound of the present invention.

The present invention is further illustrated by the following examples.

EXAMPLES

The following abbreviations are used herein:

| Abbreviation | Meaning |
| --- | --- |
| AcCl | Acetyl chloride |
| Ac$_2$O | Acetic anhydride |
| AcOH | Acetic acid |
| AcOEt | Ethyl acetate (also referred to as EtOAc) |
| AcONa | Sodium acetate |
| AlCl$_3$ | Aluminum chloride |
| Al$_2$O$_3$ | Aluminium oxide |
| Anh. | Anhydrous |
| aq | Aqueous solution |

-continued

| Abbreviation | Meaning |
|---|---|
| BINAP | 2,2'-Bis(diphenylphosphino)-1,1'-binaphathalene |
| Boc$_2$O | Di-tert-butyl-dicarbonate |
| Brettphos | 2-(Dicyclohexylphosphino)-3,6-dimethoxy-2',4',6'-triisopropyl-1,1'-biphenyl |
| tBuONa/t-BuONa | Sodium tert-butoxide |
| CH$_3$CN/ACN | Acetonitrile |
| CH$_3$I | Iodomethane |
| CHCl$_3$ | Chloroform |
| CH(OEt)$_3$ | Triethyl orthoformate |
| Conc. | Concentrated |
| Cs$_2$CO$_3$ | Cesium carbonate |
| CuCl$_2$ | Copper(II) chloride |
| CuI | Copper(I) iodide |
| d | Deuterated |
| DBU | 1,8-Diazabicyclo(5.4.0)undec-7-en |
| DCC | N,N'-dicyclohexylcarbodiimide |
| DCE | 1,2-Dichloroethane |
| DCM | Dichloromethane |
| DIAD | Diisopropyl azodicarboxylate |
| DIBAL-H | Diisobutylaluminium hydride |
| DIPA | Diisopropylamine |
| DIPEA/DIEA | N,N-diisopropylethylamine, Hunig's base |
| DMAP | 4-(Dimethylamino)pyridine |
| DMF | N,N-Dimethylformamide |
| DMSO | Dimethylsulfoxide |
| DMSO-d$_6$ | Deuterated dimethylsulfoxide |
| EDC | N-(3-Dimethylaminopropyl)-N-ethylcarbodiimide |
| eq | Equivalent |
| ESI-MS | Electrospray Ionisation - Mass spectrometry |
| Et | Ethyl |
| Et$_2$O | Diethyl ether |
| EtOH | Ethanol |
| Et$_3$N | Triethylamine |
| FCC | Flash column chromatography |
| H$_2$ | Molecular hydrogen |
| HATU | 1-[Bis(dimethylamino)methylene]-1H-1,2,3-triazolo[4,5-b]pyridinium 3-oxid hexafluorophosphate |
| HBTU | N,N,N',N'-Tetramethyl-O-(1H-benzotriazol-1-yl)uronium hexafluorophosphate |
| HCl | Hydrochloric acid |
| HCOOH | Formic acid |
| Hex | Hexane |
| H$_2$O | Water |
| HPLC | High-performance liquid chromatography |
| H$_2$SO$_4$ | Sulfuric acid |
| i-PrOH | Isopropanol |
| K | Potassium |
| K$_2$CO$_3$ | Potassium carbonate |
| KHMDS | Potassium bis(trimethylsilyl)amide |
| KI | Potassium iodide |
| KOH | Potassium hydroxide |
| LAH | Lithium aluminium hydride |
| LC-MS | Liquid chromatography - mass spectrometry |
| MeOH | Methanol |
| MeONa | Sodium methoxide |
| MgSO$_4$ | Magnesium sulfate |
| MnO$_2$ | Manganese(IV) oxide |
| MOMCl/Cl-MOM | Chloromethyl methyl ether |
| MsCl | Methanesulfonyl chloride |
| 3Å MS | 3Å molecular sieves |
| 4Å MS | 4Å molecular sieves |
| MW | Microwave |
| N/M | Molar concentration [mol/dm$^3$] |
| Na | Sodium |
| NaBH$_4$ | Sodium borohydride |
| NaBH$_3$CN | Sodium cyanoborohydride |
| NaBH(OAc)$_3$ | Sodium triacetoxyborohydride |
| NaH | Sodium hydride |
| NaHCO$_3$ | Sodium bicarbonate |
| NaNO$_2$ | Sodium nitrite |
| NaOAc | Sodium acetate |
| NaOH | Sodium hydroxide |
| Na$_2$SO$_4$ | Sodium sulfate |
| nBuOH | n-Butanol |
| NH$_3$ | Ammonia |
| NH$_2$—NH$_2$ | Hydrazine |
| NH$_2$—NH$_2$·H$_2$O | Hydrazine monohydrate |
| NH$_4$Cl | Ammonium chloride |
| NH$_4$HCO$_3$ | Ammonium bicarbonate |
| NMM | N-methylmorpholine |
| NMP | N-methyl-2-pyrrolidone |
| NMR | Nuclear magnetic resonance |
| on/o.n. | Overnight |
| PBr$_3$ | Phosphorus tribromide |
| Pd/C | Palladium (0) on carbon |
| PdCl$_2$(PPh$_3$)$_2$ | Bis(triphenylphosphine)palladium(II) dichloride |
| Pd$_2$(dba)$_3$ | Tris(dibenzylideneacetone)dipalladium(0) |
| Pd(dppf)Cl$_2$·DCM | [1,1'-Bis(diphenylphosphino)ferrocene]dichloropalladium(II), complex with di-chloromethane |
| Pd(OH)$_2$/C | Palladium(II) hydroxide on carbon |
| Pd(PPh$_3$)$_4$ | Tetrakis(triphenylphosphine)palladium(0) |
| PhOPh | Diphenyl ether |
| POCl$_3$ | Phosphorus (V) oxychloride |
| prep-HPLC | Preparative high-performance liquid chromatography |
| prep-TLC | Preparative thin layer chromatography |
| Pt/C | Platinum (0) on carbon |
| PtO$_2$ | Platinum dioxide |
| PTSA | p-Toluenesulfonic acid |
| rac | Racemate/racemic |
| RP-FCC/RPFCC/RPFCC | Reversed phase flash column chromatography |
| RT/r.t. | Room temperature, i.e. 20-25° C. |
| SiHP | Silica PuriFlash Columns High Performance, 60 A-500 m$^2$/g |
| SiC18/Si-C18 | Silica PuriFlash Columns High Performance C18, 15 μm |
| Si-Diol | Silica PuriFlash Columns Diol, 50 μm |
| Si—NH$_2$/SiNH$_2$ | Amino silica PuriFlash Columns, μm |
| SOCl$_2$ | Thionyl chloride |
| SPhos | (2-Dicyclohexylphosphino-2',6'-dimethoxybiphenyl) |
| Pd G3 | [2-(2'-Amino-1,1'-bi-phenyl)]palladium(II) Methanesulfonate |
| T3P | 1-Propanephosphonic anhydride |
| TBAB | Tetrabutylammonium bromide |
| TBSCl | tert-Butyldimethylsilyl chloride |
| tBuOK | Potassium tert-butoxide |
| TEA | Triethylamine |
| TESCl | Chlorotriethylsilane |
| TFA | Trifluoroacetic acid |
| TIPSCl | Triisopropylsilyl chloride |
| THF | Tetrahydrofurane |
| TLC | Thin layer chromatography |
| TPP/PPh$_3$ | Triphenylphosphine |
| UPLC | Ultra performance liquid chromatography |
| UPLC-MS | Ultra performance liquid chromatography tandem mass spectrometer |
| Xantphos | (9,9-dimethyl-9H-xanthene-4,5-diyl)bis(diphenylphosphine) |
| ZnCl$_2$ | Zinc chloride |

The compounds of the present invention can be prepared according to the procedures of the following Schemes and Examples, using appropriate materials and are further exemplified by the following specific examples.

Unless otherwise specified, all starting materials are obtained from commercial suppliers and used without further purifications. Unless otherwise specified, all temperatures are expressed in ° C. and all reactions are conducted at rt.

Methods and Analytical Data:
General:

Microwave heating was done using a Biotage Emrys Initiator microwave. Column chromatography was carried out using an Isco Rf200d or an Interchim Puriflash 450. Solvent removal was carried out using either a Büchi rotary evaporator or a Genevac centrifugal evaporator. Preparative LC/MS was conducted using a Waters mass directed auto-purification system and a Waters 19×100 mm XBridge 5 micron C18 column under basic mobile phase conditions or an equivalent Waters CSH C18 column under acidic conditions. NMR spectra were recorded using a Bruker 300 MHz or 400 MHz spectrometer. Chemical shifts (δ) are reported in ppm relative to the residual solvent signal (measurement range—6.4 kHz). 1H NMR data are reported as follows: chemical shift (multiplicity, coupling constants and number of hydrogens). Multiplicity is abbreviated as follows: s (singlet), d (doublet), t (triplet), q (quartet), m (multiplet), dd (doublet of doublets), dt (doublet of triplets). ESI-MS: Desolvatation Gas Flow 993 l/h; Desolvatation temperature 500° C.; cone gas: 50 l/min; 500-1000 m/z; polarity: positive and/or negative.

Preparative HPLC Conditions for the Purification of Target Compounds:
Chromatography Conditions 1:
Prep HPLC Instrument: Shimadzu
    Column: Gemini-NX 5 μm C18 110 Å, 21.2*250 mm
    Detector: SPD −20A/20AV UV-VIS
    Flow Rate: 20 mL/min
Representative Mobile Phase:
(1)
    Mobile Phase: A: 0.01% formic acid in water or TFA
    Mobile Phase: B: 0.01% formic acid in ACN or TFA
(2)
    Mobile Phase: A: 0.01% NH4OH in water
    Mobile Phase: B: 0.01% NH4OH in ACN
Chromatography Conditions 2:
Prep HPLC Instrument: Shimadzu
    Column: Chiralpak AD-H, 5 μm, 20*250 mm
    Detector: SPD −20A/20AV UV-VIS
    Flow Rate: 20 mL/min
Representative Mobile Phase:
    Mobile Phase: A: EtOH
    Mobile Phase: B: hexane UPLC, HPLC and MS data provided in the examples described below were registered on:
L C-MS analyses on Shimadzu:
    Method name: lc-ms1-2-ba
Equipment:
    Shimadzu LC-MS 2020
    HPLC with UV-Vis or DAD detector
    column: Waters Acquity UPLC HSS C18, 50 mm×2.1 mm×1.8 μm
Eluents:
    (A) 0.1% formic acid in ACN
    (B) 0.1% formic acid in water
Analytical Method:
    Autosampler: injection volume: 1 μL
    Pump:
Time [min] Flow [ml/min] % B

| Time [min] | Flow [ml/min] | % B |
| --- | --- | --- |
| 0.00 | 0.5 | 95 |
| 0.00 | 0.5 | 95 |
| 4.00 | 0.5 | 5 |
| 5.00 | 0.5 | 5 |
| 5.20 | 0.5 | 95 |
| 6.00 | 0.5 | 95 |

Column compartment: column temperature: 25° C.; time of analysis: 6 mi
Detector: wave length: 254, 230, 270, 280 nm
LC-MS Analyses on Bruker Amazon SL
    Method name: lc-ms1-2-ba
Equipment:
    MS Bruker Amazon SL
    LC Dionex Ultimate 3000
    HPLC with UV-Vis or DAD detector
    column: Waters Acquity UPLC HSS C18, 50 mm×2.1 mm×1.8 μm
Eluents:
    (A) 0.1% formic acid in ACN
    (B) 0.1% formic acid in water
Analytical Method:
    Auto sampler: injection volume: 1 μL
    Pump:

| Time [min] | Flow [ml/min] | % B |
| --- | --- | --- |
| 0.00 | 0.5 | 95 |
| 0.00 | 0.5 | 95 |
| 4.00 | 0.5 | 5 |
| 5.00 | 0.5 | 5 |
| 5.20 | 0.5 | 95 |
| 6.00 | 0.5 | 95 |

Column compartment: column temperature: 25° C.; time of analysis: 6 min
Detector: wave length: 254, 230, 270, 280 nm
LC-MS Analyses on Bruker Amazon SL
    Method name: BCM-30
Equipment:
    MS Bruker Amazon SL
    LC Dionex Ultimate 3000
    HPLC with UV-Vis or DAD detector
    column: Waters Symmetry C18 3.9×150 mm 5 μm
Eluents:
    (A) 0.1% formic acid-water solution
    (B) 0.1% formic acid-ACN solution
Analytical Method:
    Autosampler: injection volume: 3 μL
    Pump:
    flow: 1.2 ml/min
Time [min] [%] B

| Time [min] | [%] B |
| --- | --- |
| 0.0 | 20 |
| 20.0 | 80 |
| 22.0 | 80 |
| 22.5 | 95 |
| 25.0 | 95 |
| 25.3 | 20 |
| 30.0 | 20 |

Column compartment: column temperature: 25° C.; time of analysis: 30 min
Detector: wave length: 254 nm
LC-MS Analyses on Corona Ultra:
    Method name: BCM-30
Equipment:
    Corona ultra
    LC Dionex Ultimate 3000
    column: Waters Symmetry C18 3.9×150 mm 5 μm Eluents:
(A) 0.1% formic acid-water solution
(B) 0.1% formic acid-ACN solution Analytical Method:
Autosampler: injection volume: 3 μL
Pump:
flow: 1.2 ml/min
Time [Min] [%] B

| Time [min] | [%] B |
| --- | --- |
| 0.0 | 20 |
| 20.0 | 80 |
| 22.0 | 80 |
| 22.5 | 95 |
| 25.0 | 95 |
| 25.3 | 20 |
| 30.0 | 20 |

Synthetic Procedures:

The following compounds are commercially available and/or can be prepared in a number of ways well known to one skilled in the art of organic synthesis. More specifically, disclosed compounds can be prepared using the reactions and techniques described herein. In the description of the synthetic methods described below, it is to be understood that all proposed reaction conditions, including choice of solvent, reaction atmosphere, reaction temperature, duration of the experiment, and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

Procedure 1. Preparation of
3-(chloromethyl)-4H-chromen-4-one

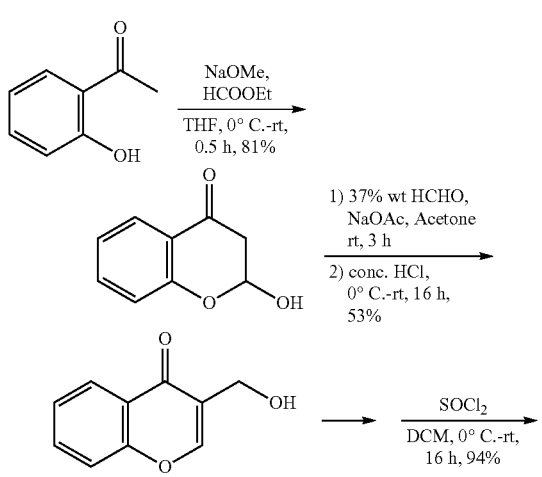

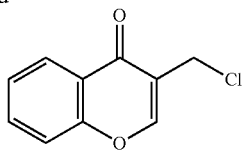

a. 2-hydroxy-3,4-dihydro-2H-1-benzopyran-4-one

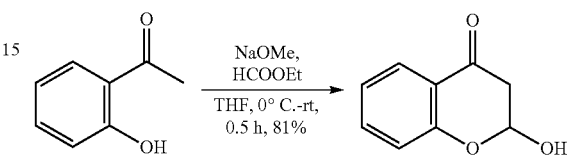

Sodium methoxide (7.14 g, 132.21 mmol, 3 eq.) was suspended in ethyl formate (70.89 mL, 881.38 mmol, 20 eq.) at 0° C. Cooling bath was removed and 1-(2-hydroxyphenyl)ethan-1-one (6.00 g, 44.07 mmol, 1 eq.) was added dropwise at rt as a solution in THF (3 mL). The reaction was monitored by TLC (SiHP, Hexane: AcOEt 2:1) and terminated after 0.5 h by the addition of water (20 mL) and AcOH (2 mL). The phases were separated and the aqueous phase was extracted with AcOEt three times. Organic layers were combined, washed with saturated $NaHCO_3$ aqueous solution, dried over $MgSO_4$, filtered off and concentrated in vacuo to afford the title compound (7.00 g, 42.60 mmol, yield 81%) as a white solid that was taken to the next step without additional purification. ESI-MS: 165 $[M+H]^+$ $^1$H NMR (300 MHz, DMSO-$d_6$): δ 7.72 (dd, J=7.7, 1.6 Hz, 1H), 7.62-7.53 (m, 2H), 7.10-6.98 (m, 2H), 5.86-5.78 (m, 1H), 3.10-2.99 (m, 1H), 2.67 (dd, J=16.5, 4.2 Hz, 1H).

b. 3-(hydroxymethyl)-4H-chromen-4-one

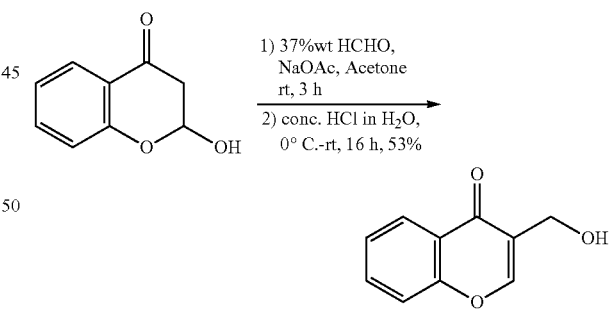

To a solution of 2-hydroxy-3,4-dihydro-2H-1-benzopyran-4-one (6.00 g, 36.55 mmol, 1 eq.) and NaOAc (150 mg, 1.83 mmol, 0.05 eq.) in acetone (30 mL), 37% wt formaldehyde aqueous solution (3.36 mL, 43.86 mmol, 1.2 eq.) was added dropwise. The reaction was continued at rt for 3 h and monitored by TLC (SiHP, Hexane: AcOEt 1:1). Afterwards, concentrated HCl solution in water was added and the reaction was continued for further 16 h. The reaction was quenched with saturated $NaHCO_3$ aqueous solution and the mixture was extracted with AcOEt three times. Organic layers were combined, dried over $MgSO_4$, filtered off and concentrated. The residue was purified by FCC (SiHP, Hexane: AcOEt 50%) to afford the title compound (3.86 g, 21.90 mmol, yield 53%) as a white solid. ESI-MS: 177 [M+H]+

$^1$H NMR (300 MHz, DMSO-d$_6$) δ 8.23 (t, J=1.3 Hz, 1H), 8.07 (dd, J=8.1, 1.7 Hz, 1H), 7.87-7.77 (m, 1H), 7.65 (dd, J=8.4, 1.0 Hz, 1H), 7.54-7.45 (m, 1H), 5.14 (t, J=5.3 Hz, 1H), 4.38 (dd, J=5.3, 1.3 Hz, 2H).

c. 3-(chloromethyl)-4H-chromen-4-one

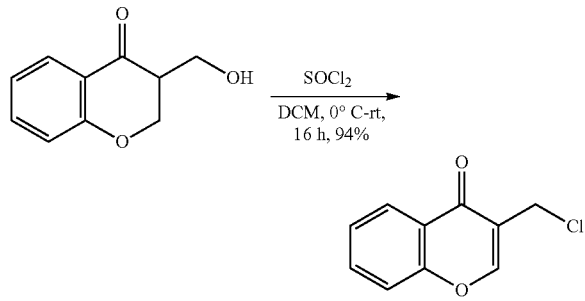

To a cooled suspension of 3-(hydroxymethyl)-4H-chromen-4-one (3.16 g, 17.94 mmol, 1 eq.) in DCM (35 mL), thionyl chloride (3.90 mL, 53.81 mmol, 3 eq.) was added dropwise. The reaction was continued at rt for 16 h and monitored by TLC (SiHP, Hexane: AcOEt 4:1) and LC-MS. Afterwards, the reaction mixture was cooled down to 0° C., quenched with saturated NaHCO$_3$ aqueous solution, diluted in water and extracted with DCM. The layers were separated. Organic layer was dried over MgSO$_4$, filtered off and concentrated. The residue was purified by FCC (SiHP, Hexane: AcOEt 15%) to afford the title compound (3.5 g, 17.98 mmol, yield 94%) as a white solid. ESI-MS: 195 [M+H]+

$^1$H NMR (300 MHz, DMSO-d$_6$) δ 8.66 (s, 1H), 8.10 (dd, J=8.0, 1.7 Hz, 1H), 7.89-7.80 (m, 1H), 7.68 (dd, J=8.7, 1.1 Hz, 1H), 7.58-7.50 (m, 1H), 4.59 (d, J=0.6 Hz, 2H).

Procedure 2. Preparation of 4-oxo-4H-chromene-3-carbaldehyde

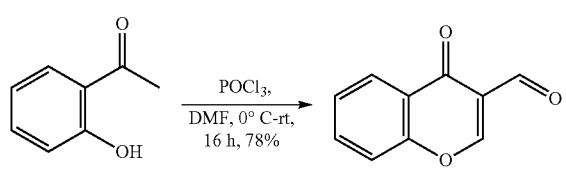

To a cooled solution of 1-(2-hydroxyphenyl)ethan-1-one (2.00 g, 14.69 mmol, 1 eq.) in DMF (10 mL), POCl$_3$ (4.10 mL, 44.07 mmol, 3 eq.) was added dropwise. The reaction was allowed to reach rt over 16 h. When the reaction was complete, the mixture was poured onto ice and stirred until the precipitation stopped. The precipitate was filtered off, washed with ice cold water and recrystallized from MeOH to afford the title compound (2.16 g, 11.50 mmol, yield 78%) as a yellow solid. ESI-MS: 175 [M+H]+

$^1$H NMR (300 MHz, DMSO-d$_6$) δ 10.14 (s, 1H), 8.94 (s, 1H), 8.16 (dd, J=8.1, 1.7 Hz, 1H), 7.94-7.85 (m, 1H), 7.77 (dd, J=8.6, 1.1 Hz, 1H), 7.67-7.55 (m, 1H).

Procedure 3. Preparation of [3-(1H-imidazol-1-yl)propyl](pyridin-4-ylmethyl)amine

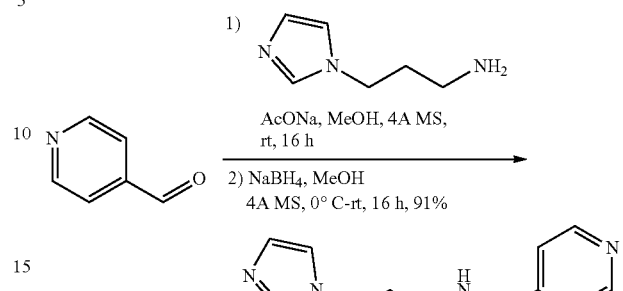

A mixture of 3-(1H-imidazol-1-yl)propan-1-amine (3.68 g, 29.41 mmol, 1.05 eq.), pyridine-4-carboxaldehyde (3.00 g, 28.01 mmol, 1 eq.), sodium acetate (2.30 g, 28.01 mmol, 1 eq.) in MeOH (15 mL) was stirred at rt for 16 h over activated 4 Å molecular sieves. Then, the mixture was cooled down to 0° C. and sodium borohydride (1.08 g, 28.57 mmol, 1.02 eq.) was added portionwise over 30 min. The reaction was allowed to reach rt over 3 h. When the reaction was complete, the mixture was filtered through celite, washed with MeOH and the solvent was removed in vacuo. Alkaline extraction between DCM and NaOH (10%, 2N or 5N) aqueous solution was performed. The layers were separated. Organic layer was dried, filtered off and concentrated to afford the title amine (5.80 g, 26.80 mmol, yield 91%) as a yellow oil. ESI-MS: 217 [M+H]+

$^1$H NMR (300 MHz, DMSO-d$_6$) δ 8.52-8.46 (m, 2H), 7.58 (d, J=1.2 Hz, 1H), 7.37-7.31 (m, 2H), 7.15-7.11 (m, 1H), 6.88-7.84 (m, 1H), 4.02 (t, J=7.0 Hz, 2H), 3.69 (s, 2H), 2.41 (t, J=7.0 Hz, 2H), 2.34 (s, 1H), 1.92-1.78 (m, 2H).

Procedure 4. Preparation of 1-(2-hydroxy-3,4-dimethylphenyl)ethan-1-one

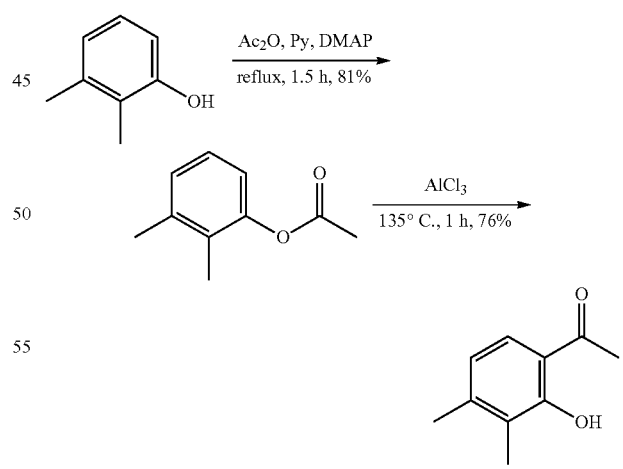

a. 2,3-dimethylphenyl acetate

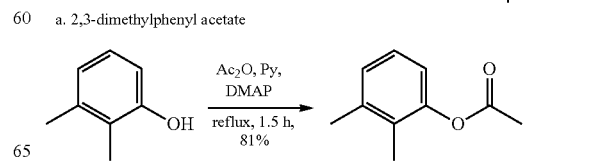

A mixture of 2,3-dimethylphenol (700 mg, 5.73 mmol, 1 eq.), acetic anhydride (1.73 mL, 18.34 mmol, 3.2 eq.), DMAP (70 mg, 0.57 mmol, 0.1 eq.) and pyridine (20 μL, 0.23 mmol, 0.05 eq.) was refluxed for 1.5 h. Afterwards, the mixture was cooled down and poured onto 2% HCl aqueous solution/ice and extracted four times with Et$_2$O. Organic layers were combined, washed four times with 2% NaOH aqueous solution, dried, filtered off and concentrated to afford the title compound (762 mg, 4.64 mmol, yield 81%) as a yellow oil. ESI-MS: 165 [M+H]$^+$ $^1$H NMR (300 MHz, Chloroform-d) δ 7.17-7.00 (m, 2H), 6.91-6.81 (m, 1H), 2.33 (s, 3H), 2.30 (s, 3H), 2.08 (s, 3H).

b. 1-(2-hydroxy-3,4-dimethylphenyl)ethan-1-one

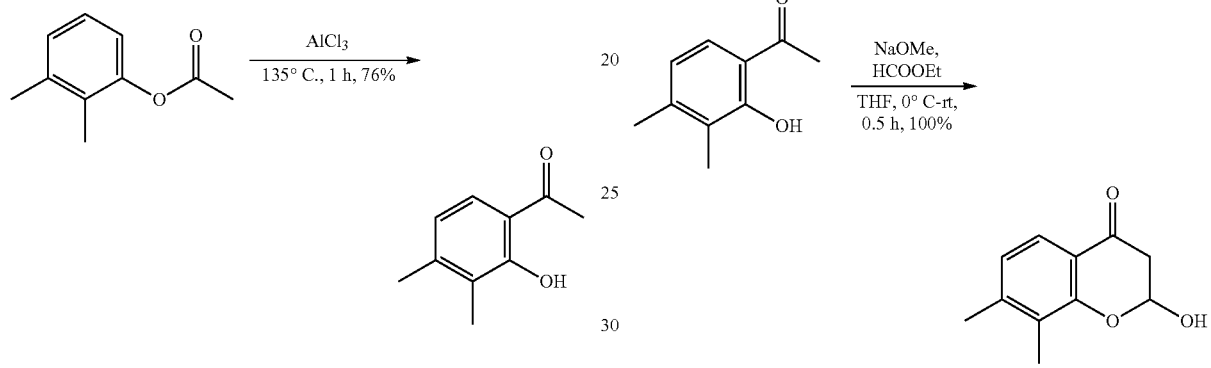

To a flask containing 2,3-dimethylphenyl acetate (1.85 g, 11.27 mmol, 1.0 eq.), AlCl$_3$ (1.73 g, 16.90 mmol, 1.5 eq.) was added portionwise. The reaction was continued at 135° C. for 1 h. The resulting solid was then hydrolyzed with a mixture of ice and diluted HCl aqueous solution and extracted with AcOEt three times. Organic layers were combined, washed with diluted NaOH aqueous solution, dried, filtered off and concentrated in vacuo. The oily residue was purified by FCC (SiHP, Hexane: AcOEt 4:1) to afford the title compound (1.40 g, 8.53 mmol, yield 76%) as a white solid. ESI-MS: 165 [M+H]$^+$ $^1$H NMR (300 MHz, DMSO-d$_6$) δ 12.71 (s, 1H), 7.68 (d, J=8.2 Hz, 1H), 6.80 (d, J=8.2 Hz, 1H), 2.61 (s, 3H), 2.28 (s, 3H), 2.09 (s, 3H).

Procedure 5. Preparation of 3-(hydroxymethyl)-7,8-dimethyl-4H-chromen-4-one

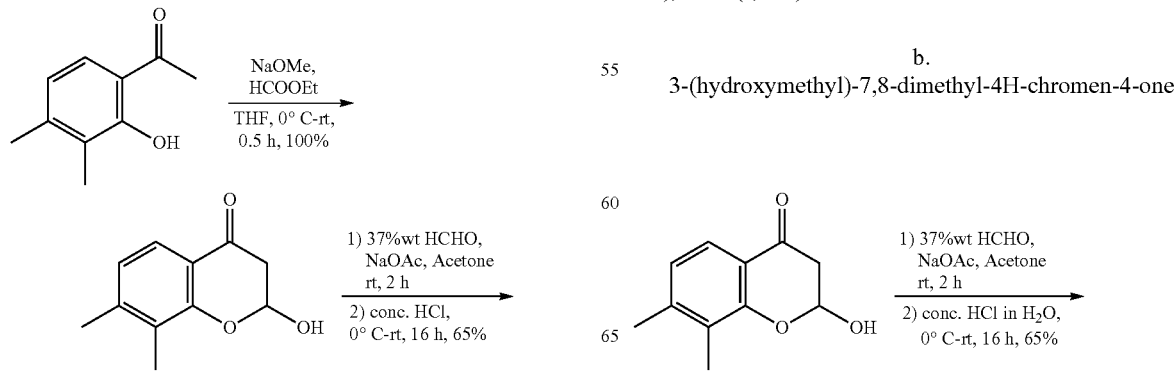

a. 2-hydroxy-7,8-dimethyl-3,4-dihydro-2H-1-benzopyran-4-one

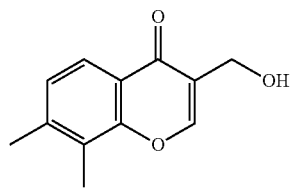

Sodium methoxide (3.38 g, 62.49 mmol, 3 eq.) was suspended in ethyl formate (33.51 mL, 416.57 mmol, 20 eq.) at 0° C. Cooling bath was removed and 1-(2-hydroxy-3,4-dimethylphenyl)ethan-1-one (3.42 g, 20.83 mmol, 1 eq.) was added dropwise at rt as a solution in THF (7 mL). The reaction was monitored by TLC and terminated after 0.5 h by the addition of water (20 mL) and AcOH (2 mL). The phases were separated and the aqueous phase was extracted with AcOEt three times. Organic layers were combined, washed with saturated NaHCO$_3$ aqueous solution, dried over MgSO$_4$, filtered off and concentrated in vacuo to afford the title compound (4.00 g, 20.81 mmol, yield 100%) as a white solid that was taken to the next step without additional purification. ESI-MS: 193 [M+H]$^+$ $^1$H NMR (300 MHz, DMSO-d$_6$) δ 7.52-7.43 (m, 2H), 6.86 (d, J=8.0 Hz, 1H), 5.82 (td, J=4.6, 3.3 Hz, 1H), 3.02-2.92 (m, 1H), 2.62 (dd, J=16.6, 4.6 Hz, 1H), 2.27 (s, 3H), 2.12 (s, 3H).

b. 3-(hydroxymethyl)-7,8-dimethyl-4H-chromen-4-one

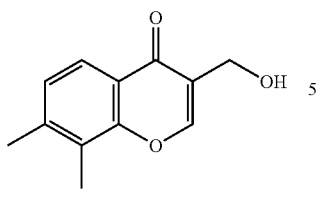

To a solution of 2-hydroxy-7,8-dimethyl-3,4-dihydro-2H-1-benzopyran-4-one (4.00 g, 20.81 mmol, 1 eq.) and NaOAc (85 mg, 1.04 mmol, 0.05 eq.) in acetone (15 mL), 37% wt formaldehyde aqueous solution (2.00 mL, 24.97 mmol, 1.2 eq.) was added dropwise. The reaction was continued at rt for 2 h and monitored by TLC. Afterwards, concentrated HCl solution in water was added and the reaction was continued for further 16 h. The reaction was neutralized with saturated NaHCO$_3$ aqueous solution and the mixture was extracted with AcOEt three times. Organic layers were combined, dried over MgSO$_4$, filtered off and concentrated. The residue was purified by FCC (SiHP, Hexane: AcOEt 1:1) to afford the title compound (2.74 g, 13.42 mmol, yield 65%) as a white solid. ESI-MS: 205 [M+H]$^+$ $^1$H NMR (300 MHz, DMSO-d$_6$) δ 8.22 (t, J=1.3 Hz, 1H), 7.80 (d, J=8.1 Hz, 1H), 7.29 (d, J=8.1 Hz, 1H), 5.09 (t, J=5.4 Hz, 1H), 4.37 (dd, J=5.4, 1.3 Hz, 2H), 2.40 (s, 3H), 2.35 (s, 3H).

Procedure 6. Preparation of 3-(chloromethyl)-7,8-dimethyl-4H-chromen-4-one

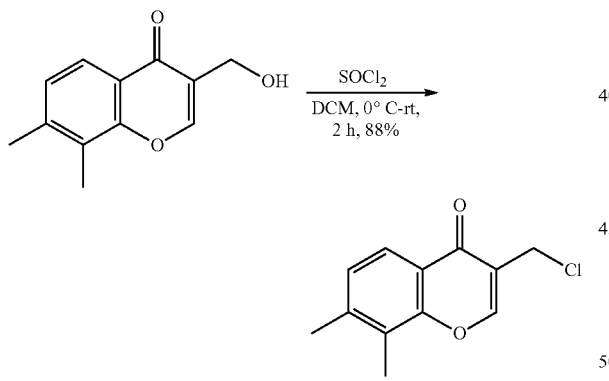

To a cooled suspension of 3-(hydroxymethyl)-7,8-dimethyl-4H-chromen-4-one (1.75 g, 8.60 mmol, 1 eq.) in DCM (10 mL), thionyl chloride (1.88 mL, 25.71 mmol, 3 eq.) was added dropwise. The reaction was continued at rt for 2 h and monitored by TLC. Afterwards, the reaction mixture was cooled down to 0° C., quenched with saturated NaHCO$_3$ aqueous solution, diluted in water and extracted with DCM. The layers were separated. Organic layer was dried over MgSO$_4$, filtered off and concentrated to afford the title compound (1.67 g, 7.50 mmol, yield 88%) as a brown solid. ESI-MS: 224 [M+H]$^+$ $^1$H NMR (300 MHz, DMSO-d$_6$) δ 8.66 (s, 1H), 7.83 (d, J=8.1 Hz, 1H), 7.34 (d, J=8.1 Hz, 1H), 4.58 (s, 2H), 2.41 (s, 3H), 2.35 (s, 3H).

Procedure 7. Preparation of 3-(bromomethyl)-7,8-dimethyl-4H-chromen-4-one

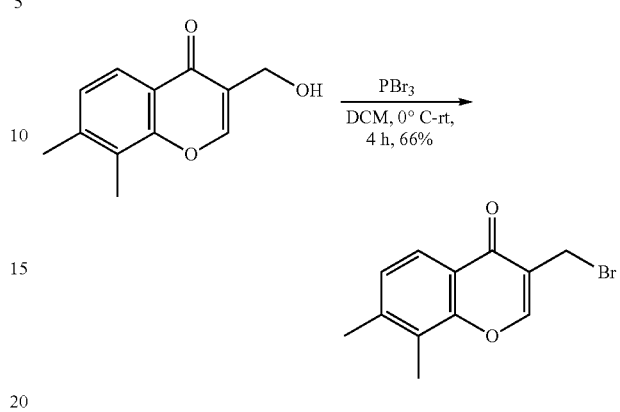

To a cooled suspension of 3-(hydroxymethyl)-7,8-dimethyl-4H-chromen-4-one (300 mg, 1.469 mmol, 1 eq.) in DCM (2 mL), PBr$_3$ (276 µL, 2.94 mmol, 2 eq.) was added dropwise. The reaction was continued at rt for 4 h and monitored by TLC (SiHP, Hexane: AcOEt 4:1) and LC-MS. Afterwards, the reaction mixture was cooled down to 0° C., quenched with ice, diluted in water and extracted with DCM. Organic layer was dried over Na$_2$SO$_4$, filtered off and concentrated in vacuo. The residue was purified by FCC (SiHP, Hexane: AcOEt 4:1) to afford the title compound (260 mg, 0.97 mmol, yield 66%) as beige crystals. ESI-MS: 268 [M+H]$^+$ $^1$H NMR (300 MHz, DMSO-d$_6$) δ 8.71 (s, 1H), 7.83 (d, J=8.2 Hz, 1H), 7.34 (d, J=8.2 Hz, 1H), 4.49 (s, 2H), 2.41 (s, 3H), 2.35 (s, 3H).

Procedure 8. Preparation of 7,8-dimethyl-4-oxo-4H-chromene-3-carbaldehyde

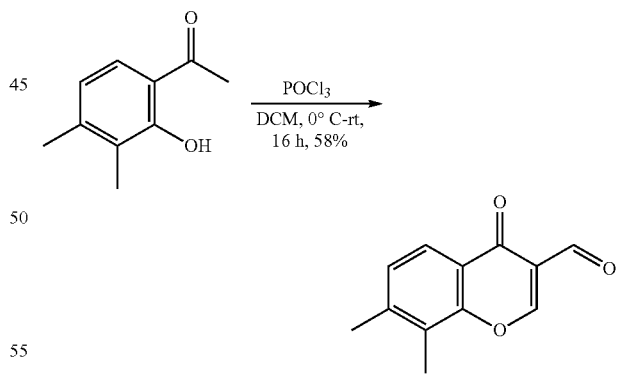

To a cooled solution of 1-(2-hydroxy-3,4-dimethylphenyl)ethan-1-one (377 mg, 2.296 mmol, 1 eq.) in DMF (4.5 mL), POCl$_3$ (859 µL, 9.184 mmol, 4 eq.) was added dropwise. The reaction was allowed to reach rt over 16 h. When the reaction was complete, the mixture was poured onto ice and stirred until the precipitation stopped. The precipitate was filtered off and washed with ice cold water. The precipitate was purified by FCC (SiHP, Hexane: AcOEt 2:1) to afford the product (270 mg, 1.30 mmol, yield 58%) as a white solid. ESI-MS: 203 [M+H]$^+$ ¹H NMR (300 MHz, Chloroform-d) δ 10.42 (s, 1H), 8.59 (s, 1H), 8.06 (d, J=8.1 Hz, 1H), 7.32 (d, J=8.1 Hz, 1H), 2.44 (s, 3H), 2.41 (s, 3H).

Procedure 9.1. Preparation of 3-({[3-(1H-imidazol-1-yl)propyl](pyridin-4-ylmethyl)amino}methyl)-7,8-dimethyl-4H-chromen-4-one

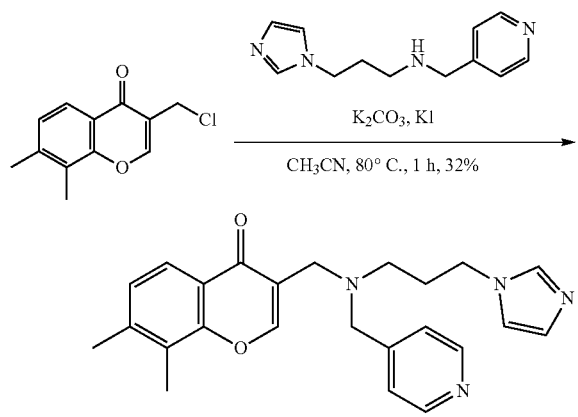

To a suspension of [3-(1H-imidazol-1-yl)propyl](pyridin-4-ylmethyl)amine (249 mg, 1.078 mmol, 1.2 eq.), KI (149 mg, 0.898 mmol, 1 eq.) and K₂CO₃ (372 mg, 2.695 mmol, 3 eq.) in CH₃CN (5 mL), 3-(chloromethyl)-7,8-dimethyl-4H-chromen-4-one (200 mg, 0.898 mmol, 1 eq.) was added portionwise at rt. The reaction was continued at 80° C. for 1 h and monitored by TLC and LC-MS. Afterwards, the reaction was quenched with water, and extracted with DCM. The layers were separated. Organic layer was dried over MgSO₄, filtered off and concentrated in vacuo. The residue was purified by FCC (deactivated SiHP, DCM: MeOH 9:1) to afford the title compound (114 mg, 0.283 mmol, yield 32%) as a yellow oil. ESI-MS: 404 [M+H]⁺

The product was converted into hydrochloric acid salt following Procedure 10.

¹H NMR (400 MHz, DMSO-d₆) δ 8.47-8.42 (m, 2H), 8.34 (s, 1H), 7.82 (d, J=8.1 Hz, 1H), 7.55 (d, J=1.2 Hz, 1H), 7.37-7.33 (m, 2H), 7.30 (d, J=8.2 Hz, 1H), 7.10 (t, J=1.3 Hz, 1H), 6.79 (d, J=1.1 Hz, 1H), 3.97 (t, J=7.1 Hz, 2H), 3.62 (s, 2H), 3.45 (s, 2H), 2.40 (s, 3H), 2.39-2.36 (m, 2H), 2.35 (s, 3H), 2.00-1.89 (m, 2H).

Procedure 9.2. Preparation of 3-({[3-(1H-imidazol-1-yl)propyl](pyridin-4-ylmethyl)amino}methyl)-7,8-dimethyl-4H-chromen-4-one

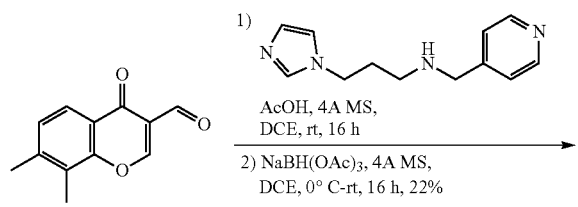

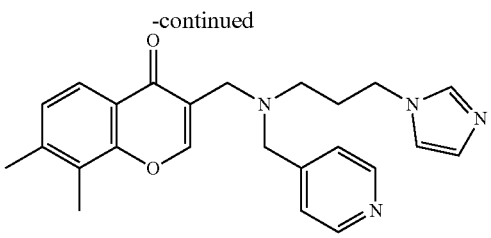

A mixture of [3-(1H-imidazol-1-yl)propyl](pyridin-4-ylmethyl)amine (149 mg, 0.688 mmol, 1,15 eq.), 7,8-dimethyl-4-oxo-4H-chromene-3-carbaldehyde (121 mg, 0.598 mmol, 1 eq.) and glacial AcOH (1 µL, 0.06 mmol, 0.1 eq.) in DCE (5 mL) was stirred at rt for 16 h over activated 4 Å molecular sieves. Then, the mixture was cooled down to 0° C. and sodium triacetoxyborohydride (190 mg, 0.898 mmol, 1.5 eq.) was added portionwise. The reaction was allowed to reach rt over 16 h. The reaction mixture was filtered through celite and washed with DCM. The filtrate was extracted with water. Organic layer was dried, filtered off and concentrated in vacuo. The residue was purified by prep-HPLC to afford a formic acid salt of the title compound (52 mg, 0.129 mmol, yield 22%) as a yellow oil. ESI-MS: 404 [M+H]⁺

¹H NMR (300 MHz, DMSO-d₆) δ 8.50-8.41 (m, 2H), 8.34 (s, 1H), 8.14 (s, 1H), 7.82 (d, J=8.1 Hz, 1H), 7.56 (d, J=1.2 Hz, 1H), 7.40-7.25 (m, 3H), 7.10 (d, J=1.3 Hz, 1H), 6.79 (d, J=1.1 Hz, 1H), 3.97 (t, J=7.1 Hz, 2H), 3.62 (s, 2H), 3.45 (s, 2H), 2.40 (s, 3H), 2.39-2.36 (m, 2H), 2.35 (s, 3H), 2.00-1.90 (m, 2H).

Procedure 10. Preparation of 3-({[3-(1H-imidazol-1-yl)propyl](pyridin-4-ylmethyl)amino}methyl)-7,8-dimethyl-4H-chromen-4-one hydrochloride

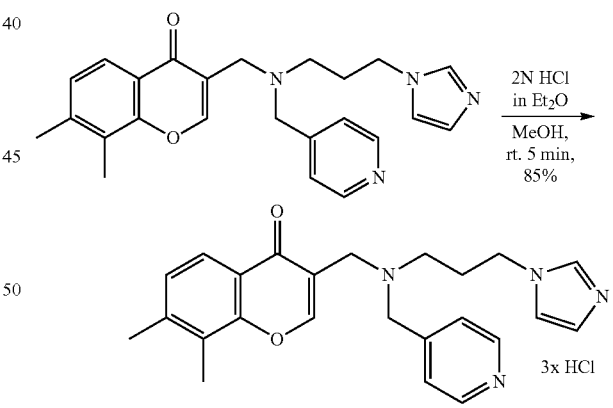

3-({[3-(1H-imidazol-1-yl)propyl](pyridin-4-ylmethyl)amino}methyl)-7,8-dimethyl-4H-chromen-4-one (10 mg, 0.024 mmol, 1 eq.) was dissolved in MeOH (1 mL) and treated with 2N HCl in Et₂O (2 mL). Solvents were removed in vacuo. The procedure was repeated several times and the residue was lyophilized to afford the title compound (11 mg, 0.021 mmol, yield 85%) as an orange solid. ESI-MS: 404 [M+H]⁺

¹H NMR (300 MHz, Deuterium Oxide) δ 8.73-8.70 (m, 1H), 8.65-8.60 (m, 2H), 8.32 (s, 1H), 8.09-8.04 (m, 2H), 7.70 (d, J=8.2 Hz, 1H), 7.48-7.43 (m, 1H), 7.36-7.30 (m, 2H), 4.53 (s, 2H), 4.30 (t, J=7.0 Hz, 2H), 4.10 (s, 2H), 3.22-3.12 (m, 2H), 2.51-2.38 (m, 2H), 2.38 (s, 3H), 2.32 (s, 3H).

Procedure 11. Preparation of 4-(1H-imidazol-1-yl)butan-1-amine

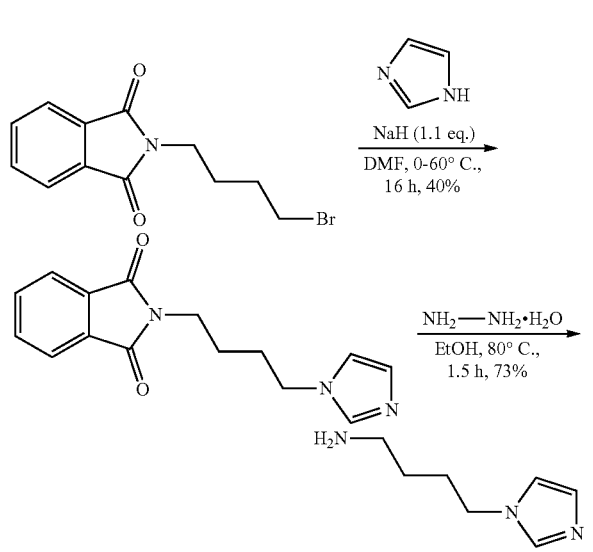

a. 2-[4-(1H-imidazol-1-yl)butyl]-2,3-dihydro-1H-isoindole-1,3-dione

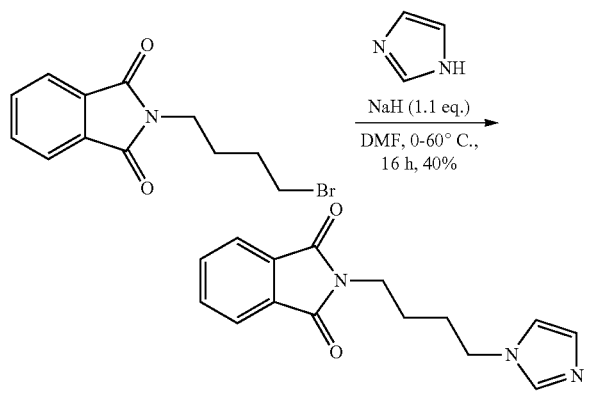

To a cooled solution of 1H-imidazole (200 mg, 3.085 mmol, 1.05 eq) in DMF (7 mL), NaH 60% in mineral oil (136 mg, 3.393 mmol, 1.1 eq.) was added portionwise and the mixture was stirred for 10 min. Afterwards, a solution of 2-(4-bromobutyl)-2,3-dihydro-1H-isoindole-1,3-dione (870 mg, 3.085 mmol, 1 eq.) in DMF (3 mL) was added dropwise. The reaction was continued at 60° C. for further 16 h. The reaction was quenched with water and diluted in AcOEt. The layers were separated. Organic layer was dried, filtered off and concentrated in vacuo. The residue was purified by FCC (SiHP, DCM: MeOH 95:5) to afford the title compound (323 mg, 1.2 mmol, yield 40%) as a white solid. ESI-MS: 270 [M+H]$^+$ $^1$H NMR (300 MHz, Chloroform-d) δ 7.89-7.85 (m, 2H), 7.77-7.73 (m, 2H), 7.50 (t, J=1.1 Hz, 1H), 7.07 (t, J=1.1 Hz, 1H), 6.93 (t, J=1.3 Hz, 1H), 4.02 (t, J=7.0 Hz, 2H), 3.74 (t, J=6.8 Hz, 2H), 1.91-1.79 (m, 2H), 1.78-1.64 (m, 2H).

b. 4-(1H-imidazol-1-yl)butan-1-amine

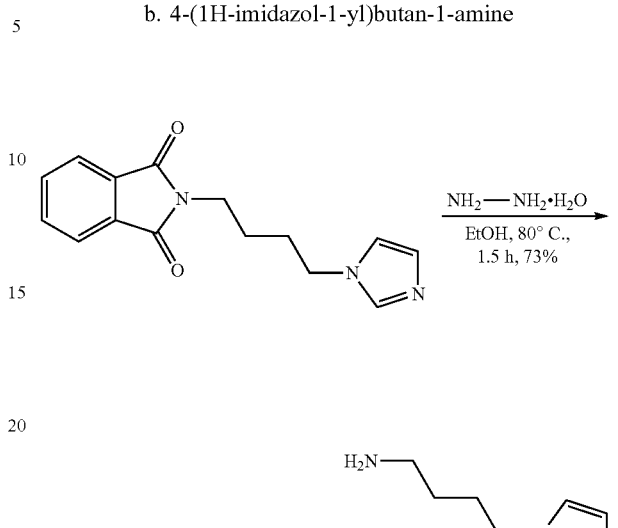

To a solution of 2-[4-(1H-imidazol-1-yl)butyl]-2,3-dihydro-1H-isoindole-1,3-dione (150 mg, 0.557 mmol, 1.0 eq.) in EtOH (5 mL), hydrazine monohydrate 65% w in water (0.046 mL, 0.613 mmol, 1.1 eq.) was added and the mixture heated to 80° C. and stirred for 1.5 h. White precipitate was filtered off and washed with EtOH. The filtrate was concentrated in vacuo. The residue was purified by FCC (Si-Diol, DCM: MeOH 4:1) afford the title compound (70 mg, 0.503 mmol, yield 73%) as a yellow oil. ESI-MS: 140 [M+H]$^+$ $^1$H NMR (300 MHz, Chloroform-d) δ 7.44-7.41 (m, 1H), 6.95-6.92 (m, 1H), 6.89-6.86 (m, 1H), 3.91 (t, J=7.1 Hz, 2H), 2.63 (t, J=7.2 Hz, 2H), 1.81-1.69 (m, 2H), 1.45-1.32 (m, 2H).

Procedure 12. Preparation of N-(3-Aminopropyl)-2-pyrrolidinone

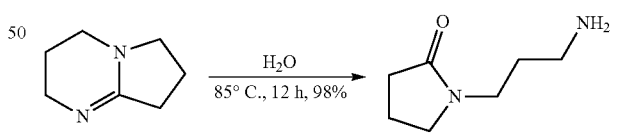

A mixture of 1,5-Diazabicyclo[4.3.0]non-5-ene (300 mg, 2.416 mmol, 1 eq.) and water (43 mg, 43 μL, 2.416 mmol, 1 eq.) was heated under reflux for 12 h at 85° C. Reaction mixture was diluted with DCM and dried with sodium sulfate. The mixture was then filtered and concentrated under reduced pressure to afford the title compound (480 mg, 2.36 mmol, yield 98%) as a colorless oil.

$^1$H NMR (300 MHz, DMSO-d$_6$) δ 3.36-3.27 (m, 2H), 3.25-3.17 (m, 2H), 3.14-3.05 (m, 1H), 2.49-2.44 (m, 1H), 2.25-2.15 (m, 2H), 1.98-1.85 (m, 3H), 1.77-1.74 (m, 1H), 1.75-1.62 (m, 1H), 1.53-1.43 (m, 1H).

Procedure 13. 1-[4-(benzyloxy)-2-hydroxyphenyl]ethan-1-one

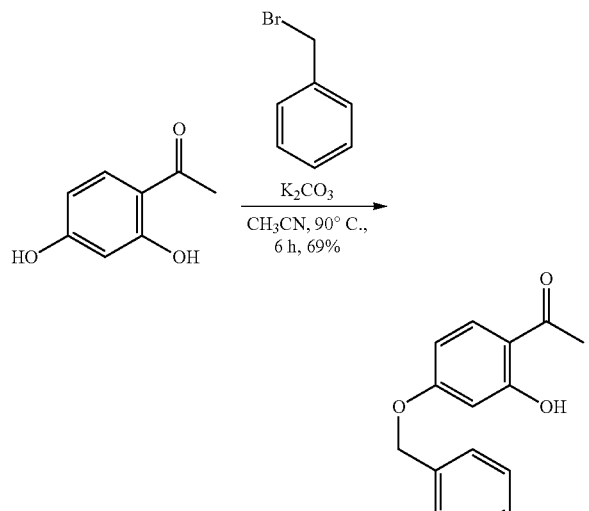

2',4'-dihydroxyacetophenone (2.0 g, 13.145 mmol, 1 eq.) was dissolved in CH$_3$CN (15 ml). Potassium carbonate (2 g, 14.46 mmol, 1.1 eq.) was added to the solution, and the mixture was refluxed for 1 hour. After 1 hour, a mixture of benzyl bromide (2.2 g, 12.89 mmol, 0.98 eq.) and CH$_3$CN (5 mL) was added dropwise. The reaction mixture was then refluxed for additional 5 h and quenched by the removal of the potassium carbonate. The filtrate was diluted in AcOEt and washed with dilute HCl and water. The residue was purified by FCC (SiHP, Hex: AcOEt 10%) to afford the title compound as a white solid (2.2 g, 9.08 mmol, yield 69%). ESI-MS: 244 [M+H]$^+$ $^1$H NMR (300 MHz, DMSO-d$_6$) δ 12.61 (s, 1H), 7.85 (d, J=8.9 Hz, 1H), 7.49-7.30 (m, 5H), 6.65-6.53 (m, 2H), 5.19 (s, 2H), 2.56 (s, 3H).

Procedure 14. 7-hydroxy-3-(hydroxymethyl)-4H-chromen-4-one

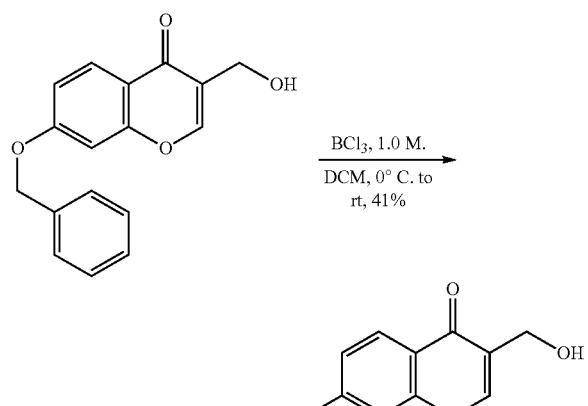

To an ice bath-cooled suspension of 7-(benzyloxy)-3-(hydroxymethyl)chromen-4-one (778 mg, 2.76 mmol, 1 eq.) in DCM (3 mL), 1M solution of boron trichloride in DCM (484 mg, 4.13 mmol, 1.5 eq.) was added dropwise. The mixture was stirred for 15 min at 0° C. and the stirring was continued for 1 hour at rt. The reaction was quenched with saturated NaHCO$_3$ and extracted with CHCl$_3$: iPrOH. Organic layer was filtered and evaporated. The residue was purified by FCC (SiHP, DCM: MeOH 10%) to afford the title compound as a white solid (218 mg, 1.13 mmol, yield 41%). ESI-MS: 193.5 [M+H]$^+$ $^1$H NMR (300 MHz, DMSO-d$_6$) δ 8.08-8.04 (m, 1H), 7.89 (d, J=8.7 Hz, 1H), 6.91 (dd, J=8.7, 2.3 Hz, 1H), 6.85-6.82 (m, 1H), 5.05 (t, J=5.4 Hz, 1H), 4.33 (dd, J=5.3, 1.4 Hz, 2H), 3.17 (d, J=5.1 Hz, 1H).

Procedure 15. Preparation of 7-(4-fluorophenyl)-3-({[3-(1H-imidazol-1-yl)propyl](pyridin-4-ylmethyl)amino}methyl)-4H-chromen-4-one

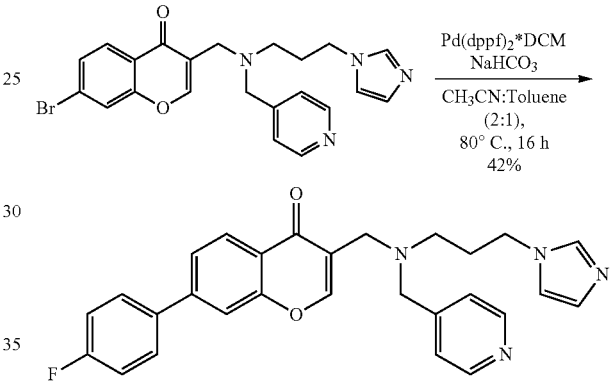

7-bromo-3-({[3-(1H-imidazol-1-yl)propyl](pyridin-4-ylmethyl)amino}methyl)-4H-chromen-4-one (50 mg, 0.215 mmol, 1 eq.) and 4-fluorophenylboronic acid (27 mg, 0.194 mmol, 0.9 eq.) were dissolved in the mixture of acetonitrile and toluene (1:1 v/v) under argon atmosphere. Afterwards, saturated NaHCO$_3$ (1 mL) and Pd(dppf)Cl$_2$.DCM (18 mg, 0.22 mmol, 0.01 eq.) were added and the reaction was continued at 80° C. for 16 h. Afterwards, the reaction mixture was cooled down to rt and filtrated through celite. The filtrate was extracted with AcOEt. Organic layer was dried over magnesium sulfate, filtered and concentrated. The residue was purified by prep-HPLC to afford the title compound as a yellow oil (44 mg, 0.09 mmol yield 42%). ESI-MS: 470 [M+H]$^+$ $^1$H NMR (400 MHz, DMSO-d$_6$) δ 8.50-8.43 (m, 2H), 8.36 (s, 1H), 8.13 (d, J=8.3 Hz, 1H), 7.93 (d, J=1.7 Hz, 1H), 7.92-7.87 (m, 2H), 7.80 (dd, J=8.4, 1.7 Hz, 1H), 7.56 (s, 1H), 7.41-7.32 (m, 4H), 7.13-7.09 (m, 1H), 6.82-6.78 (m, 1H), 3.98 (t, J=7.1 Hz, 2H), 3.64 (s, 2H), 3.48 (s, 2H), 2.40 (t, J=6.8 Hz, 2H), 2.00-1.91 (m, 2H).

The title compound was converted into hydrochloric acid salt following Procedure 10.

$^1$H NMR (400 MHz, Deuterium Oxide) δ 8.77 (t, J=1.5 Hz, 1H), 8.72-8.67 (m, 2H), 8.32 (s, 1H), 8.12-8.04 (m, 3H), 7.85-7.76 (m, 4H), 7.52 (t, J=1.8 Hz, 1H), 7.40-7.37 (m, 1H), 7.32-7.25 (m, 2H), 4.40 (s, 2H), 4.37 (t, J=7.0 Hz, 2H), 3.91 (s, 2H), 3.14-3.00 (m, 2H), 2.45-2.36 (m, 2H).

Procedure 16. Preparation of 3-({[3-(1H-imidazol-1-yl)propyl][(pyridin-4-yl)methyl]amino}methyl)-4-oxo-4H-chromene-7-carbonitrile

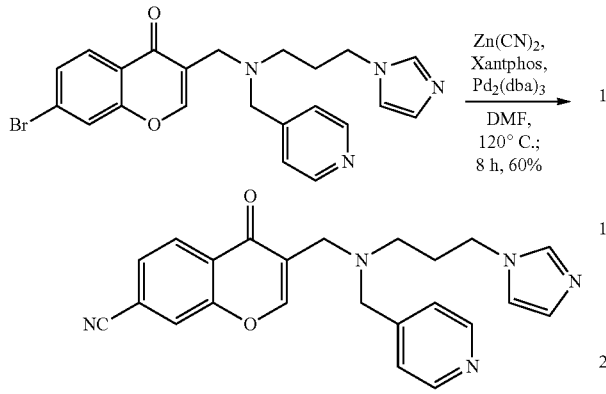

7-bromo-3-({[3-(1H-imidazol-1-yl)propyl][(pyridin-4-yl)methyl]amino}methyl)-4H-chromen-4-one (100 mg, 0.221 mmol, 1 eq.) and zinc cyanide (52 mg, 0.441 mmol, 2 eq.) were suspended in DMF, degassed with argon, and tris(dibenzylideneacetone)dipalladium(0) (10 mg, 0.011 mmol, 0.05 eq.) and (9,9-dimethyl-9H-xanthene-4,5-diyl)bis(diphenylphosphine) (13 mg, 0.022 mmol, 0.1 eq.) were added. The reaction was degassed with argon again and continued at 120° C. for 8 h. Afterwards, the reaction mixture was cooled down to room temperature, taken up in ethyl acetate, and washed with water and brine. Organic layer was dried over magnesium sulfate, filtered off and concentrated in vacuo. The residue was purified by FCC (SiHP, DCM: MeOH 9:1) to afford the title compound (80 mg, 0.188 mmol, yield 60%) as a beige powder. ESI-MS: 400 [M+H]+

$^1$H NMR (300 MHz, DMSO-d$_6$) δ 8.47-8.42 (m, 3H), 8.37-8.35 (m, 1H), 8.22-8.18 (m, 1H), 7.95 (s, 1H), 7.88 (dd, J=8.2, 1.5 Hz, 1H), 7.36-7.32 (m, 2H), 7.31-7.29 (m, 1H), 6.98-6.93 (m, 1H), 4.07 (t, J=7.2 Hz, 2H), 3.63 (s, 2H), 3.47 (s, 2H), 2.40 (t, J=6.7 Hz, 2H), 2.06-1.96 (m, 2H).

Procedure 17. Preparation of [(2-fluoropyridin-4-yl)methyl][3-(1H-imidazol-1-yl)propyl]amine

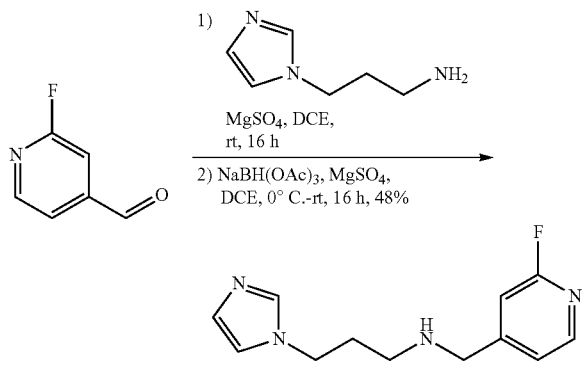

A suspension of 3-(1H-imidazol-1-yl)propan-1-amine (200 mg, 1.599 mmol, 1.00 eq), 2-fluoropyridine-4-carboxaldehyde (200 mg, 1.599 mmol, 1.00 eq) and anhydrous MgSO$_4$ (385 mg, 3.197 mmol, 2 eq) in DCE (8 mL) was stirred at rt for 72 h. Then, the mixture was cooled down to 0° C. and sodium triacetoxyborohydride (474 mg, 2.238 mmol, 1.4 eq.) was added in one portion. The reaction was allowed to reach rt over 16 h. The reaction mixture was diluted in water and washed with DCM. Aqueous layer was basified with 5N NaOH and extracted with DCM. The layers were separated. Organic layer was dried, filtered off and concentrated to afford the title compound (200 mg, 0.854 mmol, yield 48%) as a transparent oil. ESI-MS: 235 [M+H]+

$^1$H NMR (300 MHz, DMSO-d$_6$) δ 8.17-8.13 (m, 1H), 7.60-7.57 (m, 1H), 7.34-7.28 (m, 1H), 7.14 (t, J=1.3 Hz, 1H), 7.12 (bs, 1H), 6.87-6.86 (m, 1H), 4.02 (t, J=7.0 Hz, 2H), 3.75 (s, 2H), 2.41 (t, J=6.7 Hz, 2H), 1.90-1.80 (m, 2H).

Procedure 18. Preparation of 3-({[(2-fluoropyridin-4-yl)methyl][3-(1H-imidazol-1-yl)propyl]amino}methyl)-7,8-dimethyl-4H-chromen-4-one

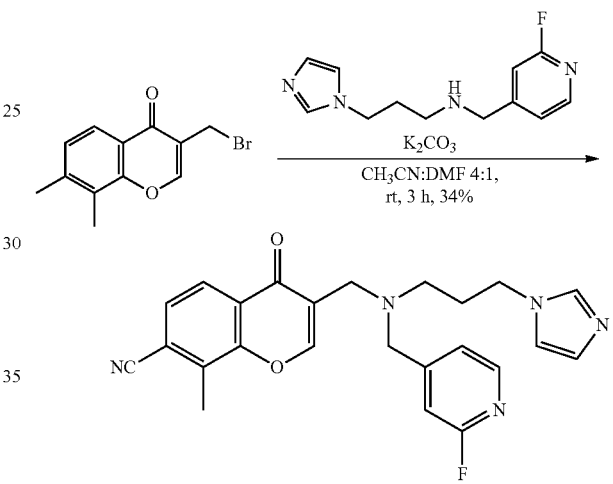

To a suspension of [(2-fluoropyridin-4-yl)methyl][3-(1H-imidazol-1-yl)propyl]amine (71 mg, 0.305 mmol, 1.1 eq.) and K$_2$CO$_3$ (115 mg, 0.831 mmol, 3 eq.) in CH$_3$CN (4 mL), 3-(bromomethyl)-7,8-dimethyl-4H-chromen-4-one (74 mg, 0.277 mmol, 1 eq.) was added dropwise as DMF solution at rt. The reaction was continued for 3 h and monitored by TLC and LC-MS. Afterwards, the reaction was quenched with water, and extracted with DCM. The layers were separated. Organic layer was dried over MgSO$_4$, filtered off and concentrated in vacuo. The residue was purified by FCC (deactivated SiHP, DCM: MeOH 92:8) to afford the title compound (41 mg, 0.098 mmol, yield 34%) as a yellow oil. ESI-MS: 421 [M+H]+

$^1$H NMR (400 MHz, DMSO-d$_6$) δ 8.36 (s, 1H), 8.12 (d, J=5.1 Hz, 1H), 7.82 (d, J=8.1 Hz, 1H), 7.57 (s, 1H), 7.34-7.29 (m, 2H), 7.17 (s, 1H), 7.12 (d, J=1.3 Hz, 1H), 6.80 (d, J=1.3 Hz, 1H), 3.98 (t, J=7.1 Hz, 2H), 3.69 (s, 2H), 3.46 (s, 2H), 2.41 (s, 3H), 2.38 (d, J=6.8 Hz, 2H), 2.36 (s, 3H), 2.02-1.90 (m, 2H).

The product was transformed into hydrochloric acid salt following Procedure 10.

$^1$H NMR (400 MHz, Deuterium Oxide) δ 8.82-8.80 (m, 1H), 8.41 (s, 1H), 8.15 (d, J=5.2 Hz, 1H), 7.80-7.76 (m, 1H), 7.57-7.53 (m, 1H), 7.47-7.44 (m, 1H), 7.43-7.39 (m, 1H), 7.22 (s, 1H), 4.55 (s, 2H), 4.40 (t, J=6.9 Hz, 2H), 4.35 (s, 2H), 3.38-3.30 (m, 2H), 2.62-2.52 (m, 2H), 2.47 (s, 3H), 2.40 (s, 3H).

Procedure 19. Preparation of 3-({[3-(1H-imidazol-1-yl)propyl][(pyridin-4-yl)methyl]amino}methyl)-1-methyl-1,4-dihydroquinolin-4-one

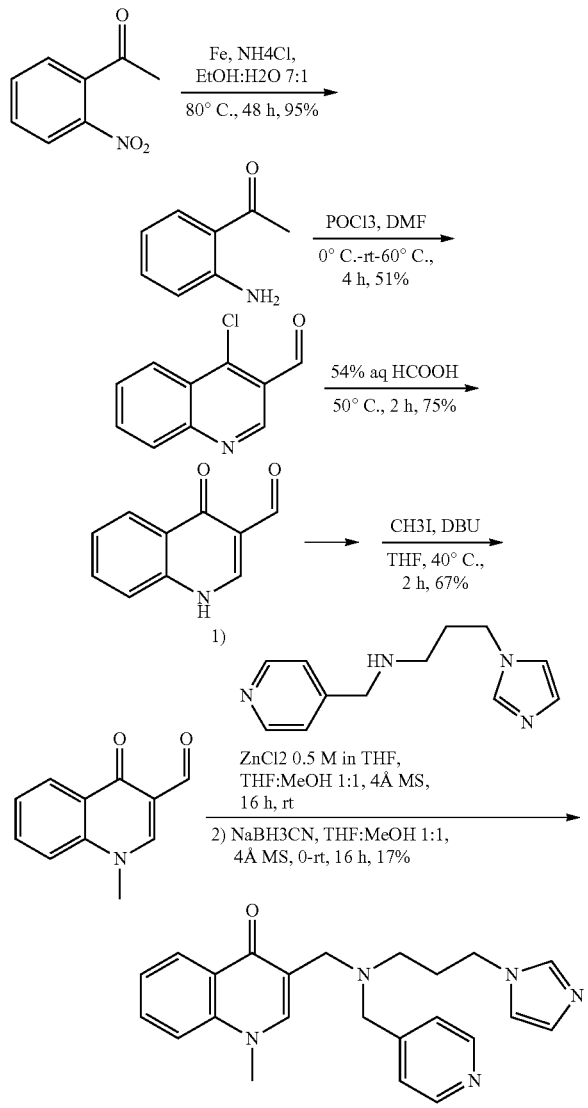

a. 1-(2-aminophenyl)ethan-1-one

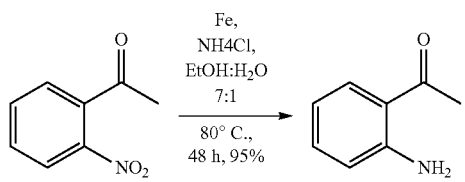

1-(2-nitrophenyl)ethan-1-one (3.30 g, 19.98 mmol, 1 eq), iron (5.58, 99.91 mmol, 5 eq) and NH4Cl (0.53 g, 9.99 mmol, 0.5 eq) were suspended in EtOH:H2O 7:1 (33:7 ml) and heated in a sealed tube for 48 h. The resulting mixture was filtered through celite and washed with methanol. Filtrate was concentrated in vacuo to afford the title compound (2.70 g, 20.00 mmol, yield 95%) as an yellow oil that was taken to the next step without additional purification. ESI-MS: 136 [M+H]$^+$ $^1$H NMR (300 MHz, Chloroform-d) δ 7.74 (dd, J=8.3, 1.6 Hz, 1H), 7.33-7.25 (m, 1H), 6.72-6.63 (m, 2H), 6.29 (s, 2H), 2.60 (s, 3H).

b. 4-chloroquinoline-3-carbaldehyde

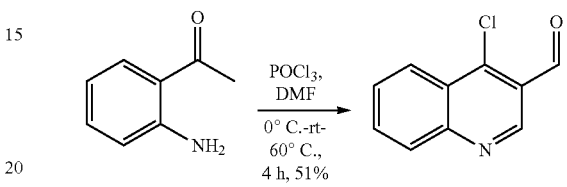

To an anh. DMF (20 mL), POCl$_3$ (8.27 mL, 88.8 mmol, 6 eq) was added dropwise at 0° C. Then 1-(2-aminophenyl)ethan-1-one (2.00 g, 14.8 mmol, 1 eq) in anh. DMF (5 mL) was added dropwise, and the reaction was heated for 4 h at 60° C. Afterwards, the reactions was cooled down to 0° C., quenched with water. Then solution was neutralized with saturated NaHCO$_3$ aqueous solution, diluted in water and extracted with DCM. The layers were separated. Organic layer was dried over MgSO$_4$, filtered off and concentrated in vacuo to afford the title compound (1.43 g, 7.49 mmol, yield 51%) as an orange solid that was taken to the next step without additional purification. ESI-MS: 192 [M+H]$^+$ c. 4-oxo-1,4-dihydroquinoline-3-carbaldehyde

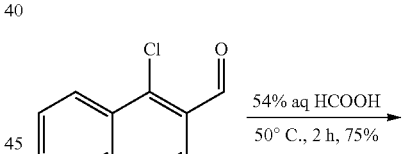

4-chloroquinoline-3-carbaldehyde (1.10 g, 5.74 mmol, 1 eq) was suspended in 54% aqueous solution HCOOH (13.41 mL). The reaction was carried out at 50° C. for 2 h. The resulting mixture was being frozen in a fridge for 16 h. Precipitate was filtered off and washed with water to give product (0.75 g, 4.33 mmol, yield 75%) as an orange solid. ESI-MS: 174 [M+H]$^+$ $^1$H NMR (400 MHz, DMSO-d$_6$) δ 12.69 (s, 1H), 10.20 (s, 1H), 8.49 (s, 1H), 8.22 (dd, J=8.0, 1.5 Hz, 1H), 7.77 (m, 1H), 7.67 (dd, J=8.3, 1.1 Hz, 1H), 7.48 (m, 1H).

d. 1-methyl-4-oxo-1,4-dihydroquinoline-3-carbaldehyde

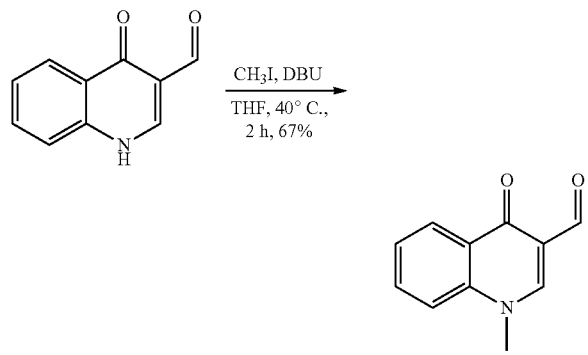

4-oxo-1,4-dihydroquinoline-3-carbaldehyde (0.50 g, 2.89 mmol, 1 eq) was suspended in THF (13 mL). DBU (1.01 g, 7.22, 2.5 eq) was added, followed by methyl iodide (4.10 g, 28.8 mmol, 10 eq). The reaction was carried out at 40° C. for 2 h. Afterwards, reactions was quenched with water and extracted with DCM. The layers were separated. Organic layer was dried over MgSO4, filtered off and concentrated in vacuo. The residue was purified by crystallization from hot EtOH to afford the title compound (0.36 g, 1.94 mmol, yield 67%) as a beige solid. ESI-MS: 188 [M+H]$^+$ $^1$H NMR (400 MHz, DMSO-d$_6$) δ 10.19 (s, 1H), 8.63 (s, 1H), 8.31 (dd, J=8.0, 1.6 Hz, 1H), 7.87 (m, 1H), 7.80 (dd, J=8.6, 1.1 Hz, 1H), 7.57 (m, 1H), 3.98 (s, 3H).

e. 3-({[3-(1H-imidazol-1-yl)propyl][(pyridin-4-yl)methyl]amino}methyl)-1-methyl-1,4-dihydroquinolin-4-one

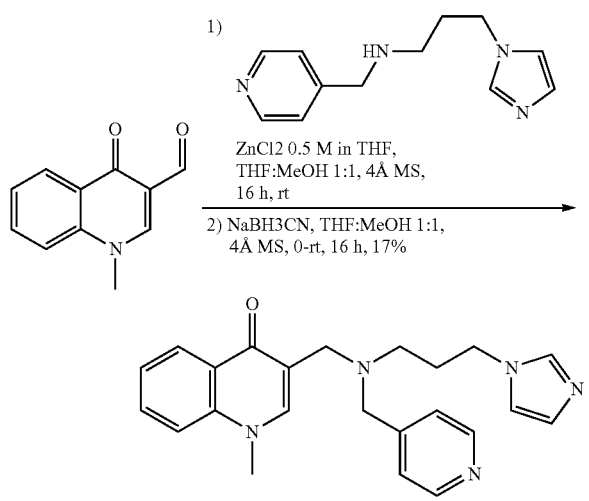

A mixture of 1-methyl-4-oxo-1,4-dihydroquinoline-3-carbaldehyde (69 mg, 0.37 mmol, 1 eq), [3-(1H-imidazol-1-yl)propyl][(pyridin-4-yl)methyl]amine (80 mg, 0.37 mmol, 1 eq) and 0.5M ZnCl$_2$ in THF (0.46 mL) was stirred in THF:MeOH 1:1 (3 mL) at rt for 16 h over activated 4 Å molecular sieves. Then, the mixture was cooled down to 0° C. and NaBH$_3$CN (33 mg, 0.52 mmol, 1.4 eq) was added portionwise. The reaction was allowed to reach rt over 16 h. The reaction mixture was filtered through celite. Solvents were evaporated. The residue was dissolved in DCM and washed with water. The layers were separated. Organic layer was dried over MgSO4, filtered off and concentrated in vacuo. The residue was purified by FCC (deactivated SiHP, DCM:MeOH 95:5) to afford the title compound (25 mg, 0.064 mmol, yield 17%) as a yellow oil. ESI-MS: 388 [M+H]$^+$ $^1$H NMR (400 MHz, DMSO-d$_6$) δ 8.46 (s, 2H), 8.23 (dd, J=8.0, 1.6 Hz, 1H), 7.99 (s, 1H), 7.75 (s, 1H), 7.66 (d, J=8.5 Hz, 1H), 7.59 (s, 1H), 7.41 (s, 1H), 7.38-7.37 (m, 2H), 7.12 (s, 1H), 6.80 (s, 1H), 4.00 (t, J=7.1 Hz, 2H), 3.86 (s, 3H), 3.62 (s, 2H), 3.49 (s, 2H), 2.39-2.36 (m, 2H), 2.01-1.93 (m, 2H).

The title compound was converted into hydrochloric acid salt following Procedure 10 (24 mg, 0.048 mmol, yield 98%). ESI-MS 388 [M+H]$^+$ $^1$H NMR (300 MHz, Deuterium Oxide) δ 8.74 (s, 1H), 8.60 (s, 2H), 8.15 (s, 1H), 8.09 (s, 3H), 7.88 (s, 1H), 7.74 (d, J=8.7 Hz, 1H), 7.56 (ddd, J=8.2, 7.0, 1.0 Hz, 1H), 7.48-7.46 (m, 1H), 7.36-7.34 (m, 1H), 4.75 (s, 2H, overlapping with solvent peak), 4.39 (s, 2H), 4.33 (t, J=7.1 Hz, 2H), 3.93 (s, 3H), 3.43-3.37 (m, 2H), 2.57-2.50 (m, 2H).

Procedure 20. Preparation of 1-[2-hydroxy-4-(4-methylpiperazin-1-yl)phenyl]ethan-1-one

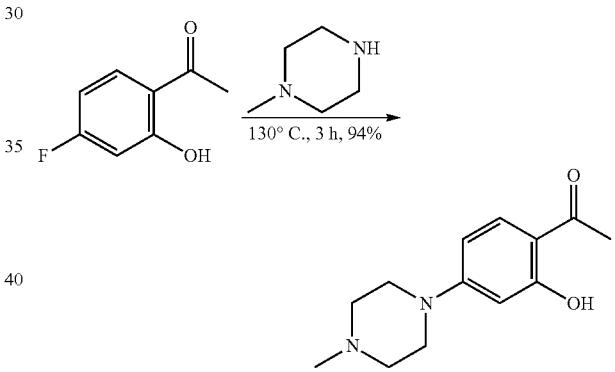

1-(4-fluoro-2-hydroxyphenyl)ethan-1-one (0.5 g, 3.24 mmol, 1 eq) was suspended in neat 1-methylpiperazine (1.44 mL, 12.98 mmol, 4 eq) and heated at 130° C. for 3 h. The reaction mixture was cooled down to rt and purified by FCC (SiHP, DCM: MeOH 95:5) to afford the title compound (715 mg, 3.05 mmol, yield 94%) as a white solid.

$^1$H NMR (400 MHz, DMSO-d$_6$) δ 12.74 (s, 1H), 7.66 (d, J=9.2 Hz, 1H), 6.53 (dd, J=9.2, 2.6 Hz, 1H), 6.26 (d, J=2.5 Hz, 1H), 3.35 (dd, J=6.3, 4.0 Hz, 4H), 2.47 (s, 3H), 2.41-2.36 (m, 4H), 2.20 (s, 3H).

Procedure 21. Preparation of 3-(chloromethyl)-2-methyl-4H-chromen-4-one

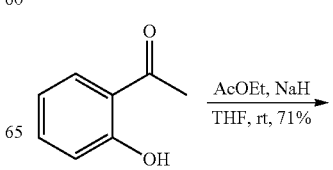

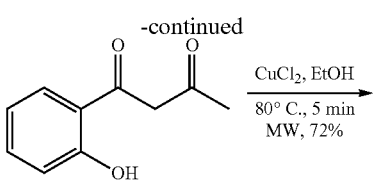

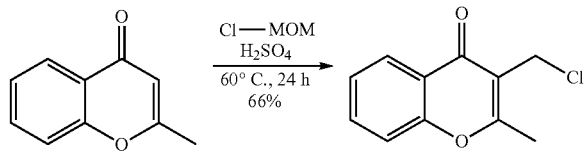

a. 1-(2-hydroxyphenyl)butane-1,3-dione

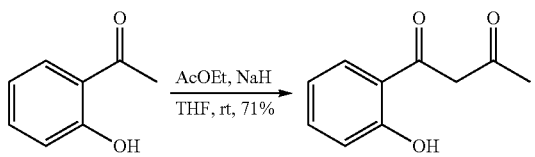

A mixture of 1-(2-hydroxyphenyl)ethan-1-one (3 g, 22 mmol, 1 eq) and AcOEt (0.9 mL, 55 mmol, 2.5 eq) in THF (5 mL) was added dropwise to the suspension of NaH (60% in mineral oil, 4.4 g, 110 mmol, 5 eq) in THF (5 mL) at room temperature. A vigorous reaction was observed and the temperature rose to reflux. After addition was completed, the reaction mixture was stirred further for 5 min, quenched by pouring onto ice, acidified to pH 6 with 6N aq. HCl and extracted with AcOEt. The organic layers were combined, dried over anhydrous magnesium sulfate and evaporated. The residue was purified by FCC (SiHP; Hex: AcOEt, 4:1) to afford the product (2.79 g, 15.7 mmol, yield 71%) as a beige solid. ESI-MS: 177.6 [M−H]⁻ b. 2-methyl-4H-chromen-4-one

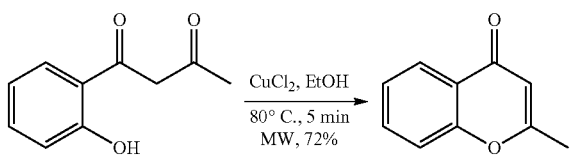

To a solution of 1-(2-hydroxyphenyl)butane-1,3-dione (1.5 g, 8.42 mmol, 1 eq) in EtOH (5 mL), CuCl$_2$ (113 mg, 0.84 mmol, 0.1 eq) was added. The reaction mixture was heated in a microwave at 80° C. for 45 min. Subsequently, the mixture was cooled down to rt, added to water and extracted with DCM. Combined organic layers were dried with magnesium sulfate and concentrated. The residue was purified by FCC (SiHP; Hex:AcOEt; 100:0 to 4:1) to afford the product (0.97 g, 6.05 mmol, 72%) as a brown solid. ESI-MS: 161 [M+H]⁺

¹H NMR (300 MHz, DMSO-d$_6$) δ 8.00 (dd, J=7.9, 1.7 Hz, 1H), 7.77 (ddd, J=8.7, 7.1, 1.7 Hz, 1H), 7.60 (dd, J=8.5, 1.1 Hz, 1H), 7.46 (ddd, J=8.1, 7.1, 1.1 Hz, 1H), 6.25 (d, J=0.8 Hz, 1H), 2.39 (d, J=0.7 Hz, 3H).

c. 3-(chloromethyl)-2-methyl-4H-chromen-4-one

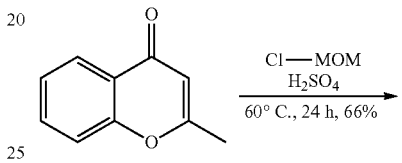

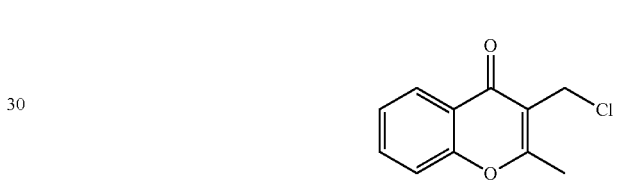

Sulfuric acid (96%, 0.5) was added dropwise to a solution of 2-methyl-4H-chromen-4-one (0.3 g, 1.87 mmol, 1 eq) in chloromethyl methyl ether (2.85 mL, 37.5 mmol, 20 eq). The reaction mixture was stirred at 60° C. for 24 h. Additional portion of sulfuric acid (96%, 0.5 mL) was added and the reaction mixture was heated at 80° C. for 62 h. Subsequently the reaction mixture was cooled down to rt, diluted with water and extracted with DCM. Combined organic layers were dried with magnesium sulfate and concentrated. The residue was purified by FCC (SiHP; Hexane:AcOEt; 100:0 to 4:1) to afford the product (0.258 g, 1.24 mmol, yield 66%) as a white solid.

¹H NMR (300 MHz, DMSO-d$_6$) δ 8.06 (dd, J=8.0, 1.7 Hz, 1H), 7.81 (ddd, J=8.7, 7.1, 1.7 Hz, 1H), 7.62 (dd, J=8.4, 1.0 Hz, 1H), 7.50 (ddd, J=8.1, 7.1, 1.1 Hz, 1H), 4.72 (s, 2H), 2.57 (s, 3H)

Procedure 22. Preparation of 7-bromo-3-(chloromethyl)-6-fluoro-2-methyl-4H-chromen-4-one

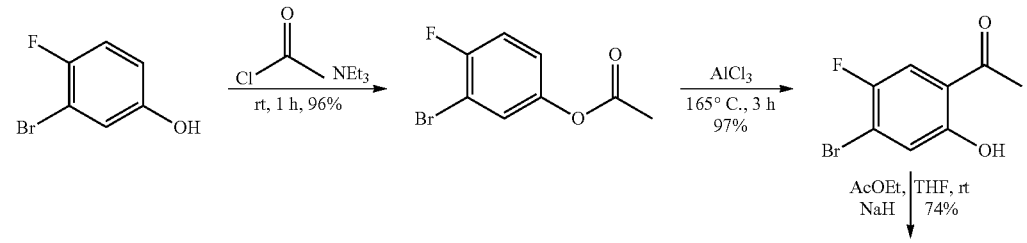

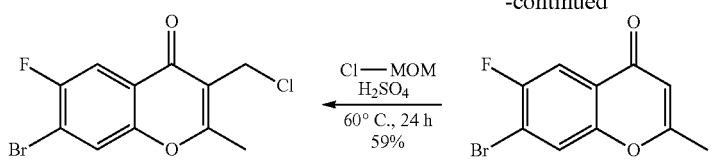
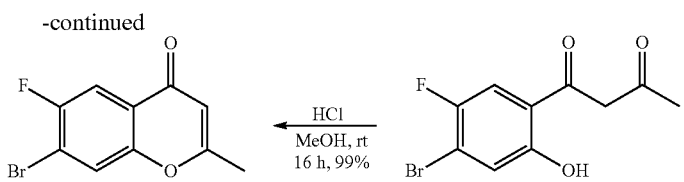

a. 3-bromo-4-fluorophenyl acetate c. 1-(4-bromo-5-fluoro-2-hydroxyphenyl)butane-1,3-dione

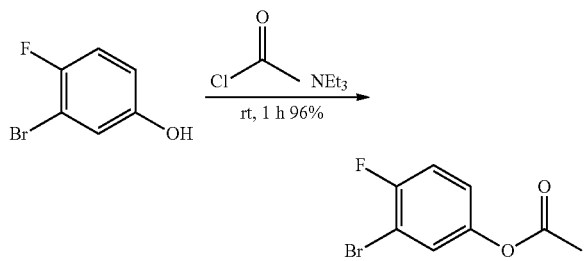

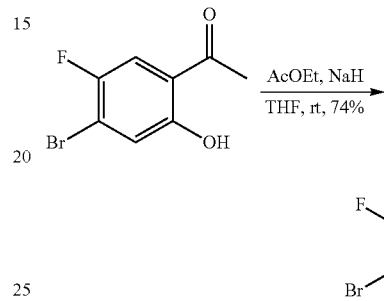

To a solution of 3-bromo-4-fluorophenol (3 g, 15.7 mmol, 1 eq) in anhydrous DCM were added AcCl (1.33 mL, 17.3 mmol, 1.1 eq) and Et$_3$N (2.41 mL, 17.3 mmol, 1.1 eq) and the mixture was stirred at rt for 1 h. Subsequently water was added and the mixture was extracted with DCM. Combined organic layers were dried over magnesium sulfate, concentrated and the residue was purified by FCC (SiHP; Hex:AcOEt; 100:0 to 4:1) to afford the product (3.5 g, 15 mmol, yield 96%) as a yellowish solid.

$^1$H NMR (300 MHz, DMSO-d$_6$) δ 7.60 (dd, J=6.0, 2.8 Hz, 1H), 7.44 (t, J=8.8 Hz, 1H), 7.22 (ddd, J=9.0, 4.2, 2.8 Hz, 1H), 2.26 (s, 3H).

b. 1-(4-bromo-5-fluoro-2-hydroxyphenyl)ethan-1-one

The title compound was synthesized following the approach outlined in Procedure 21a substituting 1-(2-hydroxyphenyl)ethan-1-one with 1-(4-bromo-5-fluoro-2-hydroxyphenyl)ethan-1-one. The product (3.5 g, 12.7 mmol, yield 74%) was obtained as a yellow solid. ESI-MS: 275 [M+H]$^+$ d. 7-bromo-6-fluoro-2-methyl-4H-chromen-4-one

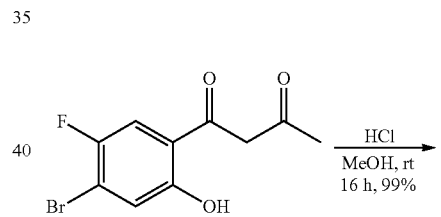

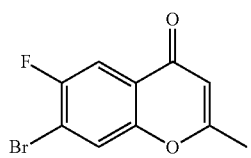

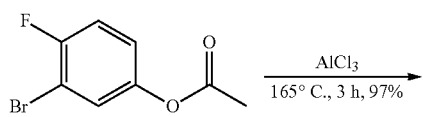

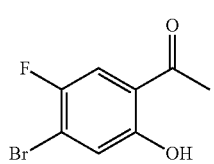

The title compound was synthesized following the approach outlined in Procedure 4b substituting 2,3-dimethylphenyl acetate with 3-bromo-4-fluorophenyl acetate and performing the reaction at 165° C. for 3 h. The product (3.3 g, 14.6 mmol, yield 97%) was obtained as a yellow oil. ESI-MS: 231 [M–H]$^-$ $^1$H NMR (400 MHz, DMSO-d$_6$) δ 11.64 (s, 1H), 7.80 (d, J=9.4 Hz, 1H), 7.34 (d, J=5.8 Hz, 1H), 2.61 (s, 3H).

The title compound was synthesized following the approach outlined in Procedure 24b substituting 1-(4-bromo-2-hydroxyphenyl)butane-1,3-dione with 1-(4-bromo-5-fluoro-2-hydroxyphenyl)butane-1,3-dione. The product (3.93 g, 15.3 mmol, yield 99.8%) was obtained as a yellow solid.

e. 7-bromo-3-(chloromethyl)-6-fluoro-2-methyl-4H-chromen-4-one

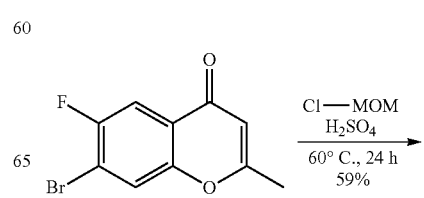

-continued

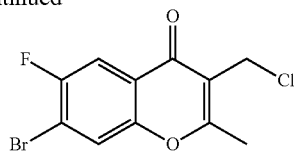

The title compound was synthesized following the approach outlined in Procedure 21c substituting 2-methyl-4H-chromen-4-one with 7-bromo-6-fluoro-2-methyl-4H-chromen-4-one. The product (1.05 g, 3.44 mmol, yield 59%) was obtained as a white solid. ESI-MS: 305 [M+H]+

$^1$H NMR (400 MHz, DMSO-$d_6$) δ 8.21 (d, J=5.5 Hz, 1H), 7.86 (d, J=8.2 Hz, 1H), 4.70 (s, 2H), 2.56 (s, 3H)

Procedure 23. Preparation of 2,4-difluorophenyl acetate

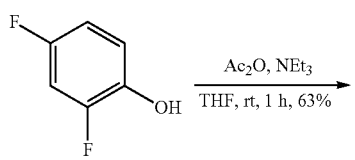

To a solution of 2,4-difluorophenol (3 g, 23.1 mmol, 1 eq) in anhydrous THF (25 mL) were added acetic anhydride (3.27 mL, 34.6 mmol, 1.5 eq) and Et3N (5.14 mL, 37 mmol, 1.6 eq) and the mixture was stirred at rt for 1 h. Subsequently water and AcOEt were added and the mixture was extracted with AcOEt. Combined organic layers were washed with brine, dried over magnesium sulfate, concentrated and the residue was purified by FCC (SiHP; Hex:AcOEt; 100:0 to 9:1) to afford the product (2.5 g, 14.5 mmol, yield 63%) as a yellow oil.

Procedure 24. Preparation of 7-bromo-2-methyl-4H-chromen-4-one

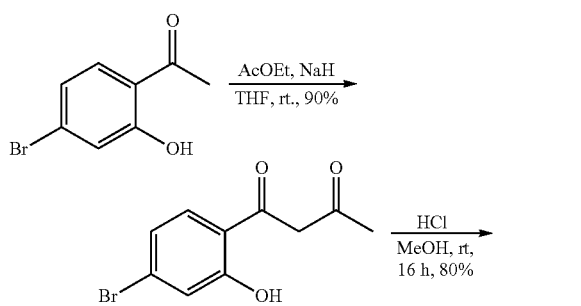

a. 1-(4-bromo-2-hydroxyphenyl)butane-1,3-dione

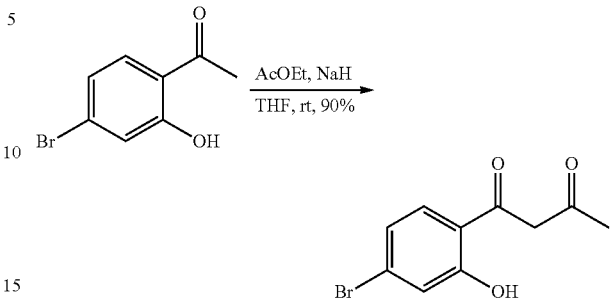

The title compound was synthesized following the approach outlined in Procedure 21a substituting 1-(2-hydroxyphenyl)ethan-1-one with 1-(4-bromo-2-hydroxyphenyl)ethan-1-one. The product (3.84 g, 14.9 mmol, yield 90%) was obtained as a beige solid. ESI-MS: 257 [M+H]+ b. 7-bromo-2-methyl-4H-chromen-4-one

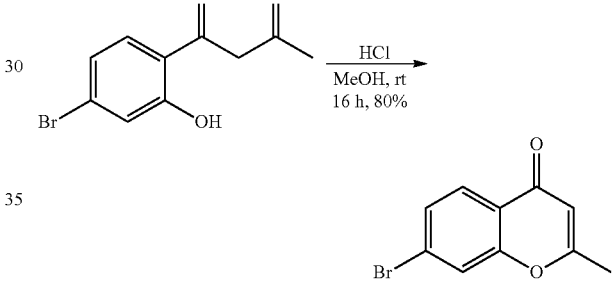

Concentrated HCl (1 mL) was added to a solution of 1-(4-bromo-2-hydroxyphenyl)butane-1,3-dione (3.82 g, 14.9 mmol) in methanol (30 mL) and the mixture allowed to stir at room temperature overnight. The mixture was concentrated under reduce pressure, the residue was diluted with AcOEt and the mixture was washed successively with solution of saturated NaHCO$_3$, water and brine. The organic layer was dried over magnesium sulfate and concentrated under reduce pressure. The residue was purified by FCC (SiHP; Hex:AcOEt; 100:0 to 2:1) to afford the product (2.83 g, 11.9 mmol, yield 80%) as a yellowish solid.

$^1$H NMR (400 MHz, DMSO-$d_6$) δ 7.95 (d, J=1.8 Hz, 1H), 7.91 (d, J=8.5 Hz, 1H), 7.64 (dd, J=8.5, 1.8 Hz, 1H), 6.28 (d, J=0.9 Hz, 1H), 2.38 (d, J=0.8 Hz, 3H).

Procedure 25. Preparation of 1-[5-fluoro-2-hydroxy-4-(4-methylpiperazin-1-yl)phenyl]ethan-1-one

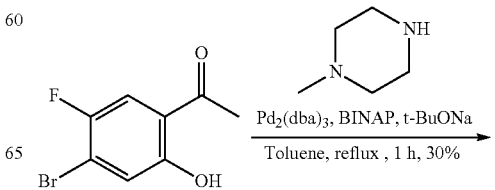

-continued

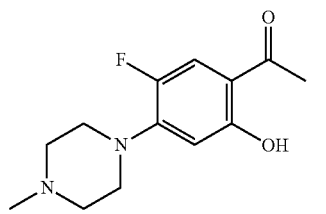

To a stirred solution of 1-(4-bromo-5-fluoro-2-hydroxyphenyl)ethan-1-one (2.67 g, 11.5 mmol, 1 eq) in anhydrous toluene (20 mL) was added 1-methylpiperazine (1.9 mL, 17.1 mmol, 1.5 eq), tris(dibenzylideneacetone)dipalladium (0) ($Pd_2(dba)_3$, 0.33 g, 0.57 mmol, 0.05 eq), sodium tert-butoxide (3.3 g, 34.4 mmol, 3 eq) and 2,2'-Bis(diphenylphosphino)-1,1'-binaphthalene (BINAP, 0.71 g, 1.15 mmol, 0.1 eq). The resulting solution was heated to reflux under argon for 1 h. Subsequently the mixture was cooled to rt and 20 mL of AcOEt and 20 mL of water were added and the mixture was filtered. The water phase was separated and washed with AcOEt (5×20 mL). Combined organic phases were washed with brine, dried over sodium sulfate and concentrated under reduce pressure. The residue was purified by FCC (SiHP; DCM:MeOH; gradient: 100:0 to 9:1) to give the product (874 mg, 3.46 mmol, yield 30%) as a brown solid. ESI-MS: 253 $[M+H]^+$ $^1$H NMR (400 MHz, DMSO-$d_6$) δ 12.31 (s, 1H), 7.62 (d, J=14.7 Hz, 1H), 6.40 (d, J=7.7 Hz, 1H), 3.23-3.17 (m, 4H), 2.52 (s, 3H), 2.46-2.42 (m, 4H), 2.21 (s, 3H)

Procedure 26. Preparation of 1-(1-hydroxy-7-methoxynaphthalen-2-yl)ethan-1-one

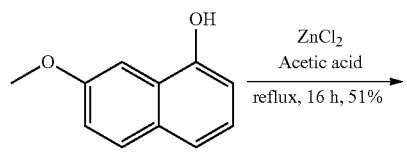

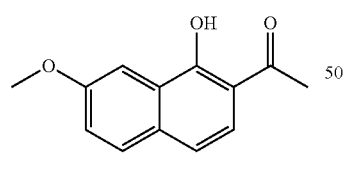

ZnCl₂ (3.13 g, 22.96 mmol, 10 eq was dissolved in acetic acid (5.25 mL, 91.85 mmol, 40 eq). 7-methoxy-1-naphthol (0.4 g, 2.296 mmol, 1 eq) was added, the reaction vessel was sealed and the reaction mixture was stirred at 130° C. for 16 h. Subsequently the reaction mixture was poured onto water, filtered and washed with water. The obtained black solid was dissolved in DCM/AcOEt and the mixture was washed with water, saturated NaHCO₃, dried over anhydrous sodium sulfate and evaporated under reduce pressure. The residue was purified by FCC (SiHP; Hex:AcOEt; 100:0 to 4:1) to afford the product (251 mg, 1.16 mmol, yield 51%) as a yellow solid. ESI-MS: 217 $[M+H]^+$ Procedure 27. Preparation of 2-methyl-4-oxo-4H-benzo[h]chromene-3-carbaldehyde

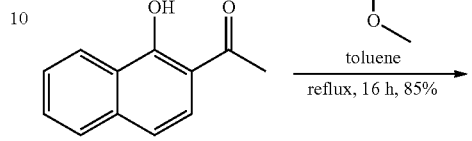

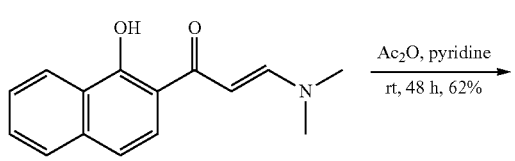

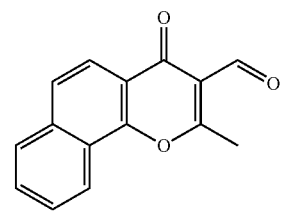

a. 3-(dimethylamino)-1-(1-hydroxynaphthalen-2-y) prop-2-en-1-one

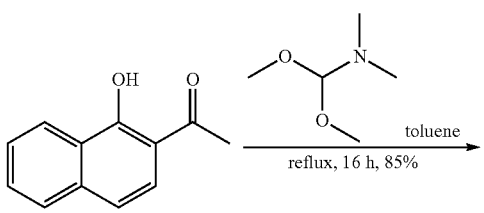

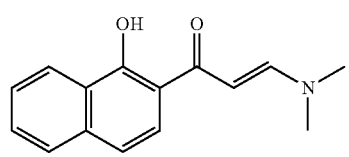

A mixture of 1-(1-hydroxynaphthalen-2-yl)ethanone (2 g, 10.7 mmol, 1 eq) and N,N-dimethylformamide dimethyl acetal (2.14 mL, 16.1 mmol, 1.5 eq) in dry toluene (25 mL) was refluxed for 16 h. Subsequently, the mixture was concentrated. A yellow precipitate formed which was filtered, washed with petroleum ether and dried to provide the desired product. The filtrate was evaporated and the residue was purified by FCC (SiHP; Hex:AcOEt; 100:0 to 2:1) and combined with the obtained yellow precipitate to afford the product (2.2 g, 9.12 mmol, yield 85%) as a yellow solid. ESI-MS: 242 [M+H]+ b. 2-methyl-4-oxo-4H-benzo[h]chromene-3-carbaldehyde

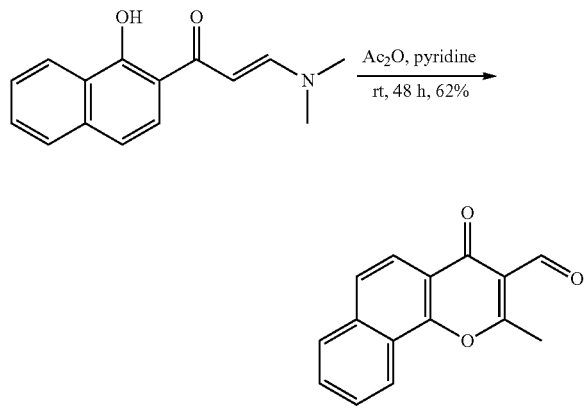

To a solution of the 3-(dimethylamino)-1-(1-hydroxynaphthalen-2-yl)prop-2-en-1-one (2.2 g, 9.12 mmol, 1 eq) in dry pyridine (9.6 mL) was added acetic acid anhydride (27.6 mL, 291.8 mmol, 32 eq) and the mixture was stirred at rt for 48 h. A precipitate formed which was filtered, washed with petroleum ether and recrystallised from ethanol to provide the desired product. The filtrate was evaporated and the residue was purified by FCC (SiHP; Hexane:AcOEt; 100:0 to 4:1) and combined with the obtained precipitate to afford the product (1.35 g, 5.67 mmol, yield 62%) as white crystals. ESI-MS: 239 [M+H]+

$^1$H NMR (300 MHz, DMSO-$d_6$) δ 8.97 (s, 1H), 8.51-8.45 (m, 1H), 8.18-8.13 (m, 1H), 8.12-7.99 (m, 2H), 7.90-7.79 (m, 2H), 2.65 (s, 3H).

Procedure 28. Preparation of 3-({[3-(1H-imidazol-1-yl)propyl]amino}methyl)-2-methyl-4H-benzo[h]chromen-4-one

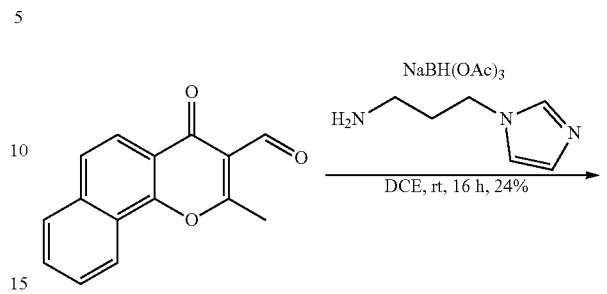

3-(1H-imidazol-1-yl)propan-1-amine (0.05 mL, 0.42 mmol, 1 eq) and 2-methyl-4-oxo-4H-benzo[h]chromene-3-carbaldehyde (100 mg, 0.42 mmol, 1 eq) were dissolved in anhydrous DCE (3 mL) and stirred under argon atmosphere at rt for 1 h. Sodium triacetoxyborohydride (125 mg, 0.59 mmol, 1.4 eq) was added and the reaction mixture was stirred at rt for 16 h. Subsequently the reaction was quenched by the addition of saturated NaHCO$_3$ (2 mL). The mixture was partioned between water and DCM and the aqueous phase was extracted 3 times with DCM. Combined organic layers were dried over magnesium sulfate, filtered and concentrated. The residue was purified by FCC (SIHP 15 um; DCM:MeOH; 100:0 to 9:1) to afford the product (35 mg, 0.10 mmol, yield 24%) as a yellow solid. ESI-MS: 348 [M+H]+

Procedure 29. Preparation of 6-fluoro-2-methyl-7-(morpholin-4-yl)-3-({[3-(pyridin-3-yl)propyl][(pyridin-4-yl)methyl]amino}methyl)-4H-chromen-4-one

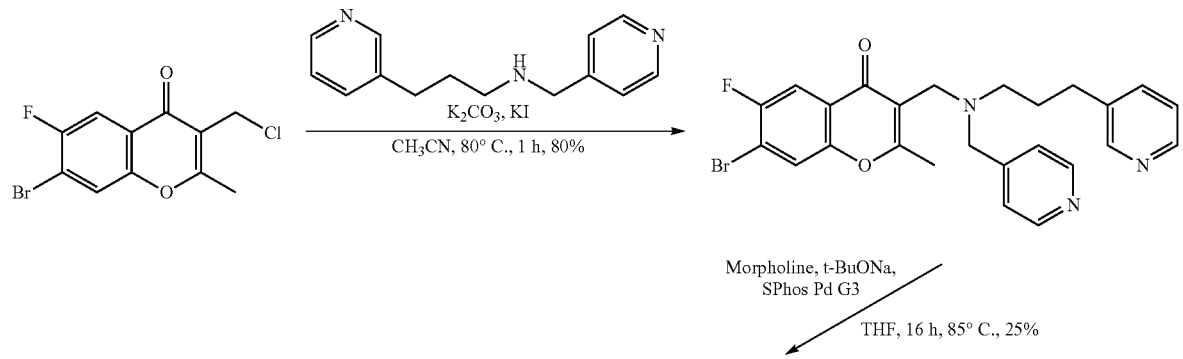

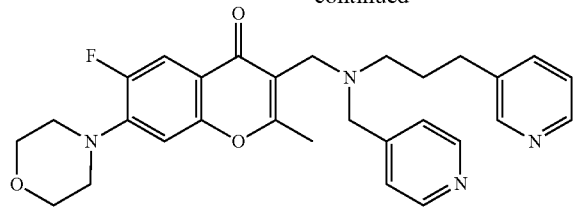

a. 7-bromo-6-fluoro-2-methyl-3-({[3-(pyridin-3-yl)propyl][(pyridin-4-yl)methyl]amino}methyl)-4H-chromen-4-one

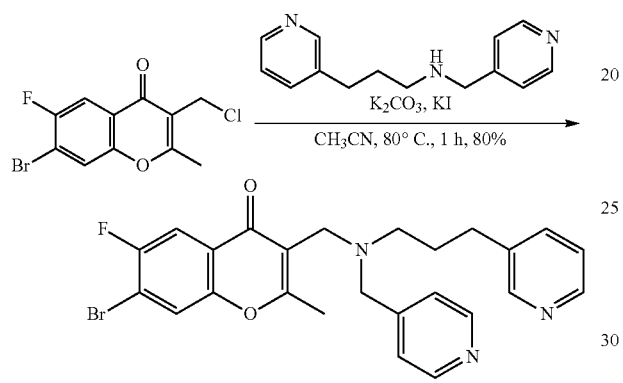

The title compound was synthesized following the approach outlined in Procedure 9.1 substituting 3-(chloromethyl)-7,8-dimethyl-4H-chromen-4-one with 7-bromo-3-(chloromethyl)-6-fluoro-2-methyl-4H-chromen-4-one and [3-(1H-imidazol-1-yl)propyl](pyridin-4-ylmethyl)amine with [3-(pyridin-3-yl)propyl][(pyridin-4-yl)methyl]amine. The product (780 mg, 1.57 mmol, yield 80%) was obtained as a yellow oil. ESI-MS: 496 [M+H]$^+$ b. 6-fluoro-2-methyl-7-(morpholin-4-yl)-3-({[3-(pyridin-3-yl)propyl][(pyridin-4-yl)methyl]amino}methyl)-4H-chromen-4-one

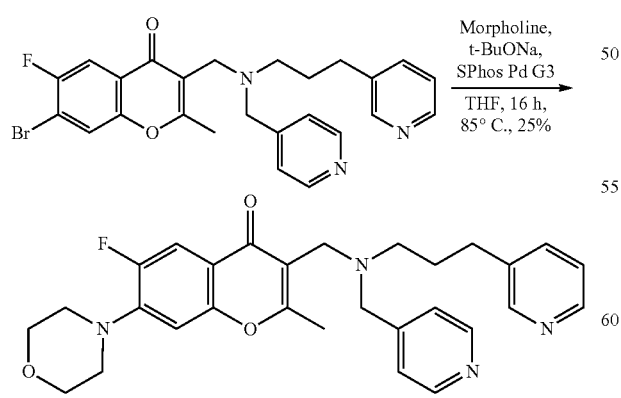

7-bromo-6-fluoro-2-methyl-3-({[3-(pyridin-3-yl)propyl][(pyridin-4-yl)methyl]amino}methyl)-4H chromen-4-one (80 mg, 0.16 mmol, 1 eq), morpholine (0.017 mL, 0.19 mmol, 1.2 eq) and sodium tert-butoxide (19 mg, 0.19 mmol, 1.2 eq) were dissolved in THF (2 mL) under argon atmosphere. (2-Dicyclohexylphosphino-2',6'-dimethoxybiphenyl) [2-(2'-amino-1,1'-biphenyl)]palladium(II) methanesulfonate (Sphos Pd G3, 13 mg, 0.016 mmol, 0.1 eq) was added and the reaction was heated at 85° C. for 16 h. Subsequently, the reaction mixture was cooled down to rt, filtered through Celite® and the filtrate was extracted with AcOEt. Organic phase was dried over magnesium sulfate, filtered and concentrated. The residue was purified by FCC (SiHP; DCM:MeOH; gradient: 100:0 to 9:1) and repurified by preparative HPLC to afford the product (20 mg, 0.04 mmol, yield 25%) as a yellow oil. ESI-MS: 503 [M+H]$^+$ Procedure 30. Preparation of 1-cyclopropyl-6,7-difluoro-4-oxo-1,4-dihydroquinoline-3-carbaldehyde

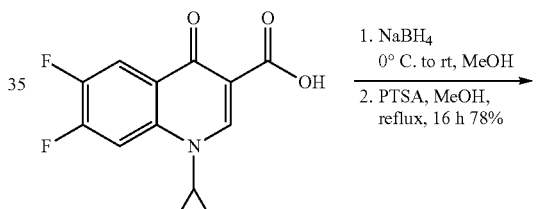

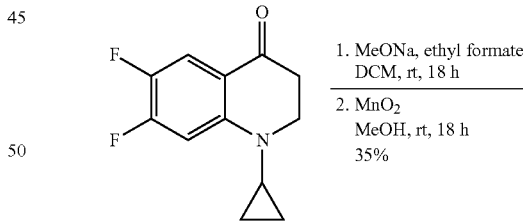

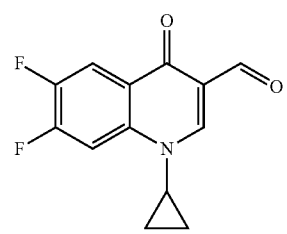

81 a. 1-cyclopropyl-6,7-difluoro-1,2,3,4-tetrahydroquinolin-4-one

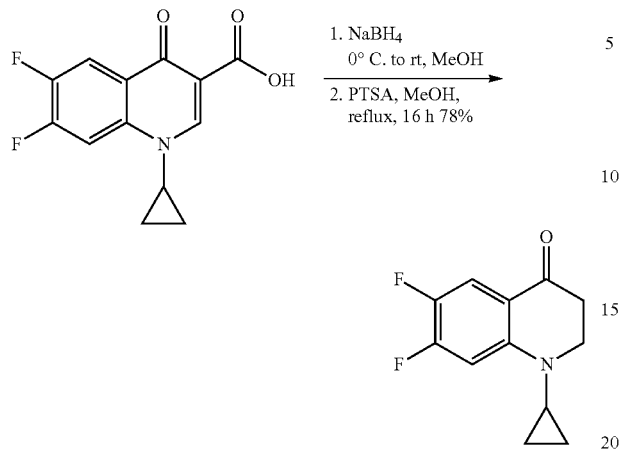

To a stirring solution of 1-cyclopropyl-6,7-difluoro-4-oxo-1,4-dihydroquinoline-3-carboxylic acid (0.2 g, 0.75 mmol, 1 eq) in anhydrous methanol (5 mL) under inert atmosphere at 0° C. was added sodium borohydride (0.128 g, 3.39 mmol, 4.5 eq) slowly over 30 minutes. The mixture was allowed to warm up to rt, p-toluenesulfonic acid (0.014 g, 0.075 mmol, 0.10 eq) was added and the reaction mixture was heated at reflux for 3.5 h. Subsequently the mixture was allowed to cool to rt and the solvent was removed in vacuo. The residue was dissolved in a mixture of hot chloroform and water and extracted with chloroform (3×). Combined organic phases were dried over magnesium sulfate, filtered and concentrated under reduced pressure. FCC (SiHP; Hex:AcOEt; gradient: 100:0 to 4:1) afforded the product (0.132 g, 0.59 mmol, yield 78%) as a yellowish solid. ESI-MS: 224 [M+H]$^+$.

b. 1-cyclopropyl-6,7-difluoro-4-oxo-1,4-dihydroquinoline-3-carbaldehyde

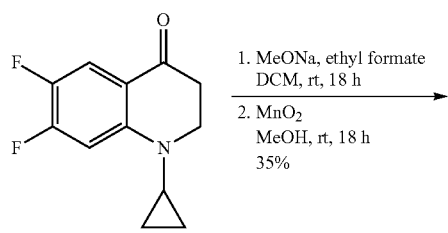

82

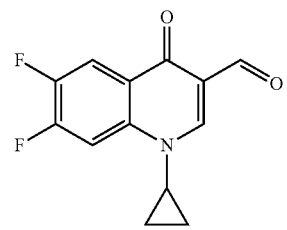

To a mixture of sodium methoxide (0.12 g, 2.22 mmol, 3.9 eq) and ethyl formate (0.180 mL, 2.24 mmol, 3.94 eq) under inert atmosphere was added a solution of 1-cyclopropyl-6,7-difluoro-1,2,3,4-tetrahydroquinolin-4-one (0.127 g, 0.57 mmol, 1 eq) in anhydrous DCM (5 mL) and the mixture was stirred at rt for 18 h. Subsequently the reaction mixture was poured into ice-water. Phases were separated and the organic layer was washed with 3 M sodium hydroxide (2×). Combined aqueous phases were acidified to pH 6 with concentrated hydrochloric acid and then extracted with DCM (3×). Combined organic phases were dried with magnesium sulfate, filtered and concentrated under reduced pressure. The residue was dissolved in anhydrous methanol (5 mL) and manganese dioxide (0.225 g, 2.59 mmol, 5 eq) was added. After stirring at room temperature for 18 h, the mixture was filtered through Celite® and the filter cake was washed with methanol and DCM. The filtrate was concentrated in vacuo and the residue was purified by FCC (SiHP, Hexane:AcOEt; 100:0 to 1:1) to afford the product as a white solid (0.045 g, 0.18 mmol, yield 35%). ESI-MS: 250 [M+H]$^+$.

$^1$H NMR (400 MHz, DMSO-d$_6$) δ 10.12 (s, 1H), 8.41 (s, 1H), 8.23 (dd, J=12.1, 6.7 Hz, 1H), 8.15 (dd, J=10.6, 8.8 Hz, 1H), 3.73-3.65 (m, 1H), 1.31-1.25 (m, 2H), 1.18-1.12 (m, 2H).

Procedure 31. Preparation of 3-({[3-(1H-1,3-benzodiazol-1-yl)propyl][(2-methoxypyridin-4-yl)methyl]amino}methyl)-4H-pyrido[1,2-a]pyrimidin-4-one

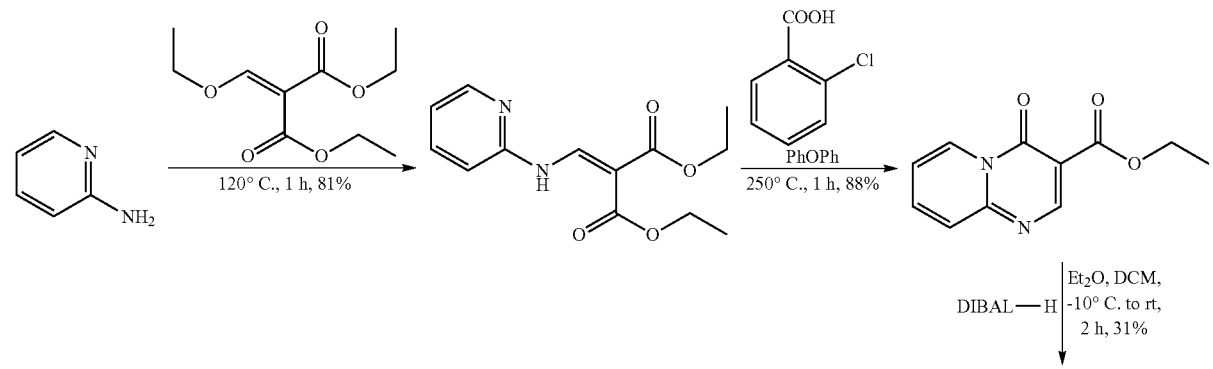

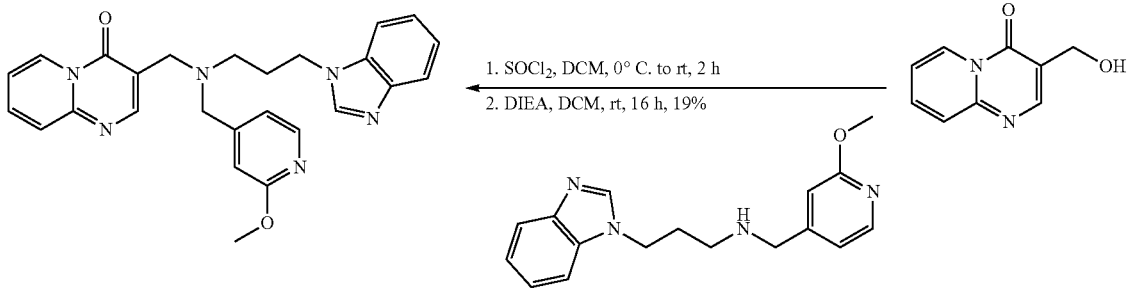

a. 1,3-d/ethyl 2-{[(pyridin-2-yl)amino]methylidene}propanedioate

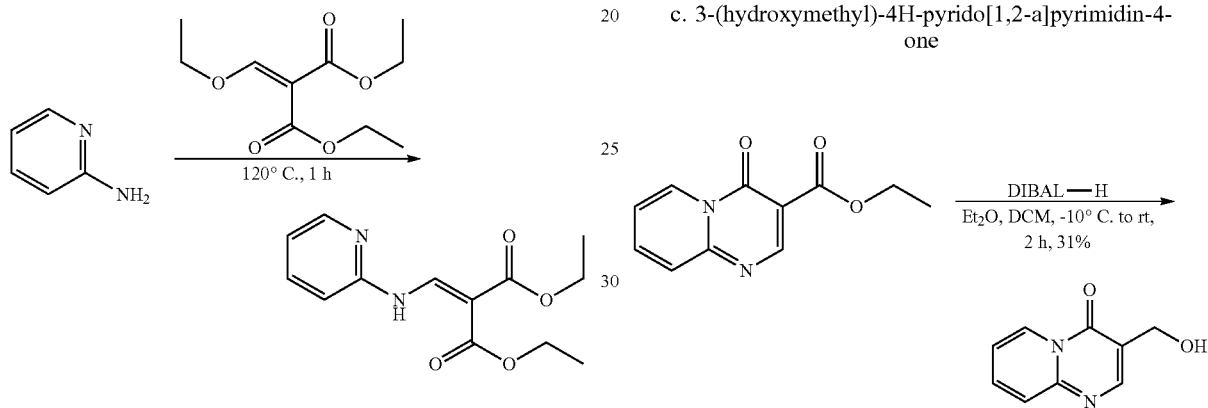

A mixture of 2-aminopyridine (4.35 g, 46.3 mmol, 1 eq) and diethyl ethoxymethylenemalonate (10.00 g, 46.3 mmol, 1 eq) was heated at 120° C. for 1 h. Subsequently the mixture was evaporated to dryness to give a residue which was triturated with cyclohexane to provide the product as a yellow solid (9.90 g, 37.5 mmol, yield 81%).

b. ethyl 4-oxo-4H-pyrido[1,2-a]pyrimidine-3-carboxylate

A mixture containing 1,3-diethyl 2-{[(pyridin-2-yl)amino]methylidene}propanedioate (9.90 g, 37.5 mmol, 1 eq), diphenyl ether (78 mL) and a catalytic amount of 2-chlorobenzoic acid was heated by microwave irradiation at 250° C. for 1 h. Reaction mixture was directly purified by FCC (SiHP, Hexane: AcOEt 0-100%) to afford the product (7.20 g, 33.0 mmol, yield 88%) as a yellow solid.

c. 3-(hydroxymethyl)-4H-pyrido[1,2-a]pyrimidin-4-one

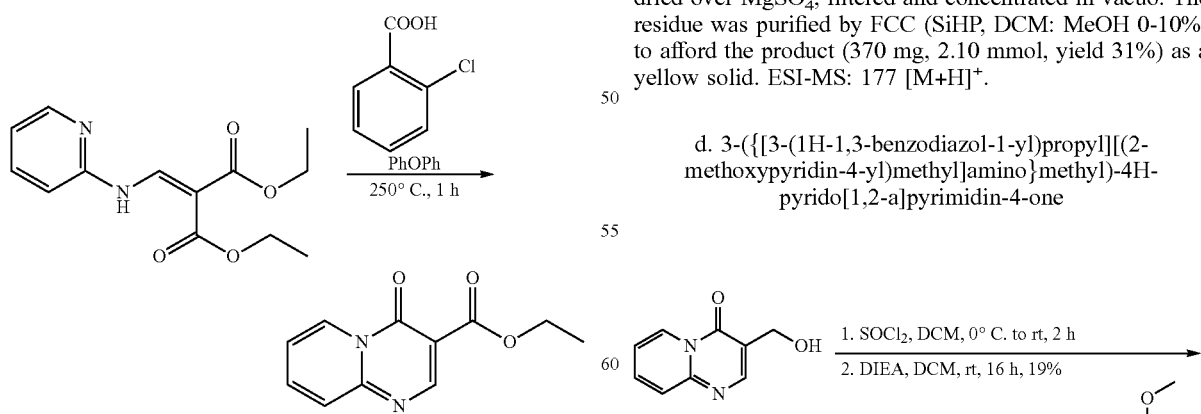

Ethyl 4-oxo-4H-pyrido[1,2-a]pyrimidine-3-carboxylate (1.5 g, 6.87 mmol, 1 eq) was dissolved in a mixture of anhydrous DCM and anhydrous diethyl ether (40 mL, 1:1) and cooled to −10° C. in an ice bath. A solution of 1M DIBAL-H in toluene (17 mL, 17.2 mmol, 2.5 eq) was added dropwise over 15 min. The resulting bright yellow solution was stirred under argon for 2 h. The reaction mixture was warmed to rt and quenched carefully with solid K/Na tartrate solution. Resulted solution was diluted with 100 mL DCM, dried over MgSO₄, filtered and concentrated in vacuo. The residue was purified by FCC (SiHP, DCM: MeOH 0-10%) to afford the product (370 mg, 2.10 mmol, yield 31%) as a yellow solid. ESI-MS: 177 [M+H]⁺.

d. 3-({[3-(1H-1,3-benzodiazol-1-yl)propyl][(2-methoxypyridin-4-yl)methyl]amino}methyl)-4H-pyrido[1,2-a]pyrimidin-4-one

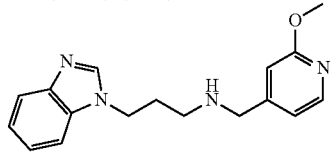

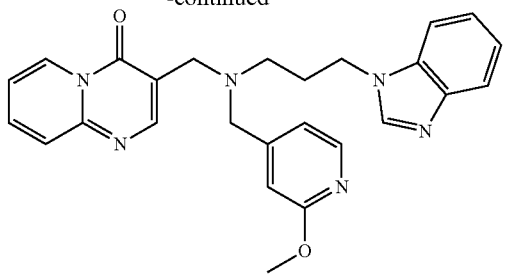

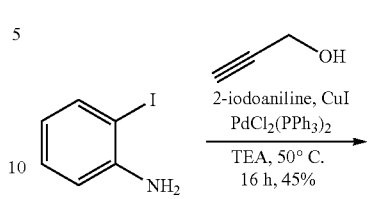

3-(hydroxymethyl-4H-pyrido[1,2-a]pyrimidin-4-one (80.0 mg, 0.45 mmol, eq) was dissolved in anhydrous DCM (3 mL) and cooled to 0° C. Thionyl chloride (132 μL, 1.82 mmol, 4 eq) was added dropwise and the resulting reaction mixture was stirred at 0° C.-rt for 2 h. Subsequently the reaction mixture was concentrated in vacuo. The residue was dried and redissolved in anhydrous DCM (3 mL), [3-(1H-1,3-benzodiazol-1-yl)propyl][(6-methoxypyridin-3-yl)methyl]amine (269 mg, 0.91 mmol, 2 eq) was added, followed by a dropwise addition of DIEA (395 μL, 2.27 mmol, 5 eq) and the reaction mixture was stirred under argon at rt over weekend. Subsequently the reaction mixture was concentrated in vacuo and the residue was purified by FCC (SiHP, DCM: MeOH 0-10%) and prep-HPLC to afford the formic acid salt of the product (43 mg, 0.09 mmol, yield 19%) as a viscous yellow oil. ESI-MS: 455 [M+H]$^+$.

$^1$H NMR (400 MHz, DMSO-d$_6$) δ 8.98 (ddd, J=7.2, 1.6, 0.8 Hz, 1H), 8.33 (s, 1H), 8.15 (s, 1H), 8.13 (s, 1H), 7.99 (dd, J=5.2, 0.7 Hz, 1H), 7.93 (ddd, J=9.0, 6.7, 1.6 Hz, 1H), 7.66 (dt, J=9.0, 1.1 Hz, 1H), 7.60-7.54 (m, 2H), 7.36 (td, J=6.9, 1.4 Hz, 1H), 7.22-7.12 (m, 2H), 6.93 (dd, J=5.3, 1.3 Hz, 1H), 6.78 (s, 1H), 4.27 (t, J=7.2 Hz, 2H), 3.78 (s, 3H), 3.60 (d, J=4.6 Hz, 4H), 2.46 (t, J=6.6 Hz, 2H), 2.05 (p, J=6.9 Hz, 2H).

Procedure 32. Preparation of 3-({[(2-methoxypyridin-4-yl)methyl][3-(pyridin-3-yl)propyl]amino}methyl)-1-methyl-1,4-dihydrocinnolin-4-one a. 3-(2-aminophenyl)prop-2-yn-1-ol PdCl$_2$(PPh$_3$)$_2$ (647 mg, 0.91 mmol, 0.1 eq) and CuI (87 mg, 0.46 mmol, 0.05 eq) were added to a solution of 2-iodoaniline (2.0 g, 9.1 mmol, 1 eq) in anhydrous TEA (25 mL) at 0° C. under argon followed by dropwise addition of propargyl alcohol (0.56 mL, 9.6 mmol, 1.05 eq). The resulting mixture was stirred at 50° C. overnight. Subsequently the reaction was quenched with water, and extracted with AcOEt. Combined organic phases were filtered through a Celite® pad, the filtrate was washed with brine, dried over Na$_2$SO$_4$, filtered and concentrated in vacuo. The residue was purified by FCC (SiHP, DCM: MeOH 0-10%; and SiHP, Hexane: AcOEt 0-50%) to afford the product (0.60 g, 4.08 mmol, yield 45%) as a brown oil. ESI-MS: 148 [M+H]$^+$ $^1$H NMR (300 MHz, DMSO-d$_6$) δ 7.12-7.00 (m, 2H), 6.67 (dd, J=8.2, 1.1 Hz, 1H), 6.48 (td, J=7.5, 1.2 Hz, 1H), 5.34 (s, 2H), 5.24 (t, J=5.9 Hz, 1H), 4.32 (d, J=5.9 Hz, 2H).

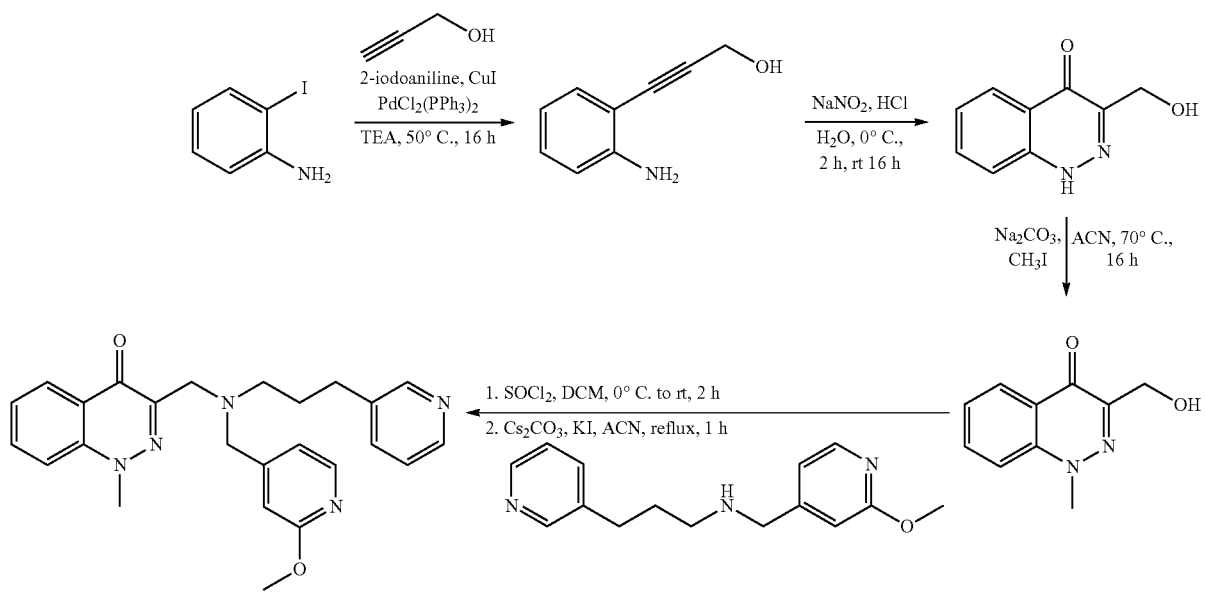

b. 3-(hydroxymethyl)-1,4-dihydrocinnolin-4-one

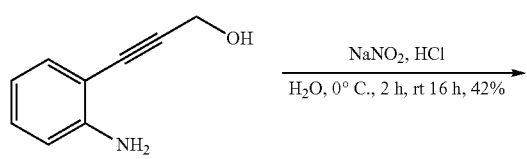

A solution of 3-(2-aminophenyl)prop-2-yn-1-ol (600 mg, 4.1 mmol, 1 eq) in 2N HCl (12 mL), was cooled to 0° C. and NaNO₂ (450 mg, 6.5 mmol, 1.6 eq) was added portionwise maintaining the temperature between 0-5° C. The resulting solution was stirred at 0° C. for 2 h and then at rt overnight. Subsequently the mixture was concentrated, and the solution was extracted with AcOEt (3×). Combined organic phases were washed with brine, dried over Na₂SO₄, filtered and concentrated. The residue was purified by FCC (SiHP, DCM: MeOH 0-10%) to afford the product (300 mg, 1.70 mmol, yield 42%) as a brown solid.

c. 3-(hydroxymethyl)-1-methyl-1,4-dihydrocinnolin-4-one

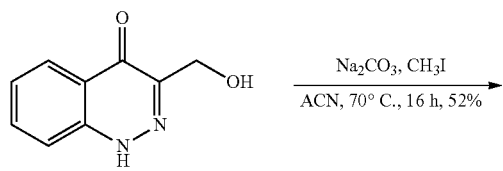

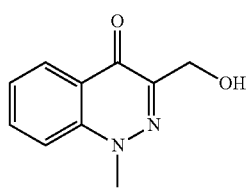

A mixture of 3-(hydroxymethyl)-1,4-dihydrocinnolin-4-one (130 mg, 0.70 mmol, 1 eq), Na₂CO₃ (116 mg, 1.10 mmol, 1.48 eq), and CH₃I (0.23 mL, 3.69 mmol, 5 eq) in anhydrous ACN (3 mL) was heated at 70° C. overnight. Reaction mixture was concentrated in vacuo, diluted with water and extracted with CHCl₃: iPrOH. Combined organic phases were dried over Na₂SO₄, filtered and concentrated. The residue was purified by FCC (SiHP, DCM: MeOH 0-10%) to afford the product (85 mg, 0.45 mmol, yield 52%) as a brown solid. ESI-MS: 191 [M+H]⁺.

¹H NMR (300 MHz, DMSO-d₆) δ 8.14 (dd, J=8.2, 1.5 Hz, 1H), 7.87 (ddd, J=8.5, 6.9, 1.6 Hz, 1H), 7.78-7.73 (m, 1H), 7.49 (ddd, J=8.0, 6.9, 1.1 Hz, 1H), 4.99 (t, J=6.0 Hz, 1H), 4.51 (d, J=5.9 Hz, 2H), 4.10 (s, 3H).

d. 3-({[3-(1H-imidazol-1-yl)propyl][(2-methoxypyridin-4-yl)methyl]amino}methyl)-1-methyl-1,4-dihydrocinnolin-4-one

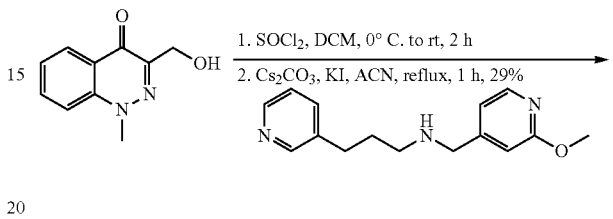

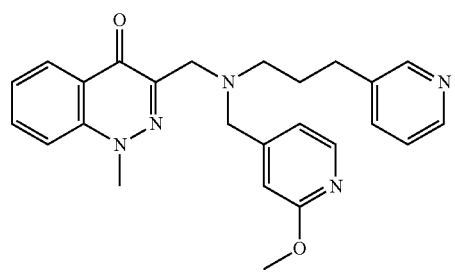

A solution of 3-(hydroxymethyl)-1-methyl-1,4-dihydrocinnolin-4-one (83.0 mg, 0.44 mmol, 1 eq) in anhydrous DCM (3 mL) was cooled to 0° C., thionyl chloride (127 µL, 1.75 mmol, 4 eq) was added dropwise and the resulting reaction mixture was stirred for 2 h allowing to warm up to rt. Subsequently the reaction mixture was concentrated in vacuo. The residue was dried and redissolved in anhydrous ACN (3 mL). A suspension of KI (66 mg, 0.40 mmol, 1 eq), Cs₂CO₃ (389 mg, 1.19 mmol, 3 eq.) and [(2-methoxypyridin-4-yl)methyl][3-(pyridin-3-yl)propyl]amine (118 mg, 0.46 mmol, 1.05 eq) was added and the reaction mixture was heated at 80° C. for 1 h. Subsequently the reaction was quenched with water and extracted with DCM. Combined organic phases were dried over Na₂SO₄, filtered and concentrated in vacuo. The residue was purified by FCC (SiHP, DCM: MeOH 0-10%) to afford the product (50 mg, 0.10 mmol, yield 29%) as an orange oil. ESI-MS: 430 [M+H]⁺.

¹H NMR (300 MHz, DMSO-d₆) δ 8.37 (d, J=2.2 Hz, 1H), 8.32 (dd, J=4.8, 1.6 Hz, 1H), 8.13 (dd, J=8.1, 1.5 Hz, 1H), 7.98 (d, J=5.2 Hz, 1H), 7.85 (ddd, J=8.6, 6.9, 1.6 Hz, 1H), 7.71 (d, J=8.7 Hz, 1H), 7.56 (dt, J=7.8, 2.0 Hz, 1H), 7.48 (ddd, J=8.0, 6.9, 1.0 Hz, 1H), 7.19 (ddd, J=7.7, 4.8, 0.9 Hz, 1H), 6.92 (dd, J=5.3, 1.3 Hz, 1H), 6.77 (s, 1H), 4.03 (s, 3H), 3.76 (s, 3H), 3.71 (s, 2H), 3.67 (s, 2H), 2.60 (t, J=7.6 Hz, 2H), 1.81 (p, J=7.0 Hz, 2H).

Procedure 33. Preparation of
3-(6-methoxypyridin-3-yl)propan-1-amine

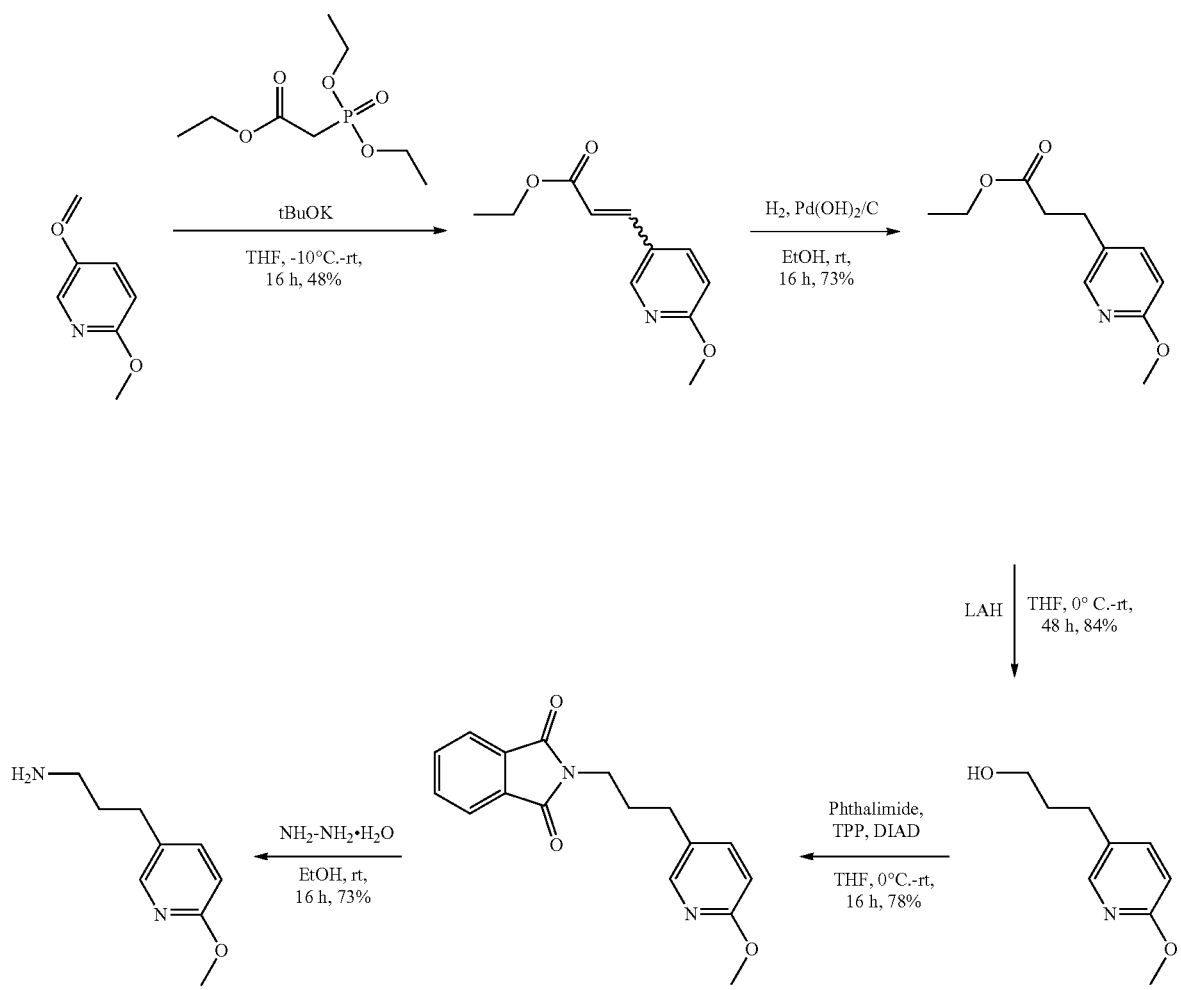

a. ethyl 3-(6-methoxypyridin-3-yl)prop-2-enoate

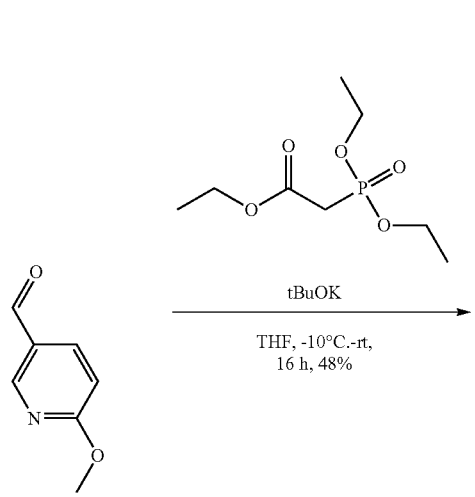

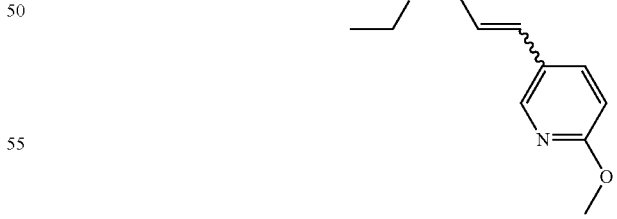

To a cooled suspension of potassium tert-butoxide (818 mg, 7.29 mmol, 1 eq) in anhydrous THF (5 mL), triethyl phosphonoacetate (1.74 mL, 8.75 mmol, 1.2 eq) was added dropwise and stirred for 30 min. Then, a solution of 6-methoxynicotinaldehyde (1.00 g, 7.29 mmol, 1 eq) in anhydrous THF (2 mL) was added. The reaction was continued at rt for 16 h. The mixture was poured into ice-cold water and extracted with AcOEt. Organic layer was dried, filtered off and concentrated. The residue was purified by FCC (SiHP, Hex: DCM 100%) to afford the title compound (1.04 g, 5.02 mmol, yield 48%) as a yellow oil. ESI-MS: 208 [M+H]$^+$ $^1$H NMR (400 MHz, Chloroform-d) δ 8.28 (d, J=2.4 Hz, 1H), 7.82-7.74 (m, 1H), 7.68-7.60 (m, 1H), 6.80-6.75 (m, 1H), 6.35 (d, J=16.0 Hz, 1H), 4.28 (q, J=7.1 Hz, 2H), 3.98 (s, 3H), 1.35 (t, J=7.1 Hz, 3H).

b. ethyl 3-(6-methoxypyridin-3-yl)propanoate

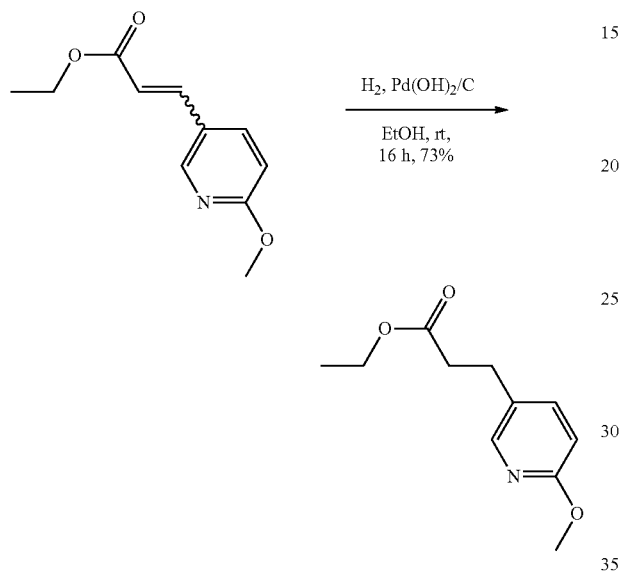

A solution of ethyl 3-(6-methoxypyridin-3-yl)prop-2-enoate (840 mg, 4.05 mmol, 1 eq) in EtOH (40 mL) was degassed and purged with argon several times. Palladium hydroxide on carbon (40 mg) was added. The reaction was carried out at rt under hydrogen atmosphere for 16 h. The mixture was filtered through Celite® and washed with AcOEt. The filtrate was concentrated in vacuo and purified by FCC (SiHP, Hex: AcOEt 15%) to afford the title compound (770 mg, 3.68 mmol, yield 73%) as a yellow oil. ESI-MS: 210 [M+H]$^+$ $^1$H NMR (400 MHz, Chloroform-d) δ 8.02 (dd, J=2.4, 0.8 Hz, 1H), 7.45 (dd, J=8.5, 2.5 Hz, 1H), 6.70 (dd, J=8.5, 0.8 Hz, 1H), 4.15 (q, J=7.1 Hz, 2H), 3.93 (s, 3H), 2.89 (t, J=7.6 Hz, 2H), 2.60 (t, J=8.0, 7.2 Hz, 2H), 1.26 (t, J=7.2 Hz, 3H).

c. 3-(6-methoxypyridin-3-yl)propan-1-ol

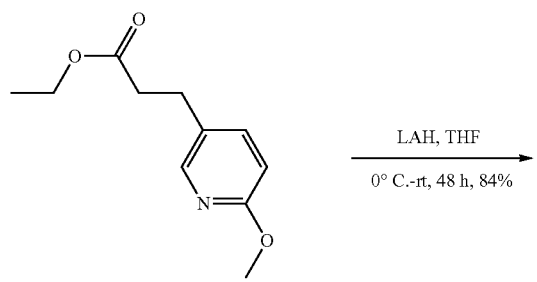

-continued

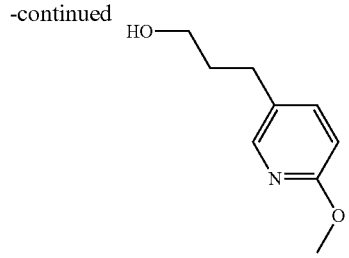

To a cooled solution of ethyl 3-(6-methoxypyridin-3-yl)propanoate (550 mg, 2.63 mmol, 1 eq) in anhydrous THF (10 mL), 2M lithium aluminium hydride in THF (1.84 mL, 3.68 mmol, 1.4 eq) was added dropwise. The reaction was carried out for 48 h, cooled to 0° C. quenched carefully with sat. Na2SO4 and the mixture was extracted with DCM. Organic layer was dried, filtered off and concentrated to afford the title compound (550 mg, 3.29 mmol, yield 84%) as a white oil. ESI-MS: 168 [M+H]$^+$ $^1$H NMR (300 MHz, Chloroform-d) δ 8.01 (dd, J=2.5, 0.8 Hz, 1H), 7.44 (dd, J=8.5, 2.5 Hz, 1H), 6.70 (dd, J=8.5, 0.7 Hz, 1H), 3.93 (s, 3H), 3.69 (t, J=6.4 Hz, 2H), 2.66 (dd, J=8.7, 6.7 Hz, 2H), 1.93-1.80 (m, 2H).

d. 2-[3-(6-methoxypyridin-3-yl)propyl]-2,3-dihydro-1H-isoindole-1,3-dione

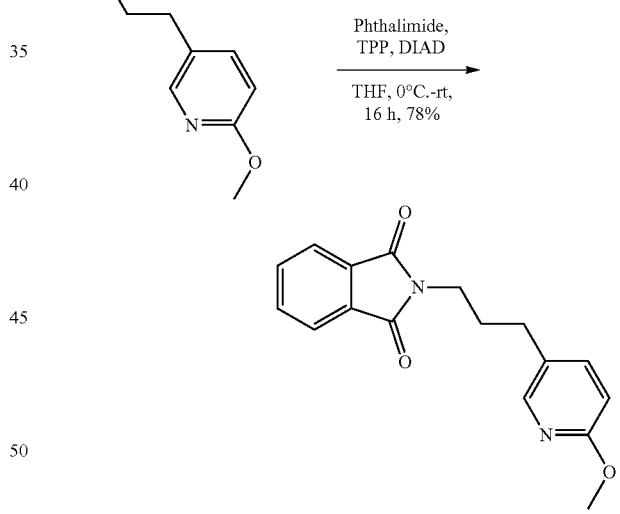

Phthalimide (484 mg, 3.29 mmol, 1 eq) and triphenylphosphine (863 mg, 3.29 mmol, 1 eq) were dissolved in THF (4 mL) and cooled to 0° C. A solution of DIAD (646 μL, 3.29 mmol, 1 eq) and 3-(6-methoxypyridin-3-yl)propan-1-ol (550 mg, 3.29 mmol, 1 eq) in THF (2 mL) was added dropwise. The reaction was carried out for 16 h. The mixture was diluted in AcOEt and washed with brine. Organic layer was dried, filtered off and concentrated. The residue was purified by FCC (SiHP, Hex: AcOEt 100%) to afford the title compound (1.52 g, yield 78%) as a yellow oil. ESI-MS: 297 [M+H]$^+$ $^1$H NMR (300 MHz, Chloroform-d) δ 8.02-7.97 (m, 1H), 7.92-7.82 (m, 2H), 7.80-7.69 (m, 2H), 7.45 (dd, J=8.5, 2.5

Hz, 1H), 6.67 (dd, J=8.5, 0.7 Hz, 1H), 3.90 (s, 3H), 3.76 (t, J=7.1 Hz, 2H), 2.67-2.58 (m, 2H), 2.07-1.94 (m, 2H).

e. 3-(6-methoxypyridin-3-yl)propan-1-amine

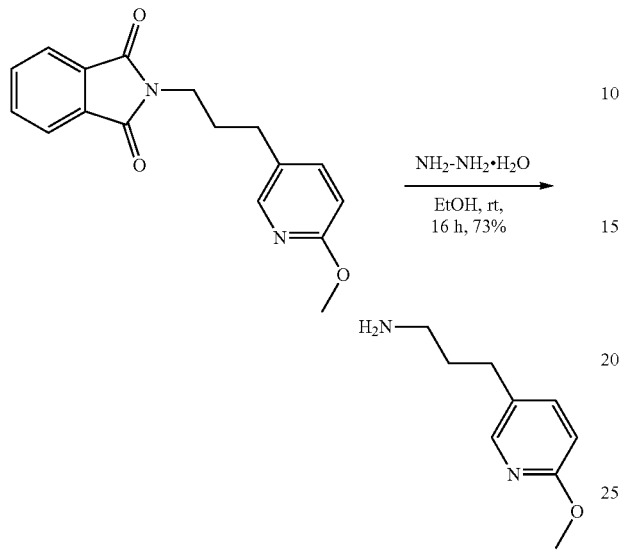

To a solution of 2-[3-(6-methoxypyridin-3-yl)propyl]-2,3-dihydro-1H-isoindole-1,3-dione (1.52 g, 3.96 mmol, 1 eq) in EtOH (9 mL), hydrazine monohydrate 65% wt in water (649 μL, 8.703 mmol, 2.2 eq.) was added dropwise. The reaction was carried out at rt for 16 h. White precipitate was filtered off and washed with EtOH. The filtrate was concentrated in vacuo, diluted in DCM and washed with 5M NaOH. Organic layer was dried, filtered off and concentrated to afford the title compound (960 mg, 5.78 mmol, yield 73%) as a yellow oil. ESI-MS: 167 [M+H]⁺

¹H NMR (400 MHz, Chloroform-d) δ 8.02-7.97 (m, 1H), 7.43 (dd, J=8.4, 2.5 Hz, 1H), 6.73-6.67 (m, 1H), 6.45 (s, 2H), 3.94-3.92 (m, 3H), 2.77-2.72 (m, 2H), 2.62-2.57 (m, 2H), 1.80-1.70 (m, 2H).

Procedure 34. Preparation of 4-(1H-1,3-benzodiazol-1-yl)butan-2-amine

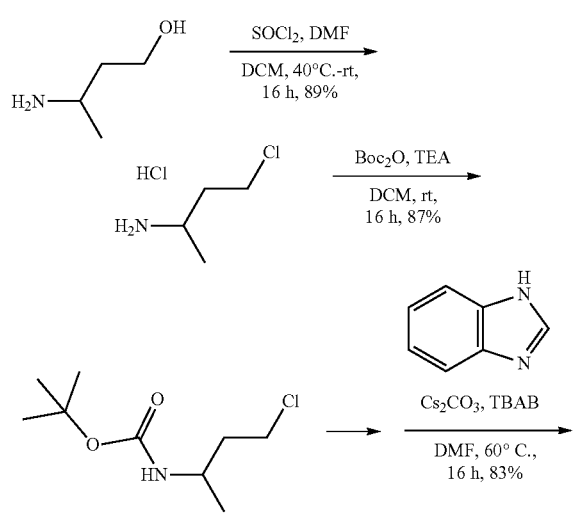

-continued

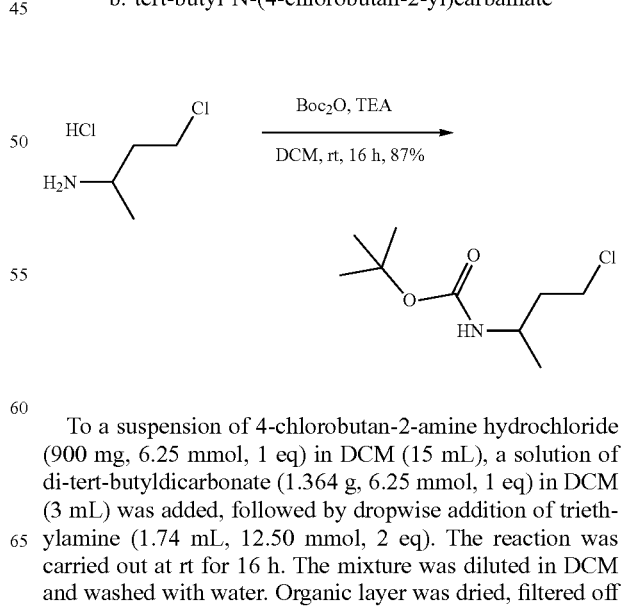

a. 4-chlorobutan-2-amine hydrochloride

To a solution of 3-aminobutan-1-ol (500 mg, 5.61 mmol, 1 eq) in anhydrous DCM (25 mL), catalytic amount of DMF (43 μL, 0.56 mmol, 0.1 eq) was added, followed by dropwise addition of thionyl chloride (610 μL, 8.414 mmol, 1.5 eq). The reaction was carried out 40° C. for 1 h, and continued at rt for further 16 h. The solvents were removed in vacuo. The residue was triturated using Et₂O to afford the title compound (900 mg, 6.25 mmol, yield 89%) as a brown solid. ESI-MS: 108 [M+H]⁺.

¹H NMR (300 MHz, DMSO-d₆) δ 8.33-8.06 (m, 3H), 3.86-3.65 (m, 2H), 3.33-3.23 (m, 1H), 2.19-1.84 (m, 2H), 1.23 (d, J=6.6 Hz, 3H).

b. tert-butyl N-(4-chlorobutan-2-yl)carbamate

To a suspension of 4-chlorobutan-2-amine hydrochloride (900 mg, 6.25 mmol, 1 eq) in DCM (15 mL), a solution of di-tert-butyldicarbonate (1.364 g, 6.25 mmol, 1 eq) in DCM (3 mL) was added, followed by dropwise addition of triethylamine (1.74 mL, 12.50 mmol, 2 eq). The reaction was carried out at rt for 16 h. The mixture was diluted in DCM and washed with water. Organic layer was dried, filtered off and concentrated to afford the title compound (1.25 g, 6.02 mmol, yield 87%) as a brown oil.

$^1$H NMR (300 MHz, Chloroform-d) δ 4.39 (s, 1H), 3.66-3.51 (m, 2H), 1.98-1.85 (m, 2H), 1.47 (s, 9H), 1.19 (d, J=6.7 Hz, 3H).

c. tert-butyl N-[4-(1H-1,3-benzodiazol-1-yl)butan-2-yl]carbamate

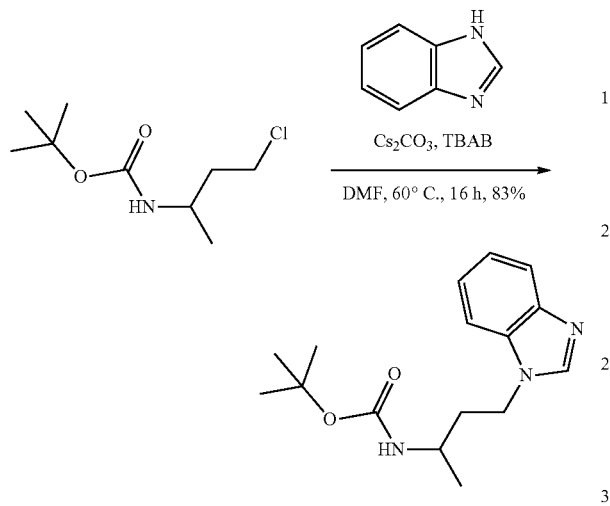

To a suspension of 1H-benzimidazole (300 mg, 2.54 mmol, 1 eq), cesium carbonate (1.24 g, 3.81 mmol, 1.5 eq) and tetrabutylammonium bromide (982 mg, 3.05 mmol, 1.2 eq) in DMF (6 mL), a solution of tert-butyl N-(4-chlorobutan-2-yl)carbamate (633 mg, 3.05 mmol, 1.2 eq) in DMF (1.5 mL) was added. The reaction was carried out at 60° C. for 16 h. The mixture was diluted in AcOEt and washed with water. Organic layer was dried, filtered off and concentrated. The residue was purified by FCC (SiHP, DCM:MeOH 95:5) to afford the title compound (643 mg, 2.22 mmol, yield 83%) as a white solid. ESI-MS: 290 [M+H]$^+$ d. 4-(1H-1,3-benzodiazol-1-yl)butan-2-amine

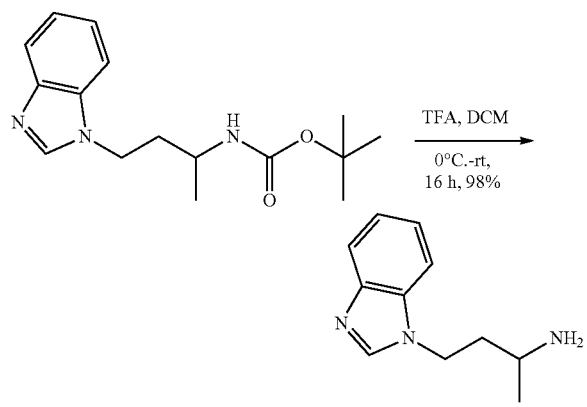

To a cooled solution of tert-butyl N-[4-(1H-1,3-benzodiazol-1-yl)butan-2-yl]carbamate (630 mg, 2.18 mmol, 1 eq) in DCM (8 mL) trifluoroacetic acid (2 mL) was added dropwise. The reaction was continued for 16 h. The mixture was diluted in DCM and washed with 15% NaOH. Organic layer was dried, filtered off and concentrated to afford the title compound (427 mg, 2.26 mmol, yield 98%) as a yellow oil. ESI-MS: 190 [M+H]$^+$ $^1$H NMR (300 MHz, Chloroform-d) δ 7.95 (s, 1H), 7.86-7.79 (m, 1H), 7.49-7.42 (m, 1H), 7.38-7.23 (m, 2H), 4.42-4.21 (m, 2H), 2.94-2.80 (m, 1H), 2.05-1.91 (m, 1H), 1.87-1.73 (m, 1H), 1.15 (d, J=6.3 Hz, 3H).

Procedure 35. Preparation of tert-butyl N-[3-(pyrimidin-5-yl)propyl]carbamate

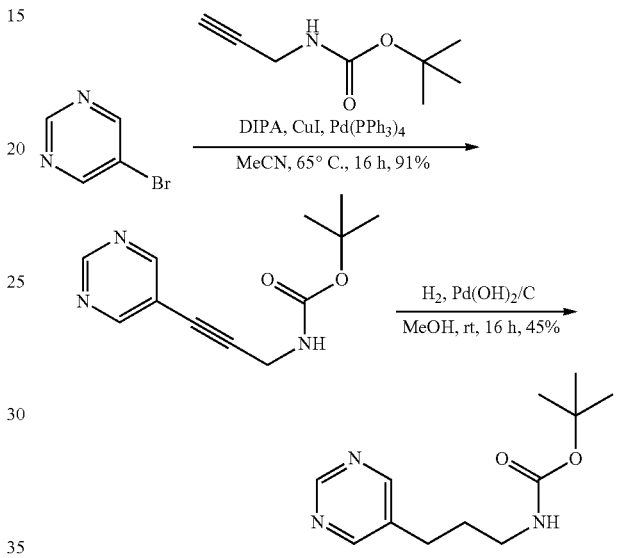

a. tert-butyl N-[3-(pyrimidin-5-yl)prop-2-yn-1-yl]carbamate

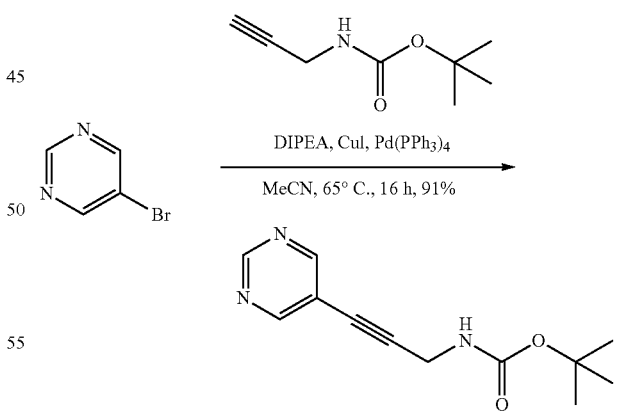

To a stirred suspension of 5-bromopyrimidine (500 mg, 3.145 mmol, 1 eq) and tert-butyl N-(prop-2-yn-1-yl)carbamate (537 mg, 3.46 mmol, 1.1 eq) in anhydrous acetonitrile (10 mL), anhydrous diisopropylamine (666 μL, 4.72, mmol, 1.5 eq), copper(I) iodide (60 mg, 0.314 mmol, 10%$_{mol}$) and tetrakis(triphenylphosphine)palladium(0) (363 mg, 0.314 mmol, 10 %$_m$ol) were added. The suspension was degassed and the reaction was continued at 65° C. for 16 h. The mixture was filtered through Celite® pad and washed with AcOEt. The solvents were removed in vacuo. The residue was purified by FCC (SiHP, Hex: AcOEt 50%) to afford the title compound (700 mg, 3 mmol, yield 91%) as an orange solid. ESI-MS: 234 [M+H]⁺

¹H NMR (300 MHz, Chloroform-d) δ 9.15 (s, 1H), 8.78 (s, 2H), 4.98 (s, 1H), 4.21 (d, J=5.6 Hz, 2H), 1.48 (s, 9H).

b. tert-butyl N-[3-(pyridin-5-y)propyl]carbamate

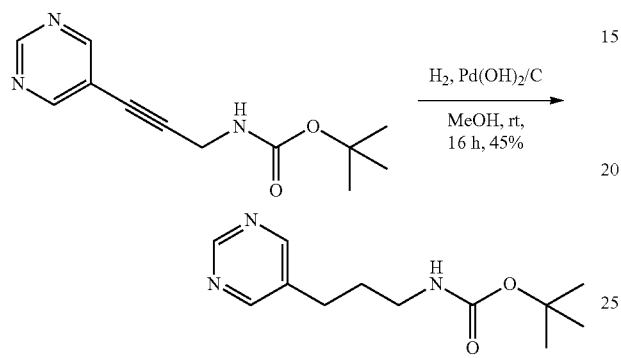

A solution of tert-butyl N-[3-(pyrimidin-5-yl)prop-2-yn-1-yl]carbamate (700 mg, 3.00 mmol, 1 eq) in MeOH (40 mL) was degassed and purged with argon several times. Palladium hydroxide on carbon (70 mg) was added. The reaction was carried out at rt under hydrogen atmosphere for 16 h. The mixture was filtered through Celite® and washed with AcOEt. The filtrate was concentrated in vacuo and purified by FCC (SiHP, Hex: AcOEt 65%) to afford the title compound (360 mg, 1.52 mmol, yield 45%) as a yellow oil. ESI-MS: 238 [M+H]⁺

¹H NMR (300 MHz, Chloroform-d) δ 9.10 (s, 1H), 8.61 (s, 2H), 4.67 (s, 1H), 3.22 (q, J=6.7 Hz, 2H), 2.67 (dd, J=9.1, 6.7 Hz, 2H), 1.94-1.79 (m, 2H), 1.46 (s, 9H).

Procedure 36. Preparation of 4-(3-{[(2-methoxy-pyridin-4-yl)methyl]({4-oxo-4H-benzo[h]chromen-3-y}methyl)amino}propyl)-1,2-dihydropyridin-2-one

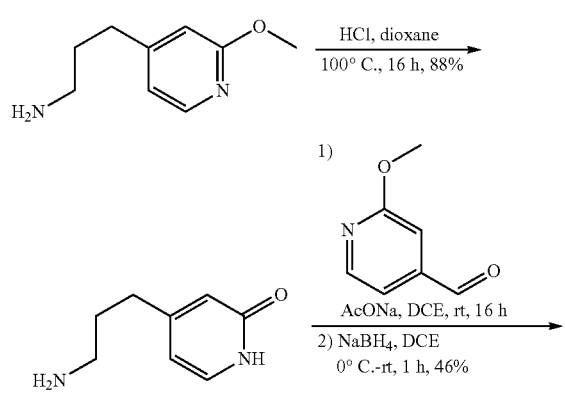

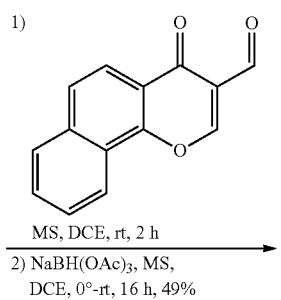

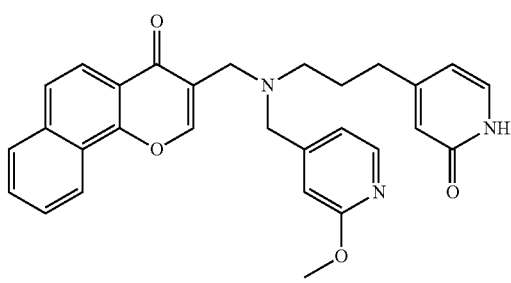

a. 4-(3-aminopropyl)-1,2-dihydropyridin-2-one

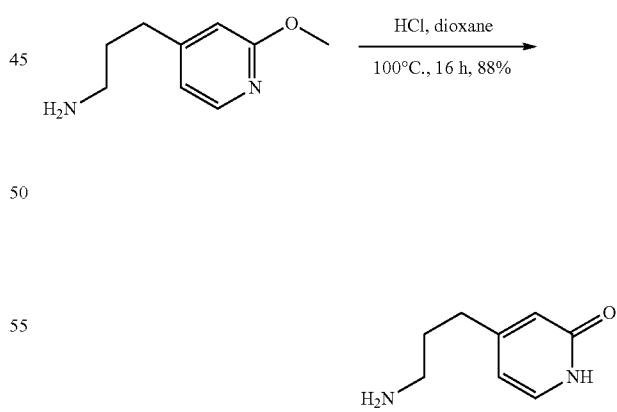

4M HCl in dioxane (0.43 mL, 1.7 mmol, 2 eq) was added to a mixture of 3-(2-methoxypyridin-4-yl)propan-1-amine TFA salt (0.240 g, 0.857 mmol, 1 eq) and 1,4-dioxane (5 mL). The reaction mixture was heated overnight at 100° C. Then, the mixture was cooled down to rt and evaporated in vacuo to afford HCl salt of the title compound (0.153 g, 0.8 mmol, yield 88%) as an orange oil. MS: 153 [M+H]⁺ b. 4-(3-{[(2-methoxypyridin-4-yl)methyl]amino}propyl)-1,2-dihydropyridin-2-one c. 4-(3-{[(2-methoxypyridin-4-yl)methyl]({4-oxo-4H-benzo[h]chromen-3-yl}methyl)amino}propyl)-1,2-dihydropyridin-2-one

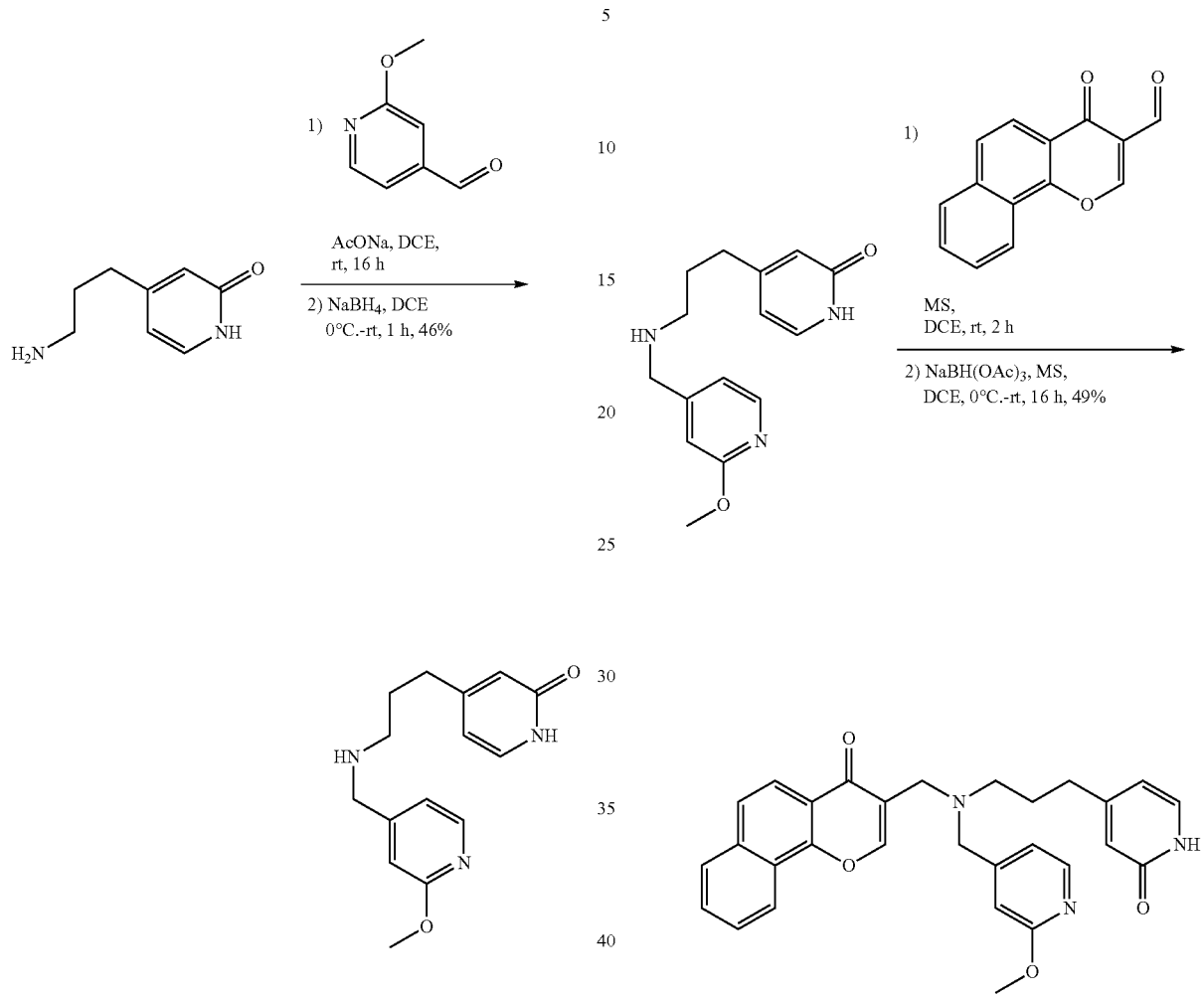

A mixture of HCl salt of 4-(3-aminopropyl)-1,2-dihydropyridin-2-one (0.172 g, 0.911 mmol, 1 eq), 2-methoxypyridine-4-carbaldehyde (0.110 mL, 0.911 mmol, 1 eq), NaOAc (0.075 g, 0.911 mmol, 1 eq) and anhydrous DCE (5 mL) was stirred overnight at rt under argon. Then, the mixture was cooled to 0° C. and NaBH$_4$ (0.035 g, 0.930 mmol, 1.02 eq) was added portionwise over 15 min. The mixture was stirred at RT for 1 hour and then partitioned between DCM and 10% NaOH. The organic layers were washed with brine, dried over MgSO$_4$, filtered and concentrated in vacuo. The residue was purified was purified using FCC (SiHP, DCM:MeOH 100:0 to 90:10) to afford the title compound (0.125 g, 0.4 mmol, yield 46%) as an orange oil. ESI-MS: 274 [M+H]$^+$ $^1$H NMR (400 MHz, Chloroform-d) δ 12.48 (s, 1H), 8.13-8.11 (m, 1H), 7.28-7.23 (m, 1H), 6.89-6.82 (m, 1H), 6.76-6.69 (m, 1H), 6.40 (dd, J=1.7, 0.8 Hz, 1H), 6.17-6.13 (m, 1H), 3.95 (s, 3H), 3.77 (s, 2H), 2.71-2.64 (m, 2H), 2.61-2.53 (m, 2H), 1.88-1.76 (m, 2H), 1.66 (s, 1H).

A mixture of 4-(3-{[(2-methoxypyridin-4-yl)methyl]amino}propyl)-1,2-dihydropyridin-2-one (0.104 g, 0.379 mmol, 1 eq), 4-oxo-4H-benzo[h]chromene-3-carbaldehyde (0.085 g, 0.379 mmol, 1 eq), dry molecular sieves 3A and DCE (4 mL) was stirred at RT for 2 h. Then, the mixture was cooled to 0° C. and NaBH(OAc)$_3$ (0.112 g, 0.531 mmol, 1.4 eq) was added and the reaction was continued overnight. The reaction mixture was quenched with NaHCO$_3$ aqueous solution and extracted with DCM. The combined organic layers were washed with brine, dried over Na$_2$SO$_4$ and concentrated in vacuo. The residue was by FCC (SiHP, DCM:MeOH 100:0 to 95:5) to afford the title compound (0.090 g, 0.2 mmol, yield 49%) as a colorless oil. ESI-MS: 482 [M+H]$^+$ $^1$H NMR (400 MHz, DMSO-d$_6$) δ 11.28 (s, 1H), 8.51 (s, 1H), 8.51-8.48 (m, 1H), 8.16-8.09 (m, 1H), 8.06-7.99 (m, 2H), 7.96-7.90 (m, 1H), 7.87-7.76 (m, 2H), 7.19 (d, J=6.7 Hz, 1H), 6.99 (dd, J=5.3, 1.3 Hz, 1H), 6.81 (d, J=1.3 Hz, 1H), 6.11 (d, J=1.6 Hz, 1H), 6.05 (dd, J=6.7, 1.7 Hz, 1H), 3.77 (s, 3H), 3.65 (s, 2H), 3.55 (s, 2H), 2.47 (d, J=7.1 Hz, 2H), 2.41 (t, J=7.7 Hz, 2H), 1.78 (p, J=7.3 Hz, 2H).

Procedure 37. Preparation of 6-fluoro-3-({[3-(pyridin-3-yl)propyl][(pyridin-4-yl)methyl]amino}methyl)-4H-benzo[h]chromen-4-one

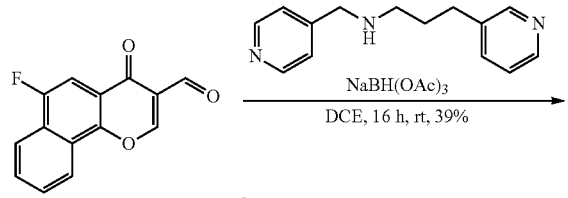

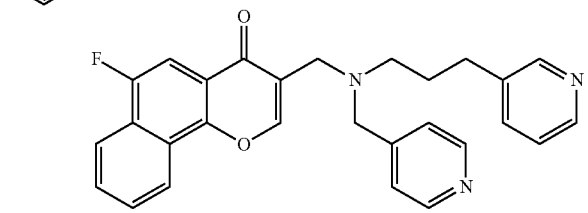

A mixture of 6-fluoro-4-oxo-4H-benzo[h]chromene-3-carbaldehyde (0.100 g, 0.41 mmol, 1 eq), [3-(pyridin-3-yl)propyl][(pyridin-4-yl)methyl]amine (0.094 g, 0.41 mmol, 1 eq), NaBH(OAc)₃ (0.123 g, 0.58 mmol, 1.4 eq) and DCE (3 mL) was stirred overnight at rt. The reaction was quenched with DCM and the mixture was washed with NaHCO₃ solution, brine, dried over Na₂SO₄, filtered and evaporated in vacuo. The residue was purified by FCC (SiHP, DCM:MeOH 100:0 to 90:10) to afford the title compound (0.074 g, 0.16 mmol, yield 39%) as a yellow oil. ESI-MS: 454 [M+H]⁺

¹H NMR (300 MHz, DMSO-d₆) δ 8.58-8.53 (m, 2H), 8.50-8.47 (m, 2H), 8.43-8.40 (m, 1H), 8.34-8.30 (m, 1H), 8.26-8.20 (m, 1H), 8.00-7.90 (m, 2H), 7.71 (d, J=10.5 Hz, 1H), 7.64-7.59 (m, 1H), 7.45-7.41 (m, 2H), 7.25-7.20 (m, 1H), 3.74 (s, 2H), 3.58 (s, 2H), 2.62 (t, J=7.7 Hz, 2H), 1.86 (p, 2H).

Procedure 38. Preparation of 6-fluoro-2-methyl-4-oxo-3-({[3-(pyridin-3-yl)propyl][(pyridin-4-yl)methyl]amino}methyl)-4H-chromene-7-carboxylic acid

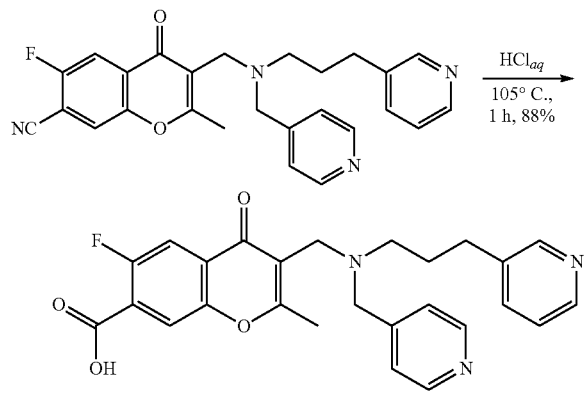

6-fluoro-2-methyl-4-oxo-3-({[3-(pyridin-3-yl)propyl][(pyridin-4-yl)methyl]amino}methyl)-4H-chromene-7-carbonitrile was suspended in 10M HCl and heated at 105° C. for 1 h. Then, the reaction mixture was evaporated in vacuo and the residue was purified by prep-HPLC to afford the title compound (0.033 g, 0.07 mmol, yield 88.7%) as a white solid. ESI-MS: 462 [M+H]⁺

¹H NMR (300 MHz, Deuterium Oxide) δ 8.88-8.79 (m, 2H), 8.74-8.62 (m, 2H), 8.53 (d, J=8.2 Hz, 1H), 8.27-8.19 (m, 2H), 8.07-7.90 (m, 2H), 7.76 (d, J=9.6 Hz, 1H), 4.41 (s, 2H), 3.50-3.38 (m, 2H), 2.97 (t, J=7.9 Hz, 2H), 2.59 (s, 3H), 2.37 (td, J=9.9, 8.2, 6.1 Hz, 2H).

Procedure 39. Preparation of 6-fluoro-2-methyl-7-(piperazin-1-yl)-3-({[3-(pyridin-3-yl)propyl][(pyridin-4-yl)methyl]amino}methyl)-4H-chromen-4-one

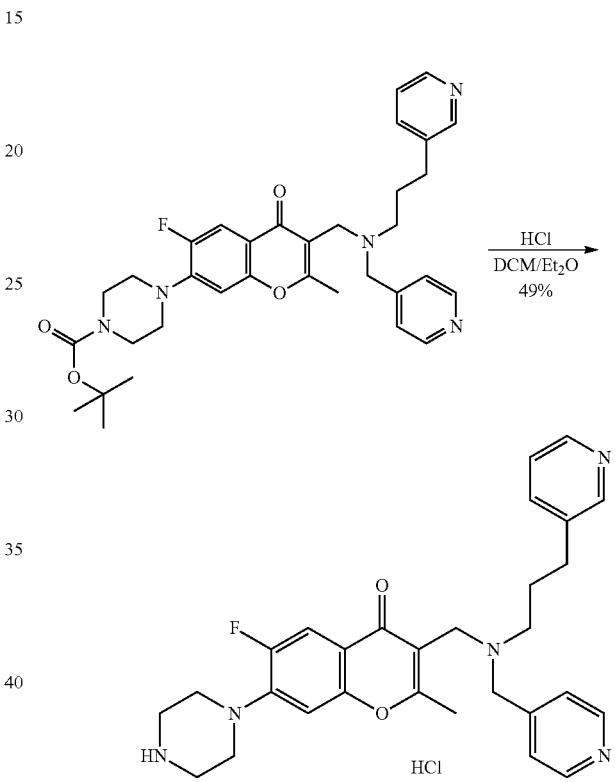

tert-butyl 4-[6-fluoro-2-methyl-4-oxo-3-({[3-(pyridin-3-yl)propyl][(pyridin-4-yl)methyl]amino}methyl)-4H-chromen-7-yl]piperazine-1-carboxylate (0.080 g, 0.13 mmol, 1 eq) was dissolved in DCM (5 mL) and the mixture was placed in an ice bath. 2N HCl in diethyl ether (1 mL) was added and the reaction mixture was stirred for 1 h. Then, additional 2N HCl in diethyl ether (1 mL) was added. The mixture was partitioned between 1 M NaOH and CHCl₃/isopropanol mixture. The organic layer was dried over Na₂SO₄, filtered and evaporated in vacuo. The residue was purified by FCC (SiHP, DCM:MeOH 100:0 to 80:20). The obtained sample was diluted with DCM (5 mL) and 2N HCl in diethyl ether (2 mL). The mixture was stirred for 5 min, afterwards it was evaporated in vacuo and freeze-dried to afford hydrochloric acid salt of the product as brown solid (0.033 g, 0.13 mmol, yield 49%). ESI-MS: 502 [M+H]⁺

¹H NMR (300 MHz, Deuterium Oxide) δ 8.80-8.76 (m, 2H), 8.72-8.70 (m, 1H), 8.67-8.63 (m, 1H), 8.55-8.50 (m, 1H), 8.17-8.12 (m, 2H), 8.03-7.97 (m, 1H), 7.67 (d, J=12.5 Hz, 1H), 7.22 (d, J=7.0 Hz, 1H), 4.74 (s, 2H), 4.39 (s, 2H), 3.60-3.54 (m, 4H), 3.50-3.39 (m, 6H), 2.97 (t, J=7.9 Hz, 2H), 2.55 (s, 3H), 2.41-2.28 (m, 2H), 1.24 (s, 1H).

Procedure 40. Preparation of 3-({[(2-methoxypyridin-4-yl)methyl][3-(7H-purin-7-yl)propyl]amino}methyl)-1-methyl-1,4-dihydroquinolin-4-one

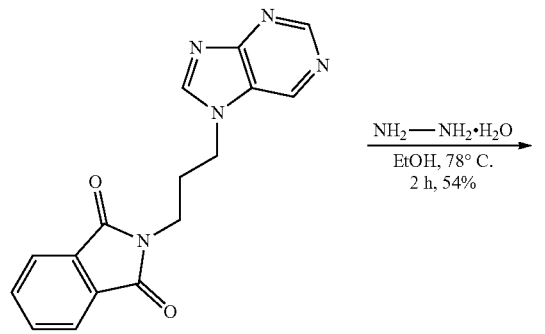

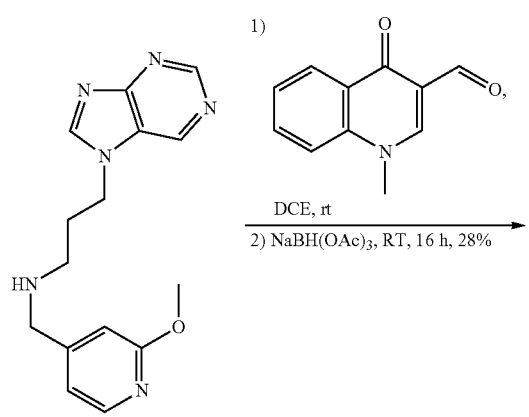

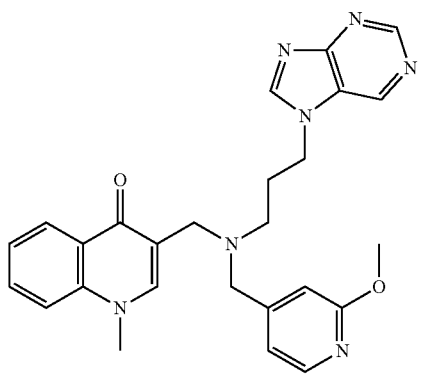

a. 3-(7H-purin-7-yl)propan-1-amine

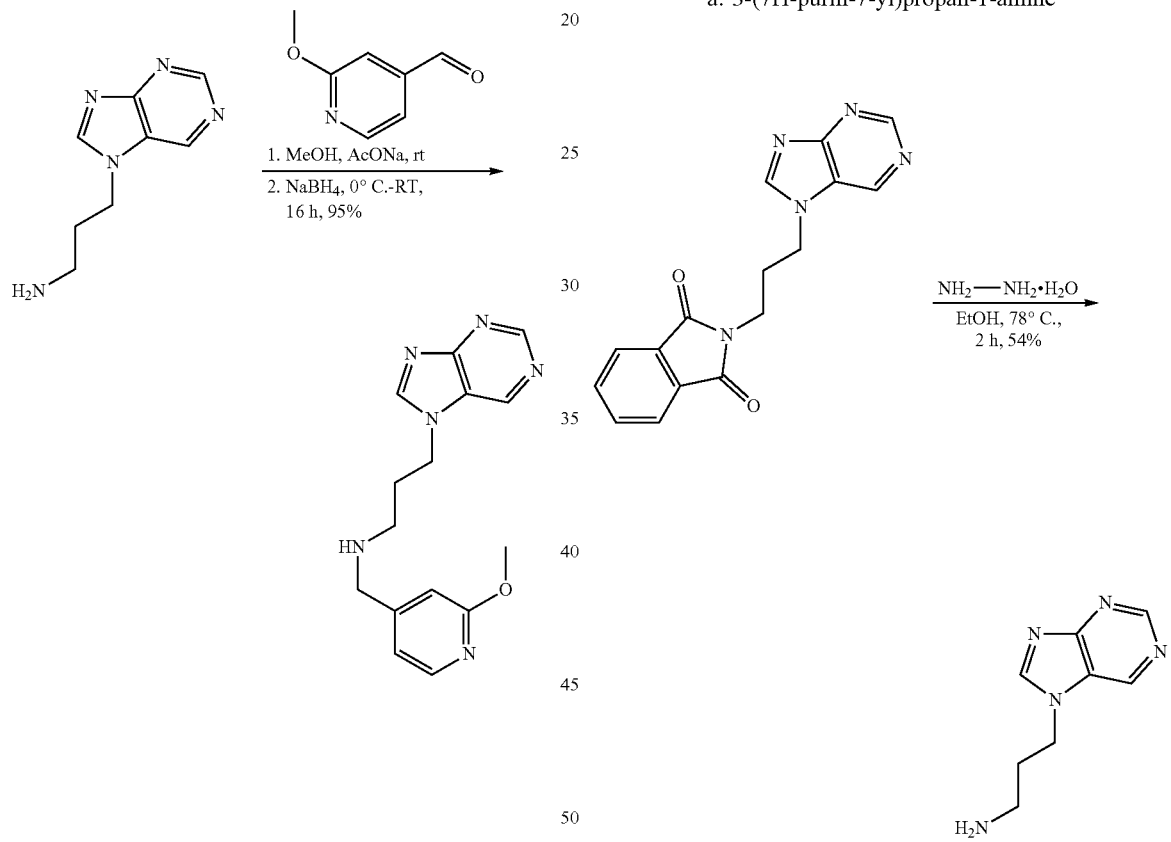

In a pressure vessel were placed 2-[3-(7H-purin-7-yl)propyl]-2,3-dihydro-1H-isoindole-1,3-dione (0.957 g, 3.114 mmol, 1 eq), and hydrazine monohydrate (3.02 mL, 62.28 mmol, 20 eq) in EtOH (100 mL). The mixture was stirred at 78° C. for 2 h. Afterwards, the precipitate was filtered off and the filtrate was concentrated in vacuo. The residue washed two times with ethanol and partitioned between 1M HCl and AcOEt. The inorganic phase was then washed two times with AcOEt and basified to pH 14. The product was diluted with the mixture of DCM:isopropanol (4:1 v/v) and butanol. The organic layers were combined, dried over Na$_2$SO$_4$, filtered and evaporated in vacuo. The product (0.3 g, 1.69 mmol, yield 54%) as an orange oil was used in the next step without further purification. ESI-MS: 178 [M+H]$^+$ b. [(2-methoxypyridin-4-y)methyl/3-(7H-purin-7-yl)propyl]amine

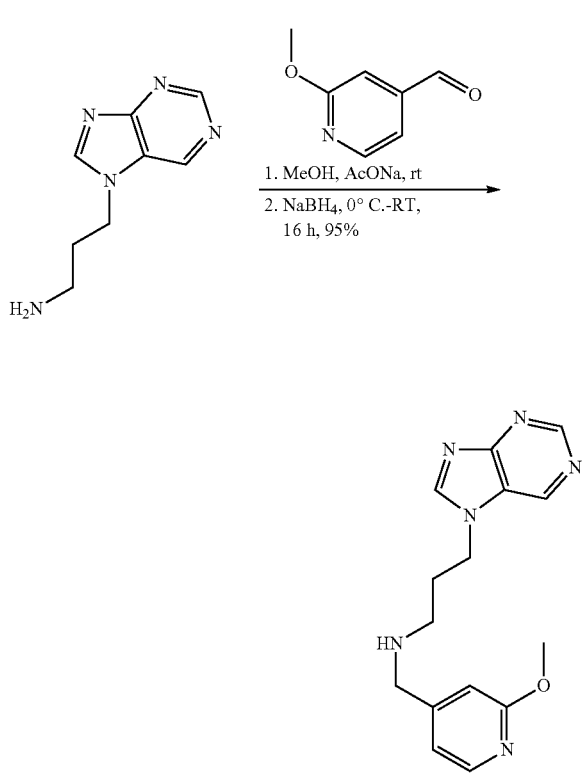

The title compound was synthesized following the approach outlined in Procedure 3 substituting 3-(1H-imidazol-1-yl)propan-1-amine with 3-(7H-purin-7-yl)propan-1-amine and pyridine-4-carboxaldehyde with 2-methoxypyridine-4-carboxaldehyde. Crude product was used in the next step without further purification (0.32 g, 1.07 mmol, yield 95%) as an orange oil. ESI-MS: 299 [M+H]$^+$ c. 3-({[(2-methoxypyridin-4-yl)methyl][3-(7H-purin-7-yl)propyl]amino}methyl)-1-methyl-1,4-dihydroquinolin-4-one

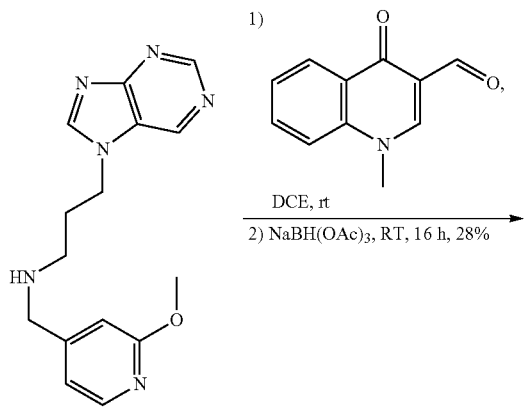

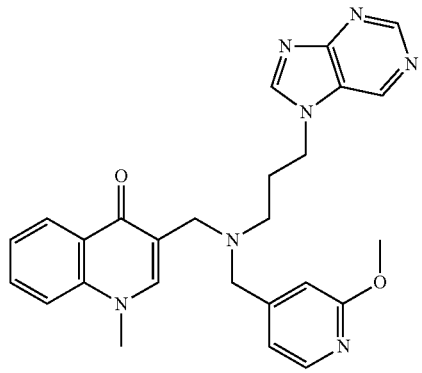

1-methyl-4-oxo-1,4-dihydroquinoline-3-carbaldehyde (0.063 g, 0.3 mmol, 1 eq) and [(2-methoxypyridin-4-yl)methyl][3-(7H-purin-7-yl)propyl]amine (0.100 g, 0.3 mmol, 1 eq) were dissolved in DCE (6 mL) and stirred overnight at rt. After that the reaction mixture was cooled to 0° C. and NaBH(OAc)$_3$. The reaction was continued at rt overnight. After that the solvent was evaporated in vacuo and the residue was purified by RP-FCC (SiC18, H$_2$O: CH$_3$CN) to afford the title compound (0.045 g, 0.1 mmol, yield 28%) as a yellow solid. ESI-MS: 470 [M+H]$^+$ $^1$H NMR (400 MHz, DMSO-d$_6$) δ 9.31 (s, 1H), 8.95 (s, 1H), 8.71 (s, 1H), 8.23 (dd, J=8.1, 1.6 Hz, 1H), 8.00-7.96 (m, 2H), 7.75 (ddd, J=8.6, 6.9, 1.7 Hz, 1H), 7.65 (d, J=8.4 Hz, 1H), 7.41 (ddd, J=8.0, 6.9, 1.0 Hz, 1H), 6.90 (dd, J=5.2, 1.3 Hz, 1H), 6.75 (s, 1H), 4.45 (t, J=7.2 Hz, 2H), 3.83 (s, 3H), 3.78 (s, 3H), 3.56 (s, 2H), 3.50 (s, 2H), 2.42 (t, J=6.6 Hz, 2H), 2.19-2.10 (m, 2H).

Procedure 41. Preparation of 6-(dimethylamino)pyridine-3-carbaldehyde

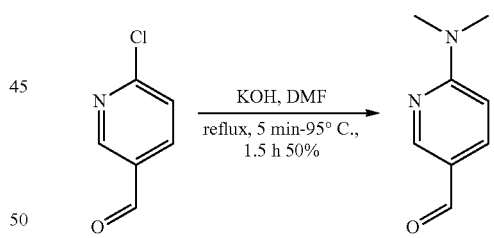

A mixture of DMF (10 mL) and 10M KOH (4 mL) was heated at reflux for 5 min. 6-chloropyridine-3-carbaldehyde (1 g, 7.06 mmol, 1 eq) was added and the resulting mixture was heated for 1.5 h at 95° C. 10 M KOH (1 mL) was added every hour for 3 following hours. The mixture was diluted with water (20 mL) and extracted three times with DCM (20 mL). The combined organic layers were dried over Na$_2$SO$_4$, filtered and concentrated in vacuo. The residue was purified was purified by FCC (SiHP, hexane:AcOEt 100:0 to 0:100) to afford the titled compound (0.534 g, 3.55 mmol, yield 50%) as a yellow solid. ESI-MS: 151.3 [M+H]$^+$ $^1$H NMR (300 MHz, DMSO-d$_6$) δ 9.73 (d, J=0.6 Hz, 1H), 8.58 (dd, J=2.4, 0.7 Hz, 1H), 7.86 (dd, J=9.0, 2.4 Hz, 1H), 6.76 (dd, J=9.1, 0.7 Hz, 1H), 3.16 (s, 6H).

Procedure 42. Preparation of tert-butyl N-[3-(isoquinolin-4-yl)prop-2-yn-1-yl]carbamate

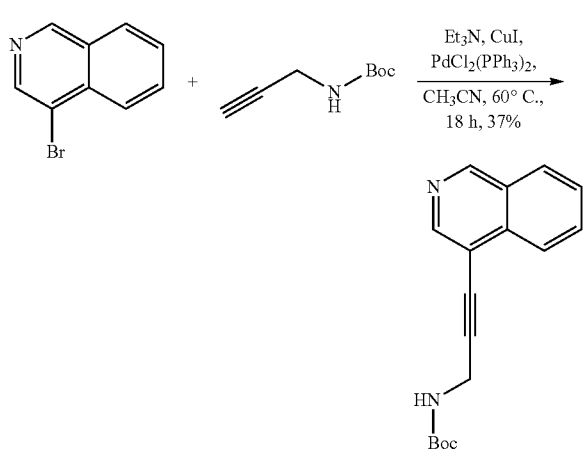

To a solution of tert-butyl N-(prop-2-yn-1-yl)carbamate (0.746 g, 4.806 mmol, 1 eq) in CH$_3$CN were added Et$_3$N (0.670 mL, 4.806 mmol, 1 eq), CuI (0.018 g, 0.096 mmol, 0.02 eq), 4-bromoisoquinoline (1 g, 4.806 mmol, 1 eq) and PdCl$_2$(PPh$_3$)$_2$ (0.034 g, 0.048 mmol, 0.01 eq) under argon. The reaction was carried out at 60° C. After stirring for 18 h, the reaction mixture was diluted with AcOEt (30 mL), washed two times with water (20 mL) and brine (10 mL). The organic layer was dried over Na$_2$SO$_4$ and evaporated and the residue was purified by FCC (SiHP, hexane:AcOEt 100:0 to 30:70) to afford the titled compound (0.508 g, 1.8 mmol, yield 37%) as a brown oil. ESI-MS: 283 [M+H]$^+$ $^1$H NMR (300 MHz, DMSO-d$_6$) δ 9.34 (s, 1H), 8.63 (s, 1H), 8.40-8.06 (m, 2H), 7.91 (ddd, J=8.3, 6.9, 1.3 Hz, 1H), 7.79 (ddd, J=8.2, 7.0, 1.2 Hz, 1H), 7.53 (s, 1H), 4.14 (d, J=5.7 Hz, 2H), 1.44 (s, 9H).

Procedure 43. Preparation of 3-({[3-(1H-imidazol-1-yl)propyl][(pyridin-4-yl)methyl]amino}methyl)-1,4-dihydroquinolin-4-one

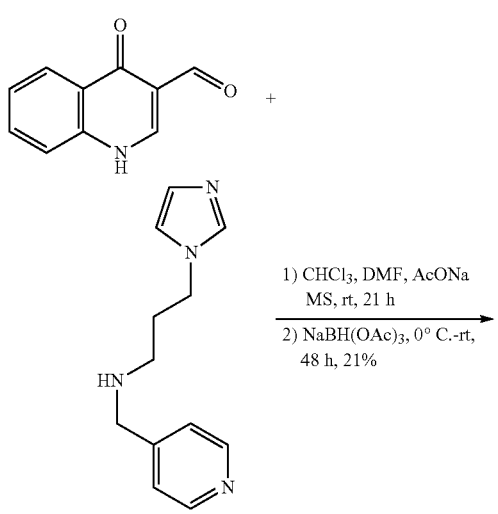

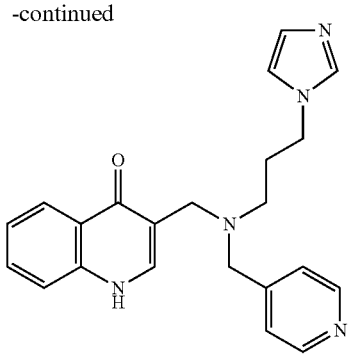

To a suspension of [3-(1H-imidazol-1-yl)propyl][(pyridin-4-yl)methyl]amine (0.066 g, 0.303 mmol, 1.05 eq) in CHCl3/DMF (5:7 v/v) (12 mL) was added 4-oxo-1,4-dihydroquinoline-3-carbaldehyde (0.050 g, 0.289 mmol, 1 eq), glacial acetic acid (0.017 mL) and 3A molecular sieves. After 21 h of stirring the reaction mixture was cooled down to 0° C. and NaBH(OAc)$_3$ (0.086 g, 0.404 mmol, 1.4 eq) was added. The reaction mixture was allowed to reach rt and was stirred for 48 h. Afterwards the reaction was quenched with water (2 mL) and the mixture was filtered through Celite® and was concentrated in vacuo. The residue was dissolved in AcOEt (20 mL) and washed with two times with water (20 mL). The combined aqueous layers were extracted two times with AcOEt (20 mL). The combined organic layers were dried over Na$_2$SO$_4$, filtered and concentrated in vacuo. The residue was purified by FCC (SiHP, DCM:MeOH 100:0 to 85:15) to afford the titled compound (0.023 g, 0.061 mmol, yield 21%) as a colorless oil. ESI-MS: 372 [M+H]$^+$ $^1$H NMR (300 MHz, Methanol-d$_4$) δ 8.46-8.34 (m, 2H), 8.29 (dd, J=8.3, 1.4 Hz, 1H), 7.97 (s, 1H), 7.69 (ddd, J=8.4, 6.9, 1.5 Hz, 1H), 7.63-7.60 (m, 1H), 7.58-7.52 (m, 1H), 7.47-7.36 (m, 3H), 7.18-7.03 (m, 1H), 6.95-6.81 (m, 1H), 4.10 (t, J=6.9 Hz, 2H), 3.70 (s, 2H), 3.65 (s, 2H), 2.52 (t, J=6.8 Hz, 2H), 2.21-1.99 (m, 2H).

Procedure 44. Preparation of 9-(3-{[(pyridin-4-yl)methyl][(2,7,8-trimethyl-4-oxo-4H-chromen-3-yl)methyl]amino}propyl)-6,9-dihydro-1H-purin-6-one

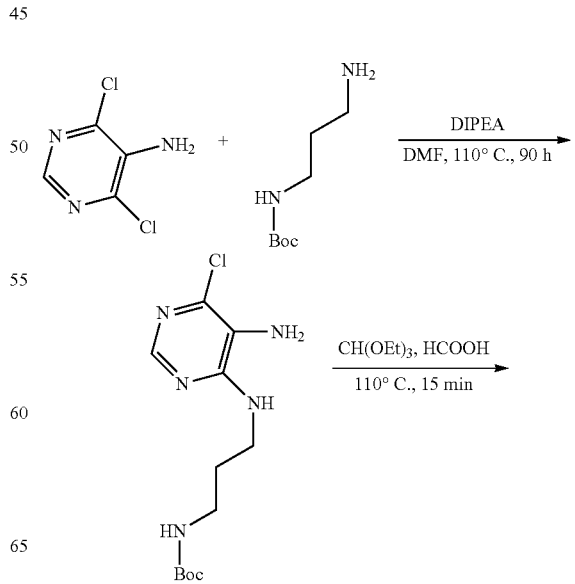

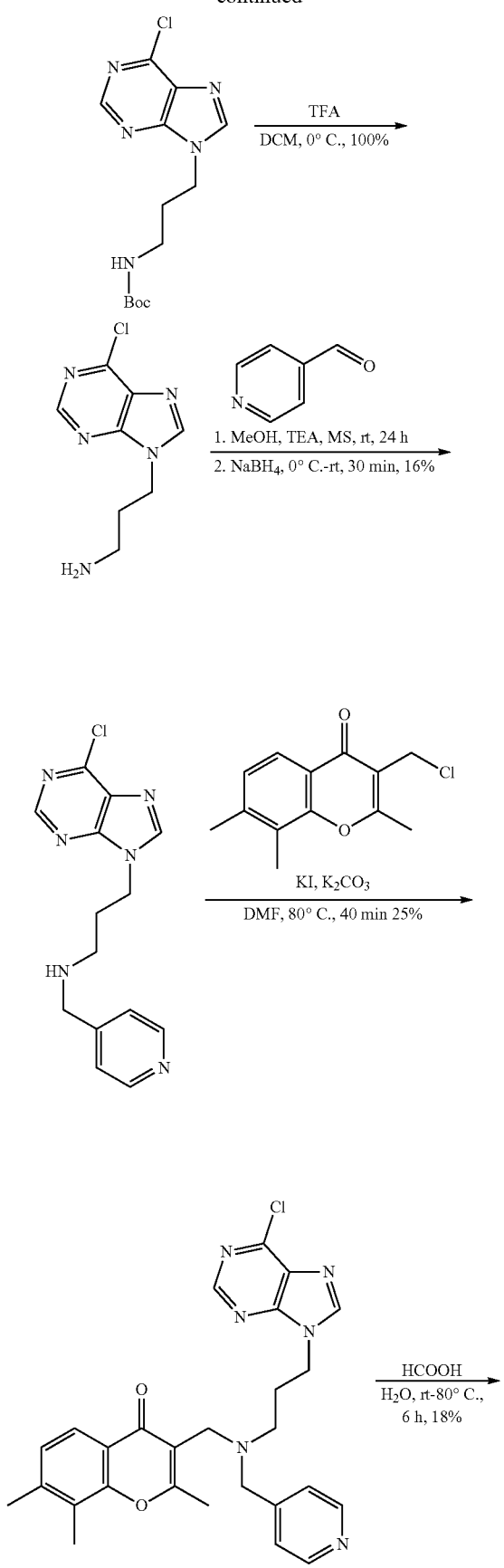

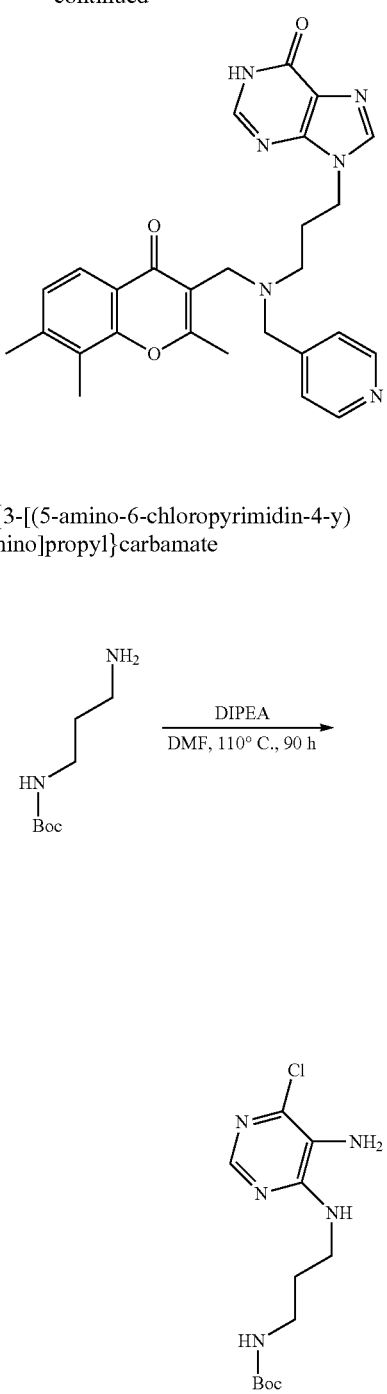

a. tert-butyl N-{3-[(5-amino-6-chloropyrimidin-4-y) amino]propyl}carbamate

A mixture of 4,6-dichloropyrimidin-5-amine (2 g, 12.17 mmol, 1 eq), tert-butyl N-(3-aminopropyl)carbamate (2.55 g, 14.63 mmol, 1.2 eq) and DMF was heated in a sealed tube at 110° C. for 90 h. The mixture was diluted with AcOEt, washed with water two times and brine. The organic layer was dried over MgSO₄ and evaporated. The crude product was used in the next step without purification. ESI-MS: 302 [M+H]⁺ b. tert-butyl N-[3-(6-chloro-9H-purin-9-yl)propyl]carbamate

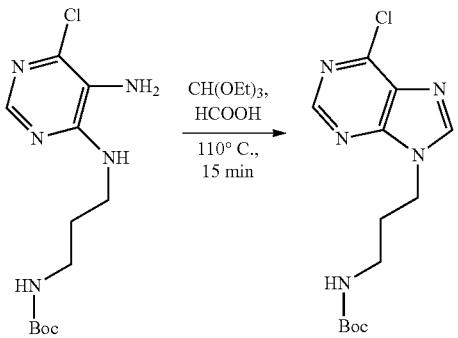 [SMILES: CC(C)(C)OC(=O)NCCCNc1ncnc(Cl)c1N ; CC(C)(C)OC(=O)NCCCn1cnc2c(Cl)ncnc21]

A mixture of tert-butyl {3-[(5-amino-6-chloropyrimidin-4-yl)amino]propyl}carbamate (3.5 g, 11.59 mmol), triethyl orthoformate (60 mL) and formic acid (6 mL) was heated at 110° C. for 15 h. The reaction mixture was evaporated. The residue was dissolved in AcOEt, washed twice with water (20 mL), brine (10 mL), dried over $Na_2SO_4$, filtered and evaporated. The residue was purified twice by FCC (SiHP, hexane: AcOEt 100:0 to 0:100) to afford the titled compound (1.4 g, 4.49 mmol, yield 38.7% over two steps) as a yellow oil. ESI-MS: 312 $[M+H]^+$ $^1$H NMR (300 MHz, DMSO-$d_6$) δ 8.79 (s, 1H), 8.72 (s, 1H), 6.93 (t, J=5.7 Hz, 1H), 4.30 (t, J=6.9 Hz, 2H), 2.95 (q, J=6.4 Hz, 2H), 2.11-1.84 (m, 2H), 1.37 (s, 9H).

c. 3-(6-chloro-9H-purin-9-yl)propan-1-amine

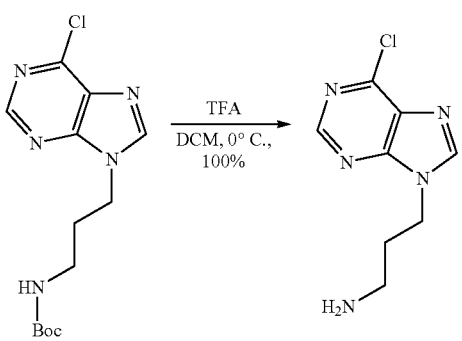 [SMILES: CC(C)(C)OC(=O)NCCCn1cnc2c(Cl)ncnc21 ; NCCCn1cnc2c(Cl)ncnc21]

tert-butyl N-[3-(6-chloro-9H-purin-9-yl)propyl]carbamate was dissolved in DCM (10 mL) and then TFA/DCM 1:1 mixture (10 mL) was added at 0° C. After 1 h the mixture was evaporated and dried on high vacuum. The crude product (0.56 g, 1.28 mmol, 100%) as TFA salt (brownish oil) was used in the next step without purification. ESI-MS: 212 $[M+H]^+$ d. [3-(6-chloro-9H-purin-9-yl)propyl][(pyridin-4-yl)methyl]amine

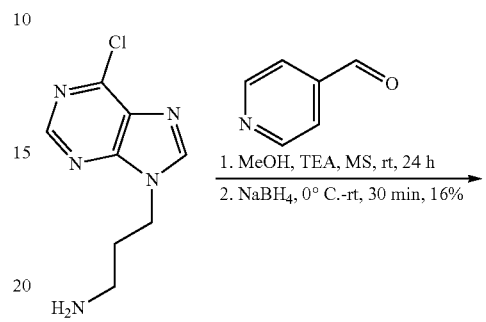

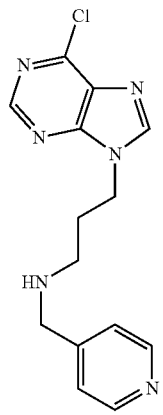

To a solution of TFA salt of 3-(6-chloro-9H-purin-9-yl)propan-1-amine (0.564 g, 1.28 mmol, 1 eq) in anh. MeOH (10 mL) were added pyridine-4-carbaldehyde (0.127 mL, 1.35 mmol, 1.05 eq) and activated molecular sieves 3 Å under argon. After 24 h of stirring the reaction mixture was cooled down to 0° C. and $NaBH_4$ (0.049 g, 1.28 mmol, 1 eq) was added and the reaction mixture was allowed to reach rt. After 30 min the reaction mixture was quenched with water (1 mL) at 0° C., filtered through Celite® and concentrated in vacuo. The residue was dissolved in DCM (20 mL), washed two times with water (20 mL). The combined aqueous layers were extracted two times with DCM (20 mL). The combined organic layers were dried over $Na_2SO_4$, filtered and concentrated in vacuo. The residue was purified by FCC (SiHP, DCM:MeOH 100:0 to 85:15) to afford the titled compound (0.065 g, 0.21 mmol, yield 16%) as an orange oil. ESI-MS: 303 $[M+H]^+$

113 e. 3-({[3-(6-chloro-9H-purin-9-yl)propyl][(pyridin-4-yl)methyl]amino}methyl)-2,7,8-trimethyl-4H-chromen-4-one

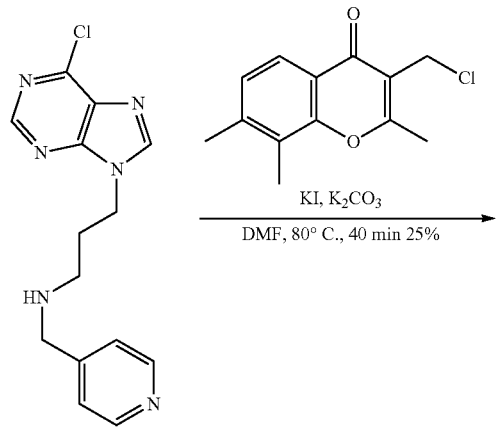

A mixture of [3-(6-chloro-9H-purin-9-yl)propyl][(pyridin-4-yl)methyl]amine (0.065 g, 0.21 mmol, 1 eq), 3-(chloromethyl)-2,7,8-trimethyl-4H-chromen-4-one (0,053 g, 0.22 mmol, 1.05 eq), KI (0.037 g, 0.22 mmol, 1.05 eq), $K_2CO_3$ (0.089 g, 0.64 mmol, 3 eq) and DMF (5 mL) was heated at 80° C. for 40 min. The reaction mixture was diluted with AcOEt (20 mL) and washed two times with water (20 mL), dried over $Na_2SO_4$, filtered and evaporate. The residue was purified by FCC (SiHP, DCM:MeOH 100:0 to 95:5) to afford the titled compound (0.028 g, 0.05 mmol, yield 25%) as a brown oil. ESI-MS: 503 [M+H]$^+$

114 f. 9-(3-{[(pyridin-4-yl)methyl][(2,7,8-trimethyl-4-oxo-4H-chromen-3-yl)methyl]amino}propyl)-6,9-dihydro-1H-purin-6-one

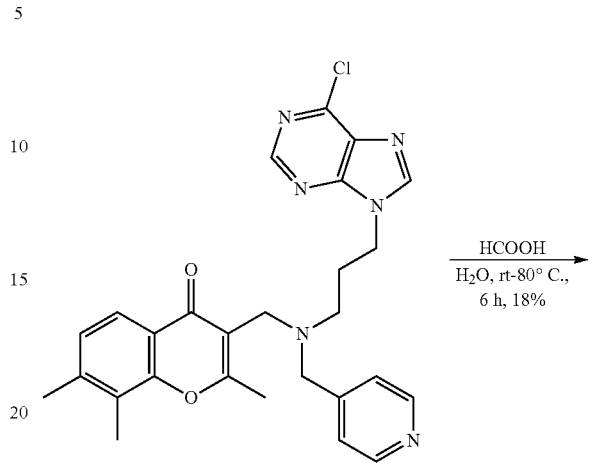

A solution of 3-({[3-(6-chloro-9H-purin-9-yl)propyl][(pyridin-4-yl)methyl]amino}methyl)-2,7,8-trimethyl-4H-chromen-4-one (0.028 g, 0.05 mmol) in 50% formic acid (1 mL) was stirred at rt for 1 h. Then temperature was increased to 40° C. and the reaction mixture was stirred for additional 3 h. Afterwards the mixture was concentrated in vacuo. The residue was purified by FCC (SiHP, DCM:MeOH 100:0 to 85:15) to afford the titled compound (0.005 g, 0.01 mmol, yield 18%) as a colorless oil. ESI-MS: 485 [M+H]

$^1$H NMR (300 MHz, Chloroform-d) δ 8.60-8.37 (m, 2H), 8.09 (s, 1H), 7.94 (d, J=8.1 Hz, 1H), 7.85 (s, 1H), 7.27-6.98 (m, 3H), 4.46-4.06 (m, 2H), 3.62 (s, 2H), 3.59 (s, 2H), 2.58 (t, J=6.7 Hz, 2H), 2.49 (s, 3H), 2.42 (s, 3H), 2.38 (s, 3H), 2.16 (p, J=7.0 Hz, 2H).

Procedure 45. Preparation of 3-({[3-(6-amino-9H-purin-9-yl)propyl][(pyridin-4-yl)methyl]amino}methyl)-2,7,8-trimethyl-4H-chromen-4-one

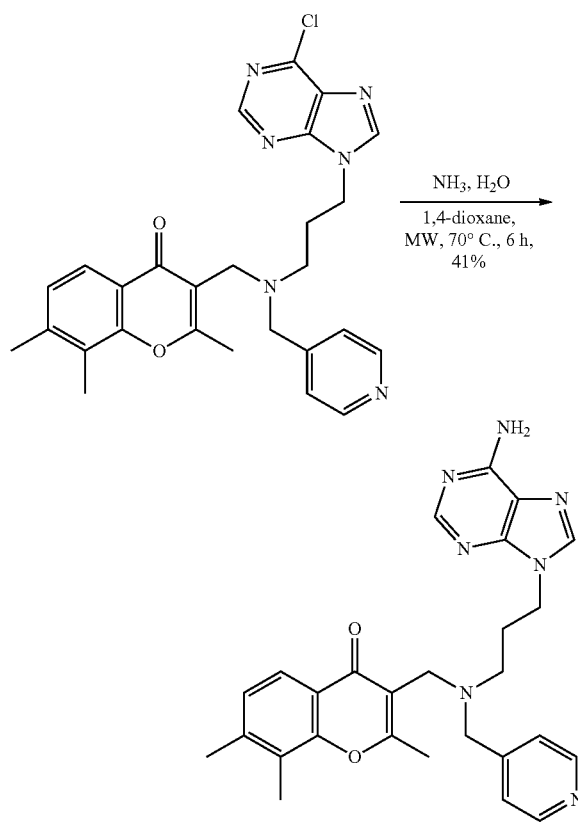

To a solution of 3-({[3-(6-chloro-9H-purin-9-yl)propyl][(pyridin-4-yl)methyl]amino}methyl)-2,7,8-trimethyl-4H-chromen-4-one (0.020 g, 0.04 mmol) in 1,4-dioxane (1 mL) placed in microwave tube 28% aqueous ammonia solution was added (2 mL) and the reaction mixture was heated by microwave irradiation at 70° C. for 6 h. Then the mixture was concentrated in vacuo and the residue was purified by FCC (SiHP, DCM:MeOH 100:0 to 90:10) to afford the titled compound (8 mg, 0.016 mmol, yield 41%) as a white solid after lyophilization. ESI-MS: 484 [M+H]+

$^1$H NMR (300 MHz, Methanol-$d_4$) δ 8.42-8.31 (m, 2H), 8.14 (s, 1H), 8.05 (s, 1H), 7.75 (d, J=8.1 Hz, 1H), 7.55-7.34 (m, 2H), 7.22 (d, J=8.2 Hz, 1H), 4.25 (t, J=6.8 Hz, 2H), 3.66 (s, 2H), 3.56 (s, 2H), 2.54 (t, J=6.8 Hz, 2H), 2.45 (s, 3H), 2.43 (s, 3H), 2.36 (s, 3H), 2.19 (p, J=6.8 Hz, 2H).

Procedure 46. Preparation of 1-(3-{[(2-methoxypyridin-4-yl)methyl][(1-methyl-4-oxo-1,4-dihydroquinolin-3-yl)methyl]amino}propyl)-1H-1,2,3-triazole-4-carboxamide

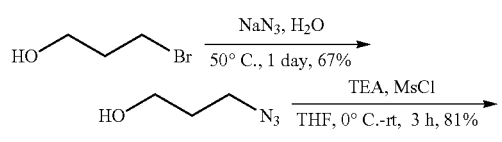

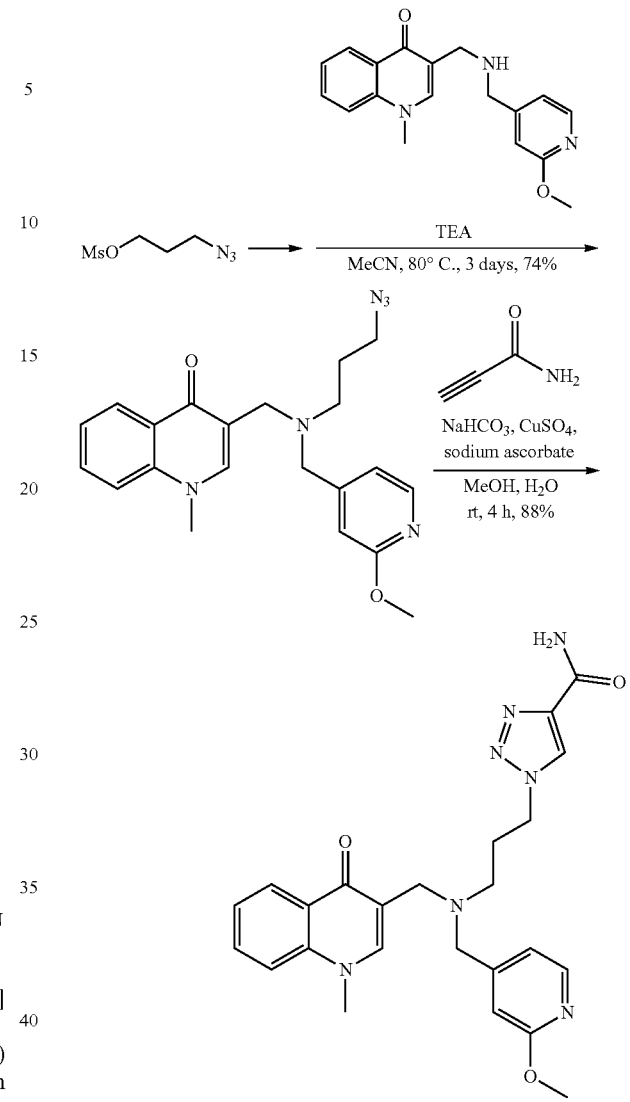

a. 3-azidopropan-1-ol

To a solution of 3-bromo-1-propanol (1 g, 7.2 mmol, 1 eq.) in water (10 mL), sodium azide (935 mg, 14.4 mmol, 2 eq.) was added. The reaction was carried out at 50° C. for 24 h. The resulting mixture was cooled down to rt and partitioned between DCM (300 mL) and water (300 mL). Organic layer was dried over magnesium sulfate, filtered off and concentrated in vacuo. The residue was purified by FCC (SiHP, Hexane:AcOEt 7:3) to afford the title compound as a transparent oil (490 mg, 4.85 mmol yield 67%).

$^1$H NMR (300 MHz, Chloroform-d) δ 4.05-3.69 (m, 2H), 3.53-3.32 (m, 2H), 2.09-1.75 (m, 2H).

b. 3-azidopropyl methanesulfonate

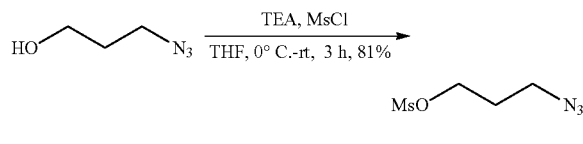

To a solution of 3-azidopropan-1-ol (490 mg, 4.85 mmol, 1 eq) in anhydrous THF (15 mL), TEA (1.1 mL, 7.8 mmol, 1.6 eq) was added. Reaction mixture was cooled to 0° C. and methanesulfonyl chloride (0.56 mL, 7.3 mmol, 1.5 eq) was added dropwise. Reaction was allowed to warm to rt and stirred for 3 h. The resulting mixture was partitioned between DCM (200 mL) and sat. NaHCO$_3$(200 mL). Organic layer was washed with brine (100 mL), dried over magnesium sulfate, filtered off and concentrated in vacuo. The residue was purified by FCC (SiHP, Hexane:AcOEt 7:3) to afford the title compound as a transparent oil (705 mg, 3.93 mmol, yield 81%).

c. 3-{[(3-azidopropyl)[(2-methoxypyridin-4-yl)methyl]amino]methyl}-1-methyl-1,4-dihydroquinolin-4-one

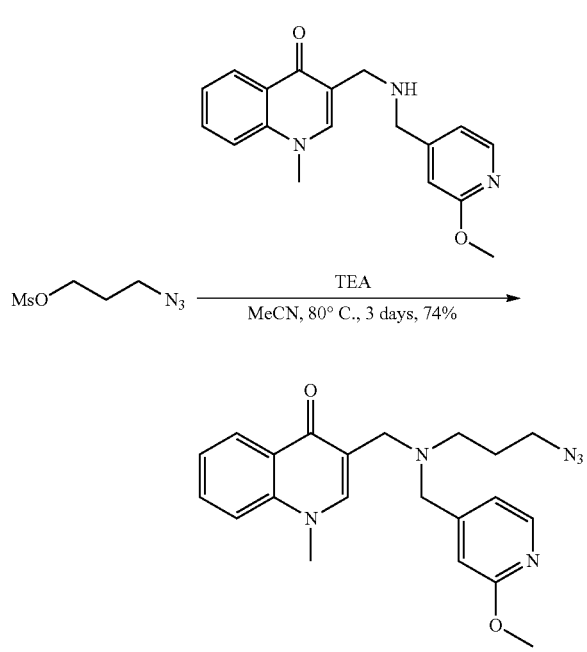 [SMILES: COc1cc(CNCc2cn(C)c3ccccc3c2=O)ccn1 ; CS(=O)(=O)OCCCN=[N+]=[N-] ; COc1cc(CN(CCCN=[N+]=[N-])Cc2cn(C)c3ccccc3c2=O)ccn1]

To a stirred solution of 3-({[(2-methoxypyridin-4-yl)methyl]amino}methyl)-1-methyl-1,4-dihydroquinolin-4-one (300 mg, 0.97 mmol, 1 eq) and 3-azidopropyl methanesulfonate (348 mg, 1.94 mmol, 2 eq) in anhydrous MeCN (5 mL), TEA (27 µL, 1.94 mmol, 2 eq) was added. The reaction was carried out at 80° C. for 72 h. Solvent was evaporated under reduced pressure. The residue was purified by FCC (SiHP, DCM: MeOH 95:5) to afford the product (270 mg, 0.71 mmol, yield 74%) as a transparent oil. ESI-MS: 393 [M+H]$^+$ d. 1-(3-{[(2-methoxypyridin-4-yl)methyl][(1-methyl-4-oxo-1,4-dihydroquinolin-3-yl)methyl]amino}propyl)-1H-1,2,3-triazole-4-carboxamide

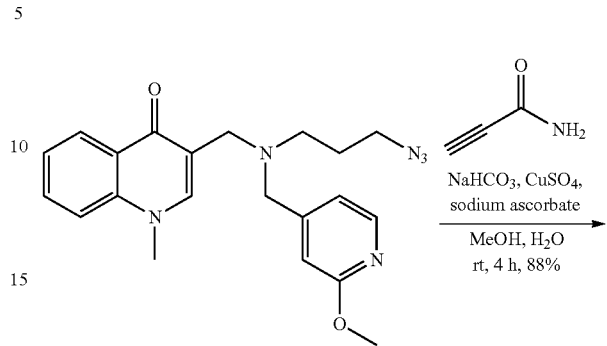

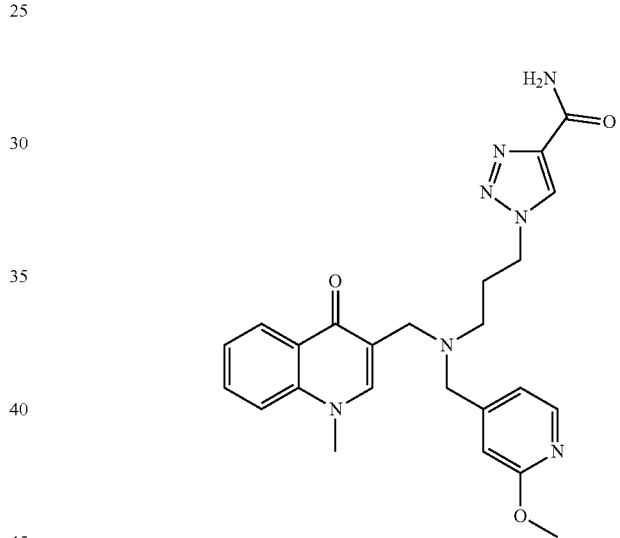

To a stirred solution of 3-{[(3-azidopropyl)[(2-methoxypyridin-4-yl)methyl]amino]methyl}-1-methyl-1,4-dihydroquinolin-4-one (88 mg, 0.22 mmol, 1 eq) in a mixture of MeOH and water (v/v 1:1), propriolamide (19 mg, 0.27 mmol, 1.2 eq) was added. Then saturated NaHCO$_3$ (19 mg, 0.23 mmol, 1.01 eq.), CuSO$_4$.5H$_2$O (2 mg, 0.008 mmol, 0.05 eq) and sodium ascorbate (5 mg, 0.025 mmol, 0.25 eq) were added. The reaction was carried out at rt for 4 h. The resulting solution was filtered through Celite® pad and concentrated under reduced pressure. The residue was purified by FCC (SiHP, DCM:MeOH 9:1) to give the product (91 mg, 0.20 mmol, yield 88%) as a white solid. ESI-MS: 462 [M+H]$^+$ $^1$H NMR (300 MHz, DMSO-d$_6$) δ 8.54 (s, 1H), 8.21 (dd, J=8.1, 1.6 Hz, 1H), 8.02 (d, J=5.2 Hz, 1H), 7.98 (s, 1H), 7.81-7.69 (m, 2H), 7.65 (d, J=8.5 Hz, 1H), 7.47-7.32 (m, 2H), 6.95 (dd, J=5.3, 1.3 Hz, 1H), 6.78 (s, 1H), 4.48 (t, J=7.0 Hz, 2H), 3.86 (s, 3H), 3.79 (s, 3H), 3.57 (s, 2H), 3.49 (s, 2H), 2.44-2.35 (m, 2H), 2.20-2.05 (m, 2H).

Preparation Examples

Example 1. 3-({[4-(1H-imidazol-1-yl)butyl](pyridin-4-ylmethyl)amino}methyl)-4H-chromen-4-one

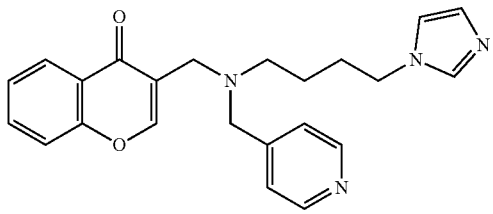 [SMILES: O=c1c(CN(CCCCn2ccnc2)Cc2ccncc2)coc2ccccc12]

Preparation of [4-(1H-imidazol-1-yl)butyl](pyridin-4-ylmethyl)amine

The title compound was synthesized following the approach outlined in Procedure 3 substituting 3-(1H-imidazol-1-yl)propan-1-amine with 4-(1H-imidazol-1-yl)butan-1-amine. The residue was purified by FCC (Si—CN, DCM: MeOH 95:5) to afford the product (40 mg, 0.174 mmol, yield 37%) as a transparent oil. ESI-MS: 231 [M+H]$^+$ $^1$H NMR (400 MHz, Chloroform-d) δ 8.57 (s, 2H), 7.50 (s, 1H), 7.27 (s, 2H), 7.08-7.08 (m, 1H), 6.93-6.91 (m, 1H), 3.98 (t, J=7.0 Hz, 2H), 3.81 (s, 2H), 2.65 (t, J=7.0 Hz, 2H), 1.90-1.85 (m, 2H), 1.55-1.50 (m, 2H).

Preparation of 3-({[4-(1H-imidazol-1-yl)butyl](pyridin-4-ylmethyl)amino}methyl)-4H-chromen-4-one The title compound was synthesized following the approach outlined in Procedure 9.2 substituting [3-(1H-imidazol-1-yl)propyl](pyridin-4-ylmethyl)amine with [4-(1H-imidazol-1-yl)butyl](pyridin-4-ylmethyl)amine and 7,8-dimethyl-4-oxo-4H-chromene-3-carbaldehyde with 4-oxo-4H-chromene-3-carbaldehyde. The residue was purified by FCC (Si-Diol, DCM: MeOH 98:2) to afford the product (8 mg, 0.021 mmol, yield 12%) as a yellow oil. ESI-MS: 389 [M+H]$^+$ $^1$H NMR (400 MHz, DMSO-d$_6$) δ 8.48-8.44 (m, 2H), 8.32 (s, 1H), 8.07 (dd, J=8.0, 1.7 Hz, 1H), 7.80 (ddd, J=8.7, 7.1, 1.7 Hz, 1H), 7.64 (dd, J=8.5, 1.0 Hz, 1H), 7.57 (s, 1H), 7.49 (ddd, J=8.1, 7.1, 1.1 Hz, 1H), 7.38-7.34 (m, 2H), 7.11 (s, 1H), 6.85 (s, 1H), 3.90 (t, J=7.1 Hz, 2H), 3.62 (s, 2H), 3.45 (s, 2H), 2.42 (t, J=7.1 Hz, 2H), 1.76-1.61 (m, 2H), 1.50-1.37 (m, 2H).

Example 2. 3-({[(pyridin-4-yl)methyl][3-(1H-pyrrol-1-yl)propyl]amino}methyl)-4H-chromen-4-one

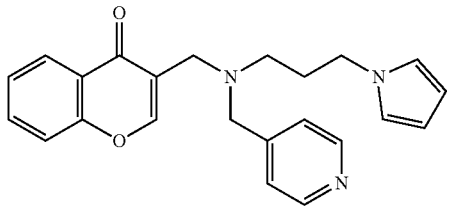 [SMILES: O=c1c(CN(CCCn2cccc2)Cc2ccncc2)coc2ccccc12]

Preparation of [3-(1H-pyrrol-1-yl)propyl][(pyridin-4-yl)methyl]amine

The title compound was synthesized following the approach outlined in Procedure 3 substituting 3-(1H-imidazol-1-yl)propan-1-amine with 3-(1H-pyrrol-1-yl)propan-1-amine. Crude product (yellowish oil) was used for the next step without further purification (0.535 g, 2.24 mmol, yield 96%). ESI-MS: 216 [M+H]$^+$ Preparation of 3-({[(pyridin-4-yl)methyl][3-(1H-pyrrol-1-yl)propyl]amino}methyl)-4H-chromen-4-one The title compound was synthesized following the approach outlined in Procedure 9.2 substituting 7,8-dimethyl-4-oxo-4H-chromene-3-carbaldehyde with 4-oxo-4H-chromene-3-carbaldehyde, and [3-(1H-imidazol-1-yl)propyl](pyridin-4-ylmethyl)amine with [3-(1H-pyrrol-1-yl)propyl][(pyridin-4-yl)methyl]amine. The residue was purified by FCC (SiHP, DCM: MeOH 9:1) to afford the title compound (211 mg, 0.54 mmol, yield 47%) as a yellow oil. ESI-MS: 374 [M+H]$^+$ $^1$H NMR (300 MHz, DMSO-d$_6$) δ 8.50-8.42 (m, 2H), 8.30 (s, 1H), 8.09 (dd, J=8.0, 1.6 Hz, 1H), 7.81 (ddd, J=8.7, 7.1, 1.7 Hz, 1H), 7.64 (dd, J=8.6, 1.0 Hz, 1H), 7.49 (ddd, J=8.1, 7.1, 1.1 Hz, 1H), 7.41-7.33 (m, 2H), 6.66-6.64 (m, 2H), 5.86-5.84 (m, 2H), 3.88 (t, J=7.0 Hz, 2H), 3.64 (s, 2H), 3.45 (s, 2H), 2.37 (t, J=6.8 Hz, 2H), 1.99-1.83 (m, 2H).

Example 3. 3-({[3-(1H-pyrazol-1-yl)propyl](pyridin-4-ylmethyl)amino}methyl)-4H-chromen-4-one

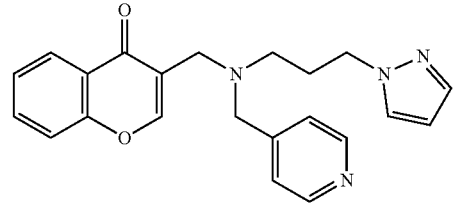 [SMILES: O=c1c(CN(CCCn2cccn2)Cc2ccncc2)coc2ccccc12]

Preparation of [3-(1H-pyrazol-1-yl)propyl](pyridin-4-ylmethyl)amine

The title compound was synthesized following the approach outlined in Procedure 3 substituting 3-(1H-imidazol-1-yl)propan-1-amine with 3-(1H-pyrazol-1-yl)propan-1-amine to afford the product (474 mg, 2.192 mmol, yield 100%) as a yellow oil. ESI-MS: 217 [M+H]$^+$ $^1$H NMR (300 MHz, DMSO-d$_6$) δ 8.50-8.44 (m, 2H), 7.68 (dd, J=2.2, 0.7 Hz, 1H), 7.41 (dd, J=1.9, 0.7 Hz, 1H), 7.36-7.30 (m, 2H), 6.22-6.18 (m, 1H), 4.17 (t, J=7.0 Hz, 2H), 3.69 (s, 2H), 2.41 (t, J=6.8 Hz, 2H), 2.33 (s, 1H), 1.99-1.83 (m, 2H).

Preparation of 3-({[3-(1H-pyrazol-1-yl)propyl](pyridin-4-ylmethyl)amino}methyl)-4H-chromen-4-one The title compound was synthesized following the approach outlined in Procedure 9.2 substituting [3-(1H-imidazol-1-yl)propyl](pyridin-4-ylmethyl)amine with [3-(1H-pyrazol-1-yl)propyl](pyridin-4-ylmethyl)amine, and 7,8-dimethyl-4-oxo-4H-chromene-3-carbaldehyde with 4-oxo-4H-chromene-3-carbaldehyde. The residue was purified by FCC (deactivated SiHP, DCM: MeOH 96:4) to afford the product (184 mg, 0.491 mmol, yield 70%) as a yellow oil. ESI-MS: 375 [M+H]+

$^1$H NMR (300 MHz, DMSO-d$_6$) δ 8.48-8.42 (m, 2H), 8.30 (s, 1H), 8.07 (dd, J=8.0, 1.7 Hz, 1H), 7.80 (ddd, J=8.6, 7.1, 1.7 Hz, 1H), 7.65-7.57 (m, 2H), 7.48 (ddd, J=8.1, 7.1, 1.1 Hz, 1H), 7.38-7.31 (m, 3H), 6.08-6.06 (m, 1H), 4.12 (t, J=6.8 Hz, 2H), 3.63 (s, 2H), 3.44 (s, 2H), 2.37 (t, J=6.8 Hz, 2H), 2.08-1.93 (m, 2H).

Example 4. 3-{[(pyridin-4-ylmethyl)[3-(1H-1,2,3-triazol-1-yl)propyl]amino]methyl}-4H-chromen-4-one

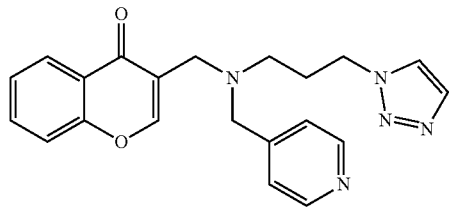 [SMILES: O=c1c(CN(CCCn2ccnn2)Cc2ccncc2)coc2ccccc12]

Preparation of (pyridin-4-ylmethyl)[3-(1H1,2,3-triazol-1-yl)propyl]amine

The title compound was synthesized following the approach outlined in Procedure 3 substituting 3-(1H-imidazol-1-yl)propan-1-amine with 3-(1H1,2,3-triazol-1-yl)propan-1-amine to afford the product (427 mg, 1.96 mmol, 70%) as a yellow oil. ESI-MS: 218 [M+H]+

Preparation of 3-{[(pyridin-4-ylmethyl)[3-(1H1,2,3-triazol-1-yl)propyl]amino]methyl}-4H chromen-4-one hydrochloride The title compound was synthesized following the approach outlined in Procedure 9.1 substituting 3-(chloromethyl)-7,8-dimethyl-4H-chromen-4-one with 3-(chloromethyl)-4H-chromen-4-one, and [3-(1H-imidazol-1-yl)propyl](pyridin-4-ylmethyl)amine with (pyridin-4-ylmethyl)[3-(1H1,2,3-triazol-1-yl)propyl]amine. The residue was purified by FCC (SiHP, AcOEt: MeOH 4:1) to afford the title compound (60 mg, 0.160 mmol, yield 31%) as a yellow oil. ESI-MS: 376 [M+H]+

The product was converted into hydrochloric acid salt using Procedure 10. Product as a yellow solid. ESI-MS: 376 [M+H]+

$^1$H NMR (400 MHz, DMSO-d$_6$) δ 12.13 (bs, 1H), 8.96 (d, J=6.0 Hz, 2H), 8.79 (s, 1H), 8.36 (s, 2H), 8.17-8.06 (m, 2H), 7.92-7.84 (m, 1H), 7.74 (d, J=8.3 Hz, 1H), 7.69 (d, J=0.8 Hz, 1H), 7.60-7.51 (m, 1H), 4.62 (bs, 2H), 4.45 (t, J=6.8 Hz, 2H), 4.19 (bs, 2H), 2.98 (bs, 2H), 2.44 (bs, 2H).

Example 5. 3-({[3-(1H-imidazol-1-yl)propyl](pyridin-4-ylmethyl)amino}methyl)-7,8-dimethyl-4H-chromen-4-one

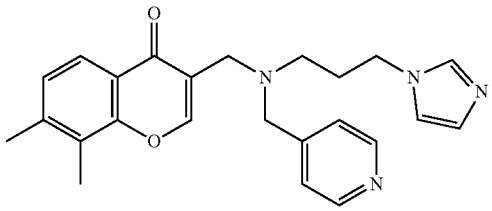 [SMILES: Cc1ccc2c(=O)c(CN(CCCn3ccnc3)Cc3ccncc3)coc2c1C]

The title compound was synthesized according to Procedure 9.1. Product as yellow oil (114 mg, 0.283 mmol, yield 32%). ESI-MS: 404 [M+H]+.

The product was converted into hydrochloric acid salt following Procedure 10.

$^1$H NMR (300 MHz, Deuterium Oxide) δ 8.73-8.70 (m, 1H), 8.65-8.60 (m, 2H), 8.32 (s, 1H), 8.09-8.04 (m, 2H), 7.70 (d, J=8.2 Hz, 1H), 7.48-7.43 (m, 1H), 7.36-7.30 (m, 2H), 4.53 (s, 2H), 4.30 (t, J=7.0 Hz, 2H), 4.10 (s, 2H), 3.22-3.12 (m, 2H), 2.51-2.38 (m, 2H), 2.38 (s, 3H), 2.32 (s, 3H).

Example 6. 3-({[3-(pyridin-2-yl)propyl][(pyridin-4-yl)methyl]amino}methyl)-4H-chromen-4-one

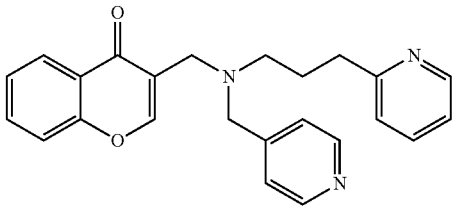 [SMILES: O=c1c(CN(CCCc2ccccn2)Cc2ccncc2)coc2ccccc12]

Preparation of [3-(pyridin-2-yl)propyl][(pyridin-4-yl)methyl]amine

The title compound was synthesized following the approach outlined in Procedure 3 substituting 3-(1H-imidazol-1-yl)propan-1-amine with (3-pyridin-2-ylpropyl)amine. Crude product was used for the next step without further purification. Product as a yellow oil (320 mg, 1.39 mmol, yield 99%). ESI-MS: 228 [M+H]+

$^1$H NMR (400 MHz, DMSO-d$_6$) δ 8.49-8.46 (m, 2H), 8.46-8.45 (m, 1H), 7.71-7.63 (m, 1H), 7.34-7.32 (m, 2H), 7.25-7.22 (m, 1H), 7.20-7.15 (m, 1H), 3.70 (s, 2H), 2.79-2.73 (m, 2H), 2.50-2.46 (m, 2H), 2.32 (s, 1H), 1.88-1.77 (m, 2H).

Preparation of 3-({[3-(pyridin-2-yl)propyl][(pyridin-4-yl)methyl]amino}methyl)-4H-chromen-4-one The title compound was synthesized following the approach outlined in Procedure 9.1 substituting 3-(chloromethyl)-7,8-dimethyl-4H-chromen-4-one with 3-(chloromethyl)-4H-chromen-4-one and [3-(1H-imidazol-1-yl)propyl](pyridin-4-ylmethyl)amine with [3-(pyridin-2-yl)propyl][(pyridin-4-yl)methyl]amine. The residue was purified by prep-HPLC to afford the title compound (35 mg, 0.086 mmol, yield 59%) as an orange oil. ESI-MS: 386 [M+H]+

$^1$H NMR (300 MHz, DMSO-d$_6$) δ 8.49-8.43 (m, 2H), 8.42-8.36 (m, 1H), 8.31 (s, 1H), 8.11-8.04 (m, 1H), 7.84-7.77 (m, 1H), 7.66-7.61 (m, 1H), 7.61-7.53 (m, 1H), 7.53-7.45 (m, 1H), 7.41-7.33 (m, 2H), 7.21-7.15 (m, 1H), 7.15-7.07 (m, 1H), 3.65 (s, 2H), 3.47 (s, 2H), 2.72 (t, J=7.1 Hz, 2H), 2.44 (t, J=7.1 Hz, 2H), 2.01-1.81 (m, 2H).

The product was converted into hydrochloric acid salt following Procedure 10. ESI-MS: 386 [M+H]+

$^1$H NMR (400 MHz, DMSO-d$_6$) δ 8.91 (d, J=5.8 Hz, 2H), 8.86-8.75 (m, 2H), 8.53-8.44 (m, 1H), 8.32-8.21 (m, 2H), 8.11-8.04 (m, 1H), 7.95 (d, J=8.0 Hz, 1H), 7.91-7.83 (m, 2H), 7.77-7.68 (m, 1H), 7.61-7.52 (m, 1H), 4.52 (s, 2H), 4.11 (s, 2H), 3.11 (t, J=7.7 Hz, 2H), 3.08-2.87 (m, 2H), 2.43-2.26 (m, 2H).

Example 7. 3-({[3-(1H-imidazol-1-yl)propyl](pyridin-4-ylmethyl)amino}methyl)-4H benzo[h]chromen-4-one

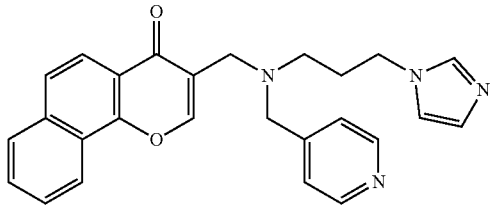 [SMILES: O=c1c(CN(CCCn2ccnc2)Cc2ccncc2)coc2c1ccc1ccccc12]

Preparation of 2-hydroxy-2H,3H,4H-naphtho[1,2-b]pyran-4-one

The title compound was prepared according to Procedure 1a. substituting 1-(2-hydroxyphenyl)ethan-1-one with 1-(1-hydroxynaphthalen-2-yl)ethan-1-one. Product as a white solid (1.1 g, 5.13 mmol, yield 96%). ESI-MS: 215 [M+H]+

$^1$H NMR (400 MHz, DMSO-d$_6$): δ8.27 (d, J=8.3 Hz, 1H), 7.94 (d, J=8.1 Hz, 1H), 7.87 (d, J=5.2 Hz, 1H), 7.77-7.68 (m, 2H), 7.65-7.61 (m, 1H), 7.52 (d, J=8.6 Hz, 1H), 6.09-6.05 (m, 1H), 3.18-3.12 (m, 1H), 2.85-2.79 (m, 1H).

Preparation of 3-(hydroxymethyl)-4H-benzo[h]chromen-4-one

The title compound was prepared according to Procedure 1b. substituting 2-hydroxy-3,4-dihydro-2H1-benzopyran-4-one with 2-hydroxy-2H,3H,4H-naphtho[1,2-b]pyran-4-one. Crude material was purified by FCC (SiHP, Hexane: AcOEt 50%) to afford the title compound as a white solid (350 mg, 1.53 mmol, yield 30%). ESI-MS: 227 [M+H]+

$^1$H NMR (300 MHz, DMSO-d$_6$): δ 8.55-8.47 (m, 1H), 8.44-8.38 (m, 1H), 8.14-8.10 (m, 1H), 8.03 (d, J=8.7 Hz, 1H), 7.94 (d, J=8.8 Hz, 1H), 7.84-7.78 (m, 2H), 5.25-5.21 (m, 1H), 4.48-4.46 (m, 2H).

Preparation of 3-(chloromethyl)-4H-benzo[h]chromen-4-one

The title compound was prepared according to Procedure 1c substituting 3-(hydroxymethyl)-4H-chromen-4-one with 3-(hydroxymethyl)-4H-benzo[h]chromen-4-one. Product as yellow solid (335 mg, 1.4 mmol, yield 90%). ESI-MS: 246 [M+H]+

$^1$H NMR (400 MHz, DMSO-d$_6$) δ 8.86 (s, 1H), 8.50 (d, J=8.0 Hz, 1H), 8.14 (d, J=7.8 Hz, 1H), 8.05 (d, J=8.7 Hz, 1H), 7.99 (d, J=8.7 Hz, 1H), 7.87-7.79 (m, 2H), 4.67 (s, 2H).

Preparation of 3-({[3-(1H-imidazol-1-yl)propyl](pyridin-4-ylmethyl)amino}methyl)-4H-benzo[h]chromen-4-one The title compound was prepared according to Procedure 9.1 substituting 3-(chloromethyl)-7,8-dimethyl-4H-chromen-4-one with 3-(chloromethyl)-4H-benzo[h]chromen-4-one. ESI-MS: 425 [M+H]+

$^1$H NMR (400 MHz, DMSO-d$_6$) δ 8.52 (s, 1H), 8.51-8.47 (m, 1H), 8.46-8.44 (m, 2H), 8.14-8.10 (m, 1H), 8.06-8.02 (m, 1H), 7.96-7.92 (m, 1H), 7.87-7.77 (m, 2H), 7.56 (s, 1H), 7.40-7.36 (m, 2H), 7.14-7.09 (m, 1H), 6.80-6.75 (m, 1H), 4.03-3.96 (m, 2H), 3.67 (s, 2H), 3.54 (s, 2H), 2.42 (t, J=6.8 Hz, 2H), 2.02-1.94 (m, 2H).

The product was converted into hydrochloric acid salt following Procedure 10. ESI-MS: 425 [M+H]+

$^1$H NMR (400 MHz, Deuterium Oxide): 8.77 (t, J=1.5 Hz, 1H), 8.75-8.72 (m, 2H), 8.47-8.43 (m, 2H), 8.20-8.16 (m, 2H), 8.02 (d, J=7.8 Hz, 1H), 7.88 (d, J=8.8 Hz, 1H), 7.84-7.73 (m, 3H), 7.52 (t, J=1.8 Hz, 1H), 7.36 (t, J=1.7 Hz, 1H), 4.60 (s, 2H), 4.35 (t, J=7.0 Hz, 2H), 4.04 (s, 2H), 3.27-3.16 (m, 2H), 2.55-2.42 (m, 2H).

Example 8. 1-(3-{[(4-oxo-4H-chromen-3-yl)methyl](pyridin-4-ylmethyl)amino}propyl)pyrrolidin-2-one

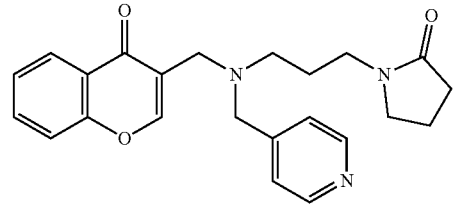 [SMILES: O=C1CCCN1CCCN(Cc1ccncc1)Cc1coc2ccccc2c1=O]

Preparation of 1-(3-{[(pyridin-4-yl)methyl]amino}propyl)pyrrolidin-2-one

The title compound was synthesized following the approach outlined in Procedure 3 substituting 3-(1H-imidazol-1-yl)propan-1-amine with N-(3-aminopropyl)-2-pyrrolidinone. Crude product (yellow oil) was used for the next step without further purification (0,323 g, 1.01 mmol, yield 72%). ESI-MS: 234 [M+H]+

Preparation of 1-(3-{[(4-oxo-4H-chromen-3-yl)methyl][(pyridin-4-yl)methyl]amino}propyl)pyrrolidin-2-one The title compound was synthesized following the approach outlined in Procedure 9.1 substituting 3-(chloromethyl)-7,8-dimethyl-4H-chromen-4-one with 3-(chloromethyl)-4H-chromen-4-one and [3-(1H-imidazol-1-yl)propyl](pyridin-4-ylmethyl)amine with 1-(3-{[(pyridin-4-yl)methyl]amino}propyl)pyrrolidin-2-one. The residue was purified by FCC (SiHP, DCM: MeOH 9:1) to afford the title compound (145 mg, 0.359 mmol, yield 47%) as an orange oil. ESI-MS: 392 [M+H]+

$^1$H NMR (300 MHz, DMSO-d$_6$) δ 8.49-8.45 (m, 2H), 8.36 (s, 1H), 8.10-8.06 (m, 1H), 7.84-7.78 (m, 1H), 7.67-

7.63 (m, 1H), 7.52-7.46 (m, 1H), 7.40-7.36 (m, 2H), 3.64 (s, 2H), 3.48 (s, 2H), 3.24 (t, J=7.0 Hz, 2H), 3.16 (t, J=7.0 Hz, 2H), 2.38 (t, J=7.1 Hz, 2H), 2.15-2.04 (m, 2H), 1.85-1.75 (m, 2H), 1.74-1.64 (m, 2H).

Example 9. 3-({[3-(1H-imidazol-1-yl)propyl](pyridin-4-ylmethyl)amino}methyl)-7-methoxy-4H-chromen-4-one

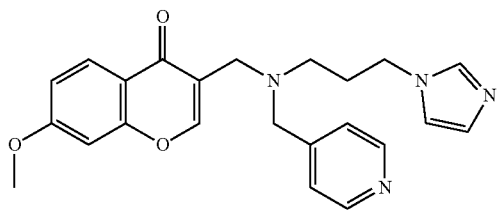 [SMILES: COc1ccc2c(=O)c(CN(CCCn3ccnc3)Cc3ccncc3)coc2c1]

Preparation of 2-hydroxy-7-methoxy-3,4-dihydro-2H1-benzopyran-4-one

The title compound was prepared according to Procedure 1a. substituting 1-(2-hydroxyphenyl)ethan-1-one with 1-(2-hydroxy-4-methoxyphenyl)ethan-1-one. Product was obtained as a white solid that was taken to the next step without additional purification (1.1 g, 5.66 mmol, yield 94%). ESI-MS: 195 [M+H]$^+$ $^1$H NMR (400 MHz, DMSO-d$_6$) δ 7.66 (d, J=8.7 Hz, 1H), 7.58 (d, J=5.0 Hz, 1H), 6.65-6.61 (m, 1H), 6.52 (d, J=2.4 Hz, 1H), 5.81-5.76 (m, 1H), 3.82 (s, 3H), 2.98-2.92 (m, 1H), 2.64-2.58 (m, 1H).

Preparation of 3-(hydroxymethyl)-7-methoxy-4H-chromen-4-one

The title compound was prepared according to Procedure 1b. substituting 2-hydroxy-3,4-dihydro-2H-1-benzopyran-4-one with 2-hydroxy-7-methoxy-3,4-dihydro-2H-1-benzopyran-4-one. Crude material was purified by FCC (SiHP, Hexane: AcOEt 50%) to afford the title compound as a white solid (690 mg, 3.36 mmol, yield 65%). ESI-MS: 207 [M+H]$^+$ $^1$H NMR (300 MHz, DMSO-d$_6$) δ 8.16-8.12 (m, 1H), 7.96 (d, J=8.9 Hz, 1H), 7.13 (d, J=2.4 Hz, 1H), 7.08-7.04 (m, 1H), 5.09 (t, J=5.4 Hz, 1H), 4.36-4.34 (m, 2H), 3.89 (s, 3H).

Preparation of 3-(chloromethyl)-7-methoxy-4H-chromen-4-one

The title compound was prepared according to Procedure 1c substituting 3-(hydroxymethyl)-4H-chromen-4-one with 3-(hydroxymethyl)-7-methoxy-4H-chromen-4-one. Product as white solid (300 mg, 1.23 mmol, 92%). ESI-MS: 226 [M+H]$^+$ $^1$H NMR (300 MHz, DMSO-d$_6$) δ 8.58 (s, 1H), 7.99 (d, J=8.9 Hz, 1H), 7.17 (d, J=2.4 Hz, 1H), 7.14-7.07 (m, 1H), 4.59-4.51 (m, 2H), 3.90 (s, 3H).

Preparation of 3-({[3-(1H-imidazol-1-yl)propyl](pyridin-4-ylmethyl)amino}methyl)-7-methoxy-4H-chromen-4-one The title compound was prepared according to Procedure 9.1 substituting 3-(chloromethyl)-7,8-dimethyl-4H-chromen-4-one with 3-(chloromethyl)-7-methoxy-4H-chromen-4-one. The residue was purified by prep-HPLC to afford a formic acid salt of the title compound (114 mg, 0.320 mmol, yield 32%) as a yellow oil. ESI-MS: 405 [M+H]$^+$ $^1$H NMR (400 MHz, DMSO-d$_6$) δ 8.48-8.43 (m, 2H), 8.24 (s, 1H), 7.97 (d, J=8.9 Hz, 1H), 7.55 (d, J=1.1 Hz, 1H), 7.40-7.32 (m, 2H), 7.12-7.09 (m, 2H), 7.08-7.04 (m, 1H), 6.80 (t, J=1.1 Hz, 1H), 3.97 (t, J=7.1 Hz, 2H), 3.89 (s, 3H), 3.62 (s, 2H), 3.44 (s, 2H), 3.17 (d, J=4.9 Hz, 1H), 2.37 (t, J=6.7 Hz, 2H), 1.99-1.89 (m, 2H).

The product was converted into hydrochloric acid salt following Procedure 10. Product as yellow crystals (140 mg, 0.96 mmol, yield 100%). ESI-MS: 405 [M+H]$^+$ $^1$H NMR (400 MHz, Deuterium Oxide) δ 8.79 (t, J=1.5 Hz, 1H), 8.79-8.73 (m, 2H), 8.33 (s, 1H), 8.22-8.16 (m, 2H), 7.97-7.95 (m, 1H), 7.54 (t, J=1.8 Hz, 1H), 7.43 (dd, J=2.0, 1.5 Hz, 1H), 7.18-7.14 (m, 2H), 4.65 (s, 2H), 4.38 (t, J=7.0 Hz, 2H), 4.19 (s, 2H), 3.96 (s, 3H), 3.32-3.22 (m, 2H), 2.59-2.44 (m, 2H).

Example 10. 7-bromo-3-({[3-(1H-imidazol-1-yl)propyl](pyridin-4 ylmethyl)amino}methyl)-4H-chromen-4-one

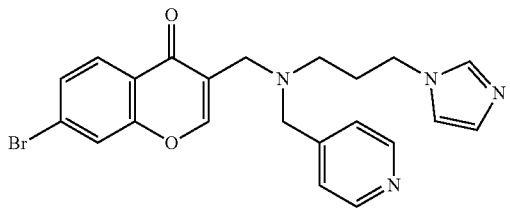 [SMILES: O=c1c(CN(CCCn2ccnc2)Cc2ccncc2)coc2cc(Br)ccc12]

Preparation of 7-bromo-2-hydroxy-3,4-dihydro-2H1-benzopyran-4-one

The title compound was prepared according to Procedure 1a. substituting 1-(2-hydroxyphenyl)ethan-1-one with 1-(4-bromo-2-hydroxyphenyl)ethan-1-one, and was taken to the next step without additional purification. Product as a pale yellow solid (3.4 g, 13.84 mmol, yield 99%). ESI-MS: 245 [M+H]$^+$ $^1$H NMR (300 MHz, DMSO-d$_6$) δ 7.75-7.71 (m, 1H), 7.64 (d, J=8.3 Hz, 1H), 7.31 (d, J=1.8 Hz, 1H), 7.28-7.22 (m, 1H), 5.89-5.83 (m, 1H), 3.13-3.03 (m, 1H), 2.74-2.64 (m, 1H).

Preparation of 7-bromo-3-(hydroxymethyl)-4H-chromen-4-one

The title compound was prepared according to Procedure 1b. substituting 2-hydroxy-3,4-dihydro-2H1-benzopyran-4-one with 7-bromo-2-hydroxy-3,4-dihydro-2H-1-benzopyran-4-one. Crude material was purified by FCC (SiHP, Hexane: AcOEt 50%) to afford the title compound as a white solid (1.980 g, 7.76 mmol, yield 56%). ESI-MS: 256 [M+H]$^+$ $^1$H NMR (300 MHz, DMSO-d$_6$) δ 8.21 (t, J=1.3 Hz, 1H), 8.02-7.95 (m, 2H), 7.69-7.63 (m, 1H), 5.17 (t, J=5.3 Hz, 1H), 4.39-4.34 (m, 2H).

Preparation of 7-bromo-3-(chloromethyl)-4H-chromen-4-one

The title compound was prepared according to Procedure 1c. substituting 3-(hydroxymethyl)-4H-chromen-4-one with 7-bromo-3-(hydroxymethyl)-4H-chromen-4-one. Product as pale yellow solid (200 mg, 0.73 mmol, yield 93%). ESI-MS: 275 [M+H]$^+$ $^1$H NMR (300 MHz, DMSO-d$_6$) δ 8.66 (s, 1H), 8.04 (d, J=1.8 Hz, 1H), 8.00 (d, J=8.5 Hz, 1H), 7.74-7.68 (m, 1H), 4.57 (s, 2H).

Preparation of 7-bromo-3-({[3-(1H-imidazol-1-yl)propyl](pyridin-4 ylmethyl)amino}methyl)-4H-chromen-4-one The title compound was prepared according to Procedure 9.1 substituting 3-(chloromethyl)-7,8-dimethyl-4H-chromen-4-one with 7-bromo-3-(chloromethyl)-4H-chromen-4-one. The residue was purified by prep-HPLC to afford the title compound (102 mg, 0.220 mmol, yield 30%) as a brown oil. ESI-MS: 454 [M+H]$^+$ $^1$H NMR (400 MHz, DMSO-d$_6$) δ 8.49-8.42 (m, 2H), 8.32 (s, 1H), 8.03-7.93 (m, 2H), 7.69-7.64 (m, 1H), 7.58-7.52 (m, 1H), 7.39-7.32 (m, 2H), 7.12-7.09 (m, 1H), 6.79 (s, 1H), 3.97 (t, J=7.1 Hz, 2H), 3.62 (s, 2H), 3.44 (s, 2H), 2.37 (t, J=6.7 Hz, 2H), 2.00-1.90 (m, 2H).

The product was converted into hydrochloric acid salt following Procedure 10. Product as yellow crystals (140 mg, 0.25 mmol, yield 100%). ESI-MS: 454 [M+H]$^+$ $^1$H NMR (400 MHz, Deuterium Oxide) δ 8.82-8.78 (m, 3H), 8.38 (s, 1H), 8.23-8.19 (m, 2H), 7.98-7.92 (m, 2H), 7.77-7.71 (m, 1H), 7.56-7.53 (m, 1H), 7.46-7.41 (m, 1H), 4.64 (s, 2H), 4.37 (t, J=7.1 Hz, 2H), 4.19 (s, 2H), 3.31-3.18 (m, 2H), 2.57-2.45 (m, 2H).

Example 11. 7-fluoro-3-({[3-(1H-imidazol-1-yl)propyl](pyridin-4-ylmethyl)amino}methyl)-4H-chromen-4-one

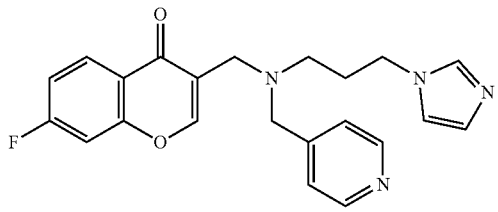 [SMILES: O=c1c(CN(CCCn2ccnc2)Cc2ccncc2)coc2cc(F)ccc12]

Preparation of 7-fluoro-2-hydroxy-3,4-dihydro-2H-1-benzopyran-4-one

The title compound was prepared according to Procedure 1a. substituting 1-(2-hydroxyphenyl)ethan-1-one with 1-(4-fluoro-2-hydroxyphenyl)ethan-1-one. Product as yellow oil (450 mg, 2.47 mmol, yield 63%). ESI-MS: 183 [M+H]$^+$

Preparation of 7-fluoro-3-(hydroxymethyl)-4H-chromen-4-one

The title compound was prepared according to the Procedure 1 b. substituting 2-hydroxy-3,4-dihydro-2H-1-benzopyran-4-one with 7-fluoro-2-hydroxy-3,4-dihydro-2H-1-benzopyran-4-one. Product as yellow solid (65 mg, 0.335 mmol, yield 16%). ESI-MS: 195 [M+H]$^+$

Preparation of 7-fluoro-3-(chloromethyl)-4H-chromen-4-one

The title compound was prepared according to the Procedure 1c. substituting 3-(hydroxymethyl)-4H-chromen-4-one with 7-fluoro-3-(hydroxymethyl)-4H-chromen-4-one. Product as yellow solid (65 mg, 0.335 mmol, yield 100%). ESI-MS: 213 [M+H]$^+$

Preparation of 7-fluoro-3-({[3-(1H-imidazol-1-yl)propyl](pyridin-4-ylmethyl)amino}methyl)-4H-chromen-4-one The title compound was prepared according to the Procedure 9.1 substituting 3-(chloromethyl)-7,8-dimethyl-4H-chromen-4-one with 7-fluoro-3-(chloromethyl)-4H-chromen-4-one. Product as yellow oil (20 mg, 0.050 mmol, yield 18%).

$^1$H NMR (300 MHz, DMSO-d$_6$) δ 8.48-8.44 (m, 2H), 8.33 (s, 1H), 8.18-8.11 (m, 1H), 7.65-7.59 (m, 1H), 7.56-7.53 (m, 1H), 7.42-7.37 (m, 1H), 7.37-7.33 (m, 2H), 7.12-7.09 (m, 1H), 6.81-6.78 (m, 1H), 3.98 (t, J=7.1 Hz, 2H), 3.63 (s, 2H), 3.45 (s, 2H), 2.38 (t, J=6.8 Hz, 2H), 2.02-1.89 (m, 2H).

The product was transformed into hydrochloric acid salt following Procedure 10. ESI-MS: 393 [M+H]$^+$.

$^1$H NMR (400 MHz, Deuterium Oxide) δ 8.71-8.69 (m, 1H), 8.67-8.64 (m, 2H), 8.27 (s, 1H), 8.09-8.03 (m, 3H), 7.47-7.44 (m, 1H), 7.37-7.30 (m, 2H), 7.30-7.26 (m, 1H), 4.40 (s, 2H), 4.29 (t, J=7.1 Hz, 2H), 3.97 (s, 2H), 3.07-3.00 (m, 2H), 2.41-2.31 (m, 2H).

Example 12. 3-({[3-(1H-imidazol-1-yl)propyl](pyridin-4-ylmethyl)amino}methyl)-7-(4-methylpiperazin-1-yl)-4H-chromen-4-one

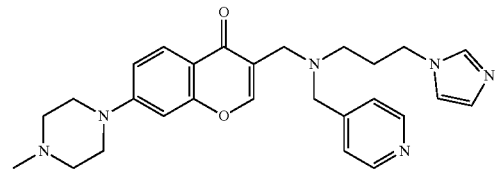 [SMILES: CN1CCN(c2ccc3c(=O)c(CN(CCCn4ccnc4)Cc4ccncc4)coc3c2)CC1]

Preparation of 1-[2-hydroxy-4-(4-methylpiperazin-1-yl)phenyl]ethan-1-one 1-(4-fluoro-2-hydroxyphenyl)ethan-1-one (0.5 g, 3.24 mmol, 1.0 eq.) and 1-methylpiperazine (1.44 mL, 12.98 mmol, 4.0 eq.) were stirred at 130° C. for 3 h. Then, the solvent was evaporated under vacuum. The residue was purified by FCC (SiHP, DCM: MeOH 5%) to afford the title compound as a white solid (715 mg, 3.05 mmol, yield 94%). ESI-MS: 236 [M+H]$^+$ $^1$H NMR (400 MHz, DMSO-d$_6$) δ 12.74 (s, 1H), 7.66 (d, J=9.2 Hz, 1H), 6.56-6.51 (m, 1H), 6.26 (d, J=2.5 Hz, 1H), 3.38-3.33 (m, 4H), 2.47 (s, 3H), 2.41-2.36 (m, 4H), 2.20 (s, 3H).

Preparation of 2-hydroxy-7-(4-methylpiperazin-1-yl)-3,4-dihydro-2H-1-benzopyran-4-one The title compound was prepared according to Procedure 1a. substituting 1-(2-hydroxyphenyl)ethan-1-one with 1-[2- hydroxy-4-(4-methylpiperazin-1-yl)phenyl]ethan-1-one, and was taken to the next step without additional purification. Product as a white solid (0.790 g, 3.01 mmol, yield 99%). ESI-MS: 263 [M+H]⁺

Preparation of 3-(hydroxymethyl)-7-(4-methylpiperazin-1-yl)-4H-chromen-4-one

The title compound was prepared according to Procedure 1b. substituting 2-hydroxy-3,4-dihydro-2H-1-benzopyran-4-one with 2-hydroxy-7-(4-methylpiperazin-1-yl)-3,4-dihydro-2H-1-benzopyran-4-one. Crude material was purified by FCC (SiHP, DCM: MeOH 10%) to afford the title compound as a white solid (200 mg, 0.73 mmol, yield 59%). ESI-MS: 275 [M+H]⁺

Preparation of 3-(chloromethyl)-7-(4-methylpiperazin-1-yl)-4H-chromen-4-one

The title compound was prepared according to Procedure 1c substituting 3-(hydroxymethyl)-4H-chromen-4-one with 3-(hydroxymethyl)-7-(4-methylpiperazin-1-yl)-4H-chromen-4-one. Product as pale yellow solid (127 mg, 0.43 mmol, yield 60%). ESI-MS: 294 [M+H]⁺

Preparation of 3-({[3-(1H-imidazol-1-yl)propyl](pyridin-4-ylmethyl)amino}methyl)-7-(4-methylpiperazin-1-yl)-4H-chromen-4-one The title compound was prepared according to Procedure 9.1 substituting 3-(chloromethyl)-7,8-dimethyl-4H-chromen-4-one with 3-(chloromethyl)-7-(4-methylpiperazin-1-yl)-4H-chromen-4-one. The residue was purified by prep-HPLC to afford the title compound (114 mg, 0.24 mmol, yield 56%) as a yellow oil. The product was transformed into hydrochloric acid salt following Procedure 10. ESI-MS: 473 [M+H]⁺

¹H NMR (400 MHz, Deuterium Oxide) δ 8.83-8.78 (m, 3H), 8.31 (s, 1H), 8.26-8.21 (m, 2H), 7.93 (d, J=9.1 Hz, 1H), 7.57-7.53 (m, 1H), 7.46-7.44 (m, 1H), 7.28-7.21 (m, 1H), 7.05 (d, J=2.4 Hz, 1H), 4.75 (s, 2H), 4.38 (t, J=7.1 Hz, 2H), 4.28 (s, 2H), 4.22-4.16 (m, 2H), 3.73-3.63 (m, 2H), 3.43-3.22 (m, 6H), 2.97 (s, 3H), 2.63-2.50 (m, 2H).

Example 13. 7-(benzyloxy)-3-({[3-(1H-imidazol-1-yl)propyl](pyridin-4-ylmethyl)amino}methyl)-4H-chromen-4-one

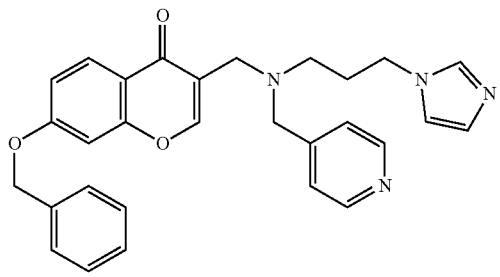 [SMILES: O=c1c(CN(CCCn2ccnc2)Cc2ccncc2)coc2cc(OCc3ccccc3)ccc12]

Preparation of 7-(benzyloxy)-2-hydroxy-3,4-dihydro-2H-1-benzopyran-4-one

The title compound was prepared according to Procedure 1a. substituting 1-(2-hydroxyphenyl)ethan-1-one with 1-[4-(benzyloxy)-2-hydroxyphenyl]ethan-1-one and was taken to the next step without additional purification. Product as a white solid (1.241 gm, 4.73 mmol, yield 53%). ESI-MS: 272 [M+H]⁺

¹H NMR (300 MHz, DMSO-d₆) δ 7.67 (d, J=8.7 Hz, 1H), 7.59 (s, 1H), 7.49-7.32 (m, 5H), 6.74-6.67 (m, 1H), 6.60 (d, J=2.4 Hz, 1H), 5.78 (s, 1H), 5.19 (s, 2H), 3.00-2.91 (m, 1H), 2.66-2.56 (m, 1H).

Preparation of 7-(benzyloxy)-3-(hydroxymethyl)-4H-chromen-4-one

The title compound was prepared according to Procedure 1b. substituting 2-hydroxy-3,4-dihydro-2H-1-benzopyran-4-one with 7-(benzyloxy)-2-hydroxy-3,4-dihydro-2H-1-benzopyran-4-one. Crude material was purified by FCC (SiHP, DCM: MeOH 10%) to afford the product as a white solid (692 mg, 2.45 mmol, yield 38%). ESI-MS: 284 [M+H]⁺

¹H NMR (300 MHz, DMSO-d₆) δ 8.16-8.12 (m, 1H), 7.97 (d, J=8.9 Hz, 1H), 7.53-7.34 (m, 5H), 7.23 (d, J=2.4 Hz, 1H), 7.16-7.11 (m, 1H), 5.26 (s, 2H), 5.09 (t, J=5.4 Hz, 1H), 4.39-4.31 (m, 2H).

Preparation of 7-(benzyloxy)-3-(chloromethyl)-4H-chromen-4-one

The title compound was prepared according to Procedure 1c. substituting 3-(hydroxymethyl)-4H-chromen-4-one with 7-(benzyloxy)-3-(hydroxymethyl)-4H-chromen-4-one. Product as yellow solid (200 mg, 0.67 mmol, yield 94%). ESI-MS: 303 [M+H]⁺

¹H NMR (300 MHz, DMSO-d₆) δ 8.58 (s, 1H), 8.00 (d, J=8.9 Hz, 1H), 7.53-7.33 (m, 5H), 7.27 (d, J=2.4 Hz, 1H), 7.21-7.14 (m, 1H), 5.27 (s, 2H), 4.56 (s, 2H).

Preparation of 7-(benzyloxy)-3-({[3-(1H-imidazol-1-yl)propyl](pyridin-4-ylmethyl)amino}methyl)-4H-chromen-4-one The title compound was prepared according to Procedure 9.1 substituting 3-(chloromethyl)-7,8-dimethyl-4H-chromen-4-one with 7-(benzyloxy)-3-(chloromethyl)-4H-chromen-4-one. The residue was purified by prep-HPLC to afford the title compound (101 mg, 0.21 mmol, yield 32%) as a yellow oil. ESI-MS: 481 [M+H]⁺

¹H NMR (400 MHz, DMSO-d₆) δ 8.48-8.44 (m, 2H), 8.23 (s, 1H), 7.98 (d, J=8.9 Hz, 1H), 7.56 (s, 1H), 7.51-7.47 (m, 2H), 7.45-7.39 (m, 2H), 7.38-7.33 (m, 3H), 7.20 (d, J=2.4 Hz, 1H), 7.15-7.11 (m, 1H), 7.10 (s, 1H), 6.80 (s, 1H), 5.26 (s, 2H), 3.97 (t, J=7.1 Hz, 2H), 3.62 (s, 2H), 3.43 (s, 2H), 2.37 (t, J=6.7 Hz, 2H), 1.98-1.90 (m, 2H).

The product was converted into hydrochloric acid salt following Procedure 10. Product as yellow crystals (120 mg, 0.2 mmol, yield 100%). ESI-MS: 481 [M+H]⁺

¹H NMR (400 MHz, Deuterium Oxide) δ 8.79-8.77 (m, 1H), 8.77-8.73 (m, 2H), 8.30 (s, 1H), 8.21-8.14 (m, 2H), 7.94 (d, J=8.7 Hz, 1H), 7.55-7.50 (m, 3H), 7.50-7.38 (m, 4H), 7.20-7.15 (m, 2H), 5.26 (s, 2H), 4.63 (s, 2H), 4.36 (t, J=7.0 Hz, 2H), 4.15 (s, 2H), 3.31-3.18 (m, 2H), 2.58-2.43 (m, 2H).

Example 14. 7,8-dimethyl-3-{[(pyridin-4-ylmethyl)[3-(1H-1,2,3-triazol-1-yl)propyl]amino]methyl}-4H-chromen-4-one

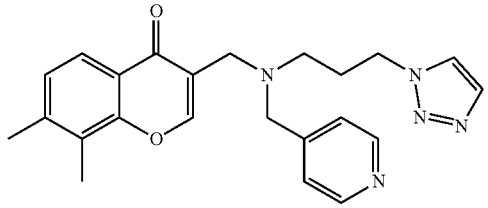 [SMILES: Cc1ccc2c(=O)c(CN(CCCn3ccnn3)Cc3ccncc3)coc2c1C]

The title compound was synthesized according to Procedure 9.1 substituting [3-(1H-imidazol-1-yl)propyl](pyridin-4-ylmethyl)amine with (pyridin-4-ylmethyl)[3-(1H1,2,3-triazol-1-yl)propyl]amine. The crude material was purified by prep-HPLC (25 mg, 0.060 mmol, yield 15%) and transformed into hydrochloride salt following Procedure 10 to afford the title compound as a yellow solid. ESI-MS: 405 [M+H]$^+$ $^1$H NMR (300 MHz, Deuterium Oxide) δ 8.88-8.79 (m, 2H), 8.41 (s, 1H), 8.28-8.19 (m, 2H), 7.98 (d, J=1.1 Hz, 1H), 7.79 (d, J=8.2 Hz, 1H), 7.70 (d, J=1.1 Hz, 1H), 7.41 (d, J=8.3 Hz, 1H), 4.81 (s, 2H), 4.60 (t, J=6.2 Hz, 2H), 4.35 (s, 2H), 3.39-3.27 (m, 2H), 2.64-2.49 (m, 2H), 2.47 (s, 3H), 2.42 (s, 3H).

Example 15. 7,8-dimethyl-3-{[(pyridin-4-ylmethyl)[3-(1H-pyrrol-1-yl)propyl]amino]methyl}-4H-chromen-4-one

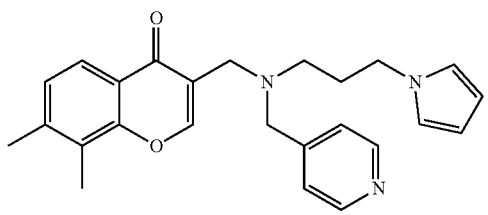 [SMILES: Cc1ccc2c(=O)c(CN(CCCn3cccc3)Cc3ccncc3)coc2c1C]

The title compound was synthesized according to Procedure 9.1 substituting [3-(1H-imidazol-1-yl)propyl](pyridin-4-ylmethyl)amine with (pyridin-4-ylmethyl)[3-(1H-pyrrol-1-yl)propyl]amine. The crude material was purified by prep-HPLC to afford the title compound as a formic acid salt (25 mg, 0.060 mmol, yield 13%). ESI-MS: 402 [M+H]$^+$ $^1$H NMR (300 MHz, DMSO-d$_6$) δ 8.51-8.42 (m, 2H), 8.30 (s, 1H), 8.13 (s, 1H), 7.81 (d, J=8.1 Hz, 1H), 7.40-7.35 (m, 2H), 7.30 (d, J=8.2 Hz, 1H), 6.69-6.60 (m, 2H), 5.89-5.81 (m, 2H), 3.87 (t, J=7.0 Hz, 2H), 3.63 (s, 2H), 3.44 (s, 2H), 2.40 (s, 3H), 2.38-2.32 (m, 5H), 1.99-1.83 (m, 2H).

Example 16. 7-hydroxy-3-({[3-(1H-imidazol-1-yl)propyl](pyridin-4-ylmethyl)amino}methyl)-4H-chromen-4-one

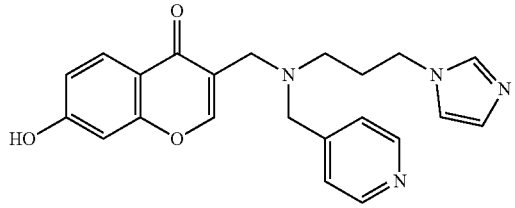 [SMILES: O=c1c(CN(CCCn2ccnc2)Cc2ccncc2)coc2cc(O)ccc12]

Preparation of 3-(chloromethyl)-7-hydroxy-4H-chromen-4-one

The title compound was prepared following Procedure 1c substituting 3-(hydroxymethyl)-4H-chromen-4-one with 7-hydroxy-3-(hydroxymethyl)-4H-chromen-4-one. Product as a yellow solid (200 mg, 0.67 mmol, yield 65%). ESI-MS: 211.4 [M+H]$^+$ $^1$H NMR (400 MHz, DMSO-d$_6$) δ 10.89 (s, 1H), 8.52 (s, 1H), 7.94 (d, J=8.8 Hz, 1H), 6.98-6.93 (m, 1H), 6.87 (d, J=2.2 Hz, 1H), 4.55 (s, 2H).

Preparation of 7-hydroxy-3-({[3-(1H-imidazol-1-yl)propyl](pyridin-4-ylmethyl)amino}methyl)-4/H chromen-4-one The title compound was prepared following Procedure 9.1 substituting 3-(chloromethyl)-7,8-dimethyl-4H-chromen-4-one with 3-(chloromethyl)-7-hydroxy-4H-chromen-4-one, with a mixture of CH$_3$CN: DMSO (1:1) as the solvent. The residue was purified by prep-HPLC to afford the title compound (40 mg, 0.1 mmol, yield 28%) as a white solid. ESI-MS: 391 [M+H]$^+$ $^1$H NMR (400 MHz, DMSO-d$_6$) δ 10.75 (s, 1H), 8.49-8.41 (m, 2H), 8.16 (s, 1H), 7.90 (d, J=8.8 Hz, 1H), 7.55 (s, 1H), 7.39-7.31 (m, 2H), 7.10 (s, 1H), 6.96-6.88 (m, 1H), 6.81 (d, J=2.2 Hz, 1H), 6.79 (s, 1H), 3.97 (t, J=7.1 Hz, 2H), 3.61 (s, 2H), 3.42 (s, 2H), 2.37 (t, J=6.8 Hz, 2H), 1.99-1.89 (m, 2H).

Example 17. 3-({[3-(1H-1,3-benzodiazol-1-yl)propyl](pyridin-4-ylmethyl)amino}methyl)-4H-chromen-4-one

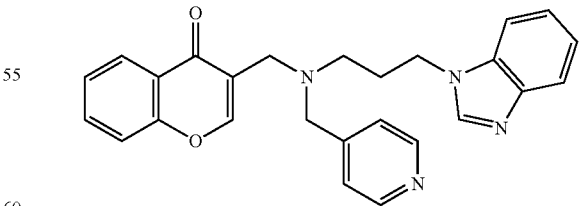

Preparation of 2-[3-(1H-1,3-benzodiazol-1-yl)propyl]-2,3-dihydro-1H-isoindole-1,3-dione The title compound was synthesized following the approach outlined in Procedure 11a substituting 1H-imidazole with 1H-1,3-benzodiazole and 2-(4-bromobutyl)-2,3-dihydro-1H-isoindole-1,3-dione with 2-(3-bromopropyl)-2,3-dihydro-1H-isoindole-1,3-dione. The residue was purified by FCC (deactivated SiHP, DCM: MeOH 99:1) to afford the product (597 mg, 1.95 mmol, yield 80%) as an oil. ESI-MS: 306 [M+H]$^+$ Preparation of 3-(1H-1,3-benzodiazol-1-yl)propan-1-amine The title compound was synthesized following the approach outlined in Procedure 11b substituting 2-[4-(1H-imidazol-1-yl)butyl]-2,3-dihydro-1H-isoindole-1,3-dione with 2-[3-(1H-1,3-benzodiazol-1-yl)propyl]-2,3-dihydro-1H-isoindole-1,3-dione to afford the product as an oil (250 mg, 1.43 mmol, yield 73%). ESI-MS: 176 [M+H]$^+$ Preparation of [3-(1H-1,3-benzodiazol-1-yl)propyl](pyridin-4-ylmethyl)amine The title compound was synthesized following the approach outlined in Procedure 3 substituting 3-(1H-imidazol-1-yl)propan-1-amine with 3-(1H-1,3-benzodiazol-1-yl)propan-1-amine. The residue was purified by FCC (deactivated SiHP, DCM: MeOH 95:5) to afford the product (170 mg, 0.638 mmol, yield 45%) as a yellow oil. ESI-MS: 267 [M+H]$^+$ Preparation of 3-({[3-(1H-1,3-benzodiazol-1-yl)propyl](pyridin-4-ylmethyl)amino}methyl)-4H-chromen-4-one The title compound was synthesized following the approach outlined in Procedure 9.1 substituting [3-(1H-imidazol-1-yl)propyl](pyridin-4-ylmethyl)amine with [3-(1H-1,3-benzodiazol-1-yl)propyl](pyridin-4-ylmethyl)amine and 3-(chloromethyl)-7,8-dimethyl-4H-chromen-4-one with 3-(chloromethyl)-4H-chromen-4-one. Product as a brown solid (50 mg, 0.117 mmol, yield 30%). ESI-MS: 425 [M+H]$^+$ $^1$H NMR (400 MHz, DMSO-d$_6$) δ 8.43-8.40 (m, 2H), 8.33 (s, 1H), 8.16 (s, 1H), 8.11-8.07 (m, 1H), 7.83-7.78 (m, 1H), 7.65-7.58 (m, 3H), 7.52-7.47 (m, 1H), 7.35-7.31 (m, 2H), 7.25-7.15 (m, 2H), 4.29 (t, J=7.2 Hz, 2H), 3.64 (s, 2H), 3.49 (s, 2H), 2.47 (t, J=6.9 Hz, 2H), 2.11-2.02 (m, 2H).

Example 18. 3-({[3-(1H-imidazol-1-yl)propyl][(2-methoxypyridin-4-yl)methyl]amino}methyl)-4H-chromen-4-one

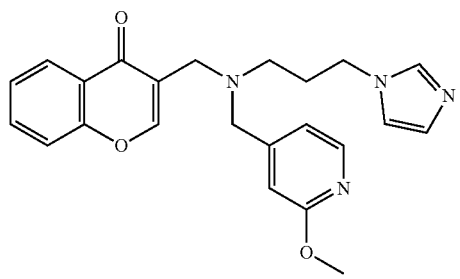 [SMILES: COc1cc(CN(CCCn2ccnc2)Cc2coc3ccccc3c2=O)ccn1]

Preparation of [3-(1H-imidazol-1-yl)propyl][(2-methoxypyridin-4-yl)methyl]amine

The title compound was synthesized following the approach outlined in Procedure 3 substituting pyridine-4-carboxaldehyde with 2-methoxypyridine-4-carboxaldehyde. Crude product, obtained as a yellow oil, was used for the next step without further purification (0,250 g, 0.98 mmol, yield 86%). ESI-MS: 247 [M+H]$^+$ $^1$H NMR (300 MHz, DMSO-d$_6$) δ 8.07 (d, J=5.2 Hz, 1H), 7.60-7.56 (m, 1H), 7.17-7.10 (m, 1H), 6.94 (dd, J=5.2, 1.3 Hz, 1H), 6.88-6.84 (m, 1H), 6.79-6.75 (m, 1H), 4.01 (t, J=7.0 Hz, 2H), 3.83 (s, 3H), 3.64 (s, 2H), 2.40 (t, J=6.7 Hz, 2H), 2.33 (s, 1H), 1.90-1.76 (m, 2H).

Preparation of 3-({[3-(1H-imidazol-1-yl)propyl][(2-methoxypyridin-4-yl)methyl]amino}methyl)-4H-chromen-4-one The title compound was synthesized following the approach outlined in Procedure 9.1 substituting [3-(1H-imidazol-1-yl)propyl](pyridin-4-ylmethyl)amine with [3-(1H-imidazol-1-yl)propyl][(2-methoxypyridin-4-yl)methyl]amine and 3-(chloromethyl)-7,8-dimethyl-4H-chromen-4-one with 3-(chloromethyl)-4H-chromen-4-one. The residue was purified by FCC (SiHP, DCM: MeOH 9:1) to afford the title compound (210 mg, 0.502 mmol, yield 57%) as an orange oil. ESI-MS: 405 [M+H]$^+$ $^1$H NMR (300 MHz, DMSO-d$_6$) δ 8.32 (s, 1H), 8.13-8.03 (m, 1H), 8.03 (d, J=5.2 Hz, 1H), 7.85-7.76 (m, 1H), 7.66-7.61 (m, 1H), 7.57-7.55 (m, 1H), 7.53-7.46 (m, 1H), 7.13-7.10 (m, 1H), 6.95 (dd, J=5.3, 1.3 Hz, 1H), 6.80-6.79 (m, 1H), 6.78 (s, 1H), 3.98 (t, J=7.1 Hz, 2H), 3.79 (s, 3H), 3.58 (s, 2H), 3.46 (s, 2H), 2.39 (t, J=6.7 Hz, 2H), 2.02-1.86 (m, 2H).

Example 19. 3-({[3-(pyridin-3-yl)propyl][(pyridin-4-yl)methyl]amino}methyl)-4H-chromen-4-one

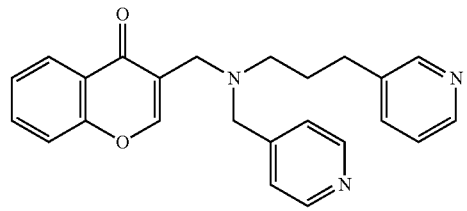 [SMILES: O=c1c(CN(CCCc2cccnc2)Cc2ccncc2)coc2ccccc12]

Preparation of [3-(pyridin-3-yl)propyl][(pyridin-4-yl)methyl]amine

The title compound was synthesized following the approach outlined in Procedure 3 substituting 3-(1H-imidazol-1-yl)propan-1-amine with 3-(pyridin-3-yl)propan-1-amine. Crude product obtained as a yellow oil was used for the next step without further purification (0.285 g, 1.24 mmol, yield 84%). ESI-MS: 228 [M+H]$^+$ $^1$H NMR (300 MHz, DMSO-d$_6$) δ 8.49-8.46 (m, 2H), 8.44-8.41 (m, 1H), 8.40-8.37 (m, 1H), 7.64-7.58 (m, 1H), 7.35-7.32 (m, 2H), 7.32-7.26 (m, 1H), 3.71 (s, 2H), 2.70-2.58 (m, 2H), 2.50-2.45 (m, 2H), 2.30 (s, 1H), 1.80-1.67 (m, 2H).

Preparation of 3-({[3-(pyridin-3-yl)propyl][(pyridin-4-yl)methyl]amino}methyl)-4H-chromen-4-one The title compound was synthesized following the approach outlined in Procedure 9.1 substituting [3-(1H-imidazol-1-yl)propyl](pyridin-4-ylmethyl)amine with [3-(pyridin-3-yl)propyl][(pyridin-4-yl)methyl]amine, and 3-(chloromethyl)-7,8-dimethyl-4H-chromen-4-one with 3-(chloromethyl)-4H-chromen-4-one. The residue was purified by FCC (SiHP, DCM: MeOH 9:1) to afford the title compound (250 mg, 0.604 mmol, yield 67%) as an orange oil. ESI-MS: 386 [M+H]$^+$ $^1$H NMR (300 MHz, DMSO-d$_6$) δ 8.48-8.44 (m, 2H), 8.39 (d, J=2.2 Hz, 1H), 8.35-8.31 (m, 2H), 8.08 (dd, J=8.0, 1.7 Hz, 1H), 7.84-7.77 (m, 1H), 7.64 (dd, J=8.5, 1.0 Hz, 1H), 7.59-7.54 (m, 1H), 7.53-7.46 (m, 1H), 7.40-7.35 (m, 2H), 7.24-7.17 (m, 1H), 3.65 (s, 2H), 3.48 (s, 2H), 2.59 (t, J=7.7 Hz, 2H), 2.44 (t, J=7.0 Hz, 2H), 1.89-1.76 (m, 2H).

The product was converted into hydrochloric acid salt following Procedure 10.

$^1$H NMR (400 MHz, DMSO-d$_6$) δ 8.96-8.91 (m, 2H), 8.90-8.88 (m, 1H), 8.84-8.78 (m, 2H), 8.53-8.47 (m, 1H), 8.36-8.28 (m, 2H), 8.10 (dd, J=8.0, 1.6 Hz, 1H), 8.05-7.99 (m, 1H), 7.93-7.84 (m, 1H), 7.77-7.71 (m, 1H), 7.62-7.53 (m, 1H), 4.60 (s, 2H), 4.21 (s, 2H), 2.99 (s, 2H), 2.84 (t, J=7.2 Hz, 2H), 2.31-2.22 (m, 2H).

Example 20. 3-({[3-(1H-imidazol-1-yl)propyl](pyridin-4-ylmethyl)amino}methyl)-4H,7H,8H,9H,10H-cyclohexa[h]chromen-4-one

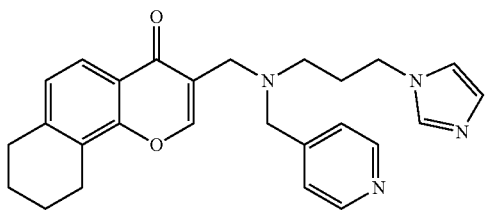 [SMILES: O=c1c(CN(CCCn2ccnc2)Cc2ccncc2)coc2c3c(ccc12)CCCC3]

Preparation of 5,6,7,8-tetrahydronaphthalen-1-yl acetate

The title compound was synthesized according to Procedure 4a substituting 2,3-dimethylphenol with 5,6,7,8-tetrahydronaphthalen-1-ol. The product was purified by FCC (SiHP, Hex: AcOEt 1:1) to afford a colorless oil (1.15 g, 6.045 mmol, yield 90%)

Preparation of 1-(1-hydroxy-5,6,7,8-tetrahydronaphthalen-2-yl)ethan-1-one

The title compound was synthesized according to Procedure 4b substituting 2,3-dimethylphenyl acetate with 5,6,7,8-tetrahydronaphthalen-1-yl acetate. Product as a yellow solid (825 mg, 4.336 mmol, yield 83%)

Preparation of 2-hydroxy-2H,3H,4H,7H,8H,9H,10H-naphtho[1,2-b]pyran-4-one

The title compound was synthesized according to Procedure 5a substituting 1-(2-hydroxy-3,4-dimethylphenyl)ethan-1-one with 1-(1-hydroxy-5,6,7,8-tetrahydronaphthalen-2-yl)ethan-1-one. Product as a yellow solid (882 mg, 4.04 mmol, yield 93%)

Preparation of 3-(hydroxymethyl)-4H,7H,8H,9H,10H-cyclohexa[h]chromen-4-one

The title compound was synthesized according to Procedure 5b substituting 2-hydroxy-7,8-dimethyl-3,4-dihydro-2H-1-benzopyran-4-one with 2-hydroxy-2H,3H,4H,7H,8H,9H,10H-naphtho[1,2-b]pyran-4-one. Product as a white solid (728 mg, 3.16 mmol, yield 78%)

Preparation of 3-(chloromethyl)-4H,7H,8H,9H,10H-cyclohexa[h]chromen-4-one

The title compound was synthesized according to Procedure 6 substituting 3-(hydroxymethyl)-7,8-dimethyl-4H-chromen-4-one with 3-(hydroxymethyl)-4H,7H,8H,9H,10H-cyclohexa[h]chromen-4-one. Product as a white solid (712 mg, 2.86 mmol, yield 91%)

Preparation of 3-({[3-(1H-imidazol-1-yl)propyl](pyridin-4-ylmethyl)amino}methyl)-4H,7H,8H,9H,10H-cyclohexa[h]chromen-4-one The title compound was synthesized according to Procedure 9.1 substituting 3-(chloromethyl)-7,8-dimethyl-4H-chromen-4-one with 3-(chloromethyl)-4H,7H,8H,9H,10H-cyclohexa[h]chromen-4-one. The crude material was purified by FCC (SiHP, AcOEt: MeOH 4:1) to afford the product as a yellow oil. ESI-MS: 429 [M+H]$^+$ The product was converted into hydrochloric acid salt following Procedure 10. to afford the title compound as a yellow solid. ESI-MS: 429 [M+H]$^+$ $^1$H NMR (400 MHz, Deuterium Oxide) δ 8.75-8.72 (m, 1H), 8.71-8.67 (m, 2H), 8.33 (s, 1H), 8.16-8.11 (m, 2H), 7.63 (d, J=8.3 Hz, 1H), 7.50-7.46 (m, 1H), 7.38-7.33 (m, 1H), 7.21 (d, J=8.3 Hz, 1H), 4.67 (s, 2H), 4.32 (t, J=7.1 Hz, 2H), 4.22 (s, 2H), 3.34-3.23 (m, 2H), 2.84-2.74 (m, 4H), 2.54-2.43 (m, 2H), 1.81-1.70 (m, 4H).

Example 21. 3-({[(pyridin-4-yl)methyl][3-(pyridin-4-yl)propyl]amino}methyl)-4H-chromen-4-one

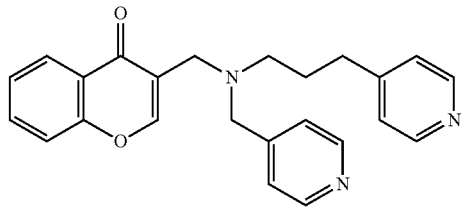 [SMILES: O=c1c(CN(CCCc2ccncc2)Cc2ccncc2)coc2ccccc12]

Preparation of [(pyridin-4-yl)methyl][3-(pyridin-4-yl)propyl]amine

The title compound was synthesized following the approach outlined in Procedure 3 substituting 3-(1H-imidazol-1-yl)propan-1-amine with 3-(4-pyridyl)propan-1-amine. Crude product obtained as a yellow oil was used in the next step without further purification (0.450 g, 1.33 mmol, yield 90%). ESI-MS: 228 [M+H]$^+$ Preparation of 3-({[(pyridin-4-yl)methyl][3-(pyridin-4-yl)propyl]amino}methyl)-4H-chromen-4-one The title compound was synthesized following the approach outlined in Procedure 9.1 substituting [3-(1H-imidazol-1-yl)propyl](pyridin-4-ylmethyl)amine with [(pyridin-4-yl)methyl][3-(pyridin-4-yl)propyl]amine, and 3-(chloromethyl)-7,8-dimethyl-4H-chromen-4-one with 3-(chloromethyl)-4H-chromen-4-one. The residue was purified by FCC (SiHP, DCM: MeOH 9:1) to afford the title compound (105 mg, 0.254 mmol, yield 59%) as an orange oil. ESI-MS: 386 [M+H]+

¹H NMR (400 MHz, DMSO-d₆) δ 8.49-8.44 (m, 2H), 8.36-8.33 (m, 2H), 8.33-8.32 (m, 1H), 8.08 (dd, J=7.9, 1.6 Hz, 1H), 7.84-7.78 (m, 1H), 7.66-7.62 (m, 1H), 7.53-7.47 (m, 1H), 7.41-7.36 (m, 2H), 7.20-7.15 (m, 2H), 3.65 (s, 2H), 3.48 (s, 2H), 2.59 (t, J=7.7 Hz, 2H), 2.43 (t, J=6.9 Hz, 2H), 1.89-1.77 (m, 2H).

Example 22. 7-bromo-3-{[(pyridin-4-ylmethyl)[3-(1H1,2,3-triazol-1-yl)propyl]amino]methyl}-4H-chromen-4-one

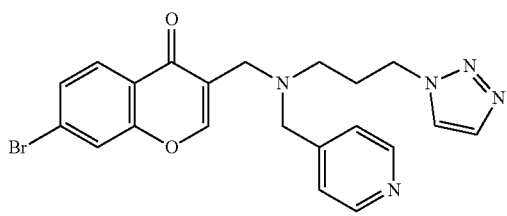

The title compound was prepared according to Procedure 9.1 substituting [3-(1H-imidazol-1-yl)propyl](pyridin-4-ylmethyl)amine with (pyridin-4-ylmethyl)[3-(1H-1,2,3-triazol-1-yl)propyl]amine, and 3-(chloromethyl)-7,8-dimethyl-4H-chromen-4-one with 7-bromo-3-(chloromethyl)-4H-chromen-4-one. The residue was purified by prep-HPLC to afford the title compound (30 mg, 0.07 mmol, yield 10%) as a brown oil. ESI-MS: 456 [M+H]+

¹H NMR (400 MHz, DMSO-d₆) δ 8.47-8.43 (m, 2H), 8.31 (s, 1H), 8.07-8.05 (m, 1H), 8.00-7.96 (m, 2H), 7.66 (dd, J=8.5, 1.8 Hz, 1H), 7.62 (d, J=0.9 Hz, 1H), 7.36-7.33 (m, 2H), 4.41 (t, J=7.1 Hz, 2H), 3.63 (s, 2H), 3.44 (s, 2H), 2.41 (t, J=6.8 Hz, 2H), 2.15-2.00 (m, 2H).

The title compound was converted into hydrochloric acid salt following Procedure 10 to afford the product as yellow crystals. ESI-MS: 456 [M+H]+

¹H NMR (400 MHz, Deuterium Oxide) δ 8.87-8.82 (m, 2H), 8.38 (s, 1H), 8.23-8.18 (m, 2H), 8.00-7.96 (m, 3H), 7.76 (dd, J=8.6, 1.8 Hz, 1H), 7.72-7.70 (m, 1H), 4.71 (s, 2H), 4.58 (t, J=6.2 Hz, 2H), 4.26 (s, 2H), 3.26-3.17 (m, 2H), 2.59-2.46 (m, 2H).

Example 23. 7-(4-fluorophenyl)-3-({[3-(1H-imidazol-1-yl)propyl](pyridin-4-ylmethyl)amino}methyl)-4H-chromen-4-one

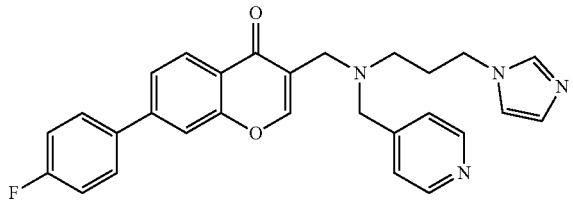 [SMILES: O=c1c(CN(CCCn2ccnc2)Cc2ccncc2)coc2cc(-c3ccc(F)cc3)ccc12]

The title compound was synthesized following Procedure 15. Product as a yellow oil (44 mg, 0.09 mmol yield 42%). ESI-MS: 470 [M+H]+

¹H NMR (400 MHz, DMSO-d₆) δ 8.50-8.43 (m, 2H), 8.36 (s, 1H), 8.13 (d, J=8.3 Hz, 1H), 7.93-7.92 (m, 1H), 7.92-7.87 (m, 2H), 7.80 (dd, J=8.4, 1.7 Hz, 1H), 7.56 (s, 1H), 7.41-7.32 (m, 4H), 7.11 (s, 1H), 6.80 (s, 1H), 3.98 (t, J=7.1 Hz, 2H), 3.64 (s, 2H), 3.48 (s, 2H), 2.40 (t, J=6.8 Hz, 2H), 2.00-1.91 (m, 2H).

The title compound was converted into hydrochloric acid salt following Procedure 10.

¹H NMR (400 MHz, Deuterium Oxide) δ 8.79-8.76 (m, 1H), 8.72-8.67 (m, 2H), 8.32 (s, 1H), 8.12-8.04 (m, 3H), 7.85-7.76 (m, 4H), 7.54-7.50 (m, 1H), 7.40-7.37 (m, 1H), 7.33-7.25 (m, 2H), 4.40 (s, 2H), 4.37 (t, J=7.0 Hz, 2H), 3.91 (s, 2H), 3.14-3.00 (m, 2H), 2.50-2.33 (m, 2H).

Example 24. 3-({[3-(1H-imidazol-1-yl)propyl][(pyridin-4-yl)methyl]amino}methyl)-4-oxo-4H-chromene-7-carbonitrile

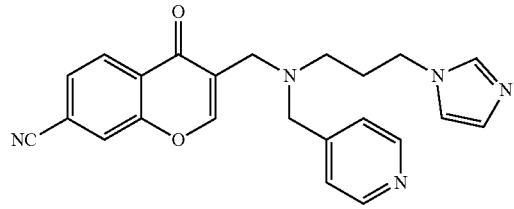 [SMILES: N#Cc1ccc2c(=O)c(CN(CCCn3ccnc3)Cc3ccncc3)coc2c1]

The title compound was synthesized following Procedure 16. Product as a beige powder (80 mg, 0.188 mmol, yield 60%). ESI-MS: 400 [M+H]+

¹H NMR (300 MHz, DMSO-d₆) δ 8.46-8.44 (m, 2H), 8.44-8.43 (m, 1H), 8.38-8.35 (m, 1H), 8.20 (d, J=8.2 Hz, 1H), 7.95 (s, 1H), 7.88 (dd, J=8.2, 1.5 Hz, 1H), 7.36-7.32 (m, 2H), 7.32-7.29 (m, 1H), 7.00-6.93 (m, 1H), 4.07 (t, J=7.2 Hz, 2H), 3.63 (s, 2H), 3.47 (s, 2H), 2.40 (t, J=6.7 Hz, 2H), 2.08-1.92 (m, 2H).

Example 25. 3-({[3-(1H-imidazol-1-yl)propyl][(2-methylpyridin-4-yl)methyl]amino}methyl)-4H-chromen-4-one

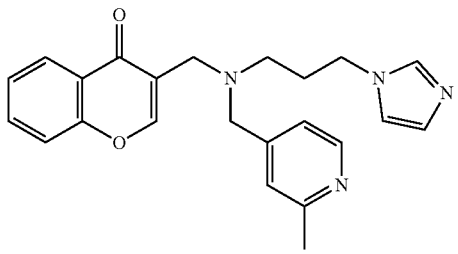 [SMILES: Cc1cc(CN(CCCn2ccnc2)Cc2coc3ccccc3c2=O)ccn1]

Preparation of [3-(1H-imidazol-1-yl)propyl][(2-methylpyridin-4-yl)methyl]amine

The title compound was synthesized following the approach outlined in Procedure 3 substituting pyridine-4-carboxaldehyde with 2-methylpyridine-4-carbaldehyde. Crude product obtained as yellow oil and was used in the next step without further purification (0.265 g, 0.99 mmol, yield 76%). ESI-MS: 232 [M+H]$^+$ $^1$H NMR (400 MHz, DMSO-d$_6$) δ 8.35-8.32 (m, 1H), 7.61-7.56 (m, 1H), 7.20-7.17 (m, 1H), 7.15-7.12 (m, 1H), 6.87-6.86 (m, 1H), 4.02 (t, J=7.0 Hz, 2H), 3.65 (s, 2H), 2.45-2.43 (m, 3H), 2.40 (t, J=6.7 Hz, 2H), 1.89-1.80 (m, 2H).

Preparation of 3-({[3-(1H-imidazol-1-yl)propyl][(2-methylpyridin-4-yl)methyl]amino}methyl)-4H-chromen-4-one The title compound was synthesized following the approach outlined in Procedure 9.1 substituting [3-(1H-imidazol-1-yl)propyl](pyridin-4-ylmethyl)amine with [3-(1H-imidazol-1-yl)propyl][(2-methylpyridin-4-yl)methyl]amine, and 3-(chloromethyl)-7,8-dimethyl-4H-chromen-4-one with 3-(chloromethyl)-4H-chromen-4-one. The residue was purified by FCC (SiHP, DCM: MeOH 9:1) to afford the title compound (170 mg, 0.416 mmol, yield 59%) as an orange oil. ESI-MS: 389 [M+H]$^+$ $^1$H NMR (400 MHz, DMSO-d$_6$) δ 8.34-8.27 (m, 2H), 8.12-8.04 (m, 1H), 7.85-7.75 (m, 1H), 7.67-7.59 (m, 1H), 7.58-7.53 (m, 1H), 7.53-7.44 (m, 1H), 7.18 (br s, 1H), 7.16-7.10 (m, 1H), 7.13-7.07 (m, 1H), 6.82-6.76 (m, 1H), 3.98 (t, J=7.1 Hz, 2H), 3.58 (s, 2H), 3.45 (s, 2H), 2.41-2.33 (m, 5H), 1.99-1.91 (m, 2H).

The product was converted into hydrochloric acid salt following Procedure 10.

$^1$H NMR (400 MHz, Deuterium Oxide) δ 8.84-8.66 (m, 1H), 8.58-8.49 (m, 1H), 8.37 (s, 1H), 8.03-7.97 (m, 1H), 7.95-7.90 (m, 2H), 7.89-7.80 (m, 1H), 7.65-7.57 (m, 1H), 7.55-7.48 (m, 2H), 7.40-7.38 (m, 1H), 4.64 (s, 2H), 4.33 (t, J=7.1 Hz, 2H), 4.27 (s, 2H), 3.42-3.26 (m, 2H), 2.63 (s, 3H), 2.58-2.43 (m, 2H).

Example 26. 3-({[(2-fluoropyridin-4-yl)methyl][3-(1H-imidazol-1-yl)propyl]amino}methyl)-7,8-dimethyl-4H-chromen-4-one

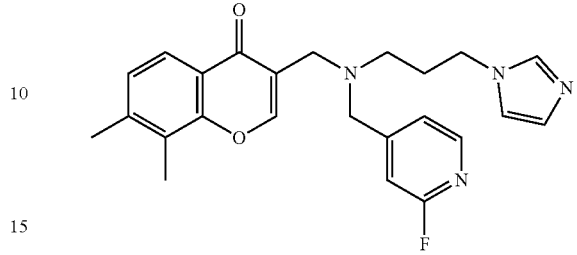

The title compound was synthesized following Procedure 18. Product as a yellow oil (41 mg, 0.098 mmol, yield 34%). ESI-MS: 421 [M+H]$^+$ $^1$H NMR (400 MHz, DMSO-d$_6$) δ 8.36 (s, 1H), 8.12 (d, J=5.1 Hz, 1H), 7.82 (d, J=8.1 Hz, 1H), 7.57 (s, 1H), 7.34-7.29 (m, 2H), 7.17 (s, 1H), 7.12 (d, J=1.3 Hz, 1H), 6.80 (d, J=1.3 Hz, 1H), 3.98 (t, J=7.1 Hz, 2H), 3.69 (s, 2H), 3.46 (s, 2H), 2.41 (s, 3H), 2.38 (d, J=6.8 Hz, 2H), 2.36 (s, 3H), 2.02-1.90 (m, 2H).

The product was transformed into hydrochloric acid salt following Procedure 10.

$^1$H NMR (400 MHz, Deuterium Oxide) δ 8.82-8.80 (m, 1H), 8.41 (s, 1H), 8.15 (d, J=5.2 Hz, 1H), 7.80-7.76 (m, 1H), 7.57-7.53 (m, 1H), 7.47-7.44 (m, 1H), 7.43-7.39 (m, 2H), 7.22 (s, 1H), 4.55 (s, 2H), 4.40 (t, J=6.9 Hz, 2H), 4.35 (s, 2H), 3.38-3.30 (m, 2H), 2.62-2.52 (m, 2H), 2.47 (s, 3H), 2.40 (s, 3H).

Example 27. 7-hydroxy-3-({[3-(1H-imidazol-1-yl)propyl][(2-methoxypyridin-4-yl)methyl]amino}methyl)-4H-chromen-4-one

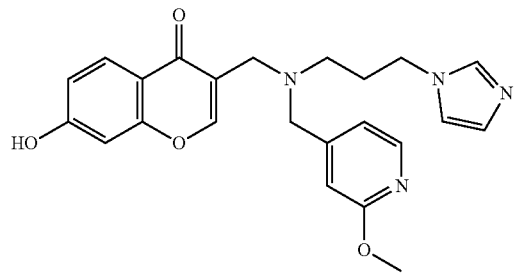 [SMILES: COc1cc(CN(CCCn2ccnc2)Cc2coc3cc(O)ccc3c2=O)ccn1]

The title compound was synthesized following Procedure 9.1 substituting [3-(1H-imidazol-1-yl)propyl](pyridin-4-ylmethyl)amine with [3-(1H-imidazol-1-yl)propyl][(2-methoxypyridin-4-yl)methyl]amine, and 3-(chloromethyl)-7,8-dimethyl-4H-chromen-4-one with 3-(chloromethyl)-7-hydroxy-4H-chromen-4-one. Crude material was purified by prep-HPLC to afford a formic acid salt of the title compound (60 mg, 0.14 mmol, yield 30%) as a white solid. ESI-MS: 421 [M+H]$^+$ $^1$H NMR (400 MHz, DMSO-d$_6$) δ 10.77 (s, 1H), 8.15 (s, 1H), 8.03 (d, J=5.2 Hz, 1H), 7.90 (d, J=8.8 Hz, 1H), 7.57 (br s, 1H), 7.12 (br s, 1H), 6.96-6.88 (m, 2H), 6.82-6.80 (m, 2H), 6.76 (s, 1H), 3.97 (t, J=7.1 Hz, 2H), 3.79 (s, 3H), 3.56 (s, 2H), 3.40 (s, 2H), 2.36 (t, J=6.7 Hz, 2H), 1.98-1.88 (m, 2H).

Example 28. 3-({[3-(pyridin-3-yl)propyl](pyridin-4-ylmethyl)amino}methyl)-4H-benzo[h]chromen-4-one

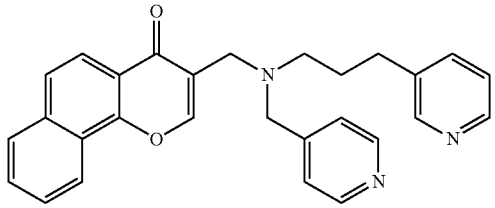 [SMILES: O=c1c(CN(CCCc2cccnc2)Cc2ccncc2)coc2c1ccc1ccccc12]

The title compound was prepared according to Procedure 9.1 substituting [3-(1H-imidazol-1-yl)propyl](pyridin-4-ylmethyl)amine with [3-(pyridin-3-yl)propyl][(pyridin-4-yl)methyl]amine, and 3-(chloromethyl)-7,8-dimethyl-4H-chromen-4-one with 3-(chloromethyl)-4H-benzo[h]chromen-4-one. Crude material was purified by prep-HPLC and converted into hydrochloric acid salt following Procedure 10. Product as yellow crystals (30 mg, 0.055 mmol, yield 50%). ESI-MS: 436 [M+H]$^+$ $^1$H NMR (400 MHz, Deuterium Oxide) δ 8.84-8.78 (m, 2H), 8.72-8.66 (m, 1H), 8.56 (s, 1H), 8.57-8.50 (m, 1H), 8.54-8.45 (m, 2H), 8.27-8.20 (m, 2H), 8.09-8.01 (m, 1H), 7.97-7.88 (m, 2H), 7.88-7.75 (m, 3H), 4.79 (s, 2H, overlapped with the solvent peak), 4.27 (s, 2H), 3.45-3.35 (m, 2H), 2.96 (t, J=7.7 Hz, 2H), 2.41-2.27 (m, 2H).

Example 29. 6-fluoro-3-({[3-(1H-imidazol-1-yl)propyl][(pyridin-4-yl)methyl]amino}methyl)-4H-chromen-4-one

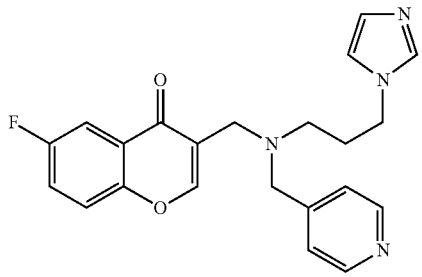 [SMILES: O=c1c(CN(CCCn2ccnc2)Cc2ccncc2)coc2ccc(F)cc12]

The title compound was synthesized following the approach outlined in Procedure 9.2 substituting 7,8-dimethyl-4-oxo-4H-chromene-3-carbaldehyde with 6-fluoro-4-oxo-4H-chromene-3-carbaldehyde. The residue was purified by FCC (deactivated SiHP, DCM: MeOH 9:1) to afford the title compound (22 mg, 0.060 mmol, yield 15%) as a yellow oil. ESI-MS: 393 [M+H]$^+$ $^1$H NMR (400 MHz, DMSO-d$_6$) δ 8.78-8.73 (m, 1H), 8.47-8.41 (m, 2H), 8.39 (s, 1H), 7.80-7.72 (m, 3H), 7.53-7.50 (m, 1H), 7.35-7.33 (m, 2H), 7.32-7.28 (m, 1H), 4.27-4.11 (m, 2H), 3.64 (s, 2H), 3.47 (s, 2H), 2.41 (t, J=6.6 Hz, 2H), 2.07-2.00 (m, 2H).

The title compound was converted into hydrochloric acid salt following Procedure 10. ESI-MS 393 [M+H]$^+$ $^1$H NMR (300 MHz, Deuterium Oxide) δ 8.73-8.65 (m, 3H), 8.32 (s, 1H), 8.11-8.05 (m, 2H), 7.72-7.55 (m, 3H), 7.48-7.44 (m, 1H), 7.37-7.33 (m, 1H), 4.46 (s, 2H), 4.29 (t, J=7.0 Hz, 2H), 4.03 (s, 2H), 3.13-3.03 (m, 2H), 2.44-2.32 (m, 2H).

Example 30. 3-({[3-(1H-imidazol-1-yl)propyl][(2-methoxypyridin-4-yl)methyl]amino}methyl)-4H-benzo[h]chromen-4-one

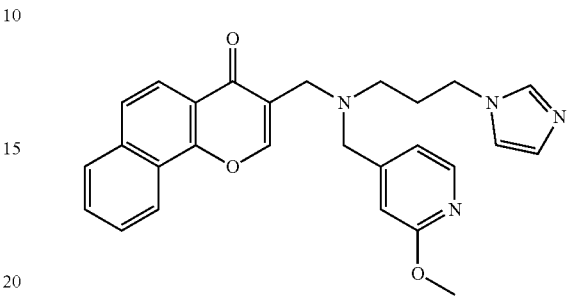

The title compound was synthesized following the approach outlined in Procedure 9.1 substituting [3-(1H-imidazol-1-yl)propyl](pyridin-4-ylmethyl)amine with [3-(1H-imidazol-1-yl)propyl][(2-methoxypyridin-4-yl)methyl]amine and 3-(chloromethyl)-7,8-dimethyl-4H-chromen-4-one with 3-(chloromethyl)-4H-benzo[h]chromen-4-one. The residue was purified by FCC (SiHP, DCM: MeOH 9:1) to afford the title compound (28 mg, 0.306 mmol, yield 20%) as a brown oil. ESI-MS: 455 [M+H]$^+$ $^1$H NMR (300 MHz, DMSO-d$_6$) δ 8.53-8.45 (m, 2H), 8.16-8.09 (m, 1H), 8.08-8.01 (m, 2H), 7.99-7.91 (m, 1H), 7.88-7.75 (m, 2H), 7.67-7.47 (m, 1H), 7.17-7.03 (m, 1H), 6.98 (dd, J=5.2, 1.3 Hz, 1H), 6.84-6.73 (m, 2H), 4.01 (t, J=7.1 Hz, 2H), 3.77 (s, 3H), 3.63 (s, 2H), 3.53 (s, 2H), 2.43 (t, J=6.8 Hz, 2H), 2.05-1.88 (m, 2H).

Example 31. 3-({[3-(1H-imidazol-1-yl)propyl][(pyridin-4-yl)methyl]amino}methyl)-1-methyl-1,4-dihydroquinolin-4-one

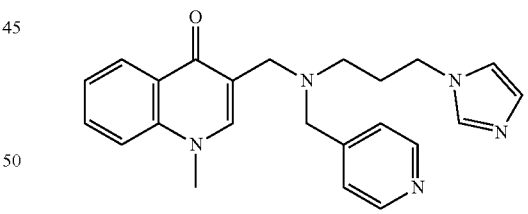

The title compound was synthesized following Procedure 19 as a yellow oil (25 mg, 0.064 mmol, yield 17%). ESI-MS: 388 [M+H]$^+$ $^1$H NMR (400 MHz, DMSO-d$_6$) δ 8.46 (s, 2H), 8.23 (dd, J=8.0, 1.6 Hz, 1H), 7.99 (s, 1H), 7.75 (s, 1H), 7.66 (d, J=8.5 Hz, 1H), 7.59 (s, 1H), 7.41 (s, 1H), 7.38-7.37 (m, 2H), 7.12 (s, 1H), 6.80 (s, 1H), 4.00 (t, J=7.1 Hz, 2H), 3.86 (s, 3H), 3.62 (s, 2H), 3.49 (s, 2H), 2.39-2.36 (m, 2H), 2.01-1.93 (m, 2H).

The title compound was converted into hydrochloric acid salt following Procedure 10 (24 mg, 0.048 mmol, yield 98%). ESI-MS 388 [M+H]$^+$ $^1$H NMR (300 MHz, Deuterium Oxide) δ 8.74 (s, 1H), 8.60 (s, 2H), 8.15 (s, 1H), 8.09 (s, 3H), 7.88 (s, 1H), 7.74 (d, J=8.7 Hz, 1H), 7.56 (ddd, J=8.2, 7.0, 1.0 Hz, 1H), 7.48-7.46 (m, 1H), 7.36-7.34 (m, 1H), 4.75 (s, 2H, overlapping with solvent peak), 4.39 (s, 2H), 4.33 (t, J=7.1 Hz, 2H), 3.93 (s, 3H), 3.43-3.37 (m, 2H), 2.57-2.50 (m, 2H).

Example 32. 3-({[3-(1H-imidazol-1-yl)propyl](pyridin-4-ylmethyl)amino}methyl)-7-(4-methoxyphenyl)-4H-chromen-4-one

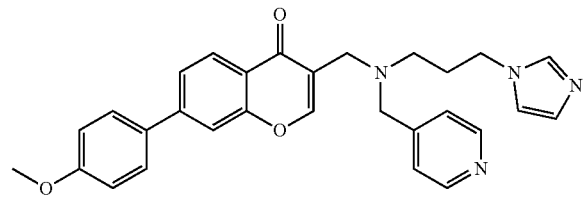 [SMILES: COc1ccc(-c2ccc3c(=O)c(CN(CCCn4ccnc4)Cc4ccncc4)coc3c2)cc1]

The title compound was prepared according to Procedure 15 substituting 4-fluorophenylboronic acid with 4-methoxyphenylboronic acid. Crude material was purified by prep-HPLC and transformed into hydrochloric acid salt following Procedure 10. Product as yellow crystals (67 mg, 0.011 mmol, yield 51%). ESI-MS: 481 [M+H]$^+$ $^1$H NMR (300 MHz, Deuterium Oxide) δ 8.84-8.76 (m, 3H), 8.33 (s, 1H), 8.24-8.17 (m, 2H), 7.96 (d, J=8.4 Hz, 1H), 7.78-7.66 (m, 4H), 7.57-7.52 (m, 1H), 7.46-7.40 (m, 1H), 7.11-7.02 (m, 2H), 4.59 (s, 2H), 4.36 (t, J=7.0 Hz, 2H), 3.99 (s, 2H), 3.87 (s, 3H), 3.26-3.14 (m, 2H), 2.54-2.40 (m, 2H).

Example 33. 3-({[3-(1H-imidazol-1-yl)propyl](pyridin-4-ylmethyl)amino}methyl)-4H-chromen-4-one

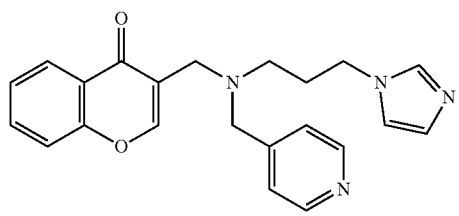 [SMILES: O=c1c(CN(CCCn2ccnc2)Cc2ccncc2)coc2ccccc12]

The title compound was synthesized following Procedure 9.1 substituting 3-(chloromethyl)-7,8-dimethyl-4H-chromen-4-one with 3-(chloromethyl)-4H-chromen-4-one. The residue was purified by prep-HPLC to afford the title compound (140 mg, 0.353 mmol, yield 34%) as a yellow oil. ESI-MS: 375 [M+H]$^+$ The product was transformed into hydrochloric acid salt following Procedure 10.

$^1$H NMR (400 MHz, DMSO-d$_6$) δ 8.49-8.42 (m, 2H), 8.36-8.30 (m, 1H), 8.12-8.04 (m, 1H), 7.86-7.76 (m, 1H), 7.69-7.60 (m, 1H), 7.58-7.53 (m, 1H), 7.54-7.45 (m, 1H), 7.41-7.32 (m, 2H), 7.16-7.00 (m, 1H), 6.82-6.71 (m, 1H), 3.98 (t, J=7.1 Hz, 2H), 3.63 (s, 2H), 3.47 (s, 2H), 2.39 (t, J=6.8 Hz, 2H), 2.00-1.92 (m, 2H).

Example 34. 3-({[3-(1H-imidazol-1-yl)propyl][(2-methoxypyridin-4-yl)methyl]amino}methyl)-7-(4-methylpiperazin-1-yl)-4H-chromen-4-one

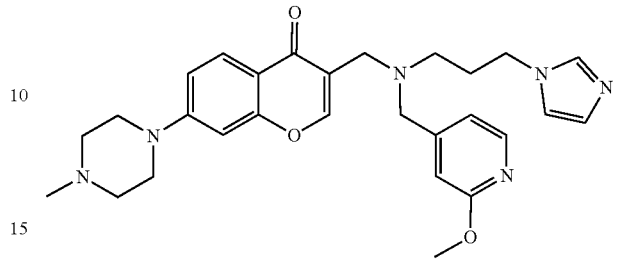

Preparation of 2-hydroxy-7-(4-methylpiperazin-1-yl)-3,4-dihydro-2H-1-benzopyran-4-one The title compound was synthesized following the approach outlined in Procedure 5a substituting 1-(2-hydroxy-3,4-dimethylphenyl)ethan-1-one with 1-[2-hydroxy-4-(4-methylpiperazin-1-yl)phenyl]ethan-1-one. The crude product (790 mg, 3.01 mmol, yield 99%) was obtained as a yellow solid and was used in the next step without further purification. ESI-MS: 261 [M–H]$^-$ Preparation of 3-(hydroxymethyl)-7-(4-methylpiperazin-1-yl)-4H-chromen-4-one The title compound was synthesized following the approach outlined in Procedure 5b substituting 2-hydroxy-7,8-dimethyl-3,4-dihydro-2H-1-benzopyran-4-one with 2-hydroxy-7-(4-methylpiperazin-1-yl)-3,4-dihydro-2H1-benzopyran-4-one. The residue was purified by FCC (SiHP; Hexane:AcOEt; 100:0 to 1:1) to afford the product (800 mg, 2.92 mmol, yield 56%) as a yellowish solid. ESI-MS: 275 [M+H]$^+$ Preparation of 3-(chloromethyl)-7-(4-methylpiperazin-1-yl)-4H-chromen-4-one The title compound was prepared according to Procedure 1c substituting 3-(hydroxymethyl)-4H-chromen-4-one with 3-(hydroxymethyl)-7-(4-methylpiperazin-1-yl)-4H-chromen-4-one. Crude product (110 mg, 0.37 mmol, yield 69%) was used directly in the next step without further purification. ESI-MS: 294 [M+H]$^+$ Preparation of 3-({[3-(1H-imidazol-1-yl)propyl][(2-methoxypyridin-4-yl)methyl]amino}methyl)-7-(4-methylpiperazin-1-yl)-4H-chromen-4-one The title compound was synthesized following the approach outlined in Procedure 9.1 substituting 3-(chloromethyl)-7,8-dimethyl-4H-chromen-4-one with 3-(chloromethyl)-7-(4-methylpiperazin-1-yl)-4H-chromen-4-one and [3-(1H-imidazol-1-yl)propyl](pyridin-4-ylmethyl)amine with [3-(1H-imidazol-1-yl)propyl][(2-methoxypyridin-4-yl)methyl]amine. The residue was purified by FCC (silica, DCM: MeOH 100:0 to 9:1) to afford the title compound (15 mg, 0.03 mmol, yield 9%) as a yellow oil. ESI-MS: 503 [M+H]$^+$ $^1$H NMR (400 MHz, DMSO-d$_6$) δ 8.11 (s, 1H), 8.03 (d, J=5.2 Hz, 1H), 7.83 (d, J=9.1 Hz, 1H), 7.54 (d, J=1.1 Hz, 1H), 7.11-7.09 (m, 2H), 6.93 (dd, J=5.3, 1.3 Hz, 1H), 6.85 (d, J=2.4 Hz, 1H), 6.81-6.76 (m, 2H), 3.96 (t, J=7.1 Hz, 2H), 3.79 (s, 3H), 3.55 (s, 2H), 3.40 (s, 2H), 3.37 (t, J=5.2 Hz, 4H), 2.45-2.41 (m, 4H), 2.40-2.32 (m, 2H), 2.22 (s, 3H), 1.98-1.88 (m, 2H).

Example 35. 3-({[3-(1H-imidazol-1-yl)propyl][(pyridin-4-yl)methyl]amino}methyl)-4H-pyrido[1,2-a]pyrimidin-4-one

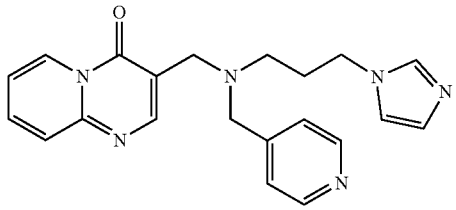 [SMILES: O=c1c(CN(CCCn2ccnc2)Cc2ccncc2)cnc2ccccn12]

The title compound was synthesized following the approach outlined in Procedure 31d substituting [3-(1H-1,3-benzodiazol-1-yl)propyl][(6-methoxypyridin-3-yl)methyl]amine with [3-(1H-imidazol-1-yl)propyl][(pyridin-4-yl)methyl]amine. The residue was purified by FCC (SiHP, DCM: MeOH 5-15%) and prep-HPLC afford a formic acid salt of the product (33 mg, 0.09 mmol, yield 7%) as a yellow oil. ESI-MS: 375 [M+H]+

The product was transformed into a hydrochloric acid salt following Procedure 10 (15 mg, 0.03 mmol, yield 95%). ESI-MS 375 [M+H]+

1H NMR (300 MHz, Deuterium Oxide) δ 9.16 (ddd, J=7.2, 1.5, 0.8 Hz, 1H), 8.86-8.75 (m, 3H), 8.48 (s, 1H), 8.37 (ddd, J=8.8, 7.0, 1.5 Hz, 1H), 8.25-8.16 (m, 2H), 7.95 (dt, J=8.9, 1.0 Hz, 1H), 7.73 (td, J=7.1, 1.3 Hz, 1H), 7.56 (t, J=1.8 Hz, 1H), 7.47 (t, J=1.7 Hz, 1H), 4.55 (s, 2H), 4.36 (t, J=7.2 Hz, 2H), 4.28 (s, 2H), 3.20-3.08 (m, 2H), 2.48 (p, J=7.4 Hz, 2H).

Example 36. 3-({[3-(1H-imidazol-1-yl)propyl][(pyridin-4-yl)methyl]amino}methyl)-2-methyl-4H-chromen-4-one

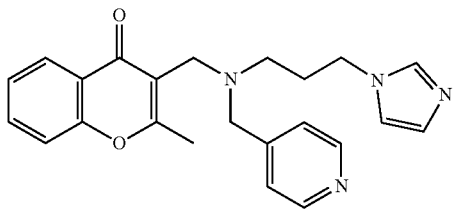 [SMILES: Cc1oc2ccccc2c(=O)c1CN(CCCn1ccnc1)Cc1ccncc1]

The title compound was synthesized following the approach outlined in Procedure 9.1 substituting 3-(chloromethyl)-7,8-dimethyl-4H-chromen-4-one with 3-(chloromethyl)-2-methyl-4H-chromen-4-one. The product (66 mg, 0.17 mmol, yield 71%) was obtained as a yellow oil. ESI-MS: 389 [M+H]+

The product was converted into hydrochloric acid salt following Procedure 10. Product as white crystals (40 mg, 0.08 mmol, yield 62%). ESI-MS: 389 [M+H]+

1H NMR (300 MHz, Deuterium Oxide) δ 8.85-8.77 (m, 3H), 8.28-8.21 (m, 2H), 8.05 (dd, J=8.1, 1.6 Hz, 1H), 7.90 (ddd, J=8.7, 7.2, 1.7 Hz, 1H), 7.67-7.55 (m, 3H), 7.47-7.45 (m, 1H), 4.76 (s, 2H), 4.45-4.36 (m, 4H), 3.46-3.38 (m, 2H), 2.65-2.52 (m, 5H)

Example 37. 7-bromo-6-fluoro-3-({[3-(1H-imidazol-1-yl)propyl][(pyridin-4-yl)methyl]amino}methyl)-4H-chromen-4-one

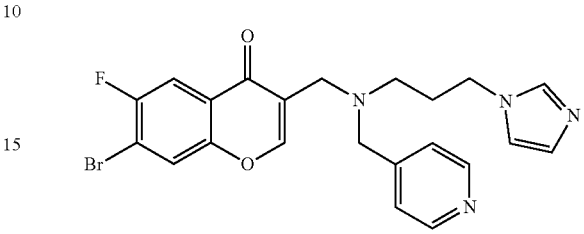

Preparation of 7-bromo-6-fluoro-2-hydroxy-3,4-dihydro-2H-1-benzopyran-4-one

The title compound was synthesized following the approach outlined in Procedure 5a substituting 1-(2-hydroxy-3,4-dimethylphenyl)ethan-1-one with 1-(4-bromo-5-fluoro-2-hydroxyphenyl)ethan-1-one. The crude product (3.3 g, 12.6 mmol, yield 98%) was obtained as an orange solid and was used in the next step without further purification. ESI-MS: 259 [M−H]−

Preparation of 7-bromo-6-fluoro-3-(hydroxymethyl)-4H-chromen-4-one

The title compound was synthesized following the approach outlined in Procedure 5b substituting 2-hydroxy-7,8-dimethyl-3,4-dihydro-2H1-benzopyran-4-one with 7-bromo-6-fluoro-2-hydroxy-3,4-dihydro-2H1-benzopyran-4-one. The residue was purified by FCC (SiHP; Hexane: AcOEt; 100:0 to 1:1) to afford the product (2.74 g, 10.0 mmol, yield 77%) as a white solid. ESI-MS: 271 [M−H]−

Preparation of 7-bromo-3-(chloromethyl)-6-fluoro-4H-chromen-4-one

The title compound was prepared according to Procedure 1c substituting 3-(hydroxymethyl)-4H-chromen-4-one with 7-bromo-6-fluoro-3-(hydroxymethyl)-4H-chromen-4-one. Product was obtained as a yellow solid (814 mg, 2.79 mmol, yield 76%). ESI-MS: 291 [M+H]+

Preparation of 7-bromo-6-fluoro-3-({[3-(1H-imidazol-1-yl)propyl][(pyridin-4-yl)methyl]amino}methyl)-4H-chromen-4-one The title compound was synthesized following the approach outlined in Procedure 9.1 substituting 3-(chloromethyl)-7,8-dimethyl-4H-chromen-4-one with 7-bromo-3-(chloromethyl)-6-fluoro-4H-chromen-4-one. The product (310 mg, 0.66 mmol, yield 64%) was obtained as a yellow oil. ESI-MS: 471 [M+H]+

The product was converted into hydrochloric acid salt following Procedure 10. Product as white crystals (58 mg, 0.10 mmol, yield 94%). ESI-MS: 471 [M+H]+

1H NMR (300 MHz, Deuterium Oxide) δ 8.86-8.80 (m, 3H), 8.41 (s, 1H), 8.25-8.19 (m, 2H), 8.10 (d, J=5.5 Hz, 1H), 7.87 (d, J=8.2 Hz, 1H), 7.59-7.54 (m, 1H), 7.51-7.45 (m, 1H), 4.58 (s, 2H), 4.39 (t, J=7.1 Hz, 2H), 4.14 (s, 2H), 3.25-3.14 (m, 2H), 2.58-2.41 (m, 2H)

Example 38. 7-(3,4-dimethoxyphenyl)-3-({[3-(1H-imidazol-1-yl)propyl][(pyridin-4-yl)methyl]amino}methyl)-4H-chromen-4-one

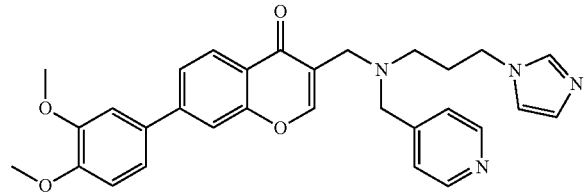 [SMILES: COc1ccc(-c2ccc3c(=O)c(CN(CCCn4ccnc4)Cc4ccncc4)coc3c2)cc1OC]

The title compound was synthesized following the approach outlined in Procedure 15 substituting 4-fluorophenylboronic acid with (3,4-dimethoxyphenyl)boronic acid. The product (20 mg, 0.053 mmol, yield 27%) was obtained as a yellow oil. ESI-MS: 511 [M+H]$^+$ The product was converted into hydrochloric acid salt following Procedure 10. Product as yellow crystals (18 mg, 0.029 mmol, yield 99%). ESI-MS: 511 [M+H]$^+$ $^1$H NMR (400 MHz, Deuterium Oxide) δ 8.78-8.75 (m, 1H), 8.75-8.71 (m, 2H), 8.27 (s, 1H), 8.16-8.12 (m, 2H), 7.90 (d, J=8.5 Hz, 1H), 7.68 (dd, J=8.6, 1.7 Hz, 1H), 7.59 (d, J=1.7 Hz, 1H), 7.55-7.50 (m, 1H), 7.41-7.37 (m, 1H), 7.26 (dd, J=8.5, 2.2 Hz, 1H), 7.12 (d, J=2.1 Hz, 1H), 7.02 (d, J=8.6 Hz, 1H), 4.46 (s, 2H), 4.35 (t, J=7.0 Hz, 2H), 3.89-3.86 (m, 5H), 3.83 (s, 3H), 3.13-3.04 (m, 2H), 2.48-2.35 (m, 2H).

Example 39. 3-({[3-(1H-imidazol-1-yl)propyl][(pyridin-4-yl)methyl]amino}methyl)-7-(2-methoxyphenyl)-4H-chromen-4-one

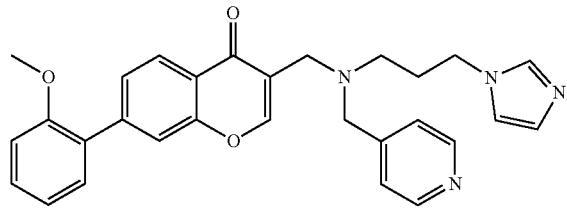 [SMILES: COc1ccccc1-c1ccc2c(=O)c(CN(CCCn3ccnc3)Cc3ccncc3)coc2c1]

The title compound was synthesized following the approach outlined in Procedure 15 substituting 4-fluorophenylboronic acid with (2-methoxyphenyl)boronic acid. The product (22 mg, 0.046 mmol, yield 32%) was obtained as a yellow oil. ESI-MS: 481 [M+H]$^+$ The product was converted into hydrochloric acid salt following Procedure 10. Product as yellow crystals (17 mg, 0.029 mmol, yield 92%). ESI-MS: 481 [M+H]$^+$ $^1$H NMR (400 MHz, Deuterium Oxide) δ 8.81-8.76 (m, 3H), 8.39 (s, 1H), 8.22-8.17 (m, 2H), 8.06 (d, J=8.4 Hz, 1H), 7.80 (d, J=1.5 Hz, 1H), 7.72 (dd, J=8.4, 1.6 Hz, 1H), 7.55-7.42 (m, 4H), 7.22 (dd, J=8.4, 1.0 Hz, 1H), 7.17 (td, J=7.5, 1.1 Hz, 1H), 4.60 (s, 2H), 4.37 (t, J=7.1 Hz, 2H), 4.11 (s, 2H), 3.87 (s, 3H), 3.26-3.18 (m, 2H), 2.54-2.43 (m, 2H).

Example 40. 3-({[3-(1H-imidazol-1-yl)propyl][(pyridin-4-yl)methyl]amino}methyl)-7-(3-methoxyphenyl)-4H-chromen-4-one

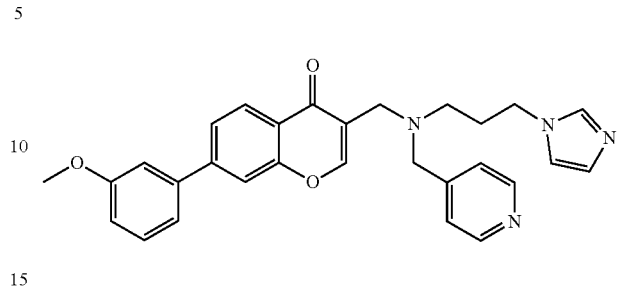

The title compound was synthesized following the approach outlined in Procedure 15 substituting 4-fluorophenylboronic acid with (3-methoxyphenyl)boronic acid. The product (19 mg, 0.04 mmol, yield 28%) was obtained as a yellow oil. ESI-MS: 481 [M+H]$^+$ The product was converted into hydrochloric acid salt following Procedure 10. Product as yellow crystals (17 mg, 0.029 mmol, yield 92%). ESI-MS: 481 [M+H]$^+$ $^1$H NMR (400 MHz, Deuterium Oxide) δ 8.79-8.73 (m, 3H), 8.32 (s, 1H), 8.18-8.12 (m, 2H), 8.00 (dd, J=8.9, 0.7 Hz, 1H), 7.79-7.75 (m, 2H), 7.54-7.50 (m, 1H), 7.49-7.43 (m, 1H), 7.41-7.39 (m, 1H), 7.38-7.34 (m, 1H), 7.26-7.22 (m, 1H), 7.09-7.03 (m, 1H), 4.50 (s, 2H), 4.35 (t, J=7.0 Hz, 2H), 3.93 (s, 2H), 3.89 (s, 3H), 3.16-3.08 (m, 2H), 2.48-2.37 (m, 2H)

Example 41. 2-methyl-3-({[3-(pyridin-3-yl)propyl][(pyridin-4-yl)methyl]amino}methyl)-4H-chromen-4-one

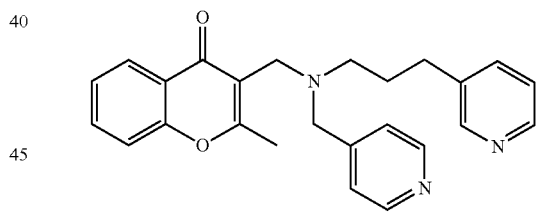

The title compound was synthesized following the approach outlined in Procedure 9.1 substituting 3-(chloromethyl)-7,8-dimethyl-4H-chromen-4-one with 3-(chloromethyl)-2-methyl-4H-chromen-4-one and [3-(1H-imidazol-1-yl)propyl](pyridin-4-ylmethyl)amine with [3-(pyridin-3-yl)propyl][(pyridin-4-yl)methyl]amine. The product (30 mg, 0.075 mmol, yield 31%) was obtained as a yellow oil. ESI-MS: 400 [M+H]$^+$ The product was converted into hydrochloric acid salt following Procedure 10. Product as white crystals (28 mg, 0.055 mmol, yield 73%). ESI-MS: 400 [M+H]$^+$ $^1$H NMR (400 MHz, Deuterium Oxide) δ 8.85-8.78 (m, 2H), 8.71 (d, J=1.9 Hz, 1H), 8.67-8.63 (m, 1H), 8.55-8.50 (m, 1H), 8.26-8.20 (m, 2H), 8.05-7.96 (m, 2H), 7.89 (ddd, J=8.7, 7.2, 1.7 Hz, 1H), 7.64-7.60 (m, 1H), 7.57 (ddd, J=8.2, 7.2, 1.0 Hz, 1H), 4.81 (s, 2H), 4.45 (s, 2H), 3.52-3.44 (m, 2H), 2.99 (t, J=7.9 Hz, 2H), 2.59 (s, 3H), 2.44-2.33 (m, 2H).

Example 42. 6-fluoro-3-({[3-(1H-imidazol-1-yl)propyl][(pyridin-4-yl)methyl]amino}methyl)-7-(4-methoxyphenyl)-4H-chromen-4-one

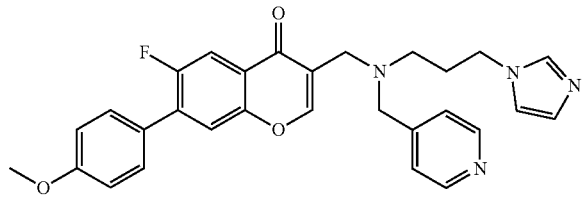 [SMILES: COc1ccc(-c2cc3occ(CN(CCCn4ccnc4)Cc4ccncc4)c(=O)c3cc2F)cc1]

The title compound was synthesized following the approach outlined in Procedure 15 substituting 7-bromo-3-({[3-(1H-imidazol-1-yl)propyl](pyridin-4-ylmethyl)amino}methyl)-4H-chromen-4-one with 7-bromo-6-fluoro-3-({[3-(1H-imidazol-1-yl)propyl][(pyridin-4-yl)methyl]amino}methyl)-4H-chromen-4-one and 4-fluorophenylboronic acid with (4-methoxyphenyl)boronic acid. The product (29 mg, 0.058 mmol, yield 55%) was obtained as a yellow oil. ESI-MS: 499 [M+H]$^+$ The product was converted into hydrochloric acid salt following Procedure 10. Product as yellow crystals (26 mg, 0.043 mmol, yield 97%). ESI-MS: 499 [M+H]$^+$ $^1$H NMR (300 MHz, Deuterium Oxide) δ 8.81-8.76 (m, 3H), 8.36 (s, 1H), 8.17 (d, J=6.4 Hz, 2H), 7.76-7.67 (m, 2H), 7.64-7.59 (m, 2H), 7.56-7.52 (m, 1H), 7.44-7.41 (m, 1H), 7.11-7.06 (m, 2H), 4.53 (s, 2H), 4.40-4.31 (m, 2H), 4.03 (s, 2H), 3.87 (s, 3H), 3.21-3.09 (m, 2H), 2.50-2.40 (m, 2H).

Example 43. 1-ethyl-3-({[3-(1H-imidazol-1-yl)propyl](pyridin-4-ylmethyl)amino}methyl)-1,4-dihydroquinolin-4-one

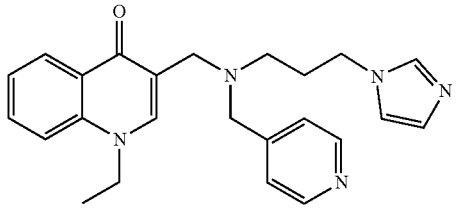 [SMILES: CCn1cc(CN(CCCn2ccnc2)Cc2ccncc2)c(=O)c2ccccc21]

Preparation of 1-ethyl-4-oxo-1,4-dihydroquinoline-3-carbaldehyde

The title compound was synthesized following the approach outlined in Procedure 19d substituting methyl iodide with ethyl iodide. The residue was purified by crystallization from hot EtOH to afford the title compound (0.16 g, 0.84 mmol, yield 63%) as a beige solid. ESI-MS: 202 [M+H]$^+$ $^1$H NMR (400 MHz, DMSO-d$_6$) δ 10.19 (s, 1H), 8.65 (s, 1H), 8.35-8.30 (m, 1H), 7.92-7.83 (m, 2H), 7.58-7.52 (m, 1H), 4.51-4.44 (m, 2H), 1.43-1.37 (m, 3H).

Preparation of 1-ethyl-3-({[3-(1H-imidazol-1-yl)propyl](pyridin-4-ylmethyl)amino}methyl)-1,4-dihydroquinolin-4-one The title compound was synthesized following the approach outlined in Procedure 9.2 substituting 7,8-dimethyl-4-oxo-4H-chromene-3-carbaldehyde with 1-ethyl-4-oxo-1,4-dihydroquinoline-3-carbaldehyde using DCM as a solvent. The residue was purified by FCC (SiHP, DCM: MeOH 95:5) to afford the title compound (50 mg, 0.12 mmol, yield 32%) as a yellow oil. ESI-MS: 402 [M+H]$^+$ $^1$H NMR (400 MHz, DMSO-d$_6$) δ 8.48-8.42 (m, 2H), 8.27-8.21 (m, 1H), 8.01 (s, 1H), 7.77-7.67 (m, 2H), 7.58-7.52 (m, 1H), 7.42-7.34 (m, 3H), 7.13-7.06 (m, 1H), 6.81-6.77 (m, 1H), 4.33 (q, J=7.1 Hz, 2H), 3.99 (t, J=7.1 Hz, 2H), 3.62 (s, 2H), 3.51 (s, 2H), 2.38 (t, J=6.7 Hz, 2H), 2.01-1.91 (m, 2H), 1.38-1.29 (m, 3H).

The product was converted into hydrochloric acid salt following Procedure 10. Product as yellow crystals. ESI-MS: 402 [M+H]$^+$ $^1$H NMR (300 MHz, Deuterium Oxide) δ 8.77-8.74 (m, 1H), 8.62-8.58 (m, 2H), 8.23 (s, 1H), 8.14-8.08 (m, 3H), 7.93-7.79 (m, 2H), 7.60-7.48 (m, 2H), 7.38-7.34 (m, 1H), 4.75 (s, 2H), 4.45-4.41 (m, 2H), 4.40-4.32 (m, 4H), 3.50-3.40 (m, 2H), 2.65-2.50 (m, 2H), 1.48-1.38 (m, 3H).

Example 44. 3-({[3-(1H-imidazol-1-yl)propyl][(2-methoxypyridin-4-yl)methyl]amino}methyl)-1-methyl-1,4-dihydroquinolin-4-one

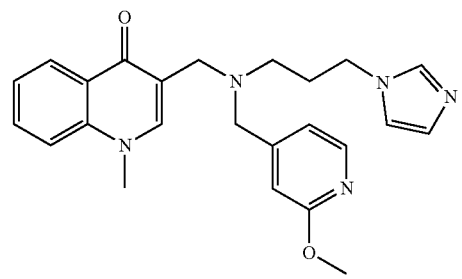 [SMILES: COc1cc(CN(CCCn2ccnc2)Cc2cn(C)c3ccccc3c2=O)ccn1]

The title compound was synthesized following the approach outlined in Procedure 9.2 substituting 7,8-dimethyl-4-oxo-4H-chromene-3-carbaldehyde with 1-methyl-4-oxo-1,4-dihydroquinoline-3-carbaldehyde and [3-(1H-imidazol-1-yl)propyl](pyridin-4-ylmethyl)amine with [3-(1H-imidazol-1-yl)propyl][(2-methoxypyridin-4-yl)methyl]amine using DCM as a solvent. The residue was purified by FCC (SiHP, DCM: MeOH 9:1) to afford the product (34 mg, 0.081 mmol, yield 21%) as a yellow oil. ESI-MS: 418 [M+H]$^+$ $^1$H NMR (300 MHz, DMSO-d$_6$) δ 8.25-8.19 (m, 1H), 8.06-8.01 (m, 1H), 7.98-7.94 (m, 1H), 7.78-7.71 (m, 1H), 7.68-7.62 (m, 1H), 7.56 (s, 1H), 7.44-7.36 (m, 1H), 7.13-7.09 (m, 1H), 7.00-6.94 (m, 1H), 6.82-6.77 (m, 2H), 4.03-3.96 (m, 2H), 3.85 (s, 3H), 3.80 (s, 3H), 3.57 (s, 2H), 3.49 (s, 2H), 2.41-2.33 (m, 2H), 2.01-1.90 (m, 2H).

Example 45. 6,8-difluoro-3-({[3-(1H-imidazol-1-yl)propyl][(pyridin-4-yl)methyl]amino}methyl)-4H-chromen-4-one

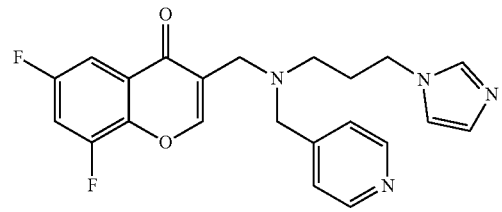 [SMILES: O=c1c(CN(CCCn2ccnc2)Cc2ccncc2)coc2c(F)cc(F)cc12]

Preparation of 1-(3,5-difluoro-2-hydroxyphenyl)ethan-1-one

The title compound was synthesized following the approach outlined in Procedure 4.b substituting 2,3-dimethylphenyl acetate with 2,4-difluorophenyl acetate and performing the reaction at 145° C. for 3 h. The product (1.89 g, 11 mmol, yield 76%) was obtained as a white solid. ESI-MS: 171 [M−H]⁻

Preparation of 6,8-difluoro-2-hydroxy-3,4-dihydro-2H-1-benzopyran-4-one

The title compound was synthesized following the approach outlined in Procedure 5a substituting 1-(2-hydroxy-3,4-dimethylphenyl)ethan-1-one with 1-(3,5-difluoro-2-hydroxyphenyl)ethan-1-one. The crude product (3.36 g) was obtained as a yellow solid and was used in the next step without further purification. ESI-MS: 201 [M+H]⁺

Preparation of 6,8-difluoro-3-(hydroxymethyl)-4H-chromen-4-one

The title compound was synthesized following the approach outlined in Procedure 5b substituting 2-hydroxy-7,8-dimethyl-3,4-dihydro-2H-1-benzopyran-4-one with 6,8-difluoro-2-hydroxy-3,4-dihydro-2H-1-benzopyran-4-one. The residue was purified by FCC (SiHP; Hexane:AcOEt; 100:0 to 1:1) to afford the product (0.43 g, 2.01 mmol, yield 24%) as a white solid. ESI-MS: 213 [M+H]⁺

Preparation of 3-(chloromethyl)-6,8-difluoro-4H-chromen-4-one

The title compound was prepared according to Procedure 1c substituting 3-(hydroxymethyl)-4H chromen-4-one with 6,8-difluoro-3-(hydroxymethyl)-4H-chromen-4-one. Product was obtained as a yellow solid (279 mg, 1.21 mmol, yield 86%). ESI-MS: 231 [M+H]⁺

Preparation of 6,8-difluoro-3-({[3-(1H-imidazol-1-yl)propyl][(pyridin-4-yl)methyl]amino}methyl)-4H-chromen-4-one The title compound was synthesized following the approach outlined in Procedure 9.1 substituting 3-(chloromethyl)-7,8-dimethyl-4H-chromen-4-one with 3-(chloromethyl)-6,8-difluoro-4H-chromen-4-one. The product (103 mg, 0.25 mmol, yield 72%) was obtained as a yellow oil. ESI-MS: 411 [M+H]⁺

¹H NMR (400 MHz, DMSO-d₆) δ 8.48-8.43 (m, 2H), 8.41 (s, 1H), 7.94 (ddd, J=11.3, 8.6, 3.0 Hz, 1H), 7.60 (ddd, J=8.3, 3.0, 1.8 Hz, 1H), 7.54 (d, J=1.1 Hz, 1H), 7.38-7.31 (m, 2H), 7.12-7.07 (m, 1H), 6.80-6.76 (m, 1H), 4.02-3.93 (m, 2H), 3.63 (s, 2H), 3.45 (s, 2H), 2.42-2.35 (m, 2H), 2.01-1.88 (m, 2H)

The product was converted into hydrochloric acid salt following Procedure 10. Product as white crystals (114 mg, 0.19 mmol, yield 96%). ESI-MS: 411 [M+H]⁺

¹H NMR (300 MHz, Deuterium Oxide) δ 8.91-8.86 (m, 2H), 8.86-8.82 (m, 1H), 8.51 (s, 1H), 8.31-8.23 (m, 2H), 7.68-7.60 (m, 2H), 7.60-7.57 (m, 1H), 7.51-7.47 (m, 1H), 4.69 (s, 2H), 4.40 (t, J=7.1 Hz, 2H), 4.25 (s, 2H), 3.34-3.23 (m, 2H), 2.60-2.47 (m, 2H).

Example 46. 3-({[3-(1H-imidazol-1-yl)propyl][(2-methoxypyridin-4-yl)methyl]amino}methyl)-2-methyl-4H-chromen-4-one

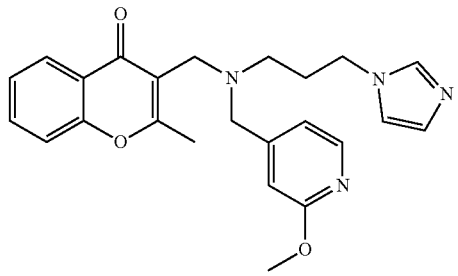 [SMILES: COc1cc(CN(CCCn2ccnc2)Cc2c(C)oc3ccccc3c2=O)ccn1]

The title compound was synthesized following the approach outlined in Procedure 9.1 substituting 3-(chloromethyl)-7,8-dimethyl-4H-chromen-4-one with 3-(chloromethyl)-2-methyl-4H-chromen-4-one and [3-(1H-imidazol-1-yl)propyl](pyridin-4-ylmethyl)amine with [3-(1H-imidazol-1-yl)propyl][(2-methoxypyridin-4-yl)methyl]amine. The product (10 mg, 0.024 mmol, yield 10%) was obtained as a yellow oil. ESI-MS: 419 [M+H]⁺

¹H NMR (300 MHz, DMSO-d₆) δ 8.04-7.98 (m, 2H), 7.75 (ddd, J=8.6, 7.1, 1.7 Hz, 1H), 7.54 (dd, J=8.5, 1.0 Hz, 1H), 7.49 (d, J=1.1 Hz, 1H), 7.44 (ddd, J=8.1, 7.1, 1.1 Hz, 1H), 7.05-7.01 (m, 1H), 6.90 (dd, J=5.2, 1.3 Hz, 1H), 6.75-6.68 (m, 2H), 3.92 (t, J=7.1 Hz, 2H), 3.76 (s, 3H), 3.50 (s, 2H), 3.49 (s, 2H), 2.46 (s, 3H), 2.34 (t, J=6.8 Hz, 2H), 1.98-1.87 (m, 2H)

Example 47. 6-fluoro-3-({[3-(1H-imidazol-1-yl)propyl][(pyridin-4-yl)methyl]amino}methyl)-4H benzo[h]chromen-4-one

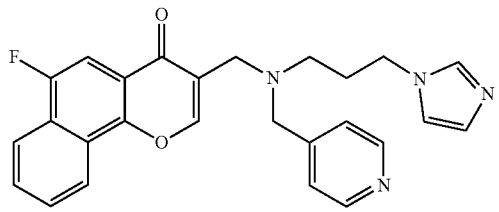 [SMILES: O=c1c(CN(CCCn2ccnc2)Cc2ccncc2)coc2c1cc(F)c1ccccc12]

Preparation of 1-(4-fluoro-1-hydroxynaphthalen-2-yl)ethan-1-one

The title compound was synthesized following the approach outlined in Procedure 26 substituting 7-methoxy-1-naphthol with 4-fluoronaphthalen-1-ol. The crude product was purified by FCC (SiHP, Hexane: AcOEt 100:0 to 90:10) to afford the title compound (0.160 g, 0.78 mmol, yield 30%) as a white solid. ESI-MS: 203 [M+H]⁻

Preparation of 6-fluoro-4-oxo-4H-benzo[h]chromene-3-carbaldehyde

The title compound was synthesized following the approach outlined in Procedure 19b substituting 1-(2-aminophenyl)ethan-1-one with 1-(4-fluoro-1-hydroxynaphthalen-2-yl)ethan-1-one. The product (0.185 g, 0.76 mmol, yield 97.5%) was obtained as a yellow solid. ESI-MS: 243 [M+H]$^+$ $^1$H NMR (300 MHz, DMSO-d$_6$) δ 10.19 (s, 1H), 9.11 (s, 1H), 8.62-8.50 (m, 1H), 8.32-8.21 (m, 1H), 8.11-7.91 (m, 2H), 7.78 (d, J=10.3 Hz, 1H).

Preparation of 6-fluoro-3-({[3-(1H-imidazol-1-yl)propyl][(pyridin-4-yl)methyl]amino}methyl)-4H-benzo[h]chromen-4-one The title compound was synthesized following the approach outlined in Procedure 37 substituting [3-(pyridin-3-yl)propyl][(pyridin-4-yl)methyl]amine with [3-(1H-imidazol-1-yl)propyl][(pyridin-4-yl)methyl]amine. The product was converted into hydrochloric acid salt following Procedure 10 without using MeOH as a solvent. Product as a yellow solid (0.006 g, 0.011 mmol, yield 6%). ESI-MS: 443 [M+H]$^+$ $^1$H NMR (300 MHz, Deuterium Oxide) δ 8.78 (t, J=1.5 Hz, 1H), 8.66-8.61 (m, 2H), 8.56 (d, J=8.3 Hz, 1H), 8.46 (s, 1H), 8.26 (d, J=7.8 Hz, 1H), 8.08 (d, J=6.6 Hz, 2H), 8.00-7.88 (m, 2H), 7.59 (d, J=10.5 Hz, 1H), 7.53 (t, J=1.8 Hz, 1H), 7.35 (t, J=1.7 Hz, 1H), 4.38 (t, J=6.9 Hz, 2H), 4.29 (s, 2H), 3.86 (s, 2H), 2.99-2.92 (m, 2H), 2.43-2.32 (m, 2H).

Example 48. 7-bromo-3-({[3-(1H-imidazol-1-yl)propyl][(pyridin-4-yl)methyl]amino}methyl)-2-methyl-4H-chromen-4-one

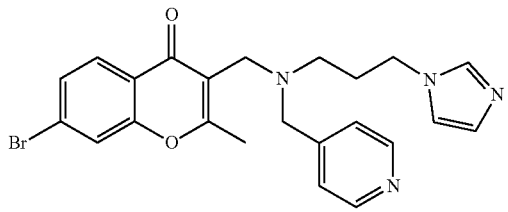 [SMILES: Cc1oc2cc(Br)ccc2c(=O)c1CN(CCCn1ccnc1)Cc1ccncc1]

Preparation of 7-bromo-3-(chloromethyl)-2-methyl-4H-chromen-4-one

The title compound was synthesized following the approach outlined in Procedure 21c substituting 2-methyl-4H-chromen-4-one with 7-bromo-2-methyl-4H-chromen-4-one. The product (787 mg, 2.74 mmol, yield 44%) was obtained as a white solid. ESI-MS: 287 [M+H]$^+$ Preparation of 7-bromo-3-({[3-(1H-imidazol-1-yl)propyl][(pyridin-4-yl)methyl]amino}methyl)-2-methyl-4H-chromen-4-one The title compound was synthesized following the approach outlined in Procedure 9.1 substituting 3-(chloromethyl)-7,8-dimethyl-4H-chromen-4-one with 7-bromo-3-(chloromethyl)-2-methyl-4H-chromen-4-one. The product (250 mg, 0.53 mmol, yield 77%) was obtained as a yellow oil. ESI-MS: 467 [M+H]$^+$ $^1$H NMR (400 MHz, DMSO-d$_6$) δ 8.45-8.39 (m, 2H), 7.94-7.87 (m, 2H), 7.61 (dd, J=8.5, 1.8 Hz, 1H), 7.48 (d, J=1.2 Hz, 1H), 7.30-7.27 (m, 2H), 7.06-7.01 (m, 1H), 6.73 (d, J=1.1 Hz, 1H), 3.92 (t, J=7.1 Hz, 2H), 3.53 (s, 2H), 3.48 (s, 2H), 2.43 (s, 3H), 2.33 (t, J=6.8 Hz, 2H), 2.00-1.88 (m, 2H).

The product was converted into hydrochloric acid salt following Procedure 10. Product as white crystals (55 mg, 0.095 mmol, yield 94%). ESI-MS: 467 [M+H]$^+$ $^1$H NMR (300 MHz, Deuterium Oxide) δ 8.86-8.78 (m, 3H), 8.26-8.20 (m, 2H), 7.94 (d, J=8.6 Hz, 1H), 7.90 (d, J=1.7 Hz, 1H), 7.74 (dd, J=8.6, 1.8 Hz, 1H), 7.61-7.57 (m, 1H), 7.50-7.46 (m, 1H), 4.67 (s, 2H), 4.42 (t, J=7.1 Hz, 2H), 4.29 (s, 2H), 3.36-3.27 (m, 2H), 2.64-2.48 (m, 5H).

Example 49. 6-fluoro-3-({[3-(1H-imidazol-1-yl)propyl][(pyridin-4-yl)methyl]amino}methyl)-7-(4-methylpiperazin-1-yl)-4H-chromen-4-one

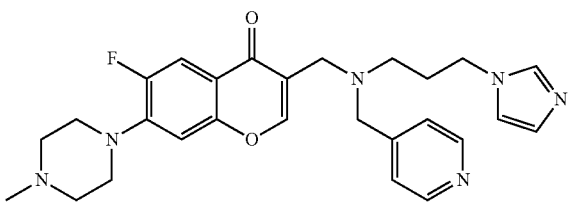 [SMILES: CN1CCN(c2cc3occ(CN(CCCn4ccnc4)Cc4ccncc4)c(=O)c3cc2F)CC1]

Preparation of 6-fluoro-2-hydroxy-7-(4-methylpiperazin-1-yl)-3,4-dihydro-2H-1-benzopyran-4-one The title compound was synthesized following the approach outlined in Procedure 5a substituting 1-(2-hydroxy-3,4-dimethylphenyl)ethan-1-one with 1-[5-fluoro-2-hydroxy-4-(4-methylpiperazin-1-yl)phenyl]ethan-1-one. FCC (SiHP; DCM:MeOH; 100:0 to 9:1) afforded the product (285 mg, 1.02 mmol, yield 29%) as a white solid. ESI-MS: 281 [M+H]$^+$ Preparation of 6-fluoro-3-(hydroxymethyl)-7-(4-methylpiperazin-1-yl)-4H-chromen-4-one The title compound was synthesized following the approach outlined in Procedure 5b substituting 2-hydroxy-7,8-dimethyl-3,4-dihydro-2H-1-benzopyran-4-one with 6-fluoro-2-hydroxy-7-(4-methylpiperazin-1-yl)-3,4-dihydro-2H-1-benzopyran-4-one. The residue was purified by FCC (SiHP; Hexane:AcOEt; 100:0 to 1:1) to afford the product (180 mg, 0.62 mmol, yield 61%) as a white solid. ESI-MS: 293 [M+H]$^+$ Preparation of 3-(chloromethyl)-6-fluoro-7-(4-methylpiperazin-1-yl)-4H-chromen-4-one The title compound was prepared according to Procedure 1c substituting 3-(hydroxymethyl)-4H chromen-4-one with 6-fluoro-3-(hydroxymethyl)-7-(4-methylpiperazin-1-yl)-4H-chromen-4-one. Product was obtained as yellow solid (160 mg, 0.51 mmol, yield 81%). ESI-MS: 311 [M+H]$^+$ Preparation of 6-fluoro-3-({[3-(1H-imidazol-1-yl)propyl][(pyridin-4-yl)methyl]amino}methyl)-7-(4-methylpiperazin-1-yl)-4H-chromen-4-one The title compound was synthesized following the approach outlined in Procedure 9.1 substituting 3-(chloromethyl)-7,8-dimethyl-4H-chromen-4-one with 3-(chloromethyl)-6-fluoro-7-(4-methylpiperazin-1-yl)-4H-chromen-4-one. The product (8 mg, 0.016 mmol, yield 15%) was obtained as a yellow oil. ESI-MS: 491 [M+H]$^+$ The product was converted into hydrochloric acid salt following Procedure 10. Product as yellow crystals (11 mg, 0.016 mmol, yield 89%). ESI-MS: 491 [M+H]$^+$ $^1$H NMR (300 MHz, Deuterium Oxide) δ 8.79-8.74 (m, 1H), 8.66-8.62 (m, 2H), 8.25 (s, 1H), 8.01 (d, J=6.3 Hz, 2H), 7.73 (d, J=12.6 Hz, 1H), 7.54-7.50 (m, 1H), 7.42-7.39 (m, 1H), 7.25 (d, J=7.1 Hz, 1H), 4.35 (t, J=7.0 Hz, 2H), 4.28 (s, 2H), 3.97-3.86 (m, 4H), 3.68 (d, J=11.9 Hz, 2H), 3.45-3.26 (m, 4H), 3.02-2.92 (m, 5H), 2.44-2.30 (m, 2H).

Example 50. 3-({[3-(1H-1,3-benzodiazol-1-yl)propyl][(pyridin-4-yl)methyl]amino}methyl)-4H-benzo[h]chromen-4-one

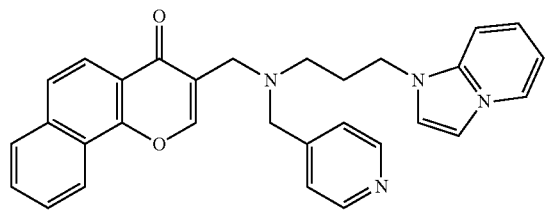

Preparation of 3-({[3-(1H-1,3-benzodiazol-1-yl)propyl][(pyridin-4-yl)methyl]amino}methyl)-4H-benzo[h]chromen-4-one The title compound was synthesized following the approach outlined in Procedure 9.1 substituting [3-(1H-imidazol-1-yl)propyl](pyridin-4-ylmethyl)amine with [3-(1H-1,3-benzodiazol-1-yl)propyl][(pyridin-4-yl)methyl]amine and 3-(chloromethyl)-7,8-dimethyl-4H-chromen-4-one with 3-(chloromethyl)-4H-benzo[h]chromen-4-one using Cs$_2$CO$_3$ as a base. The product was purified by prep-HPLC to afford the title compound (0.050 g, 0.1 mmol, yield 19%) as a yellow oil. ESI-MS: 475 [M+H]$^+$ $^1$H NMR (400 MHz, DMSO-d$_6$) δ 8.50 (s, 1H), 8.50-8.46 (m, 1H), 8.44-8.41 (m, 2H), 8.18 (s, 1H), 8.15 (s, 1H), 8.16-8.11 (m, 1H), 8.07-8.02 (m, 1H), 7.97-7.91 (m, 1H), 7.88-7.77 (m, 2H), 7.65-7.54 (m, 2H), 7.41-7.33 (m, 2H), 7.24-7.10 (m, 2H), 4.31 (t, J=7.2 Hz, 2H), 3.69 (s, 2H), 3.56 (s, 2H), 2.49 (s, 2H), 2.16-2.03 (m, 2H).

The obtained sample was converted into hydrochloric acid salt following Procedure 10 using DCM as a solvent. Product as yellow powder (0.040 g, 0.07 mmol, yield 89%). ESI-MS: 475 [M+H]$^+$ $^1$H NMR (400 MHz, Deuterium Oxide) δ 9.08 (s, 1H), 8.67-8.59 (m, 2H), 8.31-8.23 (m, 1H), 8.10 (s, 1H), 8.08-8.03 (m, 2H), 7.97-7.90 (m, 1H), 7.77-7.65 (m, 3H), 7.60-7.57 (m, 1H), 7.57-7.52 (m, 1H), 7.33-7.24 (m, 1H), 7.17-7.12 (m, 1H), 7.06-6.95 (m, 1H), 4.51-4.39 (m, 2H), 4.32 (s, 2H), 3.56 (s, 2H), 2.91-2.79 (m, 2H), 2.44-2.26 (m, 2H).

Example 51. 3-({[3-(1H-imidazol-1-yl)propyl][(2-methoxypyridin-4-yl)methyl]amino}methyl)-7,8-dimethyl-4H-chromen-4-one

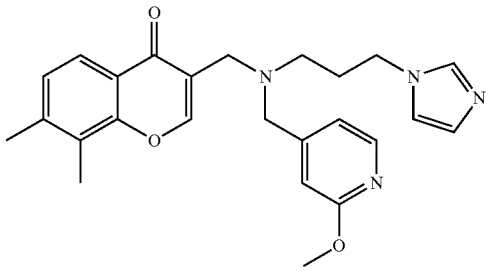 [SMILES: COc1cc(CN(CCCn2ccnc2)Cc2coc3c(C)c(C)ccc3c2=O)ccn1]

The title compound was synthesized following the approach outlined in Procedure 9.1 substituting [3-(1H-imidazol-1-yl)propyl](pyridin-4-ylmethyl)amine with [3-(1H-imidazol-1-yl)propyl][(2-methoxypyridin-4-yl)methyl]amine. The product (114 mg, 0.26 mmol, yield 39%) was obtained as a yellow oil. ESI-MS: 433 [M+H]$^+$ $^1$H NMR (400 MHz, DMSO-d$_6$) δ 8.32 (s, 1H), 8.03 (dd, J=5.2, 0.7 Hz, 1H), 7.81 (d, J=8.1 Hz, 1H), 7.56-7.53 (m, 1H), 7.30 (d, J=8.2 Hz, 1H), 7.12-7.08 (m, 1H), 6.94 (dd, J=5.3, 1.3 Hz, 1H), 6.82-6.74 (m, 2H), 3.97 (t, J=7.1 Hz, 2H), 3.79 (s, 3H), 3.57 (s, 2H), 3.44 (s, 2H), 2.42-2.32 (m, 8H), 1.99-1.89 (m, 2H).

Example 52. 9-methoxy-3-({[3-(pyridin-3-yl)propyl][(pyridin-4-yl)methyl]amino}methyl)-4H-benzo[h]chromen-4-one

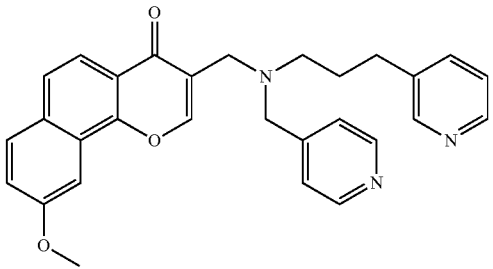 [SMILES: COc1ccc2ccc3c(=O)c(CN(CCCc4cccnc4)Cc4ccncc4)coc3c2c1]

Preparation of 2-hydroxy-9-methoxy-2H,3H,4H-naphtho[1,2-b]pyran-4-one

The title compound was synthesized following the approach outlined in Procedure 5a substituting 1-(2-hydroxy-3,4-dimethylphenyl)ethan-1-one with 1-(1-hydroxy-7-methoxynaphthalen-2-yl)ethan-1-one. The product (245 mg, 1.02 mmol, yield 87%) as a yellow solid and was used for the next step without further purification. ESI-MS: 245 [M+H]$^+$ Preparation of 3-(hydroxymethyl)-9-methoxy-4H-benzo[h]chromen-4-one The title compound was synthesized following the approach outlined in Procedure 5b substituting 2-hydroxy-7,8-dimethyl-3,4-dihydro-2H-1-benzopyran-4-one with 2-hydroxy-9-methoxy-2H,3H,4H-naphtho[1,2-b]pyran-4- one. The residue was purified by FCC (SiHP; Hexane: AcOEt; 100:0 to 1:1) to afford the product (153 mg, 0.60 mmol, yield 61%) as a white solid. ESI-MS: 255 [M−H]⁻

Preparation of 3-(chloromethyl)-9-methoxy-4H-benzo[h]chromen-4-one

The title compound was prepared according to Procedure 1c substituting 3-(hydroxymethyl)-4H-chromen-4-one with 3-(hydroxymethyl)-9-methoxy-4H-benzo[h]chromen-4-one. Product was obtained as a yellow solid (139 mg, 0.51 mmol, yield 89%). ESI-MS: 275 [M+H]P Preparation of 9-methoxy-3-({[3-(pyridin-3-yl)propyl][(pyridin-4-yl)methyl]amino}methyl)-4H benzo[h]chromen-4-one The title compound was synthesized following the approach outlined in Procedure 9.1 substituting 3-(chloromethyl)-7,8-dimethyl-4H-chromen-4-one with 3-(chloromethyl)-9-methoxy-4H-benzo[h]chromen-4-one and [3-(1H-imidazol-1-yl)propyl](pyridin-4-ylmethyl)amine with [3-(pyridin-3-yl)propyl][(pyridin-4-yl)methyl]amine. The product (80 mg, 0.17 mmol, yield 59%) was obtained as a yellow oil. ESI-MS: 466 [M+H]⁺

The product was converted into hydrochloric acid salt following Procedure 10. Product as yellow crystals (81 mg, 0.14 mmol, yield 88%). ESI-MS: 466 [M+H]⁺ 1 H NMR (300 MHz, Deuterium Oxide) δ 8.85-8.79 (m, 2H), 8.74-8.69 (m, 1H), 8.59-8.45 (m, 3H), 8.24-8.17 (m, 2H), 7.99-7.91 (m, 2H), 7.84 (d, J=8.7 Hz, 1H), 7.68 (d, J=9.8 Hz, 2H), 7.39 (dd, J=8.9, 2.9 Hz, 1H), 4.72 (s, 2H), 4.16 (s, 2H), 4.01 (s, 3H), 3.41-3.30 (m, 2H), 2.99 (t, J=7.7 Hz, 2H), 2.42-2.25 (m, 2H).

Example 53. 3-({[3-(1H-1,3-benzodiazol-1-yl)propyl][(2-methoxypyridin-4-yl)methyl]amino}methyl)-4H-benzo[h]chromen-4-one

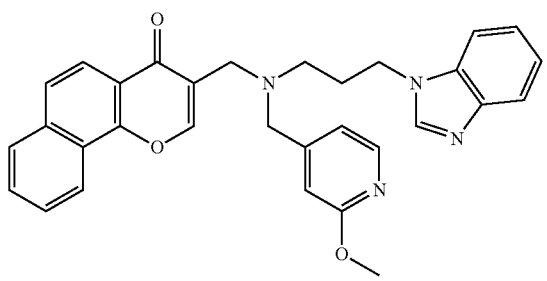 [SMILES: COc1cc(CN(CCCn2cnc3ccccc32)Cc2coc3c(ccc4ccccc43)c2=O)ccn1]

Preparation of 3-({[3-(1H-1,3-benzodiazol-1-yl)propyl][(2-methoxypyridin-4-yl)methyl]amino}methyl)-4H-benzo[h]chromen-4-one The title compound was synthesized following the approach outlined in Procedure 9.1 substituting [3-(1H-imidazol-1-yl)propyl](pyridin-4-ylmethyl)amine with [3-(1H-1,3-benzodiazol-1-yl)propyl][(2-methoxypyridin-4-yl)methyl]amine and 3-(chloromethyl)-7,8-dimethyl-4H-chromen-4-one with 3-(chloromethyl)-4H-benzo[h]chromen-4-one using Cs₂CO₃. The product was purified by FCC (SiHP, DCM: MeOH 90:10) and prep-HPLC. The obtained sample was converted into hydrochloric acid salt. Product as a beige powder (0.178 g, 0.3 mmol, yield 19%). ESI-MS: 505 [M+H]⁺

¹H NMR (400 MHz, Deuterium Oxide) δ 9.04 (s, 1H), 8.33 (d, J=7.8 Hz, 1H), 8.20 (s, 1H), 7.94 (d, J=8.1 Hz, 1H), 7.82-7.80 (m, 1H), 7.78 (d, J=8.9 Hz, 1H), 7.76-7.67 (m, 2H), 7.65 (d, J=8.5 Hz, 1H), 7.62 (d, J=8.8 Hz, 1H), 7.48-7.37 (m, 2H), 7.25 (t, J=7.7 Hz, 1H), 6.92 (dd, J=5.5, 1.5 Hz, 1H), 6.73 (s, 1H), 4.52 (t, J=6.4 Hz, 2H), 4.26 (s, 2H), 4.01 (s, 2H), 3.52 (s, 3H), 3.18-3.04 (m, 2H), 2.46 (p, J=6.6 Hz, 2H).

The compound was also converted into citrate and mesylate.

Example 54. 6-fluoro-3-({[3-(pyridin-3-yl)propyl][(pyridin-4-yl)methyl]amino}methyl)-4H benzo[h]chromen-4-one

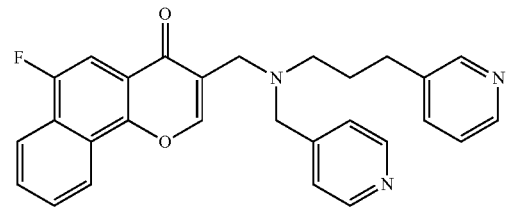 [SMILES: O=c1c(CN(CCCc2cccnc2)Cc2ccncc2)coc2c1cc(F)c1ccccc12]

Preparation of 1-(4-fluoro-1-hydroxynaphthalen-2-yl)ethan-1-one

The title compound was synthesized following the approach outlined in Procedure 26 substituting 7-methoxy-1-naphthol with 4-fluoronaphthalen-1-ol. The crude product was purified by FCC (SiHP, Hex: AcOEt 90:10) to afford the title compound (0.160 g, 0.78 mmol, yield 30%) as a white solid. ESI-MS: 203 [M+H]⁻

Preparation of 6-fluoro-4-oxo-4H-benzo[h]chromene-3-carbaldehyde

The title compound was synthesized following the approach outlined in Procedure 19b substituting 1-(2-aminophenyl)ethan-1-one with 1-(4-fluoro-1-hydroxynaphthalen-2-yl)ethan-1-one. The product (0.185 g, 0.76 mmol, yield 97.5%) was obtained as a yellow *soli*. ESI-MS: 243 [M+H]⁺

¹H NMR (300 MHz, DMSO-d₆) δ 10.19 (s, 1H), 9.11 (s, 1H), 8.62-8.50 (m, 1H), 8.32-8.21 (m, 1H), 8.11-7.91 (m, 2H), 7.78 (d, J=10.3 Hz, 1H).

Preparation of 6-fluoro-3-({[3-(pyridin-3-yl)propyl][(pyridin-4-yl)methyl]amino}methyl)-4H-benzo[h]chromen-4-one The title compound was synthesized according to Procedure 37. Product as a yellow oil (0.074 g, 0.16 mmol, yield 39. ESI-MS: 454 [M+H]⁺

¹H NMR (300 MHz, DMSO-d₆) δ 8.58-8.53 (m, 2H), 8.50-8.47 (m, 2H), 8.43-8.40 (m, 1H), 8.34-8.30 (m, 1H), 8.26-8.20 (m, 1H), 8.00-7.90 (m, 2H), 7.71 (d, J=10.5 Hz, 1H), 7.64-7.59 (m, 1H), 7.45-7.41 (m, 2H), 7.25-7.20 (m, 1H), 3.74 (s, 2H), 3.58 (s, 2H), 2.62 (t, J=7.7 Hz, 2H), 1.86 (p, 2H). Aliphatic H overlapped with solvent signals.

Example 55. 2,7,8-trimethyl-3-({[3-(pyridin-3-yl)propyl][(pyridin-4-yl)methyl]amino}methyl)-4H-chromen-4-one

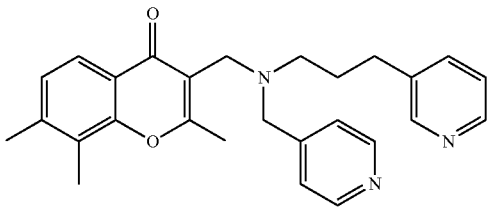 [SMILES: Cc1ccc2c(=O)c(CN(CCCc3cccnc3)Cc3ccncc3)c(C)oc2c1C]

Preparation of 1-(2-hydroxy-3,4-dimethylphenyl)butane-1,3-dione

The title compound was synthesized following the approach outlined in Procedure 21a substituting 1-(2-hydroxyphenyl)ethan-1-one with 1-(2-hydroxy-3,4-dimethylphenyl)ethan-1-one. The product (2.95 g, 14.3 mmol, yield 86%) was obtained as a yellow solid. ESI-MS: 207 [M+H]⁺

Preparation of 2,7,8-trimethyl-4H-chromen-4-one

The title compound was synthesized following the approach outlined in Procedure 24b substituting 1-(4-bromo-2-hydroxyphenyl)butane-1,3-dione with 1-(2-hydroxy-3,4-dimethylphenyl)butane-1,3-dione. The product (2.83 g, 15.1 mmol, yield 100%) was obtained as a yellow solid. ESI-MS: 189 [M+H]⁺

Preparation of 3-(chloromethyl)-2,7,8-trimethyl-4H-chromen-4-one

The title compound was synthesized following the approach outlined in Procedure 21c substituting 2-methyl-4H-chromen-4-one with 2,7,8-trimethyl-4H-chromen-4-one. The product (0.68 g, 2.87 mmol, yield 54%) was obtained as a white solid.

¹H NMR (300 MHz, DMSO-d₆) δ 7.79 (d, J=8.1 Hz, 1H), 7.31 (d, J=8.1 Hz, 1H), 4.71 (s, 2H), 2.58 (s, 3H), 2.40 (s, 3H), 2.35 (s, 3H).

The title compound was synthesized following the approach outlined in Procedure 9.1 substituting 3-(chloromethyl)-7,8-dimethyl-4H-chromen-4-one with 3-(chloromethyl)-2,7,8-trimethyl-4H-chromen-4-one and [3-(1H-imidazol-1-yl)propyl](pyridin-4-ylmethyl)amine with [3-(pyridin-3-yl)propyl][(pyridin-4-yl)methyl]amine. The product (89 mg, 0.21 mmol, yield 62%) was obtained as a yellow oil. ESI-MS: 428 [M+H]⁺

¹H NMR (300 MHz, Deuterium Oxide) δ 8.73-8.67 (m, 3H), 8.63-8.57 (m, 1H), 8.54-8.47 (m, 1H), 8.18-8.10 (m, 2H), 8.01-7.91 (m, 1H), 7.71 (d, J=8.2 Hz, 1H), 7.37 (d, J=8.3 Hz, 1H), 4.73 (s, 2H), 4.39 (s, 2H), 3.53-3.39 (m, 2H), 2.99 (t, J=7.7 Hz, 2H), 2.59 (s, 3H), 2.45 (s, 3H), 2.44-2.28 (m, 5H).

The product was converted into citrate and mesylate.

Example 56. 3-({[3-(1H-imidazol-1-yl)propyl][(pyridin-4-yl)methyl]amino}methyl)-7-(4-methoxyphenyl)-2-methyl-4H-chromen-4-one

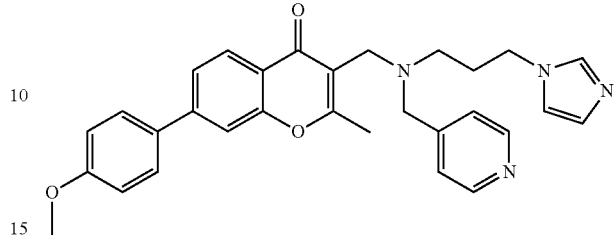

The title compound was synthesized following the approach outlined in Procedure 15 substituting 7-bromo-3-({[3-(1H-imidazol-1-yl)propyl](pyridin-4-ylmethyl)amino}methyl)-4H-chromen-4-one with 7-bromo-3-({[3-(1H-imidazol-1-yl)propyl][(pyridin-4-yl)methyl]amino}methyl)-2-methyl-4H-chromen-4-one and 4-fluorophenylboronic acid with (4-methoxyphenyl)boronic acid. The product (35 mg, 0.071 mmol, yield 41%) was obtained as a yellow oil. ESI-MS: 495 [M+H]⁺

The product was converted into hydrochloric acid salt following Procedure 10. Product as yellow crystals (39 mg, 0.065 mmol, yield 94%). ESI-MS: 495 [M+H]⁺

¹H NMR (300 MHz, Deuterium Oxide) δ 8.77-8.73 (m, 1H), 8.70-8.64 (m, 2H), 8.11-8.03 (m, 2H), 7.89 (d, J=8.4 Hz, 1H), 7.73-7.58 (m, 4H), 7.51-7.47 (m, 1H), 7.38-7.34 (m, 1H), 7.10-7.01 (m, 2H), 4.43 (s, 2H), 4.32 (t, J=7.0 Hz, 2H), 3.89 (s, 2H), 3.87 (s, 3H), 3.10 (t, J=7.8 Hz, 2H), 2.50 (s, 3H), 2.39 (t, J=7.8 Hz, 2H).

Example 57. 6-fluoro-3-({[3-(1H-imidazol-1-yl)propyl][(pyridin-4-yl)methyl]amino}methyl)-7-(3-methoxyphenyl)-4H-chromen-4-one

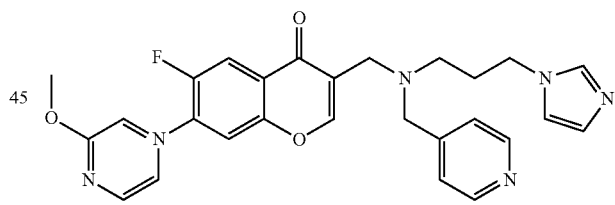

The title compound was synthesized following the approach outlined in Procedure 15 substituting 7-bromo-3-({[3-(1H-imidazol-1-yl)propyl](pyridin-4-ylmethyl)amino}methyl)-4H-chromen-4-one with 7-bromo-6-fluoro-3-({[3-(1H-imidazol-1-yl)propyl][(pyridin-4-yl)methyl]amino}methyl)-4H-chromen-4-one and 4-fluorophenylboronic acid with (3-methoxyphenyl)boronic acid. The product (32 mg, 0.064 mmol, yield 29%) was obtained as a yellow oil. ESI-MS: 499 [M+H]⁺

The product was converted into hydrochloric acid salt following Procedure 10. Product as yellow crystals (39 mg, 0.064 mmol, yield 99%). ESI-MS: 499 [M+H]⁺

¹H NMR (300 MHz, Deuterium Oxide) δ 8.82-8.76 (m, 3H), 8.38 (s, 1H), 8.21-8.14 (m, 2H), 7.79-7.72 (m, 2H), 7.55-7.41 (m, 3H), 7.28-7.05 (m, 3H), 4.52 (s, 2H), 4.35 (t, J=7.1 Hz, 2H), 4.04 (s, 2H), 3.87 (s, 3H), 3.18-3.08 (m, 2H), 2.52-2.35 (m, 2H)

Example 58. 6-fluoro-7-(4-methylpiperazin-1-yl)-3-({[3-(pyridin-3-yl)propyl](pyridin-4-ylmethyl)amino}methyl)-4H-chromen-4-one

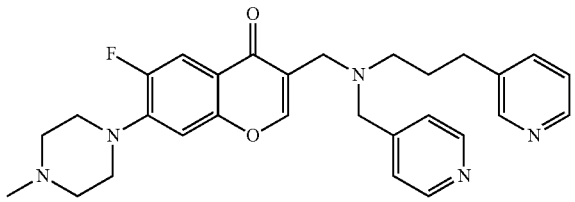 [SMILES: CN1CCN(c2cc3occ(CN(CCCc4cccnc4)Cc4ccncc4)c(=O)c3cc2F)CC1]

The title compound was synthesized following the approach outlined in Procedure 9.1 substituting 3-(chloromethyl)-7,8-dimethyl-4H-chromen-4-one with 3-(chloromethyl)-6-fluoro-7-(4-methylpiperazin-1-yl)-4H-chromen-4-one, and [3-(1H-imidazol-1-yl)propyl](pyridin-4-ylmethyl)amine with [3-(pyridin-3-yl)propyl](pyridin-4-ylmethyl)amine. The residue was purified by prep-HPLC (55 mg, 0.110 mmol, yield 36%) and converted into hydrochloric acid salt using Procedure 10. Product as a yellow solid. ESI-MS: 502 [M+H]$^+$
$^1$H NMR (300 MHz, Deuterium Oxide) δ 8.76-8.70 (m, 2H), 8.64-8.60 (m, 1H), 8.57 (d, J=5.9 Hz, 1H), 8.47-8.41 (m, 1H), 8.31 (s, 1H), 8.11-8.06 (m, 2H), 7.92 (dd, 1H), 7.64 (d, J=12.5 Hz, 1H), 7.19 (d, J=7.0 Hz, 1H), 4.66 (s, 2H), 4.23 (s, 2H), 3.88-3.79 (m, 2H), 3.63-3.55 (m, 2H), 3.35-3.17 (m, 6H), 2.90 (s, 3H), 2.86 (d, J=7.9 Hz, 2H), 2.31-2.16 (m, 2H).

Example 59. 1-{3-[({4-oxo-4H-benzo[h]chromen-3-yl}methyl)[(pyridin-4-yl)methyl]amino]propyl}-1,2-dihydropyridin-2-one

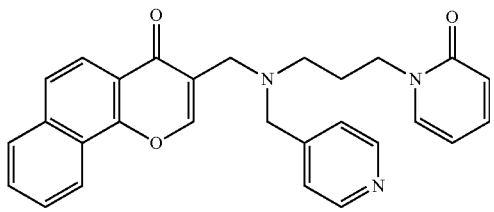 [SMILES: O=c1c(CN(CCCn2ccccc2=O)Cc2ccncc2)coc2c1ccc1ccccc12]

Preparation of 2-[3-(2-oxo-1,2-dihydropyridin-1-yl)propyl]-2,3-dihydro-1H-isoindole-1,3-dione The title compound was synthesized following the approach outlined in Procedure 11a substituting 1H-imidazole with 1,2-dihydropyridin-2-one and conducting the reaction at rt. The product was purified using FCC (SiHP, DCM:MeOH 95:5) to afford the title compound (0.339 g, 1.2 mmol, yield 55%) as a white powder. ESI-MS: 283 [M+H]$^+$
$^1$H NMR (300 MHz, DMSO-d$_6$) δ 7.95-7.77 (m, 4H), 7.76-7.64 (m, 1H), 7.46-7.30 (m, 1H), 6.40-6.32 (m, 1H), 6.24-6.14 (m, 1H), 4.01-3.81 (m, 2H), 3.65-3.52 (m, 2H), 2.09-1.87 (m, 2H).

Preparation of 1-(3-aminopropyl)-1,2-dihydropyridin-2-one

The title compound was synthesized following the approach outlined in Procedure 11b substituting 2-[4-(1H-imidazol-1-yl)butyl]-2,3-dihydro-1H-isoindole-1,3-dione with 2-[3-(2-oxo-1,2-dihydropyridin-1-yl)propyl]-2,3-dihydro-1H-isoindole-1,3-dione. The product was purified using FCC (SiNH$_2$, DCM:MeOH 9:1) to afford the title compound (0.070 g, 0.3 mmol, yield 29%) as a yellow oil. ESI-MS: 153 [M+H]$^+$ Preparation of 1-(3-{[(pyridin-4-yl)methyl]amino}propyl)-1,2-dihydropyridin-2-one The title compound was synthesized following the approach outlined in Procedure 3 substituting 3-(1H-imidazol-1-yl)propan-1-amine with 1-(3-aminopropyl)-1,2-dihydropyridin-2-one. The product was purified using FCC (SiNH$_2$, DCM:MeOH 85:15) to afford the title compound (0.079 g, 0.3 mmol, yield 69%) as an orange oil. ESI-MS: 244 [M+H]$^+$ Preparation of 1-{3-[({4-oxo-4H-benzo[h]chromen-3-yl}methyl)[(pyridin-4-yl)methyl]amino]propyl}-1,2-dihydropyridin-2-one The title compound was synthesized following the approach outlined in Procedure 9.1 substituting [3-(1H-imidazol-1-yl)propyl](pyridin-4-ylmethyl)amine with 1-(3-{[(pyridin-4-yl)methyl]amino}propyl)-1,2-dihydropyridin-2-one and 3-(chloromethyl)-7,8-dimethyl-4H-chromen-4-one with 3-(chloromethyl)-4H-benzo[h]chromen-4-one using Cs$_2$CO$_3$ as a base. The product was purified by prep-HPLC. The obtained sample was converted into hydrochloric acid salt following Procedure 10 and using DCM as a solvent. Product as yellow oil (0.006 g, 0.01 mmol, yield 4%). ESI-MS: 452 [M+H]$^+$
$^1$H NMR (400 MHz, Deuterium Oxide) δ 8.70-8.64 (m, 2H), 8.48-8.44 (m, 1H), 8.44 (s, 1H), 8.12-8.06 (m, 2H), 8.04-7.97 (m, 1H), 7.92-7.81 (m, 2H), 7.81-7.71 (m, 2H), 7.54-7.46 (m, 1H), 7.24-7.16 (m, 1H), 6.40-6.27 (m, 1H), 6.27-6.13 (m, 1H), 4.62 (s, 2H), 4.15 (s, 2H), 4.12-4.02 (m, 2H), 3.16 (t, J=7.5 Hz, 2H), 2.41-2.23 (m, 2H).

Example 60. 3-[({3-[6-(dimethylamino)pyridin-3-yl]propyl}[(pyridin-4-yl)methyl]amino)methyl]-4H-benzo[h]chromen-4-one

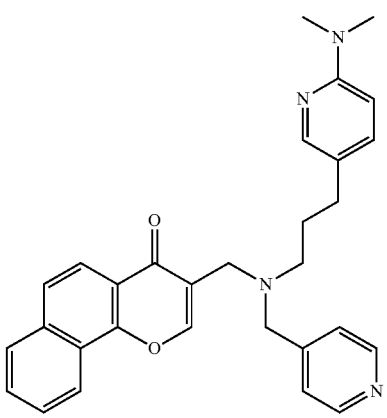 [SMILES: CN(C)c1ccc(CCCN(Cc2ccncc2)Cc2coc3c(ccc4ccccc43)c2=O)cn1]

Preparation of 6-(dimethylamino)pyridine-3-carbaldehyde

The title compound was synthesized according to Procedure 41. Product as a yellow solid (0.534 g, 3.55 mmol, yield 50%). ESI-MS: 151.3 [M+H]$^+$ $^1$H NMR (300 MHz, DMSO-d$_6$) δ 9.73 (d, J=0.6 Hz, 1H), 8.58 (dd, J=2.4, 0.7 Hz, 1H), 7.86 (dd, J=9.0, 2.4 Hz, 1H), 6.76 (dd, J=9.1, 0.7 Hz, 1H), 3.16 (s, 6H).

Preparation of ethyl 3-[6-(dimethylamino)pyridin-3-yl]prop-3-enoate

The title compound was synthesized following the approach outlined in Procedure 33a substituting 6-methoxynicotinaldehyde with 6-(dimethylamino)pyridine-3-carbaldehyde and potassium tert-butoxide with sodium tert-butoxide. The crude product was used in the next step without purification. ESI-MS: 221 [M+H]$^+$ $^1$H NMR (300 MHz, DMSO-d$_6$) δ 8.33 (d, J=2.4 Hz, 1H), 7.91 (dd, J=9.0, 2.5 Hz, 1H), 7.54 (d, J=15.9 Hz, 1H), 6.68 (d, J=9.0 Hz, 1H), 6.39 (d, J=15.9 Hz, 1H), 4.16 (q, J=7.1 Hz, 2H), 3.09 (s, 6H), 1.25 (t, J=7.1 Hz, 3H).

Preparation of ethyl 3-[6-(dimethylamino)pyridin-3-yl]propanoate

The title compound was synthesized following the approach outlined in Procedure 33b substituting 3-(6-methoxypyridin-3-yl)prop-2-enoate with ethyl 3-[6-(dimethylamino)pyridin-3-yl]prop-3-enoate. The residue was purified by FCC (SiHP, Hex: AcOEt 70:30) to afford the title compound (0.616 g, 2.771 mmol, yield 78% over two steps) as a colorless oil. ESI-MS: 223 [M+H]$^+$ $^1$H NMR (300 MHz, DMSO-d$_6$) δ 7.93 (dd, J=2.4, 0.8 Hz, 1H), 7.38 (dd, J=8.7, 2.5 Hz, 1H), 6.57 (dd, J=8.7, 0.8 Hz, 1H), 4.04 (q, J=7.1 Hz, 2H), 2.97 (s, 6H), 2.70 (t, J=7.4 Hz, 2H), 2.60-2.52 (m, 2H), 1.16 (t, J=7.1 Hz, 3H).

Preparation of 3-[6-(dimethylamino)pyridin-3-yl]propan-1-ol

The title compound was synthesized following the modified approach outlined in Procedure 33c substituting 3-(6-methoxypyridin-3-yl)propanoate with ethyl 3-[6-(dimethylamino)pyridin-3-yl]propanoate and using 15% NaOH/H$_2$O for initial quenching. The residue was purified by FCC (SiHP, DCM:MeOH 9:1) to afford the title compound (0.423 g, 2.347 mmol, yield 85%) as a colorless oil. ESI-MS: 181 [M+H]$^+$ $^1$H NMR (300 MHz, DMSO-d$_6$) δ 7.91 (d, J=2.4 Hz, 1H), 7.35 (dd, J=8.7, 2.5 Hz, 1H), 6.57 (dd, J=8.7, 0.8 Hz, 1H), 4.43 (t, J=5.1 Hz, 1H), 3.60-3.35 (m, 2H), 2.97 (s, 6H), 2.49-2.42 (m, 2H), 1.70-1.56 (m, 2H).

Preparation of 2-{3-[6-(dimethylamino)pyridin-3-yl]propyl}-2,3-dihydro-1H-isoindole-1,3-dione The title compound was synthesized following the modified approach outlined in Procedure 33d substituting 3-(6-methoxypyridin-3-yl)propan-1-ol with 3-[6-(dimethylamino)pyridin-3-yl]propan-1-ol and using additional 1 h heating at 50° C. at the end of the reaction. The product was purified by FCC (SiHP, Hex:AcOEt 3:7) to afford the title compound (0.806 g, 1.367 mmol, yield 111%) as a yellow solid. ESI-MS: 310 [M+H]$^+$ $^1$H NMR (300 MHz, DMSO-d$_6$) δ 7.95-7.89 (m, 1H), 7.86-7.79 (m, 4H), 7.37 (dd, J=8.7, 2.5 Hz, 1H), 6.53 (dd, J=8.8, 0.9 Hz, 1H), 3.58 (t, J=7.0 Hz, 2H), 2.95 (s, 6H), 2.50-2.38 (m, 2H), 1.85 (p, J=7.3 Hz, 2H).

Preparation of 5-(3-aminopropyl)-N,N-dimethylpyridin-2-amine

The title compound was synthesized following the approach outlined in Procedure 11b substituting 2-[4-(1H-imidazol-1-yl)butyl]-2,3-dihydro-1H-isoindole-1,3-dione with 2-{3-[6-(dimethylamino)pyridin-3-yl]propyl}-2,3-dihydro-1H-isoindole-1,3-dione. The residue was purified by FCC (deactivated SiHP, DCM:MeOH/1% NH$_3$ 4:1) to afford the title compound (0.107 g, 0.597 mmol, yield 66%) as a colorless oil. ESI-MS: 180 [M+H]$^+$ $^1$H NMR (300 MHz, Chloroform-d) δ 8.02 (d, J=2.4 Hz, 1H), 7.32 (dd, J=8.7, 2.5 Hz, 1H), 6.50 (dd, J=8.7, 0.8 Hz, 1H), 3.08 (s, 6H), 2.85-2.71 (m, 2H), 2.61-2.49 (m, 2H), 1.84-1.71 (m, 2H), 1.68 (s, 2H).

Preparation of N,N-dimethyl-5-(3-{[(pyridin-4-yl)methyl]amino}propyl)pyridin-2-amine The title compound was synthesized following the approach outlined in Procedure 3 substituting 3-(1H-imidazol-1-yl)propan-1-amine with 5-(3-aminopropyl)-N,N-dimethylpyridin-2-amine. The product was purified by FCC (deactivated SiHP, DCM:MeOH/1% NH3 9:10) to afford the title compound (0.040 g, 0.148 mmol, yield 58%) as a yellow oil. ESI-MS: 271 [M+H]$^+$ $^1$H NMR (300 MHz, Chloroform-d) δ 8.55-8.49 (m, 2H), 8.16-7.91 (m, 1H), 7.47-7.12 (m, 3H), 6.47 (dd, J=8.7, 0.8 Hz, 1H), 3.78 (s, 2H), 3.05 (s, 6H), 2.63 (t, J=7.1 Hz, 2H), 2.53 (t, J=7.6 Hz, 2H), 1.92 (s, 1H), 1.87-1.69 (m, 2H).

Preparation of 3-[({3-[6-(dimethylamino)pyridin-3-yl]propyl}[(pyridin-4-yl)methyl]amino)methyl]-4H-benzo[h]chromen-4-one The title compound was synthesized following the approach outlined in Procedure 9.1 substituting [3-(1H-imidazol-1-yl)propyl](pyridin-4-ylmethyl)amine with N,N-dimethyl-5-(3-{[(pyridin-4-yl)methyl]amino}propyl)pyridin-2-amine and 3-(chloromethyl)-7,8-dimethyl-4H-chromen-4-one with 3-(chloromethyl)-4H-benzo[h]chromen-4-one. The product was purified by FCC (SiHP, DCM: MeOH 95:5) to afford the title compound (0.025 g, 0.052 mmol, yield 35%) as an orange oil. ESI-MS: 479 [M+H]$^+$ $^1$H NMR (300 MHz, Chloroform-d) δ 8.54-8.51 (m, 2H), 8.50-8.44 (m, 1H), 8.22-8.11 (m, 2H), 7.98-7.89 (m, 2H), 7.77-7.74 (m, 1H), 7.73-7.60 (m, 2H), 7.35-7.28 (m, 2H), 7.22 (dd, J=8.7, 2.5 Hz, 1H), 6.37 (dd, J=8.7, 0.8 Hz, 1H), 3.68 (s, 2H), 3.62 (s, 2H), 2.98 (s, 6H), 2.65-2.34 (m, 4H), 1.94-1.76 (m, 2H).

The product was converted into hydrochloric acid salt following Procedure 10 using DCM as a solvent at 0° C. Product as a yellow solid (0.014 g, 0,022 mmol, yield 97%). ESI-MS: 479 [M+H]$^+$ $^1$H NMR (300 MHz, Deuterium Oxide) δ 8.86-8.72 (m, 2H), 8.45 (d, J=8.4 Hz, 2H), 8.23-8.07 (m, 2H), 8.08-7.99 (m, 1H), 7.89 (d, J=8.8 Hz, 1H), 7.87-7.70 (m, 3H), 7.60 (dd, J=9.5, 2.2 Hz, 1H), 7.42-7.30 (m, 1H), 6.63 (d, J=9.5 Hz, 1H), 4.68 (s, 2H), 4.10 (s, 2H), 3.13-2.93 (m, 2H), 2.50 (t, J=6.6 Hz, 2H), 2.27-1.93 (m, 2H). Aliphatic H overlapped with solvents signals.

Example 61. 3-({[3-(isoquinolin-4-yl)propyl][(pyridin-4-yl)methyl]amino}methyl)-4H-benzo[h]chromen-4-one

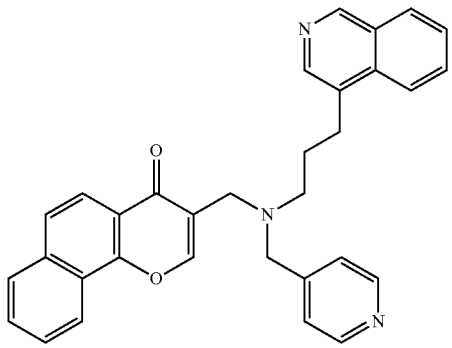 [SMILES: O=c1c(CN(CCCc2cncc3ccccc23)Cc2ccncc2)coc2c1ccc1ccccc12]

Preparation of tert-butyl N-[3-(isoquinolin-4-yl)prop-2-yn-1-yl]carbamate

The title compound was synthesized according to Procedure 42. Product as a brown oil (0.508 g, 1.8 mmol, yield 37%). ESI-MS: 283 [M+H]+

$^1$H NMR (300 MHz, DMSO-d$_6$) δ 9.34 (s, 1H), 8.63 (s, 1H), 8.40-8.06 (m, 2H), 7.91 (ddd, J=8.3, 6.9, 1.3 Hz, 1H), 7.79 (ddd, J=8.2, 7.0, 1.2 Hz, 1H), 7.53 (s, 1H), 4.14 (d, J=5.7 Hz, 2H), 1.44 (s, 9H).

Preparation of tert-butyl N-[3-(isoquinolin-4-yl)propyl]carbamate

The title compound was synthesized following the approach outlined in Procedure 35b substituting tert-butyl N-[3-(pyrimidin-5-yl)prop-2-yn-1-yl]carbamate with tert-butyl N-[3-(isoquinolin-4-yl)prop-2-yn-1-yl]carbamate. The product was purified by FCC (SiHP, Hex: AcOEt 3:7) to afford the title compound (0.358 g, 1.25 mmol, yield 69%) as a brown oil. ESI-MS: 287 [M+H]+

Preparation of 3-(isoquinolin-4-yl)propan-1-amine

The title compound was synthesized following the approach outlined in Procedure 34d substituting tert-butyl N-[4-(1H-1,3-benzodiazol-1-yl)butan-2-yl]carbamate with tert-butyl N-[3-(isoquinolin-4-yl)propyl]carbamate. The residue was purified by FCC (SiHP, DCM:MeOH 4:1) to afford the title compound (0.114 g, 0.612 mmol, yield 49%) as an brown oil. ESI-MS: 187 [M+H]+

$^1$H NMR (300 MHz, Chloroform-d) δ 9.15 (s, 1H), 8.41 (s, 1H), 8.19-7.95 (m, 2H), 7.75 (ddd, J=8.4, 6.9, 1.4 Hz, 1H), 7.63 (ddd, J=8.0, 6.9, 1.1 Hz, 1H), 3.29-3.02 (m, 2H), 2.86 (t, J=7.1 Hz, 2H), 2.00-1.85 (m, 2H), 1.53 (s, 2H).

Preparation of [3-(isoquinolin-4-yl)propyl][(pyridin-4-yl)methyl]amine

The title compound was synthesized following the approach outlined in Procedure 3 substituting 3-(1H-imidazol-1-yl)propan-1-amine with 3-(isoquinolin-4-yl)propan-1-amine. The crude product (0.145 g, 0.523 mmol, yield 88%) was used in the next step. ESI-MS: 278 [M+H]+

$^1$H NMR (300 MHz, Chloroform-d) δ 9.09 (s, 1H), 8.57-8.46 (m, 2H), 8.35 (s, 1H), 7.99-7.90 (m, 2H), 7.82-7.61 (m, 1H), 7.60-7.50 (m, 1H), 7.34-7.12 (m, 2H), 3.77 (s, 2H), 3.19-2.93 (m, 2H), 2.70 (t, J=7.0 Hz, 2H), 2.00-1.86 (m, 2H).

Preparation of 3-({[3-(isoquinolin-4-yl)propyl][(pyridin-4-yl)methyl]amino}methyl)-4H-benzo[h]chromen-4-one The title compound was synthesized following the approach outlined in Procedure 9.1 substituting [3-(1H-imidazol-1-yl)propyl](pyridin-4-ylmethyl)amine with [3-(isoquinolin-4-yl)propyl][(pyridin-4-yl)methyl]amine and 3-(chloromethyl)-7,8-dimethyl-4H-chromen-4-onem with 3-(chloromethyl)-4H-benzo[h]chromen-4-one. The residue was purified by FCC (SiHP, DCM:MeOH 95:5) to afford the title compound (0.021 g, 0.435 mmol, yield 16% over two steps) as an orange oil. ESI-MS: 486 [M+H]+

$^1$H NMR (300 MHz, Chloroform-d) δ 9.10 (s, 1H), 8.62-8.47 (m, 3H), 8.37 (s, 1H), 8.24-8.14 (m, 2H), 8.03-7.91 (m, 3H), 7.84-7.66 (m, 4H), 7.66-7.54 (m, 1H), 7.40-7.32 (m, 2H), 3.74 (s, 2H), 3.70 (s, 2H), 3.34-2.96 (m, 2H), 2.79-2.58 (m, 2H), 2.24-1.99 (m, 2H).

The product was converted into hydrochloric acid salt following Procedure 10 using DCM as a solvent at 0° C. Product as a yellow solid (0.011 g, 0.018 mmol, yield 74%). ESI-MS: 486 [M+H]+

$^1$H NMR (300 MHz, Deuterium Oxide) δ 8.96 (s, 1H), 8.78-8.68 (m, 2H), 8.30-8.11 (m, 5H), 8.07 (d, J=8.6 Hz, 1H), 8.01-7.89 (m, 2H), 7.83-7.68 (m, 4H), 7.61-7.53 (m, 1H), 7.51 (d, J=8.8 Hz, 1H), 4.63 (s, 2H), 3.96 (s, 2H), 3.19-3.05 (m, 4H), 2.30-2.14 (m, 2H).

Example 62. 3-({[3-(1H-1,3-benzodiazol-1-yl)propyl][(pyridin-4-yl)methyl]amino}methyl)-9-methoxy-4H-benzo[h]chromen-4-one

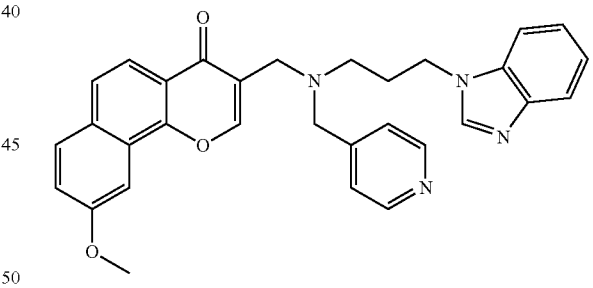

The title compound was synthesized following the approach outlined in Procedure 9.1 substituting 3-(chloromethyl)-7,8-dimethyl-4H-chromen-4-one with 3-(chloromethyl)-9-methoxy-4H-benzo[h]chromen-4-one and [3-(1H-imidazol-1-yl)propyl](pyridin-4-ylmethyl)amine with [3-(1H1,3-benzodiazol-1-yl)propyl][(pyridin-4-yl)methyl]amine. The product (50 mg, 0.10 mmol, yield 35%) was obtained as a yellow oil. ESI-MS: 505 [M+H]+

The product was converted into hydrochloric acid salt following Procedure 10. Product as white solid (52 mg, 0.085 mmol, yield 97%) ESI-MS: 505 [M+H]+

$^1$H NMR (400 MHz, DMSO-d$_6$) δ 9.15 (s, 1H), 8.74-8.68 (m, 2H), 8.14-8.10 (m, 2H), 8.08 (s, 1H), 7.91 (d, J=9.0 Hz, 1H), 7.74 (d, J=8.7 Hz, 1H), 7.66-7.63 (m, 1H), 7.55 (d, J=2.6 Hz, 1H), 7.49 (d, J=8.8 Hz, 1H), 7.40-7.32 (m, 2H), 7.24-7.18 (m, 1H), 7.07 (ddd, J=8.3, 7.3, 0.9 Hz, 1H), 4.50

(t, J=6.3 Hz, 2H), 4.34 (s, 2H), 3.99 (s, 3H), 3.50 (s, 2H), 2.88 (t, J=7.4 Hz, 2H), 2.46-2.33 (m, 2H).

Example 63. 7-bromo-6-fluoro-2-methyl-3-({[3-(pyridin-3-yl)propyl][(pyridin-4-yl)methyl]amino}methyl)-4H-chromen-4-one

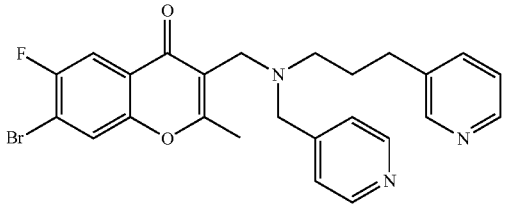 [SMILES: Cc1oc2cc(Br)c(F)cc2c(=O)c1CN(CCCc1cccnc1)Cc1ccncc1]

The title compound was synthesized following the Procedure 29a. The product (780 mg, 1.57 mmol, yield 80%) was obtained as a yellow oil. ESI-MS: 496 [M+H]+

The product was converted into hydrochloric acid salt following Procedure 10. Product as beige solid (40 mg, 0.07 mmol, yield 82%) ESI-MS: 496 [M+H]+

¹H NMR (400 MHz, Deuterium Oxide) δ 8.65-8.62 (m, 2H), 8.61-8.58 (m, 1H), 8.57-8.53 (m, 1H), 8.44-8.39 (m, 1H), 7.98-7.93 (m, 2H), 7.93-7.87 (m, 2H), 7.70 (d, J=8.1 Hz, 1H), 4.52 (s, 2H), 4.21 (s, 2H), 3.26-3.18 (m, 2H), 2.87 (t, J=7.8 Hz, 2H), 2.46 (s, 3H), 2.27-2.17 (m, 2H)

Example 64. 7-bromo-2-methyl-3-({[3-(pyridin-3-yl)propyl](pyridin-4-ylmethyl)amino}methyl)-4H-chromen-4-one

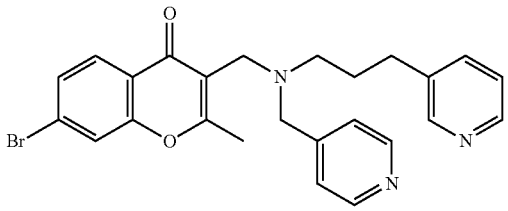 [SMILES: Cc1oc2cc(Br)ccc2c(=O)c1CN(CCCc1cccnc1)Cc1ccncc1]

Preparation of 7-bromo-2-methyl-3-({[3-(pyridin-3-yl)propyl](pyridin-4-ylmethyl)amino}methyl)-4H-chromen-4-one The title compound was synthesized following the approach outlined in Procedure 9.1 substituting 3-(chloromethyl)-7,8-dimethyl-4H-chromen-4-one with 7-bromo-3-(chloromethyl)-2-methyl-4H-chromen-4-one, and [3-(1H-imidazol-1-yl)propyl](pyridin-4-ylmethyl)amine with [(pyridin-4-yl)methyl][3-(pyridin-3-yl)propyl]amine. The product was purified by prep-HPLC and converted into hydrochloric acid salt following Procedure 10. Product as a yellow solid (53 mg, 0.090 mmol, yield 34%). ESI-MS: 478.5, 480.5 [M+H]+

¹H NMR (400 MHz, Deuterium Oxide) δ 8.73-8.67 (m, 2H), 8.64-8.60 (m, 1H), 8.57-8.53 (m, 1H), 8.46-8.40 (m, 1H), 8.10-8.05 (m, 2H), 7.93-7.88 (m, 1H), 7.83 (d, J=8.6 Hz, 1H), 7.79 (d, J=1.7 Hz, 1H), 7.63 (dd, J=8.6, 1.8 Hz, 1H), 4.64 (s, 2H), 4.29 (s, 2H), 3.36-3.27 (m, 2H), 2.88 (t, J=7.9 Hz, 2H), 2.48 (s, 3H), 2.30-2.19 (m, 2H).

Example 65. 6-fluoro-2-methyl-7-(4-methylpiperazin-1-yl)-3-({[3-(pyridin-3-yl)propyl][(pyridin-4-yl)methyl]amino}methyl)-4-chromen-4-one

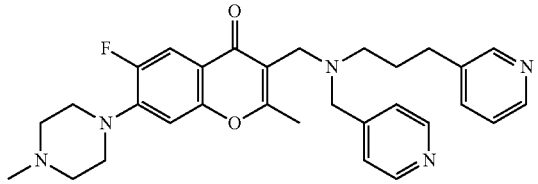 [SMILES: Cc1oc2cc(N3CCN(C)CC3)c(F)cc2c(=O)c1CN(CCCc1cccnc1)Cc1ccncc1]

The title compound was synthesized following the approach outlined in Procedure 29b substituting morpholine with 1-methylpiperazine. The product was purified using FCC (SiHP, DCM:MeOH 90:10) to afford the titled compound which was converted into hydrochloric acid salt following Procedure 10 using DCM as a solvent. Product as a yellow solid (0.022 mg, 0.035 mmol, yield 34%). ESI-MS: 516 [M+H]+

¹H NMR (400 MHz, Deuterium Oxide) δ 8.78-8.75 (m, 2H), 8.72-8.70 (m, 1H), 8.67-8.64 (m, 1H), 8.54-8.50 (m, 1H), 8.13-8.10 (m, 2H), 8.03-7.98 (m, 1H), 7.70-7.66 (m, 1H), 7.23-7.20 (m, 1H), 4.72 (s, 2H), 4.38 (s, 2H), 3.94-3.88 (m, 2H), 3.71-3.65 (m, 2H), 3.45-3.26 (m, 6H), 3.02-2.94 (m, 5H), 2.55 (s, 3H), 2.40-2.30 (m, 2H).

Example 66. 3-({[3-(6-methoxypyridin-3-yl)propyl](pyridin-4-ylmethyl)amino}methyl)-2,7,8-trimethyl-4H-chromen-4-one

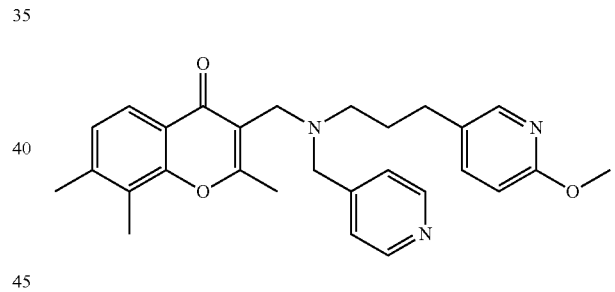

Preparation of [3-(6-methoxypyridin-3-yl)propyl](pyridin-4-ylmethyl)amine

The title compound was synthesized following the approach outlined in Procedure 3 substituting 3-(1H-imidazol-1-yl)propan-1-amine with 3-(6-methoxypyridin-3-yl)propan-1-amine to afford the product (50 mg, 0.194 mmol, yield 29%) as a transparent oil. ESI-MS: 258 [M+H]+

¹H NMR (400 MHz, Chloroform-d) δ 8.58-8.54 (m, 2H), 8.00-7.98 (m, 1H), 7.42 (dd, J=8.5, 2.5 Hz, 1H), 7.28-7.26 (m, 2H), 6.70 (d, J=8.4, 0.7 Hz, 1H), 3.93 (s, 3H), 3.82 (s, 2H), 2.70-2.65 (m, 2H), 2.65-2.60 (m, 2H), 1.86-1.77 (m, 2H).

Preparation of 3-({[3-(6-methoxypyridin-3-yl)propyl](pyridin-4-ylmethyl)amino}methyl)-2,7,8-trimethyl-4H-chromen-4-one The title compound was synthesized following the approach outlined in Procedure 9.1 substituting 3-(chloromethyl)-7,8-dimethyl-4H-chromen-4-one with 3-(chloromethyl)-2,7,8-trimethyl-4H-chromen-4-one and [3-(1H-imidazol-1-yl)propyl](pyridin-4-ylmethyl)amine with [3-(6-methoxypyridin-3-yl)propyl](pyridin-4-ylmethyl)amine. The residue was purified by prep-TLC to afford the product (16 mg, 0.035 mmol, yield 18%) as a yellow oil. ESI-MS: 458 [M+H]$^+$ $^1$H NMR (300 MHz, DMSO-d$_6$) δ 8.50-8.41 (m, 2H), 7.87 (d, J=2.4 Hz, 1H), 7.74 (d, J=8.1 Hz, 1H), 7.43 (dd, J=8.5, 2.5 Hz, 1H), 7.33 (d, J=5.1 Hz, 2H), 7.25 (d, J=8.2 Hz, 1H), 6.59 (d, J=8.4 Hz, 1H), 3.73 (s, 3H), 3.55 (s, 2H), 3.54-3.47 (m, 2H), 2.48 (s, 3H), 2.47-2.41 (m, 2H), 2.38 (s, 3H), 2.34 (s, 3H), 1.84-1.70 (m, 2H). Some aliphatic H overlapped with solvent peak.

Example 67. 3-({[3-(1H-imidazol-1-yl)propyl][(pyridin-4-yl)methyl]amino}methyl)-2-methyl-4H-benzo[h]chromen-4-one

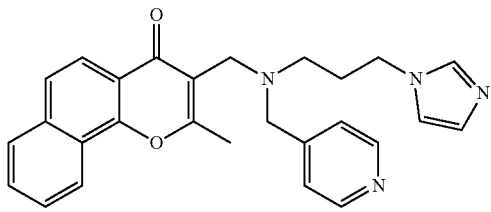 [SMILES: Cc1oc2c(ccc3ccccc32)c(=O)c1CN(CCCn1ccnc1)Cc1ccncc1]

The title compound was synthesized following the approach outlined in Procedure 28 substituting 3-(1H-imidazol-1-yl)propan-1-amine with 3-({[3-(1H-imidazol-1-yl)propyl]amino}methyl)-2-methyl-4H-benzo[h]chromen-4-one and 2-methyl-4-oxo-4H-benzo[h]chromene-3-carbaldehyde with pyridine-4-carbaldehyde. The product (35 mg, 0.08 mmol, yield 24%) was obtained as a greenish oil. ESI-MS: 439 [M+H]$^+$ The product was converted into a hydrochloric acid salt following Procedure 10. Product as yellow crystals (11 mg, 0.02 mmol, yield 98%) ESI-MS: 439 [M+H]$^+$ $^1$H NMR (300 MHz, Deuterium Oxide) δ 8.76 (t, J=1.5 Hz, 1H), 8.73-8.65 (m, 2H), 8.45-8.39 (m, 1H), 8.15-8.11 (m, 2H), 8.03-7.96 (m, 1H), 7.89-7.67 (m, 4H), 7.52-7.48 (m, 1H), 7.37-7.32 (m, 1H), 4.55 (s, 2H), 4.39-4.31 (m, 2H), 3.99 (s, 2H), 3.25-3.16 (m, 2H), 2.58 (s, 3H), 2.53-2.40 (m, 2H).

Example 68. 3-{[(3-{1H-imidazo[4,5-b]pyridin-1-yl}propyl)(pyridin-4-ylmethyl)amino]methyl}-4H-benzo[h]chromen-4-one

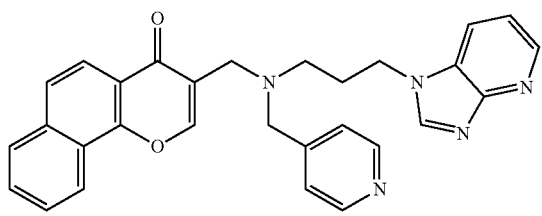 [SMILES: O=c1c(CN(CCCn2cnc3ncccc32)Cc2ccncc2)coc2c1ccc1ccccc12]

Preparation of 2-(3-{1H-imidazo[4,5-b]pyridin-1-yl}propyl)-2,3-dihydro-1H-isoindole-1,3-dione The title compound was synthesized following the approach outlined in Procedure 11a substituting 1H-imidazole with 3H-imidazo[4,5-b]pyridine and 2-(4-bromobutyl)-2,3-dihydro-1H-isoindole-1,3-dione with 2-(3-bromopropyl)-2,3-dihydro-1H-isoindole-1,3-dione. The residue was purified by FCC (SiHP, DCM: MeOH 95:5) to afford the product (120 mg, 0.380 mmol, yield 23%) as a white solid. ESI-MS: 307.4 [M+H]$^+$ $^1$H NMR (400 MHz, DMSO-d$_6$) δ 8.51 (s, 1H), 8.41 (dd, J=4.7, 1.6 Hz, 1H), 8.12 (dd, J=8.0, 1.6 Hz, 1H), 7.90-7.77 (m, 4H), 7.28 (dd, J=8.1, 4.7 Hz, 1H), 4.37 (t, J=7.1 Hz, 2H), 3.62 (t, J=6.7 Hz, 2H), 2.16 (q, J=6.9 Hz, 2H).

The structure was confirmed with 2D NMR.

Preparation of 3-{1H-imidazo[4,5-b]pyridin-1-yl}propan-1-amine

The title compound was synthesized following the approach outlined in Procedure 11b substituting 2-[4-(1H-imidazol-1-yl)butyl]-2,3-dihydro-1H-isoindole-1,3-dione with 2-(3-{1H-imidazo[4,5-b]pyridin-1-yl}propyl)-2,3-dihydro-1H-isoindole-1,3-dione to afford the product as a yellow oil (50 mg, 0.204 mmol, yield 52%). ESI-MS: 177.0 [M+H]$^+$ Preparation of (3-{1H-imidazo[4,5-b]pyridin-1-yl}propyl)(pyridin-4-ylmethyl)amine The title compound was synthesized following the approach outlined in Procedure 3 substituting 3-(1H-imidazol-1-yl)propan-1-amine with (3-{1H-imidazo[4,5-b]pyridin-1-yl}propyl)(pyridin-4-ylmethyl)amine to afford the product (50 mg, 0.127 mmol, yield 34%) as a yellow solid. ESI-MS: 268.3 [M+H]$^+$ Preparation of 3-{[(3-{1H-imidazo[4,5-b]pyridin-1-yl}propyl)(pyridin-4-ylmethyl)amino]methyl}-4H-benzo[h]chromen-4-one The title compound was synthesized following the approach outlined in Procedure 9.1 substituting 3-(chloromethyl)-7,8-dimethyl-4H-chromen-4-one with 3-(chloromethyl)-4H-benzo[h]chromen-4-one and [3-(1H-imidazol-1-yl)propyl](pyridin-4-ylmethyl)amine with (3-{1H-imidazo[4,5-b]pyridin-1-yl}propyl)(pyridin-4-ylmethyl)amine. The residue was purified by prep-HPLC and converted into hydrochloric acid salt to afford the product as a yellow solid. ESI-MS: 476.3 [M+H]$^+$ $^1$H NMR (300 MHz, Deuterium Oxide) δ 8.73 (s, 1H), 8.65-8.58 (m, 2H), 8.35-8.26 (m, 2H), 8.17 (s, 1H), 8.10-8.04 (m, 2H), 8.02-7.88 (m, 2H), 7.82-7.68 (m, 3H), 7.64-7.59 (m, 1H), 7.38-7.29 (m, 1H), 4.43-4.33 (m, 2H), 4.27 (s, 2H), 3.60-3.53 (m, 2H), 2.88-2.79 (m, 2H), 2.36-2.23 (m, 2H).

Example 69. 6-fluoro-2-methyl-7-(piperazin-1-yl)-3-({[3-(pyridin-3-yl)propyl][(pyridin-4-yl)methyl]amino}methyl)-4H-chromen-4-one

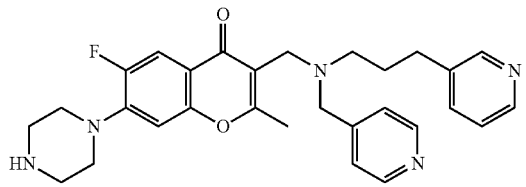 [SMILES: Cc1oc2cc(N3CCNCC3)c(F)cc2c(=O)c1CN(CCCc1cccnc1)Cc1ccncc1]

Preparation of tert-butyl 4-[6-fluoro-2-methyl-4-oxo-3-({[3-(pyridin-3-yl)propyl][(pyridin-4-yl)methyl]amino}methyl)-4H-chromen-7-yl]piperazine-1-carboxylate The title compound was synthesized following the approach outlined in Procedure 29b substituting morpholine with tert-butyl piperazine-1-carboxylate. The product was purified using FCC (SiHP, DCM: MeOH 90:10) to afford the titled compound (0.080 g, 0.133 mmol, yield 73%) as a yellow oil. ESI-MS: 602 [M+H]+

Preparation of 6-fluoro-2-methyl-7-(piperazin-1-yl)-3-({[3-(pyridin-3-yl)propyl][(pyridin-4-yl)methyl]amino}methyl)-4H-chromen-4-one The title compound was synthesized according to Procedure 39. Product as brown solid (0.033 g, 0.13 mmol, yield 49%). ESI-MS: 502 [M+H]+

$^1$H NMR (300 MHz, Deuterium Oxide) δ 8.80-8.76 (m, 2H), 8.72-8.70 (m, 1H), 8.67-8.63 (m, 1H), 8.55-8.50 (m, 1H), 8.17-8.12 (m, 2H), 8.03-7.97 (m, 1H), 7.67 (d, J=12.5 Hz, 1H), 7.22 (d, J=7.0 Hz, 1H), 4.74 (s, 2H), 4.39 (s, 2H), 3.60-3.54 (m, 4H), 3.50-3.39 (m, 6H), 2.97 (t, J=7.9 Hz, 2H), 2.55 (s, 3H), 2.41-2.28 (m, 2H), 1.24 (s, 1H).

Example 70. 6-fluoro-2-methyl-7-(morpholin-4-yl)-3-({[3-(pyridin-3-yl)propyl][(pyridin-4-yl)methyl]amino}methyl)-4H-chromen-4-one

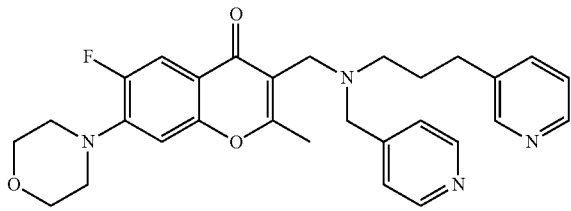 [SMILES: Cc1oc2cc(N3CCOCC3)c(F)cc2c(=O)c1CN(CCCc1cccnc1)Cc1ccncc1]

The title compound was synthesized following the Procedure 29b. Product (20 mg, 0.04 mmol, yield 25%) was obtained as a yellow oil. ESI-MS: 503 [M+H]+

The product was converted into hydrochloric acid salt following Procedure 10. Product as beige solid (11 mg, 0.018 mmol, yield 90%) ESI-MS: 503 [M+H]+

$^1$H NMR (300 MHz, Deuterium Oxide) δ 8.79-8.73 (m, 2H), 8.73-8.68 (m, 1H), 8.67-8.61 (m, 1H), 8.55-8.47 (m, 1H), 8.18-8.10 (m, 2H), 7.99 (dd, J=8.1, 5.8 Hz, 1H), 7.64 (d, J=12.6 Hz, 1H), 7.20 (d, J=7.0 Hz, 1H), 4.72 (s, 2H), 4.37 (s, 2H), 3.93 (t, J=4.7 Hz, 4H), 3.47-3.37 (m, 2H), 3.31 (t, J=4.8 Hz, 4H), 2.97 (t, J=7.8 Hz, 2H), 2.53 (s, 3H), 2.42-2.27 (m, 2H).

Example 71. 3-({[3-(1H-imidazol-1-yl)propyl](pyridin-4-ylmethyl)amino}methyl)-7-(1H-pyrazol-3-yl)-4H-chromen-4-one

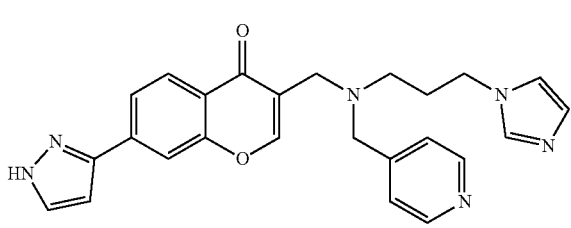 [SMILES: O=c1c(CN(CCCn2ccnc2)Cc2ccncc2)coc2cc(-c3cc[nH]n3)ccc12]

The title compound was prepared according to Procedure 15 substituting 4-fluorophenylboronic acid with (1H-pyrazol-3-yl)boronic acid. Crude material was purified by prep-HPLC. Product as yellow solid (11 mg, 0.025 mmol, yield 16%). ESI-MS: 441.2 [M+H]+

$^1$H NMR (400 MHz, DMSO-d$_6$) δ 8.48-8.45 (m, 2H), 8.33 (s, 1H), 8.16 (s, 1H), 8.09 (d, J=8.3 Hz, 1H), 8.02-7.99 (m, 1H), 7.98-7.93 (m, 1H), 7.90-7.82 (m, 1H), 7.56 (s, 1H), 7.39-7.34 (m, 2H), 7.13-7.11 (m, 1H), 6.98 (d, J=2.3 Hz, 1H), 6.81-6.78 (m, 1H), 3.99 (t, J=7.1 Hz, 2H), 3.65 (s, 2H), 3.47 (s, 2H), 2.43-2.36 (m, 2H), 2.01-1.91 (m, 2H).

Example 72. 3-({[4-(1H-1,3-benzodiazol-1-yl)butan-2-yl](pyridin-4-ylmethyl)amino}methyl)-4H-benzo[h]chromen-4-one

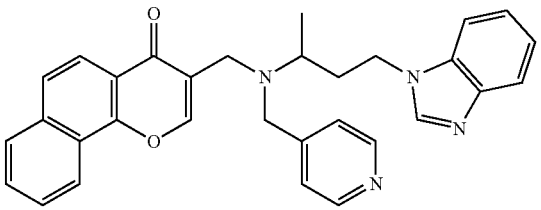 [SMILES: CC(CCn1cnc2ccccc21)N(Cc1ccncc1)Cc1coc2c(ccc3ccccc32)c1=O]

Preparation of 4-oxo-4H-benzo[h]chromene-3-carbaldehyde

The title compound was synthesized following the approach outlined in Procedure 2 substituting 1-(2-hydroxyphenyl)ethan-1-one with 1-(1-hydroxynaphthalen-2-yl)ethan-1-one to afford the product (3.25 g, 21.48 mmol, yield 67%) as a yellow solid. ESI-MS: 225.0 [M+H]+

$^1$H NMR (400 MHz, DMSO-d$_6$) δ 10.21 (d, J=1.5 Hz, 1H), 9.11 (d, J=1.6 Hz, 1H), 8.55-8.46 (m, 1H), 8.23-8.14 (m, 1H), 8.07 (qd, J=8.8, 1.5 Hz, 2H), 7.86 (ttd, J=7.1, 5.3, 1.6 Hz, 2H).

Preparation of [4-(1H-1,3-benzodiazol-1-yl)butan-2-yl](pyridin-4-ylmethyl)amine

The title compound was synthesized following the approach outlined in Procedure 3 substituting 3-(1H-imidazol-1-yl)propan-1-amine with 4-(1H-1,3-benzodiazol-1-yl)butan-2-amine to afford the product (200 mg, 0.713 mmol, yield 81%) as a yellow oil. ESI-MS: 281 [M+H]+

$^1$H NMR (400 MHz, Chloroform-d) δ 8.59-8.56 (m, 2H), 7.89 (s, 1H), 7.86-7.81 (m, 1H), 7.48-7.39 (m, 1H), 7.34-7.29 (m, 2H), 7.32-7.25 (m, 2H), 4.47-4.26 (m, 2H), 3.90 (d, J=14.3 Hz, 1H), 3.69 (d, J=14.3 Hz, 1H), 2.72-2.62 (m, 1H), 2.07-1.87 (m, 2H), 1.19 (d, J=6.3 Hz, 3H).

Preparation of 3-({[4-(1H-1,3-benzodiazol-1-yl)butan-2-yl](pyridin-4-ylmethyl)amino}methyl)-4H-benzo[h]chromen-4-one The title compound was synthesized following the approach outlined in Procedure 9.2 substituting [3-(1H-imidazol-1-yl)propyl](pyridin-4-ylmethyl)amine with [4-(1H-1,3-benzodiazol-1-yl)butan-2-yl](pyridin-4-ylmethyl) amine and 7,8-dimethyl-4-oxo-4H-chromene-3-carbaldehyde with 4-oxo-4H-benzo[h]chromene-3-carbaldehyde. The residue was purified by FCC (SiHP, DCM: MeOH 95:5) to afford the product (37 mg, 0.076 mmol, yield 34%) as a white solid. ESI-MS: 489 [M+H]+

1H NMR (400 MHz, DMSO-d6) δ 8.49 (s, 1H), 8.48-8.44 (m, 1H), 8.37-8.33 (m, 2H), 8.23 (s, 1H), 8.15-8.10 (m, 1H), 8.05 (d, J=8.8 Hz, 1H), 7.94 (d, J=8.7 Hz, 1H), 7.86-7.76 (m, 2H), 7.65-7.56 (m, 2H), 7.36-7.32 (m, 2H), 7.24-7.12 (m, 2H), 4.59-4.47 (m, 1H), 4.30-4.17 (m, 1H), 3.84 (d, J=15.4 Hz, 1H), 3.64 (dd, J=38.3, 14.7 Hz, 2H), 3.42 (d, J=14.0 Hz, 1H), 2.83-2.73 (m, 1H), 2.28-2.15 (m, 1H), 1.92-1.80 (m, 1H), 1.11 (d, J=6.5 Hz, 3H).

Example 73. 7-bromo-6-fluoro-2-methyl-3-({[3-(9H-purin-9-yl)propyl][(pyridin-4-yl)methyl]amino}methyl)-4H-chromen-4-one

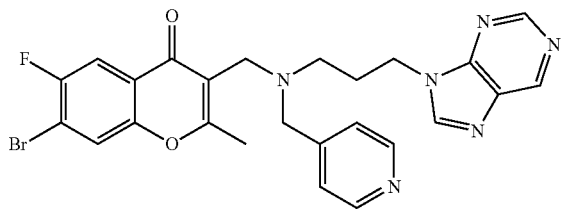 [SMILES: Cc1oc2cc(Br)c(F)cc2c(=O)c1CN(CCCn1cnc2cncnc21)Cc1ccncc1]

Preparation of 2-[3-(9H-purin-9-yl)propyl]-2,3-dihydro-1H-isoindole-1,3-dione

The title compound was synthesized following the approach outlined in Procedure 11a substituting 1H-imidazole with 9H-purine and 2-(4-bromobutyl)-2,3-dihydro-1H-isoindole-1,3-dione with 2-(3-bromopropyl)-2,3-dihydro-1H-isoindole-1,3-dione. The residue was purified by FCC (deactivated SiHP, DCM: MeOH 9:1) to afford the product (358 mg, 1.095 mmol, yield 44%) as a white solid. ESI-MS: 308.4 [M+H]+

1H NMR (400 MHz, DMSO-d6) δ 9.12 (s, 1H), 8.89 (s, 1H), 8.62 (s, 1H), 7.88-7.80 (m, 4H), 4.35 (t, J=7.1 Hz, 2H), 3.63 (t, J=6.7 Hz, 2H), 2.32-2.22 (m, 2H).

The structure was confirmed with 2D NMR.

Preparation of 3-(9H-purin-9-yl)propan-1-amine

The title compound was synthesized following the approach outlined in Procedure 11b substituting 2-[4-(1H-imidazol-1-yl)butyl]-2,3-dihydro-1H-isoindole-1,3-dione with 2-[3-(9H-purin-9-yl)propyl]-2,3-dihydro-1H-isoindole-1,3-dione to afford the product as a yellow oil (256 mg, 0.910 mmol, yield 87%). ESI-MS: 178.1 [M+H]+

1H NMR (400 MHz, DMSO-d6) δ 9.16 (s, 1H), 8.94 (s, 1H), 8.64 (s, 1H), 4.36 (t, J=7.0 Hz, 2H), 2.53 (t, J=6.7 Hz, 2H, overlapped with solvent peak), 1.99-1.87 (m, 2H).

Preparation of [3-(9H-purin-9-yl)propyl](pyridin-4-ylmethyl)amine

The title compound was synthesized following the approach outlined in Procedure 3 substituting 3-(1H-imidazol-1-yl)propan-1-amine with 3-(9H-purin-9-yl)propan-1-amine to afford the product (532 mg, 1.983 mmol, yield 77%) as a yellow solid.

1H NMR (300 MHz, DMSO-d6) δ 9.14 (s, 1H), 8.93 (s, 1H), 8.60 (s, 1H), 8.49-8.41 (m, 2H), 7.33-7.27 (m, 2H), 4.36 (t, J=7.0 Hz, 2H), 3.67 (s, 2H), 2.45 (t, J=6.7 Hz, 2H), 2.09-1.95 (m, 2H).

Preparation of 7-bromo-6-fluoro-2-methyl-3-({[3-(9H-purin-9-yl)propyl][(pyridin-4-yl)methyl]amino}methyl)-4H-chromen-4-one The title compound was synthesized following the approach outlined in Procedure 9.1 substituting 3-(chloromethyl)-7,8-dimethyl-4H-chromen-4-one with 7-bromo-3-(chloromethyl)-6-fluoro-2-methyl-4H-chromen-4-one and [3-(1H-imidazol-1-yl)propyl](pyridin-4-ylmethyl)amine with [3-(9H-purin-9-yl)propyl][(pyridin-4-yl)methyl]amine. The product (680 mg, 1.27 mmol, yield 77%) was obtained as a yellow oil. ESI-MS: 537 [M+H]+

1H NMR (300 MHz, DMSO-d6) δ 9.00 (s, 1H), 8.86 (s, 1H), 8.51 (s, 1H), 8.42-8.37 (m, 2H), 8.08 (d, J=5.6 Hz, 1H), 7.71 (d, J=8.3 Hz, 1H), 7.33-7.26 (m, 2H), 4.26 (t, J=6.9 Hz, 2H), 3.55 (s, 2H), 3.44 (s, 2H), 2.37 (s, 5H), 2.20-2.07 (m, 2H).

The product was converted into hydrochloric acid salt following Procedure 10. Product as an orange solid (60 mg, 0.093 mmol, yield 93%) ESI-MS: 537 [M+H]+

1H NMR (400 MHz, Deuterium Oxide) δ 9.20 (d, J=0.6 Hz, 1H), 9.05 (d, J=0.6 Hz, 1H), 8.89-8.83 (m, 2H), 8.73 (s, 1H), 8.29-8.25 (m, 2H), 7.97 (d, J=5.4 Hz, 1H), 7.64 (d, J=8.0 Hz, 1H), 4.75 (s, 2H), 4.53 (t, J=6.6 Hz, 2H), 4.25 (s, 2H), 3.37-3.29 (m, 2H), 2.63-2.51 (m, 2H), 2.49 (s, 3H).

Example 74. 3-({[3-(1H-imidazol-1-yl)propyl][(pyridin-4-yl)methyl]amino}methyl)-1,4-dihydroquinolin-4-one

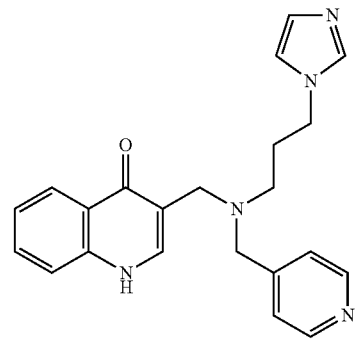 [SMILES: O=c1c(CN(CCCn2ccnc2)Cc2ccncc2)c[nH]c2ccccc12]

Preparation of 3-({[3-(1H-imidazol-1-yl)propyl][(pyridin-4-yl)methyl]amino}methyl)-1,4-dihydroquinolin-4-one The title compound was synthesized according to Procedure 43. Product as a colorless oil (0.023 g, 0.061 mmol, yield 21%). ESI-MS: 372 [M−H]−

1H NMR (300 MHz, Methanol-d4) δ 8.46-8.34 (m, 2H), 8.29 (dd, J=8.3, 1.4 Hz, 1H), 7.97 (s, 1H), 7.69 (ddd, J=8.4, 6.9, 1.5 Hz, 1H), 7.63-7.60 (m, 1H), 7.58-7.52 (m, 1H), 7.47-7.36 (m, 3H), 7.18-7.03 (m, 1H), 6.95-6.81 (m, 1H), 4.10 (t, J=6.9 Hz, 2H), 3.70 (s, 2H), 3.65 (s, 2H), 2.52 (t, J=6.8 Hz, 2H), 2.21-1.99 (m, 2H).

The product was converted into hydrochloric acid salt following Procedure 10 using DCM as a solvent at 0° C. Product as yellow solid (0.027 g, 0.056 mmol, yield 90%). ESI-MS: 374 [M+H]+

1H NMR (300 MHz, Deuterium Oxide) δ 8.70 (t, J=1.5 Hz, 1H), 8.62-8.53 (m, 2H), 8.09 (s, 1H), 8.07-8.03 (m, 2H), 8.01-7.95 (m, 1H), 7.76 (ddd, J=8.5, 7.0, 1.5 Hz, 1H), 7.65-7.55 (m, 1H), 7.52-7.42 (m, 2H), 7.38-7.31 (m, 1H), 4.70 (s, overlapped with solvent peak), 4.39 (s, 2H), 4.31 (t, J=7.0 Hz, 2H), 3.51-3.23 (m, 2H), 2.73-2.32 (m, 2H).

Example 75. 9-(3-{[(pyridin-4-yl)methyl][(2,7,8-trimethyl-4-oxo-4H-chromen-3-yl)methyl]amino}propyl)-6,9-dihydro-1H-purin-6-one

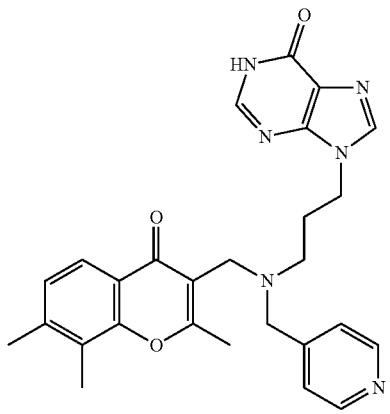 [SMILES: Cc1ccc2c(=O)c(CN(CCCn3cnc4c(=O)[nH]cnc43)Cc3ccncc3)c(C)oc2c1C]

The title compound was synthesized according to Procedure 44. Product as a colorless oil. ESI-MS: 485 [M+H]

¹H NMR (300 MHz, Chloroform-d) δ 8.60-8.37 (m, 2H), 8.09 (s, 1H), 7.94 (d, J=8.1 Hz, 1H), 7.85 (s, 1H), 7.27-6.98 (m, 3H), 4.46-4.06 (m, 2H), 3.62 (s, 2H), 3.59 (s, 2H), 2.58 (t, J=6.7 Hz, 2H), 2.49 (s, 3H), 2.42 (s, 3H), 2.38 (s, 3H), 2.16 (p, J=7.0 Hz, 2H).

The product was converted into hydrochloric acid salt following Procedure 10 using DCM as a solvent at 0° C. Product as a white solid (5 mg, 0.008 mmol, yield 81%). ESI-MS: 485 [M+H]⁺

¹H NMR (300 MHz, Deuterium Oxide) δ 8.93-8.65 (m, 2H), 8.26-8.17 (m, 2H), 8.03 (s, 1H), 7.75 (s, 1H), 7.50 (d, J=8.2 Hz, 1H), 7.25 (d, J=8.3 Hz, 1H), 4.76 (s, 2H), 4.20 (t, J=5.7 Hz, 2H), 4.14 (s, 2H), 3.31-3.06 (m, 2H), 2.37 (s, 3H), 2.34 (m, 5H), 2.26 (s, 3H).

Example 76. 3-({[3-(5,6-dimethoxy-1H-1,3-benzodiazol-1-yl)propyl](pyridin-4-ylmethyl)amino}methyl)-4H-benzo[h]chromen-4-one

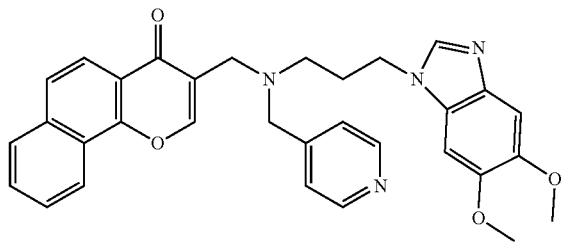 [SMILES: COc1cc2ncn(CCCN(Cc3ccncc3)Cc3coc4c(ccc5ccccc54)c3=O)c2cc1OC]

Preparation of 2-[3-(5,6-dimethoxy-1H-1,3-benzodiazol-1-yl)propyl]-2,3-dihydro-1H-isoindole-1,3-dione The title compound was synthesized following the approach outlined in Procedure 11a substituting 1H-imidazole with 5,6-dimethoxy-1H-1,3-benzodiazole and 2-(4-bromobutyl)-2,3-dihydro-1H-isoindole-1,3-dione with 2-(3-bromopropyl)-2,3-dihydro-1H-isoindole-1,3-dione. The residue was purified by FCC (deactivated SiHP, DCM:MeOH 95:5) to afford the product (219 mg, 0.600 mmol, yield 36%) as a yellow solid. ESI-MS: 366.3 [M+H]⁺

Preparation of 3-(5,6-dimethoxy-1H-1,3-benzodiazol-1-yl)propan-1-amine

The title compound was synthesized following the approach outlined in Procedure 11b substituting 2-[4-(1H-imidazol-1-yl)butyl]-2,3-dihydro-1H-isoindole-1,3-dione with 2-[3-(5,6-dimethoxy-1H-1,3-benzodiazol-1-yl)propyl]-2,3-dihydro-1H-isoindole-1,3-dione to afford the product as a yellow oil (100 mg, 0.425 mmol, yield 71%). ESI-MS: 236.1 [M+H]⁺

Preparation of [3-(5,6-dimethoxy-1H-1,3-benzodiazol-1-yl)propyl](pyridin-4-ylmethyl)amine The title compound was synthesized following the approach outlined in Procedure 3 substituting 3-(1H-imidazol-1-yl)propan-1-amine with 3-(5,6-dimethoxy-1H-1,3-benzodiazol-1-yl)propan-1-amine to afford the product (70 mg, 0.214 mmol, yield 53%) as a yellow oil.

¹H NMR (300 MHz, Chloroform-d) δ 8.60-8.54 (m, 2H), 7.78 (s, 1H), 7.30 (s, 1H), 7.28-7.24 (m, 2H), 6.87 (s, 1H), 4.29 (t, J=6.7 Hz, 2H), 3.96 (s, 3H), 3.94 (s, 3H), 3.80 (s, 2H), 2.66 (t, J=6.6 Hz, 2H), 2.12-2.00 (m, 2H).

Preparation of 3-({[3-(5,6-dimethoxy-1H-1,3-benzodiazol-1-yl)propyl](pyridin-4-ylmethyl)amino}methyl)-4H-benzo[h]chromen-4-one The title compound was synthesized following the approach outlined in Procedure 9.1 substituting 3-(chloromethyl)-7,8-dimethyl-4H-chromen-4-one with 3-(chloromethyl)-4H-benzo[h]chromen-4-one and [3-(1H-imidazol-1-yl)propyl](pyridin-4-ylmethyl)amine with [3-(5,6-dimethoxy-1H-1,3-benzodiazol-1-yl)propyl](pyridin-4-ylmethyl)amine. The residue was purified by prep HPLC to afford the product (20 mg, 0.037 mmol, yield 21%) as a white solid. ESI-MS: 535.4 [M+H]⁺

¹H NMR (400 MHz, DMSO-d₆) δ 8.51 (s, 1H), 8.49-8.45 (m, 1H), 8.44-8.41 (m, 2H), 8.16 (s, 1H), 8.15-8.11 (m, 1H), 8.03 (d, J=8.7 Hz, 1H), 7.97 (s, 1H), 7.94 (d, 1H), 7.86-7.78 (m, 2H), 7.38-7.35 (m, 2H), 7.22 (s, 1H), 7.13 (s, 1H), 4.26 (t, J=7.2 Hz, 2H), 3.78 (s, 3H), 3.75 (s, 3H), 3.69 (s, 2H), 3.56 (s, 2H), 2.49-2.44 (m, 2H), 2.12-2.02 (m, 2H).

The product was converted into a hydrochloric acid salt following Procedure 10 using DCM as a solvent. Product as yellow solid (26 mg, 0.040 mmol, yield 100%) ESI-MS: 535.2 [M+H]⁺

¹H NMR (400 MHz, Deuterium Oxide) δ 8.81 (s, 1H), 8.75-8.71 (m, 2H), 8.19-8.12 (m, 3H), 7.96 (s, 1H), 7.89 (d, J=8.0 Hz, 1H), 7.75-7.69 (m, 1H), 7.68-7.61 (m, 2H), 7.42 (d, J=8.8 Hz, 1H), 6.79 (s, 1H), 6.27 (s, 1H), 4.24-4.17 (m, 4H), 3.67 (s, 3H), 3.18 (s, 2H), 3.16 (s, 3H), 2.71 (t, J=6.8 Hz, 2H), 2.26-2.16 (m, 2H).

Example 77. 6-fluoro-3-({[(2-methoxypyridin-4-yl)methyl][3-(pyridin-3-yl)propyl]amino}methyl)-2-methyl-7-(morpholin-4-yl)-4H-chromen-4-one

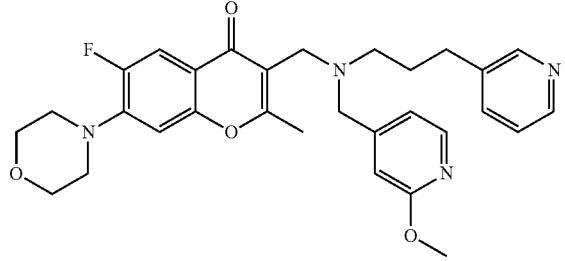 [SMILES: COc1cc(CN(CCCc2cccnc2)Cc2c(C)oc3cc(N4CCOCC4)c(F)cc3c2=O)ccn1]

Preparation of [(2-methoxypyridin-4-yl)methyl][3-(pyridin-3-yl)propyl]amine The title compound was synthesized following the approach outlined in Procedure 3 substituting 3-(1H-imidazol-1-yl)propan-1-amine with 3-(pyridin-3-yl)propan-1-amine and pyridine-4-carbaldehyde with 2-methoxypyridine-4-carbaldehyde to afford the product (150 mg, 0.583 mmol, yield 40%) as a yellow oil. ESI-MS: 258.3 [M+H]$^+$ $^1$H NMR (400 MHz, Chloroform-d) δ 8.50-8.43 (m, 2H), 8.12 (dd, J=5.3, 0.7 Hz, 1H), 7.53-7.48 (m, 1H), 7.25-7.20 (m, 1H), 6.85 (dd, J=5.3, 1.4 Hz, 1H), 6.74-6.72 (m, 1H), 3.95 (s, 3H), 3.77 (s, 2H), 2.74-2.64 (m, 4H), 1.90-1.80 (m, 2H).

Preparation of 7-bromo-6-fluoro-3-({[(2-methoxypyridin-4-yl)methyl][3-(pyridin-3-yl)propyl]amino}methyl)-2-methyl-4H-chromen-4-one The title compound was synthesized following the approach outlined in Procedure 9.1 substituting 3-(chloromethyl)-7,8-dimethyl-4H-chromen-4-one with 7-bromo-3-(chloromethyl)-6-fluoro-2-methyl-4H-chromen-4-one and [3-(1H-imidazol-1-yl)propyl](pyridin-4-ylmethyl)amine with [(2-methoxypyridin-4-yl)methyl][3-(pyridin-3-yl)propyl]amine. The residue was purified by FCC (SiHP, DCM:MeOH 9:1) to afford the title compound (104 mg, 0.19 mmol, yield 71%) as a yellow oil. ESI-MS: 526, 528 [M+H]$^+$

Preparation of 6-fluoro-3-({[(2-methoxypyridin-4-yl)methyl][3-(pyridin-3-yl)propyl]amino}methyl)-2-methyl-7-(morpholin-4-yl)-4H-chromen-4-one The title compound was synthesized following the approach outlined in Procedure 29b substituting 7-bromo-6-fluoro-2-methyl-3-({[3-(pyridin-3-yl)propyl][(pyridin-4-yl)methyl]amino}methyl)-4H chromen-4-one with 7-bromo-6-fluoro-3-({[(2-methoxypyridin-4-yl)methyl][3-(pyridin-3-yl)propyl]amino}methyl)-2-methyl-4H-chromen-4-one. The residue was purified by (SiHP, DCM:MeOH 95:5) to afford the title compound as an orange solid (22 mg, 0.04 mmol yield 43%). ESI-MS: 533.3 [M+H]$^+$ $^1$H NMR (300 MHz, Methanol-d$_4$) δ 8.34 (s, 1H), 8.29-8.23 (m, 1H), 7.96-7.92 (m, 1H), 7.66-7.57 (m, 2H), 7.28-7.22 (m, 1H), 7.03-6.98 (m, 1H), 6.95-6.91 (m, 1H), 6.72 (s, 1H), 3.91-3.85 (m, 4H), 3.83 (s, 3H), 3.60-3.55 (m, 4H), 3.29-3.24 (m, 4H), 2.73-2.65 (m, 2H), 2.57-2.50 (m, 2H), 2.48 (s, 3H), 1.99-1.84 (m, 2H).

Example 78. 7-bromo-6-fluoro-3-({[(2-methoxypyridin-4-yl)methyl][3-(9H-purin-9-yl)propyl]amino}methyl)-2-methyl-4H-chromen-4-one

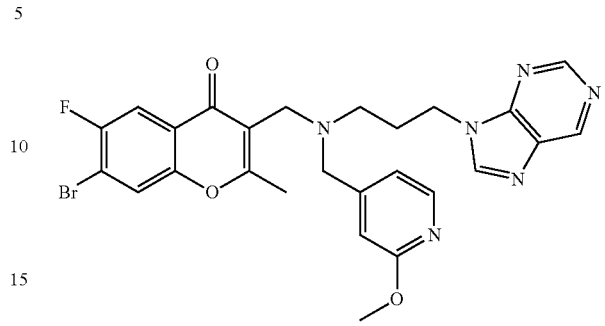

Preparation of [(2-methoxypyridin-4-yl)methyl][3-(9H-purin-9-yl)propyl]amine The title compound was synthesized following the approach outlined in Procedure 3 substituting 3-(1H-imidazol-1-yl)propan-1-amine with 3-(9H-purin-9-yl)propan-1-amine and pyridine-4-carboxaldehyde with 2-methoxypyridine-4-carboxaldehyde to afford the product (100 mg, 0.335 mmol, yield 37%) as a light yellow oil.

$^1$H NMR (400 MHz, Chloroform-d) δ 9.18 (s, 1H), 9.01 (s, 1H), 8.14-8.11 (m, 2H), 6.86-6.83 (m, 1H), 6.73-6.71 (m, 1H), 4.47 (t, J=6.9 Hz, 2H), 3.96 (s, 3H), 3.75 (s, 2H), 2.64 (t, J=6.5 Hz, 2H), 2.17-2.09 (m, 2H).

Preparation of 7-bromo-6-fluoro-3-({[(2-methoxypyridin-4-yl)methyl][3-(9H-purin-9-yl)propyl]amino}methyl)-2-methyl-4H-chromen-4-one The title compound was synthesized following the approach outlined in Procedure 9.1 substituting 3-(chloromethyl)-7,8-dimethyl-4H-chromen-4-one with 7-bromo-3-(chloromethyl)-6-fluoro-2-methyl-4H-chromen-4-one and [3-(1H-imidazol-1-yl)propyl](pyridin-4-ylmethyl)amine with [3-(9H-purin-9-yl)propyl][(2-methoxypyridin-4-yl)methyl]amine. The product (389 mg, 0.686 mmol, yield 52%) was obtained as an orange solid. ESI-MS: 567 [M+H]$^+$ $^1$H NMR (300 MHz, DMSO-d$_6$) δ 9.01 (s, 1H), 8.86 (s, 1H), 8.51 (s, 1H), 8.07 (d, J=5.6 Hz, 1H), 7.97 (d, J=5.2 Hz, 1H), 7.70 (d, J=8.3 Hz, 1H), 6.89 (dd, J=5.3, 1.3 Hz, 1H), 6.66 (s, 1H), 4.26 (t, J=6.9 Hz, 2H), 3.75 (s, 3H), 3.50 (s, 2H), 3.44 (s, 2H), 2.42-2.35 (m, 5H), 2.18-2.06 (m, 2H).

Example 79. 6-fluoro-2-methyl-7-(4-methylpiperazin-1-yl)-3-({[3-(9H-purin-9-yl)propyl][(pyridin-4-yl)methyl]amino}methyl)-4H-chromen-4-one

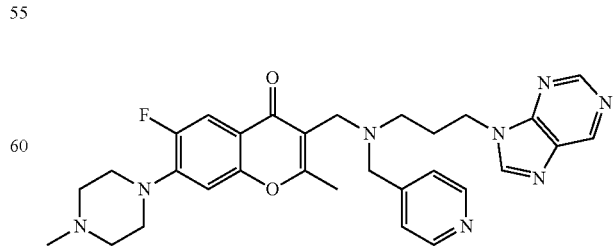

The title compound was synthesized following the approach outlined in Procedure 29b substituting 7-bromo- 6-fluoro-2-methyl-3-({[3-(pyridin-3-yl)propyl][(pyridin-4-yl)methyl]amino}methyl)-4H chromen-4-one with 7-bromo-6-fluoro-2-methyl-3-({[3-(9H-purin-9-yl)propyl][(pyridin-4-yl)methyl]amino}methyl)-4H-chromen-4-one and morpholine with 1-methylpiperazine. Product (45 mg, 0.081 mmol, yield 29%) was obtained as an orange solid. ESI-MS: 557 [M+H]+

The product was converted into hydrochloric acid salt following Procedure 10. Product as orange crystals (40 mg, 0.06 mmol, yield 96%) ESI-MS: 557 [M+H]+

¹H NMR (300 MHz, Deuterium Oxide) δ 9.24 (d, J=0.7 Hz, 1H), 9.10 (d, J=0.6 Hz, 1H), 8.91-8.86 (m, 2H), 8.80 (s, 1H), 8.35-8.28 (m, 2H), 7.56 (d, J=12.4 Hz, 1H), 7.20 (d, J=7.0 Hz, 1H), 4.84 (s, 2H), 4.56 (t, J=6.6 Hz, 2H), 4.34 (s, 2H), 3.94 (d, J=11.4 Hz, 2H), 3.70 (d, J=10.5 Hz, 2H), 3.49-3.28 (m, 6H), 3.01 (s, 3H), 2.68-2.53 (m, 2H), 2.50 (s, 3H).

Example 80. 6-fluoro-2-methyl-4-oxo-3-({[3-(pyridin-3-yl)propyl][(pyridin-4-yl)methyl]amino}methyl)-4H-chromene-7-carboxylic acid

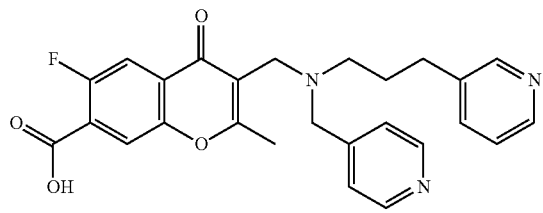 [SMILES: Cc1oc2cc(C(=O)O)c(F)cc2c(=O)c1CN(CCCc1cccnc1)Cc1ccncc1]

Preparation of 6-fluoro-2-methyl-4-oxo-3-({[3-(pyridin-3-yl)propyl][(pyridin-4-yl)methyl]amino}methyl)-4H-chromene-7-carbonitrile The title compound was synthesized following the approach outlined in Procedure 16 substituting 7-bromo-3-({[3-(1H-imidazol-1-yl)propyl][(pyridin-4-yl)methyl]amino}methyl)-4H-chromen-4-one with 7-bromo-6-fluoro-2-methyl-3-({[3-(pyridin-3-yl)propyl][(pyridin-4-yl)methyl]amino}methyl)-4H-chromen-4-one. The product was purified by FCC (SiHP, DCM:MeOH 92:8) to afford the title compound (0.085 g, 0.19 mmol, yield 47%) as an orange solid. ESI-MS: 443 [M+H]+

Preparation of 6-fluoro-2-methyl-4-oxo-3-({[3-(pyridin-3-yl)propyl][(pyridin-4-yl)methyl]amino}methyl)-4H-chromene-7-carboxylic acid The title compound was synthesized according to Procedure 38. Product as a white solid (0.033 g, 0.07 mmol, yield 88.7%). ESI-MS: 462 [M+H]+

¹H NMR (300 MHz, Deuterium Oxide) δ 8.88-8.79 (m, 2H), 8.74-8.62 (m, 2H), 8.53 (d, J=8.2 Hz, 1H), 8.27-8.19 (m, 2H), 8.07-7.90 (m, 2H), 7.76 (d, J=9.6 Hz, 1H), 4.41 (s, 2H), 3.50-3.38 (m, 2H), 2.97 (t, J=7.9 Hz, 2H), 2.59 (s, 3H), 2.37 (td, J=9.9, 8.2, 6.1 Hz, 2H). Some aliphatic H overlapped with solvent peak.

Example 81. 3-({[3-(6-amino-9H-purin-9-yl)propyl][(pyridin-4-yl)methyl]amino}methyl)-2,7,8-trimethyl-4H-chromen-4-one

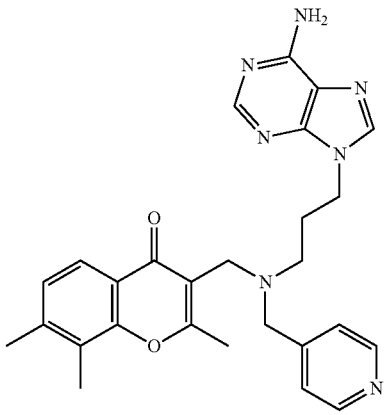 [SMILES: Cc1ccc2c(=O)c(CN(CCCn3cnc4c(N)ncnc43)Cc3ccncc3)c(C)oc2c1C]

Preparation of 3-({[3-(6-amino-9H-purin-9-yl)propyl][(pyridin-4-yl)methyl]amino}methyl)-2,7,8-trimethyl-4H-chromen-4-one The title compound was synthesized according to Procedure 45. Product as a white solid (8 mg, 0,016 mmol, yield of the last step 41%). ESI-MS: 484 [M+H]+

¹H NMR (300 MHz, Methanol-d₄) δ 8.42-8.31 (m, 2H), 8.14 (s, 1H), 8.05 (s, 1H), 7.75 (d, J=8.1 Hz, 1H), 7.55-7.34 (m, 2H), 7.22 (d, J=8.2 Hz, 1H), 4.25 (t, J=6.8 Hz, 2H), 3.66 (s, 2H), 3.56 (s, 2H), 2.54 (t, J=6.8 Hz, 2H), 2.45 (s, 3H), 2.43 (s, 3H), 2.36 (s, 3H), 2.19 (p, J=6.8 Hz, 2H).

Example 82. 3-({[3-(1H-1,3-benzodiazol-1-yl)propyl][(2-methoxypyridin-4-yl)methyl]amino}methyl)-1-methyl-1,4-dihydroquinolin-4-one

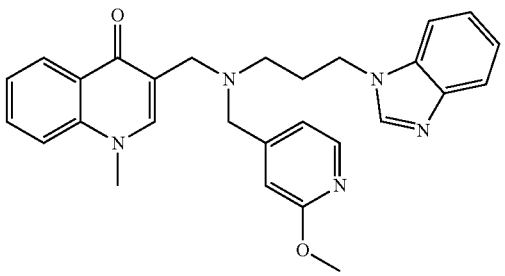 [SMILES: COc1cc(CN(CCCn2cnc3ccccc32)Cc2cn(C)c3ccccc3c2=O)ccn1]

The title compound was synthesized following the approach outlined in Procedure 9.2 substituting 7,8-dimethyl-4-oxo-4H-chromene-3-carbaldehyde with 1-methyl-4-oxo-1,4-dihydroquinoline-3-carbaldehyde and [3-(1H-imidazol-1-yl)propyl](pyridin-4-ylmethyl)amine with [3-(1H-1,3-benzodiazol-1-yl)propyl][(2-methoxypyridin-4-yl)methyl]amine using DCM as a solvent. The residue was purified by FCC (SiHP, DCM: MeOH 9:1) to afford the product (86 mg, 0.18 mmol, yield 44%) as a yellow oil. ESI-MS: 468 [M+H]+

¹H NMR (300 MHz, DMSO-d₆) δ 8.27-8.21 (m, 1H), 8.19 (s, 1H), 8.03-7.96 (m, 2H), 7.79-7.71 (m, 1H), 7.69-

7.58 (m, 3H), 7.45-7.37 (m, 1H), 7.26-7.14 (m, 2H), 6.98-6.93 (m, 1H), 6.80 (s, 1H), 4.35-4.27 (m, 2H), 3.82 (s, 3H), 3.79 (s, 3H), 3.58 (s, 2H), 3.52 (s, 2H), 2.47-2.42 (m, 2H), 2.11-2.00 (m, 2H).

The title compound was converted into hydrochloric acid salt to afford the product as a white solid. ESI-MS: 468 [M+H]$^+$ $^1$H NMR (300 MHz, Deuterium Oxide) δ 8.29 (s, 1H), 8.01-7.96 (m, 1H), 7.85-7.78 (m, 3H), 7.65-7.60 (m, 1H), 7.54-7.39 (m, 3H), 7.26-7.15 (m, 2H), 6.89-6.85 (m, 1H), 6.70 (s, 1H), 4.40-4.30 (m, 2H), 4.26 (s, 2H), 4.14 (s, 2H), 3.76 (s, 3H), 3.67 (s, 3H), 3.11-3.00 (m, 2H), 2.44-2.29 (m, 2H).

Example 83. 3-({[(2-methoxypyridin-4-yl)methyl][4-(pyridin-3-yl)butan-2-yl]amino}methyl)-4H-benzo[h]chromen-4-one

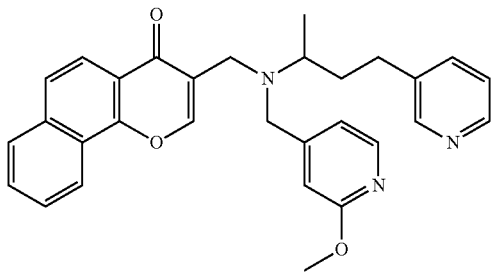 [SMILES: COc1cc(CN(Cc2coc3c(ccc4ccccc43)c2=O)C(C)CCc2cccnc2)ccn1]

Preparation of tert-butyl N-[4-(pyridin-3-yl)but-3-yn-2-yl]carbamate

The title compound was synthesized following the approach outlined in Procedure 35a substituting 5-bromopyrimidine with 3-bromopyridine and tert-butyl N-(prop-2-yn-1-yl)carbamate with tert-butyl N-(but-3-yn-2-yl)carbamate. The product was purified by FCC (SiHP, Hex:AcOEt 60:40) to afford the title compound (0.347 g, 1.4 mmol, yield 72%) as a yellow solid. ESI-MS: 247 [M+H]$^+$ $^1$H NMR (400 MHz, DMSO-d$_6$) δ 8.71 (s, 2H), 7.83 (d, J=7.8 Hz, 1H), 7.51-7.39 (m, 2H), 4.64-4.50 (m, 1H), 1.41 (s, 9H), 1.38 (d, J=7.0 Hz, 3H).

Preparation of tert-butyl N-[4-(pyridin-3-yl)butan-2-yl]carbamate

The title compound was synthesized following the approach outlined in Procedure 35b substituting tert-butyl N-[3-(pyrimidin-5-yl)prop-2-yn-1-yl]carbamate with tert-butyl N-[4-(pyridin-3-yl)but-3-yn-2-yl]carbamate. The crude product (0.319 g, 1.3 mmol, yield 94%) was obtained as an orange solid. ESI-MS: 251 [M+H]$^+$ Preparation of 4-(pyridin-3-yl)butan-2-amine The title compound was synthesized following the approach outlined in Procedure 34d substituting tert-butyl N-[4-(1H-1,3-benzodiazol-1-yl)butan-2-yl]carbamate with tert-butyl N-[4-(pyridin-3-yl)butan-2-yl]carbamate. TFA salt of the product (0.2 g, 0.7 mmol, yield 53%) was obtained as an orange oil after evaporation and lyophilization. ESI-MS: 151 [M+H]$^+$ Preparation of [(2-methoxypyridin-4-yl)methyl][4-(pyridin-3-yl)butan-2-yl]amine The title compound was synthesized following the approach outlined in Procedure 3 substituting 3-(1H-imidazol-1-yl)propan-1-amine with 4-(pyridin-3-yl)butan-2-amine and pyridine-4-carboxaldehyde with 2-methoxypyridine-4-carbaldehyde. The crude product (0.166 g, 0.5 mmol, yield 72%) was obtained as yellow oil. ESI-MS: 272 [M+H]$^+$ Preparation of 3-({[(2-methoxypyridin-4-yl)methyl][4-(pyridin-3-yl)butan-2-yl]amino}methyl)-4H-benzo[h]chromen-4-one The title compound was synthesized following the approach outlined in Procedure 9.2 substituting [3-(1H-imidazol-1-yl)propyl](pyridin-4-ylmethyl)amine with [(2-methoxypyridin-4-yl)methyl][4-(pyridin-3-yl)butan-2-yl]amine and 7,8-dimethyl-4-oxo-4H-chromene-3-carbaldehyde with 4-oxo-4H-benzo[h]chromene-3-carbaldehyde. The product was purified using FCC (SiHP, DCM: MeOH 95:5) to afford the titled compound (0.086 g, 0.2 mmol, yield 33%) as a yellow solid. ESI-MS: 480 [M+H]$^+$ $^1$H NMR (400 MHz, DMSO-d$_6$) δ 8.48-8.45 (m, 1H), 8.45-8.41 (m, 2H), 8.30-8.25 (m, 1H), 8.14-8.09 (m, 1H), 8.03-7.99 (m, 1H), 7.99-7.95 (m, 1H), 7.94-7.90 (m, 1H), 7.86-7.76 (m, 2H), 7.65-7.57 (m, 1H), 7.22-7.11 (m, 1H), 7.01-6.92 (m, 1H), 6.81 (s, 1H), 3.77 (s, 1H), 3.70 (s, 3H), 3.64-3.51 (m, 2H), 3.49-3.40 (m, 1H), 2.87-2.70 (m, 2H), 2.63-2.54 (m, 1H), 2.02-1.86 (m, 1H), 1.70-1.53 (m, 1H), 1.13-1.03 (m, 3H).

The product was converted into hydrochloric acid salt. Product as yellow solid (0.070 g, 0.1 mmol, yield 85%). ESI-MS: 480 [M+H]$^+$ $^1$H NMR (400 MHz, Deuterium Oxide) δ 8.60-8.55 (m, 1H), 8.47-8.42 (m, 1H), 8.44-8.37 (m, 1H), 8.33 (s, 1H), 8.30-8.24 (m, 1H), 8.04-7.97 (m, 1H), 7.89-7.84 (m, 1H), 7.82-7.69 (m, 5H), 6.94-6.90 (m, 1H), 6.69-6.65 (m, 1H), 4.41-4.20 (m, 4H), 3.71-3.48 (m, 1H), 3.22 (s, 3H), 3.10-2.96 (m, 1H), 2.90 (s, 1H), 2.41-2.28 (m, 1H), 2.24-2.11 (m, 1H), 1.54 (d, J=6.5 Hz, 3H).

Example 84. 6-fluoro-2-methyl-7-(4-methylpiperazin-1-yl)-3-({[3-(9H-purin-9-yl)propyl][(2-methoxypyridin-4-yl)methyl]amino}methyl)-4H-chromen-4-one

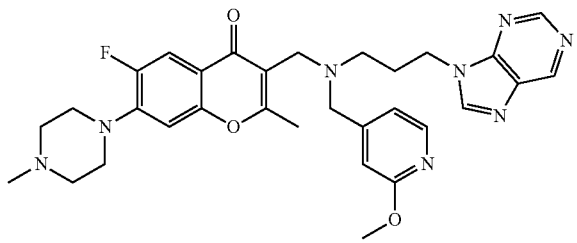 [SMILES: COc1cc(CN(CCCn2cnc3cncnc32)Cc2c(C)oc3cc(N4CCN(C)CC4)c(F)cc3c2=O)ccn1]

The title compound was synthesized following the approach outlined in Procedure 29b substituting 7-bromo-6-fluoro-2-methyl-3-({[3-(pyridin-3-yl)propyl][(pyridin-4-yl)methyl]amino}methyl)-4H chromen-4-one with 7-bromo-6-fluoro-2-methyl-3-({[3-(9H-purin-9-yl)propyl]

[(2-methoxypyridin-4-yl)methyl]amino}methyl)-4H-chromen-4-one and morpholine with 1-methylpiperazine. Product (34 mg, 0.058 mmol, yield 22%) was obtained as a grey solid. ESI-MS: 587 [M+H]$^+$ $^1$H NMR (400 MHz, DMSO-d$_6$) δ 9.02 (s, 1H), 8.86 (s, 1H), 8.51 (s, 1H), 7.99 (d, J=5.2 Hz, 1H), 7.46 (d, J=13.0 Hz, 1H), 6.97 (d, J=7.2 Hz, 1H), 6.90 (dd, J=5.2, 1.3 Hz, 1H), 6.68 (s, 1H), 4.24 (t, J=7.0 Hz, 2H), 3.77 (s, 3H), 3.49 (s, 2H), 3.42 (s, 2H), 3.19 (t, J=4.8 Hz, 4H), 2.40-2.31 (m, 5H), 2.24 (s, 3H), 2.15-2.06 (m, 2H). Aliphatic H overlapped with solvent peak.

Example 85. 3-({[3-(1H-1,3-benzodiazol-1-yl)propyl][(3-fluoropyridin-4-yl)methyl]amino}methyl)-4H-benzo[h]chromen-4-one

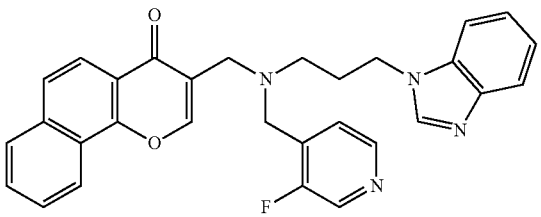 [SMILES: O=c1c(CN(CCCn2cnc3ccccc32)Cc2ccncc2F)coc2c1ccc1ccccc12]

Preparation of [3-(1H-1,3-benzodiazol-1-yl)propyl][(3-fluoropyridin-4-yl)methyl]amine The title compound was synthesized following the approach outlined in Procedure 3 substituting pyridine-4-carboxaldehyde with 3-fluoropyridine-4-carboxaldehyde and 3-(1H-imidazol-1-yl)propan-1-amine with 3-(1H-1,3-benzodiazol-1-yl)propan-1-amine to afford the product (195 mg, 0.686 mmol, yield 77%) as a yellow oil. ESI-MS: 285 [M+H]$^+$ $^1$H NMR (300 MHz, Chloroform-d) δ 8.44 (d, J=1.7 Hz, 1H), 8.40 (dd, J=4.9, 1.1 Hz, 1H), 7.92 (s, 1H), 7.87-7.80 (m, 1H), 7.48-7.40 (m, 1H), 7.36-7.29 (m, 3H), 4.35 (t, J=6.7 Hz, 2H), 3.86 (s, 2H), 2.64 (t, J=6.5 Hz, 2H), 2.13-2.01 (m, 2H).

Preparation of 3-({[3-(1H-1,3-benzodiazol-1-yl)propyl][(3-fluoropyridin-4-yl)methyl]amino}methyl)-4H-benzo[h]chromen-4-one The title compound was synthesized following the approach outlined in Procedure 9.1 substituting 3-(chloromethyl)-7,8-dimethyl-4H-chromen-4-one with 3-(chloromethyl)-4H-benzo[h]chromen-4-one and [3-(1H-imidazol-1-yl)propyl](pyridin-4-ylmethyl)amine with [3-(1H-1,3-benzodiazol-1-yl)propyl][(3-fluoropyridin-4-yl)methyl]amine. The residue was purified by prep HPLC and converted into hydrochloric acid salt following Procedure 10 to afford the product (24 mg, 0.043 mmol, yield 12%) as a yellow solid. ESI-MS: 493 [M+H]$^+$ $^1$H NMR (300 MHz, Deuterium Oxide) δ 9.12 (s, 1H), 8.50 (d, J=2.1 Hz, 1H), 8.37 (d, J=5.2 Hz, 1H), 8.27-8.21 (m, 1H), 8.20 (s, 1H), 7.91-7.84 (m, 1H), 7.76-7.57 (m, 5H), 7.47 (d, J=8.8 Hz, 1H), 7.39-7.26 (m, 1H), 7.15-7.08 (m, 1H), 4.51 (s, 2H), 4.50-4.46 (m, 2H), 3.97 (s, 2H), 3.16-3.04 (m, 2H), 2.52-2.39 (m, 2H).

Example 86. 3-({[3-(1H-1,3-benzodiazol-1-yl)propyl][(2-methoxypyridin-4-yl)methyl]amino}methyl)-4H-pyrido[1,2-a]pyrimidin-4-one

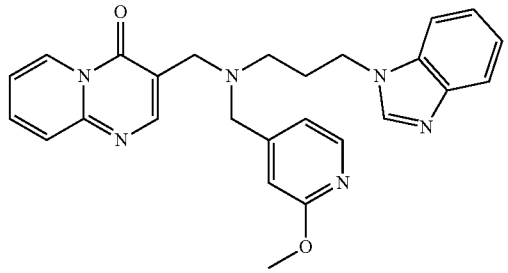 [SMILES: COc1cc(CN(CCCn2cnc3ccccc32)Cc2cnc3ccccn3c2=O)ccn1]

The title compound was synthesized following the Procedure 31. Formic acid salt of the product (43 mg, 0.09 mmol, yield 19%) was obtained as a viscous yellow oil. ESI-MS: 455 [M+H]$^+$.

$^1$H NMR (400 MHz, DMSO-d$_6$) δ 8.98 (ddd, J=7.2, 1.6, 0.8 Hz, 1H), 8.33 (s, 1H), 8.15 (s, 1H), 8.13 (s, 1H), 7.99 (dd, J=5.2, 0.7 Hz, 1H), 7.93 (ddd, J=9.0, 6.7, 1.6 Hz, 1H), 7.66 (dt, J=9.0, 1.1 Hz, 1H), 7.60-7.54 (m, 2H), 7.36 (td, J=6.9, 1.4 Hz, 1H), 7.22-7.12 (m, 2H), 6.93 (dd, J=5.3, 1.3 Hz, 1H), 6.78 (s, 1H), 4.27 (t, J=7.2 Hz, 2H), 3.78 (s, 3H), 3.60 (d, J=4.6 Hz, 4H), 2.46 (t, J=6.6 Hz, 2H), 2.05 (p, J=6.9 Hz, 2H).

Example 87. 3-({[3-(1H-1,3-benzodiazol-1-yl)propyl][(2-methoxypyridin-4-yl)methyl]amino}methyl)-2-methyl-4H-benzo[h]chromen-4-one

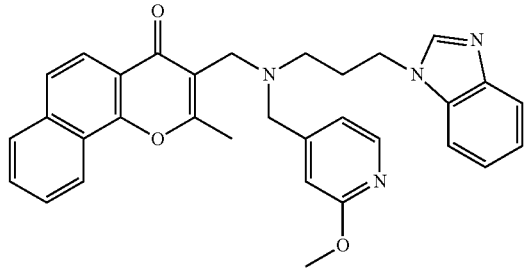 [SMILES: COc1cc(CN(CCCn2cnc3ccccc32)Cc2c(C)oc3c(ccc4ccccc43)c2=O)ccn1]

Preparation of 3-({[3-(1H-1,3-benzodiazol-1-yl)propyl]amino}methyl)-2-methyl-4H benzo[h]chromen-4-one The title compound was synthesized following the approach outlined in Procedure 28 substituting 3-(1H-imidazol-1-yl)propan-1-amine with 3-(1H-1,3-benzodiazol-1-yl)propan-1-amine. The residue was purified by FCC (SiHP, DCM: MeOH 9:1) to afford the product (50 mg, 0.126 mmol, yield 40%) as a yellow oil. ESI-MS: 398.2 [M+H]$^+$ Preparation of 3-({[3-(1H-1,3-benzodiazol-1-yl)propyl][(2-methoxypyridin-4-yl)methyl]amino}methyl)-2-methyl-4H-benzo[h]chromen-4-one The title compound was synthesized following the approach outlined in Procedure 28 substituting 3-(1H-imidazol-1-yl)propan-1-amine with 3-({[3-(1H-1,3-benzodiazol-1-yl)propyl]amino}methyl)-2-methyl-4H-benzo[h]chromen-4-one and 2-methyl-4-oxo-4H-benzo[h]chromene-3-carbaldehyde with 2-methoxypyridine-4-carbaldehyde. Product (43 mg, 0.083 mmol, yield 60%) as a light yellow oil. ESI-MS: 519.3 [M+H]$^+$ $^1$H NMR (400 MHz, DMSO-d$_6$) δ 8.51-8.46 (m, 1H), 8.12 (s, 1H), 8.11-8.08 (m, 1H), 7.99-7.95 (m, 2H), 7.91-7.87 (m, 1H), 7.83-7.75 (m, 2H), 7.56-7.51 (m, 2H), 7.20-7.14 (m, 1H), 7.13-7.08 (m, 1H), 6.91 (dd, J=5.3, 1.3 Hz, 1H), 6.73 (s, 1H), 4.23 (t, J=7.2 Hz, 2H), 3.72 (s, 3H), 3.58 (s, 2H), 3.55 (s, 2H), 2.59 (s, 3H), 2.47 (t, J=6.9 Hz, 2H), 2.10-2.01 (m, 2H).

Example 88. 3-({[3-(1H-1,3-benzodiazol-1-yl)propyl][(2-methoxypyridin-4-yl)methyl]amino}methyl)-1,4-dihydroquinolin-4-one

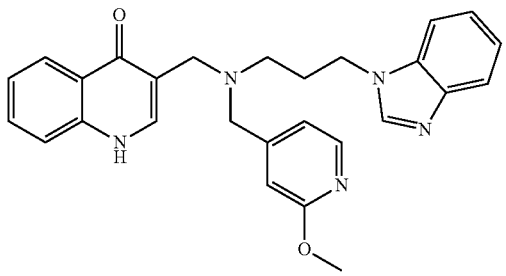 [SMILES: COc1cc(CN(CCCn2cnc3ccccc32)Cc2c[nH]c3ccccc3c2=O)ccn1]

The title compound was synthesized following the approach outlined in Procedure 9.2 substituting 7,8-dimethyl-4-oxo-4H-chromene-3-carbaldehyde with 4-oxo-1,4-dihydroquinoline-3-carbaldehyde and [3-(1H-imidazol-1-yl)propyl](pyridin-4-ylmethyl)amine with [3-(1H-1,3-benzodiazol-1-yl)propyl][(2-methoxypyridin-4-yl)methyl]amine using a mixture of DMF: CHCl$_3$ 3:1 as a solvent.

The residue was purified by prep-HPLC to afford the product (320 mg, 0.706 mmol, yield 44%) as a yellow oil. ESI-MS: 454 [M+H]$^+$ The title compound was converted into hydrochloric acid salt to afford the product as white solid. ESI-MS: 454 [M+H]$^+$ $^1$H NMR (300 MHz, Deuterium Oxide) δ 8.87 (s, 1H), 7.93-7.80 (m, 3H), 7.76-7.69 (m, 1H), 7.61-7.36 (m, 6H), 6.90-6.85 (m, 1H), 6.73-6.69 (m, 1H), 4.52-4.45 (m, 2H), 4.32 (s, 2H), 4.25 (s, 2H), 3.65 (s, 3H), 3.21-3.11 (m, 2H), 2.53-2.40 (m, 2H).

Example 89. 3-({[(2-methoxypyridin-4-yl)methyl][3-(9H-purin-9-yl)propyl]amino}methyl)-1-methyl-1,4-dihydroquinolin-4-one

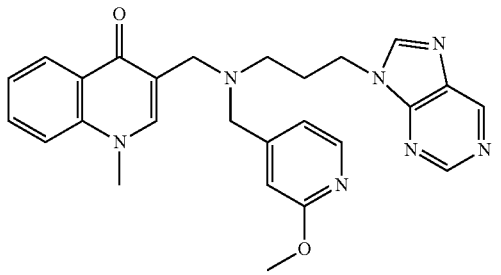 [SMILES: COc1cc(CN(CCCn2cnc3cncnc32)Cc2cn(C)c3ccccc3c2=O)ccn1]

Preparation of 3-({[(2-methoxypyridin-4-yl)methyl][3-(9H-purin-9-yl)propyl]amino}methyl)-1-methyl-1,4-dihydroquinolin-4-one The title compound was synthesized following the approach outlined in Procedure 9.2 substituting [3-(1H-imidazol-1-yl)propyl](pyridin-4-ylmethyl)amine with [(2-methoxypyridin-4-yl)methyl][3-(9H-purin-9-yl)propyl]amine and 7,8-dimethyl-4-oxo-4H-chromene-3-carbaldehyde with 1-methyl-4-oxo-1,4-dihydroquinoline-3-carbaldehyde using DCM as a solvent. The residue was purified by FCC (SiHP, DCM: MeOH 9:1) to afford the product (79 mg, 0.168 mmol, yield 50%) as a light yellow solid. ESI-MS: 470.1 [M+H]$^+$ $^1$H NMR (400 MHz, DMSO-d$_6$) δ 9.09 (s, 1H), 8.89 (s, 1H), 8.61 (s, 1H), 8.20 (dd, J=8.0, 1.6 Hz, 1H), 8.00-7.96 (m, 2H), 7.77-7.71 (m, 1H), 7.69-7.63 (m, 1H), 7.42-7.37 (m, 1H), 6.92 (dd, J=5.3, 1.3 Hz, 1H), 6.75 (s, 1H), 4.34 (t, J=7.0 Hz, 2H), 3.84 (s, 3H), 3.78 (s, 3H), 3.56 (s, 2H), 3.50 (s, 2H), 2.42 (t, J=6.7 Hz, 2H), 2.19-2.10 (m, 2H).

Example 90. 3-({[(2-chloropyridin-4-yl)methyl][3-(pyridin-3-yl)propyl]amino}methyl)-1-methyl-1,4-dihydroquinolin-4-one

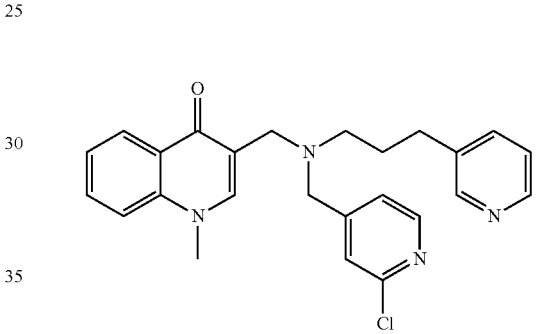

Preparation of [(2-chloropyridin-4-yl)methyl][3-(pyridin-3-yl)propyl]amine

The title compound was synthesized following the approach outlined in Procedure 3 substituting pyridine-4-carbaldehyde with 2-chloropyridine-4-carbaldehyde and 3-(1H-imidazol-1-yl)propan-1-amine with 3-(pyridin-3-yl)propan-1-amine. Crude product, obtained as a yellow oil, was used in the next step without further purification (0.230 g, 0.87 mmol, yield 83%). ESI-MS: 262 [M+H]$^+$ $^1$H NMR (400 MHz, Methanol-d$_4$) δ 8.43-8.41 (m, 1H), 8.39-8.36 (m, 1H), 8.32-8.28 (m, 1H), 7.76-7.71 (m, 1H), 7.50-7.48 (m, 1H), 7.40-7.35 (m, 2H), 3.84-3.81 (m, 2H), 2.78-2.71 (m, 2H), 2.66-2.60 (m, 2H), 1.93-1.83 (m, 2H).

Preparation of 3-({[(2-chloropyridin-4-yl)methyl][3-(pyridin-3-yl)propyl]amino}methyl)-1-methyl-1,4-dihydroquinolin-4-one The title compound was synthesized following the approach outlined in Procedure 9.2 substituting [3-(1H-imidazol-1-yl)propyl](pyridin-4-ylmethyl)amine with [(2-chloropyridin-4-yl)methyl][3-(pyridin-3-yl)propyl]amine and 7,8-dimethyl-4-oxo-4H-chromene-3-carbaldehyde with 1-methyl-4-oxo-1,4-dihydroquinoline-3-carbaldehyde using DCM as a solvent. The residue was purified by FCC (SiHP, DCM: MeOH 9:1) to afford the product (28 mg, 0.064 mmol, yield 34%) as a yellow oil. ESI-MS: 433 [M+H]$^+$ $^1$H NMR (300 MHz, DMSO-d$_6$) δ 8.43-8.38 (m, 1H), 8.37-8.31 (m, 1H), 8.29-8.25 (m, 1H), 8.24-8.18 (m, 1H), 8.02-7.98 (m, 1H), 7.80-7.70 (m, 1H), 7.68-7.62 (m, 1H), 7.60-7.54 (m, 1H), 7.52-7.49 (m, 1H), 7.46-7.36 (m, 2H), 7.24-7.16 (m, 1H), 3.84 (s, 3H), 3.66 (s, 2H), 3.51 (s, 2H), 2.64-2.57 (m, 2H), 2.45-2.41 (m, 2H), 1.89-1.75 (m, 2H).

The title compound was converted into hydrochloric acid salt to afford the product as white solid. ESI-MS: 433 [M+H]$^+$ $^1$H NMR (400 MHz, Deuterium Oxide) δ 8.65-8.61 (m, 1H), 8.57-8.52 (m, 1H), 8.47-8.41 (m, 1H), 8.09-8.05 (m, 1H), 8.04-7.99 (m, 2H), 7.93-7.88 (m, 1H), 7.87-7.81 (m, 1H), 7.72-7.68 (m, 1H), 7.54-7.48 (m, 1H), 7.36-7.29 (m, 2H), 4.42 (s, 3H), 3.88 (s, 4H), 3.44-3.36 (m, 2H), 2.96-2.90 (m, 2H), 2.36-2.26 (m, 2H).

Example 91. 3-({[(2-methoxypyridin-4-yl)methyl] [3-(7H-purin-7-yl)propyl]amino}methyl)-1-methyl-1,4-dihydroquinolin-4-one

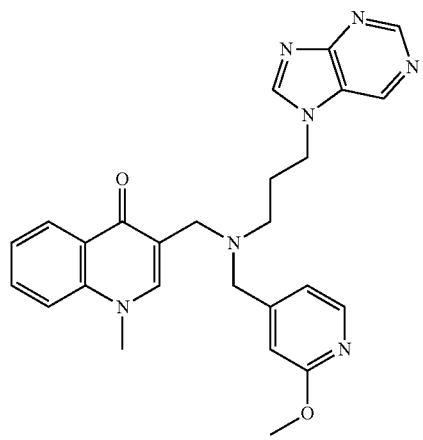 [SMILES: COc1cc(CN(CCCn2cnc3ncncc32)Cc2cn(C)c3ccccc3c2=O)ccn1]

Preparation of 2-[3-(7H-purin-7-yl)propyl]-2,3-dihydro-1H-isoindole-1,3-dione

The title compound was synthesized following the approach outlined in Procedure 11a substituting 2-(4-bromobutyl)-2,3-dihydro-1H-isoindole-1,3-dione with 2-(3-bromopropyl)-2,3-dihydro-1H-isoindole-1,3-dione and 1H-imidazole with 9H-purine. The residue was purified by FCC (SiHP, DCM:MeOH 95:5) to afford the title compound (1.52 g, 4.96 mmol, yield 59%) as a white solid. ESI-MS: 308 [M+H]$^+$ The structure was confirmed with 2D NMR.

Preparation of 3-(7H-purin-7-yl)propan-1-amine

The title compound was synthesized according to Procedure 40a. Product as an orange oil (0.3 g, 1.69 mmol, yield 54%) was used in the next step without further purification. ESI-MS: 178 [M+H]$^+$ Preparation of [(2-methoxypyridin-4-yl)methyl][3-(7H-purin-7-yl)propyl]amine The title compound was synthesized according to Procedure 40b. The crude product was used in the next step without further purification (0.32 g, 1.07 mmol, yield 95%) as an orange oil. ESI-MS: 299 [M+H]$^+$ Preparation of 3-({[(2-methoxypyridin-4-yl)methyl] [3-(7H-purin-7-yl)propyl]amino}methyl)-1-methyl-1,4-dihydroquinolin-4-one The title compound was synthesized according to Procedure 40c. Product as a yellow solid (0.045 g, 0.1 mmol, yield 28%). ESI-MS: 470 [M+H]$^+$ $^1$H NMR (400 MHz, DMSO-d$_6$) δ 9.31 (s, 1H), 8.95 (s, 1H), 8.71 (s, 1H), 8.23 (dd, J=8.1, 1.6 Hz, 1H), 8.00-7.96 (m, 2H), 7.75 (ddd, J=8.6, 6.9, 1.7 Hz, 1H), 7.65 (d, J=8.4 Hz, 1H), 7.41 (ddd, J=8.0, 6.9, 1.0 Hz, 1H), 6.90 (dd, J=5.2, 1.3 Hz, 1H), 6.75 (s, 1H), 4.45 (t, J=7.2 Hz, 2H), 3.83 (s, 3H), 3.78 (s, 3H), 3.56 (s, 2H), 3.50 (s, 2H), 2.42 (t, J=6.6 Hz, 2H), 2.19-2.10 (m, 2H).

Example 92. 7-bromo-6-fluoro-3-({[(2-methoxypyridin-4-yl)methyl](3-{1H-pyrazolo[3,4-c]pyridin-4-yl}propyl)amino}methyl)-2-methyl-4H-chromen-4-one

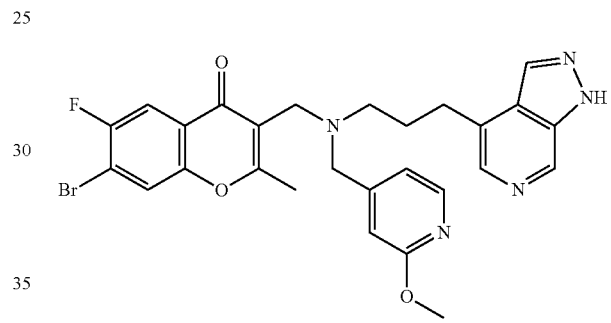

Preparation of tert-butyl N-(3-{1H-pyrazolo[3,4-c]pyridin-4-yl}prop-2-yn-1-yl)carbamate The title compound was synthesized following the approach outlined in Procedure 35a substituting 5-bromopyrimidine with 4-bromo-1H-pyrazolo[3,4-c]pyridine. The product was purified using FCC (SiHP, DCM: MeOH 95:5) to afford the title compound (0.36 g, 1.3 mmol, yield 86%) as a yellow solid. ESI-MS: 273 [M+H]$^+$ $^1$H NMR (400 MHz, DMSO-d$_6$) δ 13.90 (s, 1H), 9.04 (s, 1H), 8.27 (s, 1H), 8.22 (s, 1H), 7.48 (s, 1H), 4.11 (dd, J=5.5, 1.8 Hz, 2H), 1.43 (s, 9H).

Preparation of tert-butyl N-(3-{1H-pyrazolo[3,4-c]pyridin-4-yl}propyl)carbamate

The title compound was synthesized following the approach outlined in Procedure 35b substituting tert-butyl N-[3-(pyrimidin-5-yl)prop-2-yn-1-yl]carbamate with tert-butyl N-(3-{1H-pyrazolo[3,4-c]pyridin-4-yl}prop-2-yn-1-yl)carbamate using Parr Apparatus. The product was purified by FCC (SiHP, DCM: MeOH 95:5) to afford the title compound (0.30 g, 1.1 mmol, yield 87%) as a beige solid. ESI-MS: 277 [M+H]$^+$ $^1$H NMR (400 MHz, DMSO-d$_6$) δ 13.60 (s, 1H), 8.88 (s, 1H), 8.29 (s, 1H), 8.04 (s, 1H), 7.01-6.86 (m, 1H), 3.03-2.93 (m, 2H), 2.93-2.86 (m, 2H), 1.87-1.73 (m, 2H), 1.42-1.34 (m, 9H).

Preparation of 3-{1H-pyrazolo[3,4-c]pyridin-4-yl}propan-1-amine

The title compound was synthesized following the approach outlined in Procedure 34d substituting tert-butyl N-[4-(1H-1,3-benzodiazol-1-yl)butan-2-yl]carbamate with tert-butyl N-(3-{1H-pyrazolo[3,4-c]pyridin-4-yl}propyl)carbamate. TFA salt of the title compound (0.2 g, 0.7 mmol, yield 64%) was obtained as a yellow powder after evaporation and lyophilization. ESI-MS: 177 [M+H]$^+$

Preparation of [(2-methoxypyridin-4-yl)methyl](3-{1H-pyrazolo[3,4-c]pyridin-4-yl}propyl)amine The title compound was synthesized following the approach outlined in Procedure 3 substituting 3-(1H-imidazol-1-yl)propan-1-amine with 3-{1H-pyrazolo[3,4-c]pyridin-4-yl}propan-1-amine and pyridine-4-carboxaldehyde with 2-methoxypyridine-4-carbaldehyde. The crude product (0.070 g, 0.2 mmol, yield 25%) was obtained as an orange oil. ESI-MS: 298 [M+H]$^+$

Preparation of 7-bromo-6-fluoro-3-({[(2-methoxypyridin-4-yl)methyl](3-{1H-pyrazolo[3,4-c]pyridin-4-yl}propyl)amino}methyl)-2-methyl-4H-chromen-4-one The title compound was synthesized following the approach outlined in Procedure 9.1 substituting [3-(1H-imidazol-1-yl)propyl](pyridin-4-ylmethyl)amine with [(2-methoxypyridin-4-yl)methyl](3-{1H-pyrazolo[3,4-c]pyridin-4-yl}propyl)amine and 3-(chloromethyl)-7,8-dimethyl-4H-chromen-4-one with 7-bromo-3-(chloromethyl)-6-fluoro-2-methyl-4H-chromen-4-one using Cs$_2$CO$_3$ as a base. The product was purified by prep-HPLC to afford the title compound (0.006 g, 0.01 mmol, yield 6%) as a white powder. ESI-MS: 568 [M+H]$^+$ $^1$H NMR (400 MHz, DMSO-d$_6$) δ 13.54 (s, 1H), 8.77 (s, 1H), 8.25 (s, 1H), 8.12-8.08 (m, 1H), 8.00-7.96 (m, 1H), 7.92 (s, 1H), 7.79-7.73 (m, 1H), 6.91-6.87 (m, 1H), 6.66 (s, 1H), 3.76 (s, 3H), 3.54-3.45 (m, 4H), 2.93-2.81 (m, 2H), 2.48-2.44 (m, 2H), 2.44 (s, 3H), 2.00-1.86 (m, 2H).

Example 93. 4-(3-{[(2-methoxypyridin-4-yl)methyl]({4-oxo-4H-benzo[h]chromen-3-yl}methyl)amino}propyl)-1,2-dihydropyridin-2-one

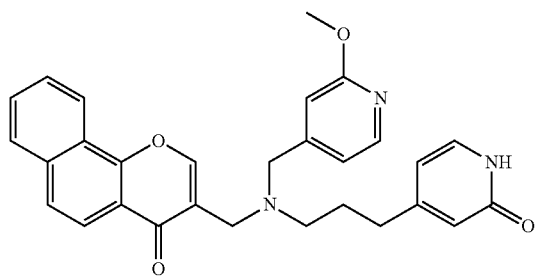 [SMILES: COc1cc(CN(CCCc2cc[nH]c(=O)c2)Cc2coc3c(ccc4ccccc43)c2=O)ccn1]

Preparation of tert-butyl N-[3-(2-methoxypyridin-4-yl)prop-2-yn-1-yl]carbamate The title compound was synthesized following the approach outlined in Procedure 35a substituting 5-bromopyrimidine with 4-bromo-2-methoxypyridine. The product was purified using FCC (SiHP, DCM: MeOH 90:10) to afford the title compound (0.80 g, 3.1 mmol, yield 96%) as a brown oil. ESI-MS: 263 [M+H]$^+$ $^1$H NMR (400 MHz, DMSO-d$_6$) δ 8.19-8.12 (m, 1H), 7.45-7.35 (m, 1H), 6.99-6.94 (m, 1H), 6.83-6.78 (m, 1H), 4.05-3.93 (m, 2H), 3.85 (s, 3H), 1.40 (s, 9H).

Preparation of tert-butyl N-[3-(2-methoxypyridin-4-yl)propyl]carbamate

The title compound was synthesized following the approach outlined in Procedure 35b substituting tert-butyl N-[3-(pyrimidin-5-yl)prop-2-yn-1-yl]carbamate with tert-butyl N-[3-(2-methoxypyridin-4-yl)prop-2-yn-1-yl]carbamate. The product (0.48 g, 1.5 mmol, yield 67%) was obtained as a yellow oil without FCC purification. ESI-MS: 267 [M+H]$^+$ $^1$H NMR (400 MHz, DMSO-d$_6$) 8.06-7.98 (m, 1H), 6.91-6.85 (m, 1H), 6.85-6.81 (m, 1H), 6.67-6.63 (m, 1H), 3.82 (s, 3H), 2.97-2.84 (m, 2H), 2.55-2.52 (m, 2H), 1.73-1.58 (m, 2H), 1.38 (s, 9H).

Preparation of 3-(2-methoxypyridin-4-yl)propan-1-amine

The title compound was synthesized following the approach outlined in Procedure 34d substituting tert-butyl N-[4-(1H-1,3-benzodiazol-1-yl)butan-2-yl]carbamate with tert-butyl N-[3-(2-methoxypyridin-4-yl)propyl]carbamate. TFA salt of the product (0.25 g, 0.8 mmol, yield 53%) as a yellow powder after solvent removal and lyophilization. ESI-MS: 167 [M+H]$^+$

Preparation of 4-(3-aminopropyl)-1,2-dihydropyridin-2-one

The title compound was synthesized according to Procedure 36a. Product as an orange oil (0.153 g, 0.8 mmmol, yield 88%). MS: 153 [M+H]$^+$

Preparation of 4-(3-{[(2-methoxypyridin-4-yl)methyl]amino}propyl)-1,2-dihydropyridin-2-one The title compound was synthesized according to Procedure 36b. Product as an orange oil (0.125 g, 0.4 mmol, yield 46%). ESI-MS: 274 [M+H]$^+$ $^1$H NMR (400 MHz, Chloroform-d) δ 12.48 (s, 1H), 8.13-8.11 (m, 1H), 7.28-7.23 (m, 1H), 6.89-6.82 (m, 1H), 6.76-6.69 (m, 1H), 6.40 (dd, J=1.7, 0.8 Hz, 1H), 6.17-6.13 (m, 1H), 3.95 (s, 3H), 3.77 (s, 2H), 2.71-2.64 (m, 2H), 2.61-2.53 (m, 2H), 1.88-1.76 (m, 2H), 1.66 (s, 1H).

Preparation of 4-(3-{[(2-methoxypyridin-4-yl)methyl]({4-oxo-4H-benzo[h]chromen-3-yl}methyl)amino}propyl)-1,2-dihydropyridin-2-one The title compound was synthesized according to Procedure 36c. Product as a colorless oil (0.090 g, 0.2 mmol, yield 49%). ESI-MS: 482 [M+H]$^+$ $^1$H NMR (400 MHz, DMSO-d$_6$) δ 11.28 (s, 1H), 8.51 (s, 1H), 8.51-8.48 (m, 1H), 8.16-8.09 (m, 1H), 8.06-7.99 (m, 2H), 7.96-7.90 (m, 1H), 7.87-7.76 (m, 2H), 7.19 (d, J=6.7 Hz, 1H), 6.99 (dd, J=5.3, 1.3 Hz, 1H), 6.81 (d, J=1.3 Hz, 1H), 6.11 (d, J=1.6 Hz, 1H), 6.05 (dd, J=6.7, 1.7 Hz, 1H), 3.77 (s, 3H), 3.65 (s, 2H), 3.55 (s, 2H), 2.47 (d, J=7.1 Hz, 2H), 2.41 (t, J=7.7 Hz, 2H), 1.78 (p, J=7.3 Hz, 2H).

Example 94. 3-({[(2-methoxypyridin-4-yl)methyl][3-(pyridin-3-yl)propyl]amino}methyl)-1-methyl-1,4-dihydrocinnolin-4-one

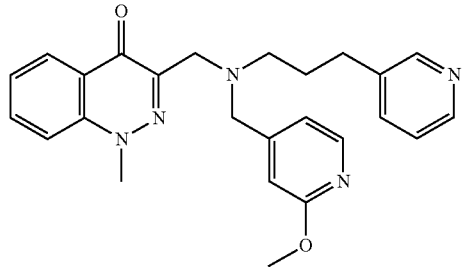 [SMILES: COc1cc(CN(CCCc2cccnc2)Cc2nn(C)c3ccccc3c2=O)ccn1]

The title compound was synthesized following the Procedure 32. Product (50 mg, 0.10 mmol, yield 29%) was obtained as an orange oil. ESI-MS: 430 [M+H]$^+$.

$^1$H NMR (300 MHz, DMSO-d$_6$) δ 8.37 (d, J=2.2 Hz, 1H), 8.32 (dd, J=4.8, 1.6 Hz, 1H), 8.13 (dd, J=8.1, 1.5 Hz, 1H), 7.98 (d, J=5.2 Hz, 1H), 7.85 (ddd, J=8.6, 6.9, 1.6 Hz, 1H), 7.71 (d, J=8.7 Hz, 1H), 7.56 (dt, J=7.8, 2.0 Hz, 1H), 7.48 (ddd, J=8.0, 6.9, 1.0 Hz, 1H), 7.19 (ddd, J=7.7, 4.8, 0.9 Hz, 1H), 6.92 (dd, J=5.3, 1.3 Hz, 1H), 6.77 (s, 1H), 4.03 (s, 3H), 3.76 (s, 3H), 3.71 (s, 2H), 3.67 (s, 2H), 2.60 (t, J=7.6 Hz, 2H), 1.81 (p, J=7.0 Hz, 2H). Some aliphatic H overlapped with solvent peak.

Example 95. 1-cyclopropyl-6,7-difluoro-3-({[(2-methoxypyridin-4-yl)methyl][3-(pyridin-3-yl)propyl]amino}methyl)-1,4-dihydroquinolin-4-one

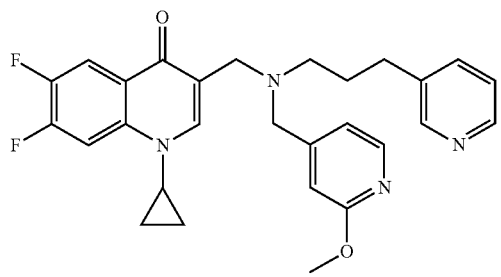 [SMILES: COc1cc(CN(CCCc2cccnc2)Cc2cn(C3CC3)c3cc(F)c(F)cc3c2=O)ccn1]

The title compound was synthesized following the approach outlined in Procedure 28 substituting 3-(1H-imidazol-1-yl)propan-1-amine with [3-(pyridin-3-yl)propyl][(2-methoxypyridin-4-yl)methyl]amine and 2-methyl-4-oxo-4H-benzo[h]chromene-3-carbaldehyde with 1-cyclopropyl-6,7-difluoro-4-oxo-1,4-dihydroquinoline-3-carbaldehyde. The product (0.035 g, 0.071 mmol, yield 40%) was obtained as a colorless oil. ESI-MS: 491 [M+H]$^+$ $^1$H NMR (400 MHz, DMSO-d$_6$) δ 8.37 (d, J=2.2 Hz, 1H), 8.35-8.31 (m, 1H), 8.06-7.98 (m, 3H), 7.90 (s, 1H), 7.60-7.54 (m, 1H), 7.24-7.19 (m, 1H), 6.93 (dd, J=5.2, 1.3 Hz, 1H), 6.76 (s, 1H), 3.79 (s, 3H), 3.57 (s, 2H), 3.55-3.49 (m, 1H), 3.48 (s, 2H), 2.59 (t, J=7.6 Hz, 2H), 2.43 (t, J=7.0 Hz, 2H), 1.86-1.76 (m, 2H), 1.27-1.20 (m, 2H), 0.99-0.93 (m, 2H).

Example 96. 3-({[(2-methoxypyridin-4-yl)methyl][3-(pyrimidin-5-yl)propyl]amino}methyl)-1-methyl-1,4-dihydroquinolin-4-one

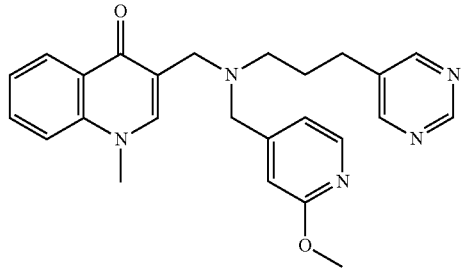 [SMILES: COc1cc(CN(CCCc2cncnc2)Cc2cn(C)c3ccccc3c2=O)ccn1]

Preparation of 3-(pyrimidin-5-yl)propan-1-amine

The title compound was synthesized following the approach outlined in Procedure 34d substituting tert-butyl N-[4-(1H-1,3-benzodiazol-1-yl)butan-2-yl]carbamate with tert-butyl N-[3-(pyrimidin-5-yl)propyl]carbamate. The residue was purified by FCC (SiNH$_2$, DCM: MeOH 98:2) to afford the product (55 mg, 0.401 mmol, yield 27%) as a yellow oil. ESI-MS: 138 [M+H]$^+$ $^1$H NMR (400 MHz, Chloroform-d) δ 9.09 (s, 1H), 8.61 (s, 2H), 2.83-2.76 (m, 2H), 2.73-2.66 (m, 2H), 1.86-1.76 (m, 2H).

Preparation of [(2-methoxypyridin-4-yl)methyl][3-(pyrimidin-5-yl)propyl]amine

The title compound was synthesized following the approach outlined in Procedure 3 substituting pyridine-4-carboxaldehyde with 2-methoxypyridine-4-carboxaldehyde and 3-(1H-imidazol-1-yl)propan-1-amine with 3-(pyrimidin-5-yl)propan-1-amine to afford the product (70 mg, 0.271 mmol, yield 71%) as a yellow oil. ESI-MS: 259 [M+H]$^+$ $^1$H NMR (400 MHz, Chloroform-d) δ 9.09 (s, 1H), 8.61 (s, 2H), 8.13 (d, J=5.2 Hz, 1H), 6.89-6.85 (m, 1H), 6.74 (s, 1H), 3.95 (s, 3H), 3.79 (s, 2H), 2.76-2.66 (m, 4H), 1.92-1.83 (m, 2H).

Preparation of 3-({[(2-methoxypyridin-4-yl)methyl][3-(pyrimidin-5-yl)propyl]amino}methyl)-1-methyl-1,4-dihydroquinolin-4-one The title compound was synthesized following the approach outlined in Procedure 9.2 substituting [3-(1H-imidazol-1-yl)propyl](pyridin-4-ylmethyl)amine with [(2-methoxypyridin-4-yl)methyl][3-(pyrimidin-5-yl)propyl]amine and 7,8-dimethyl-4-oxo-4H-chromene-3-carbaldehyde with 1-methyl-4-oxo-1,4-dihydroquinoline-3-carbaldehyde using DCM as a solvent. The residue was purified by FCC (SiHP, DCM: MeOH 94:6 with the addition of 1% NH$_3$) to afford the product (66 mg, 0.154 mmol, yield 56%) as a white solid. ESI-MS: 430 [M+H]$^+$ $^1$H NMR (300 MHz, DMSO-d$_6$) δ 8.96 (s, 1H), 8.65 (s, 2H), 8.21 (dd, J=8.0, 1.6 Hz, 1H), 8.04 (d, J=5.2 Hz, 1H), 8.00 (s, 1H), 7.79-7.70 (m, 1H), 7.65 (d, J=8.5 Hz, 1H), 7.44-7.35 (m, 1H), 6.99 (dd, J=5.3, 1.3 Hz, 1H), 6.81 (s, 1H), 3.86 (s, 3H), 3.81 (s, 3H), 3.59 (s, 2H), 3.50 (s, 2H), 2.62 (t, J=7.7 Hz, 2H), 2.42 (t, J=6.9 Hz, 2H), 1.91-1.78 (m, 2H).

Example 97. 3-({[(2-methoxypyridin-4-yl)methyl][4-(pyridin-3-yl)butan-2-yl]amino}methyl)-1-methyl-1,4-dihydroquinolin-4-one

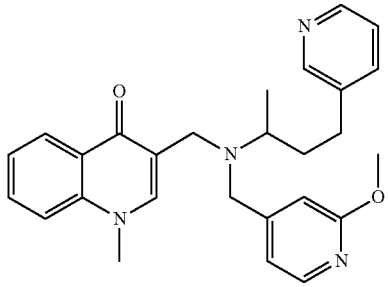 [SMILES: COc1cc(CN(Cc2cn(C)c3ccccc3c2=O)C(C)CCc2cccnc2)ccn1]

Preparation of [(2-methoxypyridin-4-yl)methyl][4-(pyridin-3-yl)butan-2-yl]amine The title compound was synthesized following the approach outlined in Procedure 3 substituting 3-(1H-imidazol-1-yl)propan-1-amine with 4-(pyridin-3-yl)butan-2-amine and pyridine-4-carbaldehyde with 2-methoxypyridine-4-carbaldehyde. The residue was purified by FCC (SiHP, DCM: MeOH 9:1) to afford the product (70 mg, 0.257 mmol, yield 35%) as a yellow oil. ESI-MS: 272 [M+H]$^+$

Preparation of 3-({[(2-methoxypyridin-4-yl)methyl][4-(pyridin-3-yl)butan-2-yl]amino}methyl)-1-methyl-1,4-dihydroquinolin-4-one The title compound was synthesized following the approach outlined in Procedure 9.2 substituting [3-(1H-imidazol-1-yl)propyl](pyridin-4-ylmethyl)amine with [(2-methoxypyridin-4-yl)methyl][4-(pyridin-3-yl)butan-2-yl]amine and 7,8-dimethyl-4-oxo-4H-chromene-3-carbaldehyde with 1-methyl-4-oxo-1,4-dihydroquinoline-3-carbaldehyde. The residue was purified by FCC (SiHP, DCM: MeOH 9:1) to afford the product (68 mg, 0.153 mmol, yield 57%) as a yellow solid. ESI-MS: 443 [M+H]$^+$ $^1$H NMR (400 MHz, DMSO-d$_6$) δ 8.42-8.40 (m, 1H), 8.33-8.26 (m, 1H), 8.24-8.18 (m, 1H), 8.01-7.97 (m, 1H), 7.92 (s, 1H), 7.77-7.69 (m, 1H), 7.62 (d, J=8.6 Hz, 1H), 7.60-7.54 (m, 1H), 7.43-7.33 (m, 1H), 7.21-7.11 (m, 1H), 7.03-6.96 (m, 1H), 6.81 (s, 1H), 3.82 (s, 3H), 3.77 (s, 3H), 3.75-3.67 (m, 1H), 3.56-3.41 (m, 3H), 2.85-2.73 (m, 1H), 2.74-2.53 (m, 2H), 2.01-1.85 (m, 1H), 1.66-1.49 (m, 1H), 1.12-1.00 (m, 3H).

Example 98. 3-({[(2-methoxypyridin-4-yl)methyl][3-(pyridin-3-yl)propyl]amino}methyl)-1,4-dihydrocinnolin-4-one

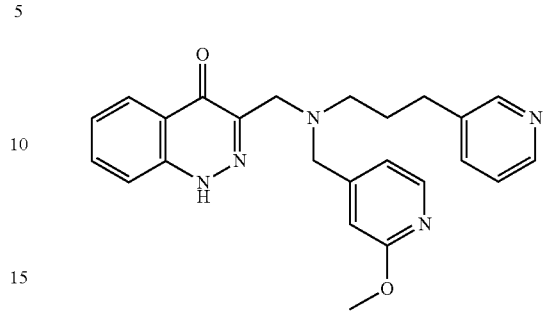

Preparation of 3-({[(2-methoxypyridin-4-yl)methyl][3-(pyridin-3-yl)propyl]amino}methyl)-1,4-dihydrocinnolin-4-one The title compound was synthesized following the approach outlined in Procedure 32d substituting 3-(hydroxymethyl)-1-methyl-1,4-dihydrocinnolin-4-one with 3-(hydroxymethyl)-1,4-dihydrocinnolin-4-one. The residue was purified by FCC (SiHP, DCM: MeOH 0-10%) and repurified by FCC (Si-Diol, AcOEt: MeOH 0-10%) to afford the product (17 mg, 0.04 mmol, yield 6%) as an orange oily solid. ESI-MS: 146 [M+H]$^+$ $^1$H NMR (300 MHz, DMSO-d$_6$) δ 13.37 (s, 1H), 8.37 (d, J=2.2 Hz, 1H), 8.32 (dd, J=4.8, 1.7 Hz, 1H), 8.06 (dd, J=8.3, 1.4 Hz, 1H), 8.01 (d, J=5.2 Hz, 1H), 7.77 (ddd, J=8.5, 6.9, 1.5 Hz, 1H), 7.58-7.51 (m, 2H), 7.40 (ddd, J=8.0, 6.9, 1.0 Hz, 1H), 7.18 (ddd, J=7.7, 4.8, 0.9 Hz, 1H), 6.94 (dd, J=5.3, 1.3 Hz, 1H), 6.80 (s, 1H), 3.78 (s, 3H), 3.73 (s, 2H), 3.68 (s, 2H), 2.61-2.54 (m, 2H), 1.86-1.73 (m, 2H). Aliphatic H overlapped with solvent peak.

Example 99. 3-({[3-(1H-1,3-benzodiazol-1-yl)propyl][(pyridin-4-yl)methyl]amino}methyl)-6,7-difluoro-2-methyl-4H-chromen-4-one

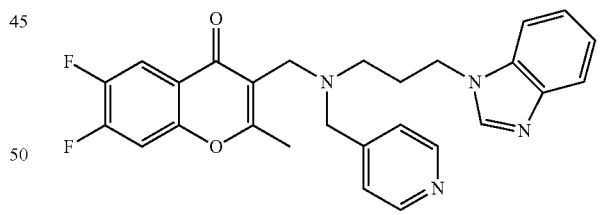

Preparation of 3,4-difluorophenyl acetate

The title compound was synthesized following the approach outlined in Procedure 22a substituting 3-bromo-4-fluorophenol with 3,4-difluorophenol. The product (19.1 g, 110.96 mmol, yield 96%) was obtained as a yellow oil. ESI-MS: 173 [M+H]$^+$

Preparation of 1-(4,5-difluoro-2-hydroxyphenyl)ethan-1-one

The title compound was synthesized following the approach outlined in Procedure 4b substituting 2,3-dimethylphenyl acetate with 3,4-difluorophenyl acetate. The product (12.96 g, 75.29 mmol, yield 64%) was obtained as a yellow solid. ESI-MS: 173 [M+H]$^+$ $^1$H NMR (300 MHz, DMSO-d$_{(6)}$) δ 12.02 (d, J=1.2 Hz, 1H), 7.96 (dd, J=11.4, 9.3 Hz, 1H), 7.07 (dd, J=12.1, 6.8 Hz, 1H), 2.61 (s, 3H).

Preparation of
1-(4,5-difluoro-2-hydroxyphenyl)butane-1,3-dione

The title compound was synthesized following the approach outlined in Procedure 21a substituting 1-(2-hydroxyphenyl)ethan-1-one with 1-(4,5-difluoro-2-hydroxyphenyl)ethan-1-one. The product (11.20 g, 52.30 mmol, yield 90%) was obtained as a yellow solid. ESI-MS: 215 [M+H]$^+$ Preparation of
6,7-difluoro-2-methyl-4H-chromen-4-one The title compound was synthesized following the approach outlined in Procedure 24b substituting 1-(4-bromo-2-hydroxyphenyl)butane-1,3-dione with 1-(4,5-difluoro-2-hydroxyphenyl)butane-1,3-dione. The product (10.10 g, 51.49 mmol, yield 98%) was obtained as a yellow solid. ESI-MS: 197 [M+H]$^+$ Preparation of 3-(chloromethyl)-6,7-difluoro-2-methyl-4H-chromen-4-one The title compound was synthesized following the approach outlined in Procedure 21c substituting 2-methyl-4H-chromen-4-one with 6,7-difluoro-2-methyl-4H-chromen-4-one. The product (3.23 g, 13.20 mmol, yield 52%) was obtained as a yellow solid. ESI-MS: 245 [M+H]$^+$ $^1$H NMR (400 MHz, DMSO-d$_6$) δ 8.00-7.93 (m, 2H), 4.70 (s, 2H), 2.56 (s, 3H).

Preparation of [3-(1H-1,3-benzodiazol-1-yl)propyl][(pyridin-4-yl)methyl]amine

The title compound was synthesized following the approach outlined in Procedure 3 substituting 3-(1H-imidazol-1-yl)propan-1-amine with 3-(1H-1,3-benzodiazol-1-yl)propan-1-amine. Product was purified by FCC (MeOH: DCM 0-10%) to provide the title compound (160 mg, 0.6 mmol, yield 51%) as a yellow oil. ESI-MS: 267 [M+H]$^+$ Preparation of 3-({[3-(1H-1,3-benzodiazol-1-yl)propyl][(pyridin-4-yl)methyl]amino}methyl)-6,7-difluoro-2-methyl-4H-chromen-4-one The title compound was synthesized following the approach outlined in Procedure 9.1 substituting 3-(chloromethyl)-7,8-dimethyl-4H-chromen-4-one with 3-(chloromethyl)-6,7-difluoro-2-methyl-4H-chromen-4-one and [3-(1H-imidazol-1-yl)propyl](pyridin-4-ylmethyl)amine with [3-(1H-1,3-benzodiazol-1-yl)propyl][(pyridin-4-yl)methyl]amine. The product (556 mg, 1.17 mmol, yield 84%) was obtained as a yellow solid. ESI-MS: 475 [M+H]$^+$ The product was converted into hydrochloric acid salt following Procedure 10. Product as a yellow crystals (121 mg, 0.21 mmol, yield 97%). ESI-MS: 475 [M+H]$^+$ $^1$H NMR (300 MHz, Deuterium Oxide) δ 9.27 (s, 1H), 8.81-8.76 (m, 2H), 8.22-8.17 (m, 2H), 7.86-7.70 (m, 3H), 7.67-7.60 (m, 2H), 7.53 (dd, J=10.2, 6.3 Hz, 1H), 4.69-4.61 (m, 4H), 4.17 (s, 2H), 3.27-3.17 (m, 2H), 2.65-2.52 (m, 2H), 2.44 (s, 3H).

Example 100. 3-({[3-(1H-1,3-benzodiazol-1-yl)propyl][(2-methylpyridin-4-yl)methyl]amino}methyl)-1-methyl-1,4-dihydroquinolin-4-one

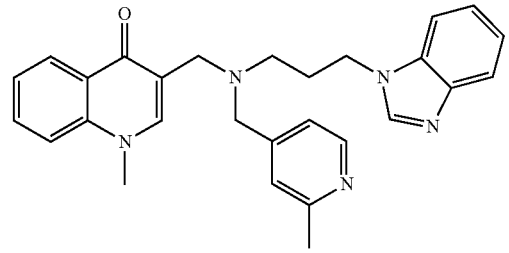 [SMILES: Cc1cc(CN(CCCn2cnc3ccccc32)Cc2cn(C)c3ccccc3c2=O)ccn1]

Preparation of [3-(1H-1,3-benzodiazol-1-yl)propyl][(2-methylpyridin-4-yl)methyl]amine The title compound was synthesized following the approach outlined in Procedure 3 substituting 3-(1H-imidazol-1-yl)propan-1-amine with 3-(1H-1,3-benzodiazol-1-yl)propan-1-amine and pyridine-4-carbaldehyde with 2-methylpyridine-4-carbaldehyde. The residue was purified by FCC (SiHP, DCM: MeOH 9:1) to afford the product (70 mg, 0.249 mmol, yield 44%) as a yellow oil. ESI-MS: 281 [M+H]$^+$ Preparation of 3-({[3-(1H-1,3-benzodiazol-1-yl)propyl][(2-methylpyridin-4-yl)methyl]amino}methyl)-1-methyl-1,4-dihydroquinolin-4-one The title compound was synthesized following the approach outlined in Procedure 9.2 substituting [3-(1H-imidazol-1-yl)propyl](pyridin-4-ylmethyl)amine with [3-(1H-1,3-benzodiazol-1-yl)propyl][(2-methylpyridin-4-yl)methyl]amine and 7,8-dimethyl-4-oxo-4H-chromene-3-carbaldehyde with 1-methyl-4-oxo-1,4-dihydroquinoline-3-carbaldehyde using DCM as a solvent. The residue was purified by FCC (SiHP, DCM: MeOH 9:1) to afford the product (26 mg, 0.057 mmol, yield 22%) as a yellow solid. ESI-MS: 452 [M+H]$^+$ $^1$H NMR (300 MHz, DMSO-d$_6$) δ 8.29-8.21 (m, 2H), 8.19 (s, 1H), 7.96 (s, 1H), 7.79-7.70 (m, 1H), 7.68-7.57 (m, 3H), 7.44-7.36 (m, 1H), 7.25-7.11 (m, 4H), 4.36-4.25 (m, 2H), 3.82 (s, 3H), 3.57 (s, 2H), 3.51 (s, 2H), 2.47-2.41 (m, 2H), 2.36 (s, 3H), 2.12-2.00 (m, 2H).

Example 101. 1-methyl-3-({[(2-methylpyridin-4-yl)methyl][3-(pyridin-3-yl)propyl]amino}methyl)-1,4-dihydroquinolin-4-one

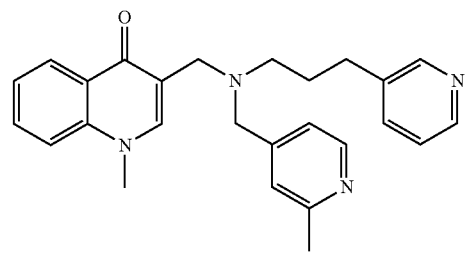 [SMILES: Cc1cc(CN(CCCc2cccnc2)Cc2cn(C)c3ccccc3c2=O)ccn1]

Preparation of 1-methyl-3-({[3-(pyridin-3-yl)propyl]amino}methyl)-1,4-dihydroquinolin-4-one The title compound was synthesized following the approach outlined in Procedure 9.2 substituting [3-(1H-imidazol-1-yl)propyl](pyridin-4-ylmethyl)amine with 3-(pyridin-3-yl)propan-1-amine and 7,8-dimethyl-4-oxo-4H-chromene-3-carbaldehyde with 1-methyl-4-oxo-1,4-dihydroquinoline-3-carbaldehyde using DCM as a solvent. The residue was purified by FCC (SiHP, DCM: MeOH 9:1) to afford the product (104 mg, 0.338 mmol, yield 70%) as a yellow oil. ESI-MS: 308 [M+H]$^+$ Preparation of 1-methyl-3-({[(2-methylpyridin-4-yl)methyl][3-(pyridin-3-yl)propyl]amino}methyl)-1,4-dihydroquinolin-4-one The title compound was synthesized following the approach outlined in Procedure 9.2 substituting [3-(1H-imidazol-1-yl)propyl](pyridin-4-ylmethyl)amine with 1-methyl-3-({[3-(pyridin-3-yl)propyl]amino}methyl)-1,4-dihydroquinolin-4-one and 7,8-dimethyl-4-oxo-4H-chromene-3-carbaldehyde with 2-methylpyridine-4-carbaldehyde using DCM as a solvent. The residue was purified by FCC (SiHP, DCM: MeOH 9:1) to afford the product (38 mg, 0.093 mmol, yield 29%) as a transparent oil. ESI-MS: 413 [M+H]$^+$ $^1$H NMR (300 MHz, DMSO-d$_6$) δ 8.42-8.37 (m, 1H), 8.35-8.29 (m, 2H), 8.25-8.18 (m, 1H), 7.98 (s, 1H), 7.78-7.71 (m, 1H), 7.69-7.63 (m, 1H), 7.60-7.53 (m, 1H), 7.44-7.36 (m, 1H), 7.23-7.17 (m, 3H), 3.85 (s, 3H), 3.59 (s, 2H), 3.50 (s, 2H), 2.64-2.56 (m, 2H), 2.45-2.38 (m, 5H), 1.88-1.78 (m, 2H).

The product was converted into hydrochloric acid salt according to Procedure 10 using DCM as a solvent. Product as a yellow solid. ESI-MS: 413 [M+H]$^+$ $^1$H NMR (400 MHz, Deuterium Oxide) δ 8.64-8.59 (m, 1H), 8.54-8.50 (m, 1H), 8.46-8.40 (m, 1H), 8.40-8.35 (m, 1H), 8.13 (s, 1H), 8.08-8.03 (m, 1H), 7.91-7.80 (m, 4H), 7.75-7.70 (m, 1H), 7.56-7.50 (m, 1H), 4.64 (s, 2H), 4.39 (s, 2H), 3.91 (s, 3H), 3.48-3.41 (m, 2H), 2.95-2.88 (m, 2H), 2.48 (s, 3H), 2.36-2.26 (m, 2H).

Example 102. 3-({[(2-methoxypyridin-4-yl)methyl][3-(pyridazin-4-yl)propyl]amino}methyl)-1-methyl-1,4-dihydroquinolin-4-one

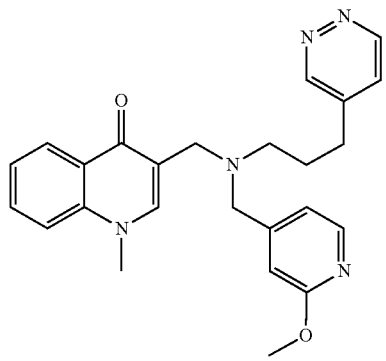 [SMILES: COc1cc(CN(CCCc2ccnnc2)Cc2cn(C)c3ccccc3c2=O)ccn1]

Preparation of [(2-methoxypyridin-4-yl)methyl][3-(pyridazin-4-yl)propyl]amine

The title compound was synthesized following the approach outlined in Procedure 3 substituting 3-(1H-imidazol-1-yl)propan-1-amine with 3-(pyridazin-4-yl)propan-1-amine dihydrochloride and pyridine-4-carbaldehyde with 2-methoxypyridine-4-carbaldehyde with the addition of TEA as a base and using DCM as a solvent. Crude product was used for the next step without further purification. Product as a yellow oil (118 mg, 0.456 mmol, yield 96%). ESI-MS: 259 [M+H]$^+$ $^1$H NMR (300 MHz, DMSO-d$_6$) δ 9.15-9.11 (m, 1H), 9.09-9.05 (m, 1H), 8.08-8.04 (m, 1H), 7.55-7.51 (m, 1H), 6.96-6.92 (m, 1H), 6.78-6.75 (m, 1H), 3.83 (s, 3H), 3.66 (s, 2H), 2.71-2.64 (m, 2H), 2.48-2.43 (m, 2H), 1.81-1.69 (m, 2H).

Preparation of 3-({[(2-methoxypyridin-4-yl)methyl][3-(pyridazin-4-yl)propyl]amino}methyl)-1-methyl-1,4-dihydroquinolin-4-one The title compound was synthesized following the approach outlined in Procedure 9.2 substituting [3-(1H-imidazol-1-yl)propyl](pyridin-4-ylmethyl)amine with [(2-methoxypyridin-4-yl)methyl][3-(pyridazin-4-yl)propyl]amine and 7,8-dimethyl-4-oxo-4H-chromene-3-carbaldehyde with 1-methyl-4-oxo-1,4-dihydroquinoline-3-carbaldehyde. The residue was purified by FCC (SiHP, DCM: MeOH 9:1) to afford the product (78 mg, 0.181 mmol, yield 40%) as a transparent oil. ESI-MS: 430 [M+H]$^+$ $^1$H NMR (400 MHz, DMSO-d$_6$) δ 9.12-9.10 (m, 1H), 8.99-8.96 (m, 1H), 8.24-8.20 (m, 1H), 8.05-8.02 (m, 1H), 7.98 (s, 1H), 7.77-7.72 (m, 1H), 7.67-7.63 (m, 1H), 7.51-7.47 (m, 1H), 7.43-7.37 (m, 1H), 7.00-6.96 (m, 1H), 6.81 (s, 1H), 3.85 (s, 3H), 3.80 (s, 3H), 3.58 (s, 2H), 3.50 (s, 2H), 2.69-2.62 (m, 2H), 2.43-2.38 (m, 2H), 1.91-1.82 (m, 2H).

The product was converted into hydrochloric acid salt according to Procedure 10 using DCM as a solvent. Product as a yellow solid. ESI-MS: 430 [M+H]$^+$ $^1$H NMR (400 MHz, Deuterium Oxide) δ 8.87 (s, 1H), 8.74-8.69 (m, 1H), 8.01-7.97 (m, 1H), 7.77-7.69 (m, 3H), 7.55-7.50 (m, 1H), 7.46-7.39 (m, 2H), 6.84-6.78 (m, 1H), 6.58 (s, 1H), 3.96-3.82 (m, 4H), 3.71 (s, 3H), 3.57 (d, J=1.0 Hz, 3H), 2.92-2.76 (m, 2H), 2.70-2.63 (m, 2H), 2.09-1.97 (m, 2H).

Example 103. 1-(3-{[(2-methoxypyridin-4-yl)methyl][(1-methyl-4-oxo-1,4-dihydroquinolin-3-yl)methyl]amino}propyl)-1H-1,2,3-triazole-4-carboxamide

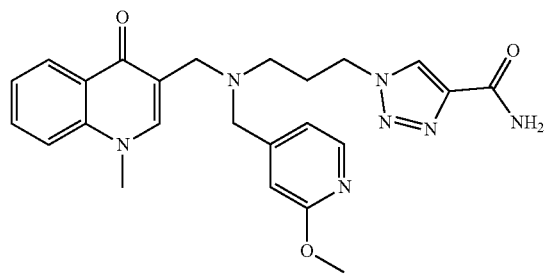 [SMILES: COc1cc(CN(CCCn2cc(C(N)=O)nn2)Cc2cn(C)c3ccccc3c2=O)ccn1]

Preparation of 3-azidopropan-1-ol

The title compound was synthesized according to Procedure 46a. The residue was purified by FCC (SiHP, Hexane:

AcOEt 7:3) to afford the title compound as a transparent oil (490 mg, 4.85 mmol yield 67%).

$^1$H NMR (300 MHz, Chloroform-d) δ 4.05-3.69 (m, 2H), 3.53-3.32 (m, 2H), 2.09-1.75 (m, 2H).

Preparation of 3-azidopropyl methanesulfonate

The title compound was synthesized according to Procedure 46b. The residue was purified by FCC (SiHP, Hexane: AcOEt 7:3) to afford the title compound as a transparent oil (705 mg, 3.93 mmol yield 81%).

Preparation of 3-{[(3-azidopropyl)[(2-methoxypyridin-4-yl)methyl]amino]methyl}-1-methyl-1,4-dihydroquinolin-4-one The title compound was synthesized according to Procedure 46c. The residue was purified by FCC (SiHP, DCM: MeOH 95:5) to afford the product (270 mg, 0.71 mmol, yield 74%) as a transparent oil. ESI-MS: 393 [M+H]$^+$ Preparation of 1-(3-{[(2-methoxypyridin-4-yl)methyl][(1-methyl-4-oxo-1,4-dihydroquinolin-3-yl)methyl]amino}propyl)-1H-1,2,3-triazole-4-carboxamide The title compound was synthesized according to Procedure 46d. The residue was purified by FCC (SiHP, DCM: MeOH 9:1) to give the product (91 mg, 0.20 mmol, yield 88%) as a white solid. ESI-MS: 462 [M+H]$^+$ $^1$H NMR (300 MHz, DMSO-d$_6$) δ 8.54 (s, 1H), 8.21 (dd, J=8.1, 1.6 Hz, 1H), 8.02 (d, J=5.2 Hz, 1H), 7.98 (s, 1H), 7.81-7.69 (m, 2H), 7.65 (d, J=8.5 Hz, 1H), 7.47-7.32 (m, 2H), 6.95 (dd, J=5.3, 1.3 Hz, 1H), 6.78 (s, 1H), 4.48 (t, J=7.0 Hz, 2H), 3.86 (s, 3H), 3.79 (s, 3H), 3.57 (s, 2H), 3.49 (s, 2H), 2.44-2.35 (m, 2H), 2.20-2.05 (m, 2H).

Biological Assays and Data:

As stated above, the compounds of the present invention are STING modulators and are useful in treating diseases by STING activity regulation. The biological activity of the compounds of present invention can be determined by any appropriate test to determine the activity of the compound as STING modulator, as well as cell lines and in vivo models.

Fluorescence Thermal Shift Assay

Compounds of the present invention were tested for binding to human STING in Fluorescence Thermal Shift assay. STING was preincubated with the compounds for 20 minutes in 50 mM Hepes, 150 mM NaCl, pH 7.5 in 16 µl volume, following by adding 4 µl of SyproOrange dye dilution (ThermoFisher, cat no. S-6651). Final STING concentration was 0.1 mg/ml. Thermal unfolding was performed in Real-Time PCR QuantStudio 6 Flex System (Applied Biosystems), from 25 to 99° C., with continuous ramp mode and ramp rate 0.033° C./s. The data were analyzed using Protein Thermal Shift Software (ThermoFisher).

Using the Fluorescence Thermal Shift assay described above, Examples 1-23, 25-34, 36-85, 87-91, 93-103 exhibited ΔTm [° C.] values in the following ranges: +=ΔTm<2.5° C.; ++=ΔTm>2.5° C. For example, ΔTm [° C.] of FTS assay for following examples are:

| Examples | [hSTING] FTS, ΔTm [° C.] for 50 µM |
|---|---|
| 1 | + |
| 2 | + |
| 3 | + |
| 4 | + |
| 5 | ++ |
| 6 | + |
| 7 | ++ |
| 8 | + |
| 9 | ++ |
| 10 | ++ |
| 11 | + |
| 12 | ++ |
| 13 | ++ |
| 14 | ++ |
| 15 | + |
| 16 | ++ |
| 17 | ++ |
| 18 | + |
| 19 | ++ |
| 20 | + |
| 21 | ++ |
| 22 | + |
| 23 | ++ |
| 25 | + |
| 26 | + |
| 27 | ++ |
| 28 | ++ |
| 29 | ++ |
| 30 | ++ |
| 31 | ++ |
| 32 | ++ |
| 33 | + |
| 34 | + |
| 36 | ++ |
| 37 | ++ |
| 38 | + |
| 39 | ++ |
| 40 | ++ |
| 41 | ++ |
| 42 | ++ |
| 43 | + |
| 44 | + |
| 45 | + |
| 46 | + |
| 47 | ++ |
| 48 | ++ |
| 49 | ++ |
| 50 | ++ |
| 51 | ++ |
| 52 | ++ |
| 53 | ++ |
| 54 | ++ |
| 55 | ++ |
| 56 | ++ |
| 57 | ++ |
| 58 | ++ |
| 59 | + |
| 60 | + |
| 61 | + |
| 62 | ++ |
| 63 | ++ |
| 64 | ++ |
| 65 | ++ |
| 66 | + |
| 67 | ++ |
| 68 | ++ |
| 69 | ++ |
| 70 | ++ |
| 71 | ++ |
| 72 | + |
| 73 | ++ |
| 74 | + |
| 75 | ++ |
| 76 | ++ |
| 77 | + |
| 78 | ++ |
| 79 | ++ |
| 80 | + |

201
-continued

| Examples | [hSTING] FTS, ΔTm [° C.] for 50 μM |
|---|---|
| 81 | ++ |
| 82 | ++ |
| 83 | + |
| 84 | ++ |
| 85 | + |
| 88 | ++ |
| 89 | + |
| 90 | ++ |
| 91 | + |
| 93 | ++ |
| 94 | ++ |
| 95 | ++ |
| 96 | ++ |
| 97 | ++ |
| 98 | ++ |
| 99 | ++ |
| 100 | ++ |
| 101 | ++ |
| 102 | + |
| 103 | + |

THP-1 Dual Reporter Assay

Compounds of the present invention were tested for their activity using THP-1 dual cells (Invivogen, cat no. thpd-nfis) allowing for simultaneous study of NF-κB pathway and the interferon regulatory factor (IRF) pathway. THP-1 dual cells contain luciferase reporter gene under the control of an ISG54 (interferon-stimulated gene) minimal promoter in conjunction with five interferon-stimulated response elements and a secreted embryonic alkaline phosphatase reporter gene under the control an IFN (interferon)-β minimal promoter fused to five copies of the NF-κB consensus transcriptional response element with three copies of the c-Rel binding site. Following 18 h of stimulation with STING agonist, medium was collected and transferred onto fresh cell culture plate. To verify activity of the IRF pathway, luminescence activity was measured with standard laboratory plate reader immediately after addition 10 μl of the medium to 50 μl of luminescence reagent (Invivogen, cat. No. rep-qlc2). To verify activity of NF-κB pathway, 20 μl of the medium was mixed with 80 μl of a detection medium (Invivogen, cat. No. rep-qb2) and incubated for 2 hours at 37° C. in a humidified atmosphere containing 5% $CO_2$. Next, absorbance at 630 nm was recorded using standard laboratory plate reader.

Compounds of the present disclosure, as exemplified in Examples, showed EC50 values in the following ranges: $+=EC_{50} \geq 20$ μM; $++=10$ μM$<EC_{50}<20$ μM; $+++=EC_{50} \leq 10$ μM.

| Examples | Structure | THP1 Dual EC50 (μM) IRF | THP1 Dual EC50 (μM) NFkB |
|---|---|---|---|
| 1 | 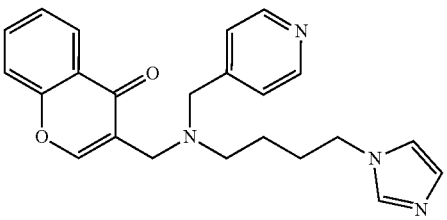 [SMILES: O=c1c(CN(CCCCn2ccnc2)Cc2ccncc2)coc2ccccc12] | ++ | + |
| 2 | 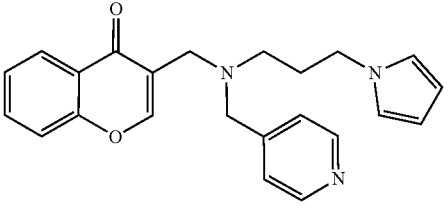 [SMILES: O=c1c(CN(CCCn2cccc2)Cc2ccncc2)coc2ccccc12] | ++ | + |
| 3 | 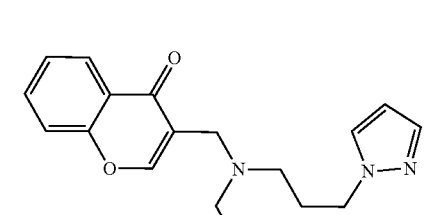 | + | + |

-continued

| Examples | Structure | THP1 Dual EC50 (μM) IRF | THP1 Dual EC50 (μM) NFkB |
|---|---|---|---|
| 4 | 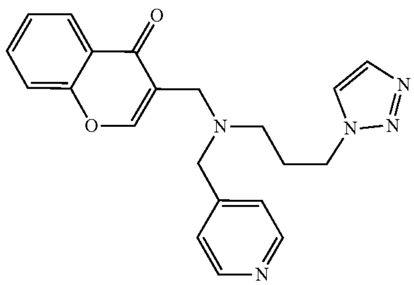 [SMILES: O=c1c(CN(CCCn2ccnn2)Cc2ccncc2)coc2ccccc12] | + | + |
| 5 | 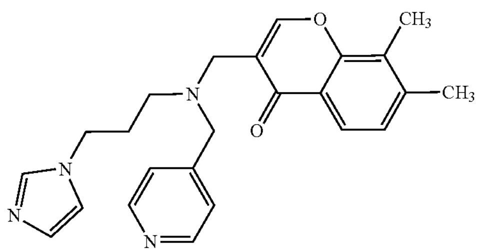 [SMILES: Cc1ccc2c(=O)c(CN(CCCn3ccnc3)Cc3ccncc3)coc2c1C] | +++ | +++ |
| 6 | 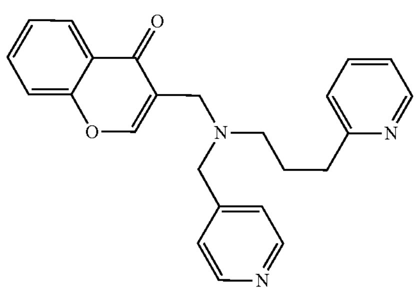 [SMILES: O=c1c(CN(CCCc2ccccn2)Cc2ccncc2)coc2ccccc12] | + | + |
| 7 | 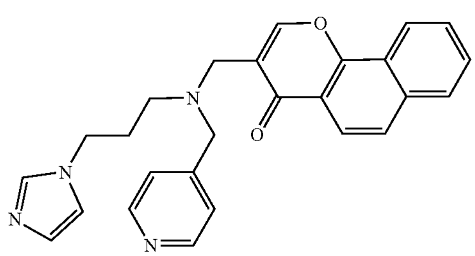 [SMILES: O=c1c(CN(CCCn2ccnc2)Cc2ccncc2)coc2c1ccc1ccccc12] | +++ | +++ |
| 8 | 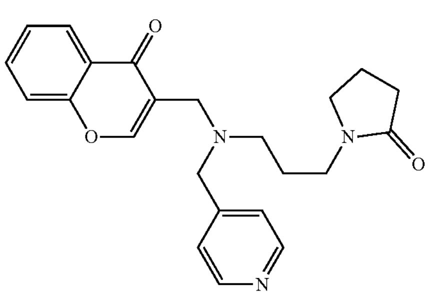 [SMILES: O=C1CCCN1CCCN(Cc1ccncc1)Cc1coc2ccccc2c1=O] | + | + |

| Examples | Structure | THP1 Dual EC50 (μM) IRF | THP1 Dual EC50 (μM) NFkB |
|---|---|---|---|
| 9 | 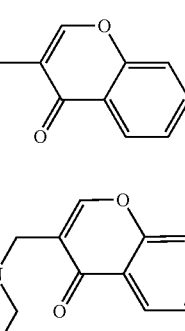 | +++ | +++ |
| 10 | 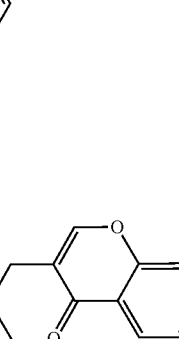 | +++ | ++ |
| 11 | 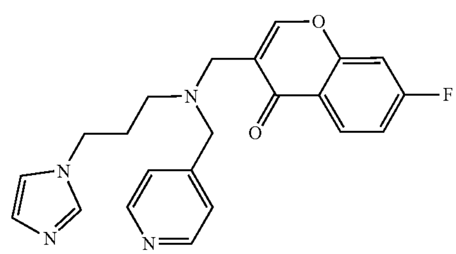 [SMILES: O=c1c(CN(CCCn2ccnc2)Cc2ccncc2)coc2cc(F)ccc12] | ++ | + |
| 12 | 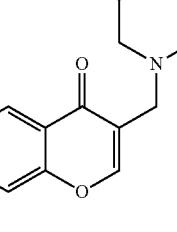 | +++ | ++ |

-continued
| Examples | Structure | THP1 Dual EC50 (μM) IRF | THP1 Dual EC50 (μM) NFkB |
|---|---|---|---|
| 13 | 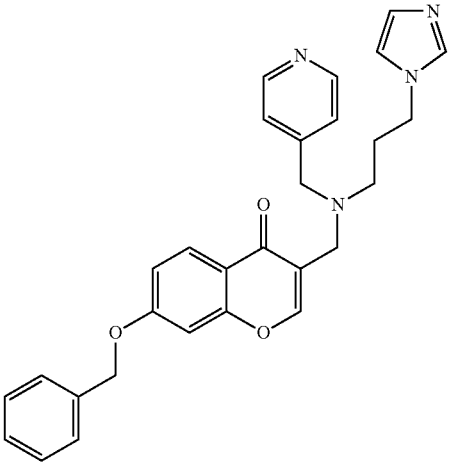 [SMILES: O=c1c(CN(CCCn2ccnc2)Cc2ccncc2)coc2cc(OCc3ccccc3)ccc12] | +++ | +++ |
| 14 | 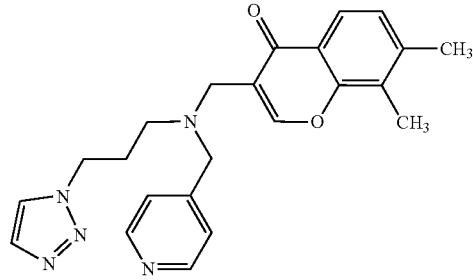 [SMILES: Cc1ccc2c(=O)c(CN(CCCn3ccnn3)Cc3ccncc3)coc2c1C] | ++ | ++ |
| 15 | 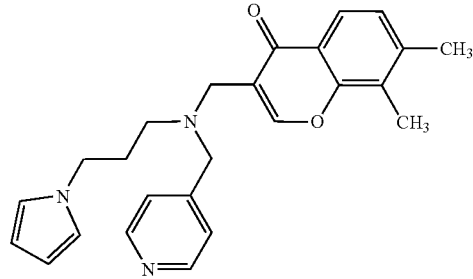 [SMILES: Cc1ccc2c(=O)c(CN(CCCn3cccc3)Cc3ccncc3)coc2c1C] | + | + |
| 16 | 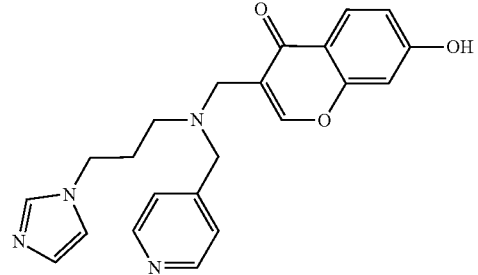 [SMILES: O=c1c(CN(CCCn2ccnc2)Cc2ccncc2)coc2cc(O)ccc12] | ++ | + |

-continued

| Examples | Structure | THP1 Dual EC50 (μM) IRF | THP1 Dual EC50 (μM) NFkB |
| --- | --- | --- | --- |
| 17 | 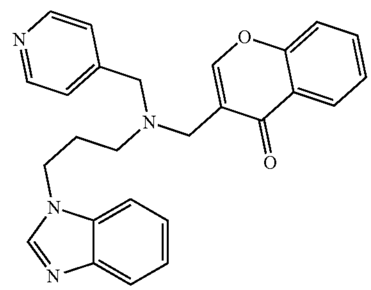 [SMILES: O=c1c(CN(CCCn2cnc3ccccc32)Cc2ccncc2)coc2ccccc12] | +++ | ++ |
| 18 | 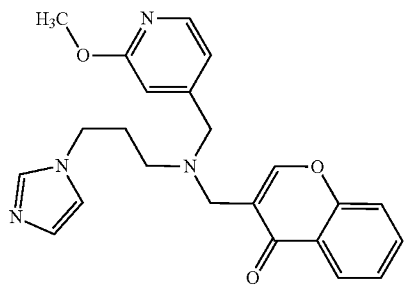 [SMILES: COc1cc(CN(CCCn2ccnc2)Cc2coc3ccccc3c2=O)ccn1] | + | + |
| 19 | 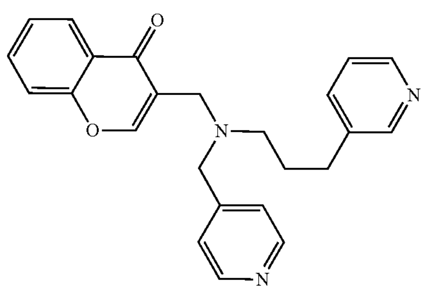 [SMILES: O=c1c(CN(CCCc2cccnc2)Cc2ccncc2)coc2ccccc12] | +++ | ++ |
| 20 | 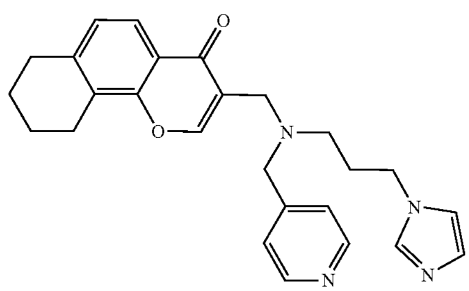 [SMILES: O=c1c(CN(CCCn2ccnc2)Cc2ccncc2)coc2c3c(ccc12)CCCC3] | +++ | +++ |
| 21 | 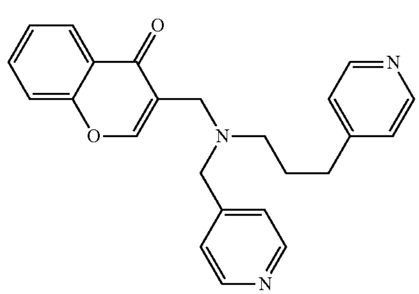 [SMILES: O=c1c(CN(CCCc2ccncc2)Cc2ccncc2)coc2ccccc12] | +++ | ++ |

-continued

| Examples | Structure | THP1 Dual EC50 (μM) IRF | THP1 Dual EC50 (μM) NFkB |
|---|---|---|---|
| 22 | 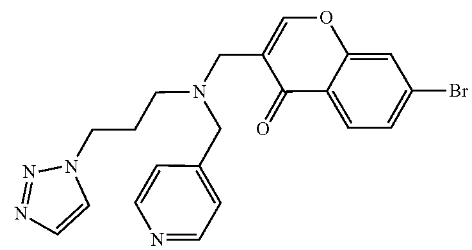 | ++ | + |
| 23 | 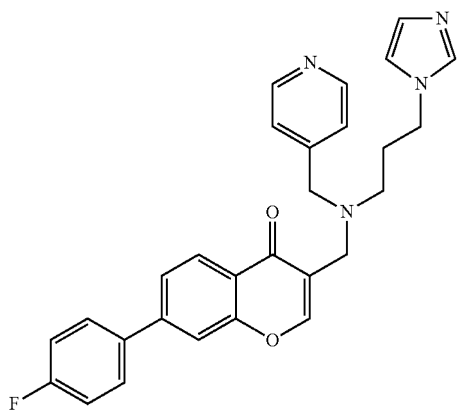 [SMILES: O=c1c(CN(CCCn2ccnc2)Cc2ccncc2)coc2cc(-c3ccc(F)cc3)ccc12] | + | + |
| 24 | 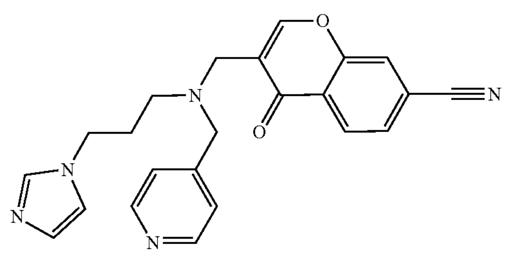 [SMILES: N#Cc1ccc2c(=O)c(CN(CCCn3ccnc3)Cc3ccncc3)coc2c1] | + | + |
| 25 | 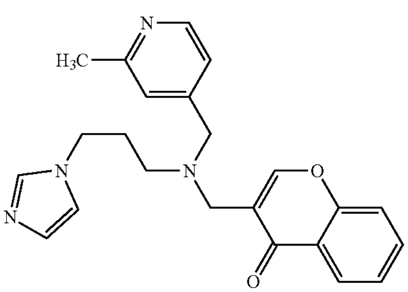 [SMILES: Cc1cc(CN(CCCn2ccnc2)Cc2coc3ccccc3c2=O)ccn1] | ++ | + |
| 26 | 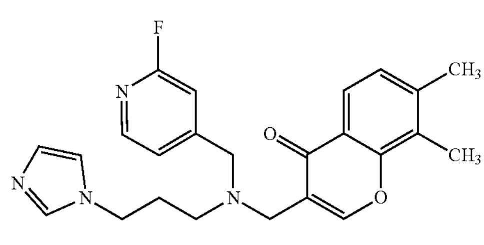 [SMILES: Cc1ccc2c(=O)c(CN(CCCn3ccnc3)Cc3ccnc(F)c3)coc2c1C] | + | + |

-continued

| Examples | Structure | THP1 Dual EC50 (μM) IRF | THP1 Dual EC50 (μM) NFkB |
|---|---|---|---|
| 27 | 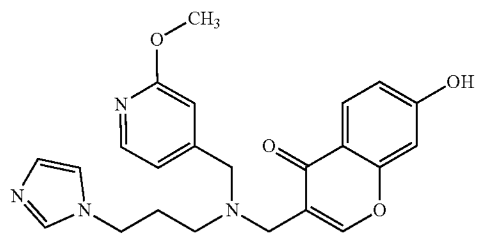 [SMILES: COc1cc(CN(CCCn2ccnc2)Cc2coc3cc(O)ccc3c2=O)ccn1] | ++ | + |
| 28 | 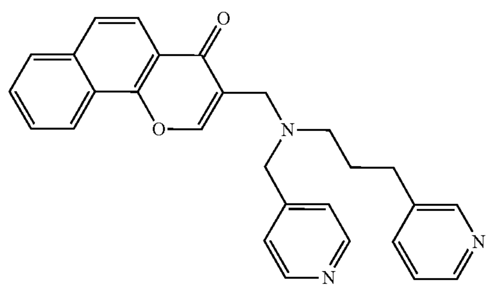 [SMILES: O=c1c(CN(CCCc2cccnc2)Cc2ccncc2)coc2c1ccc1ccccc12] | +++ | +++ |
| 29 | 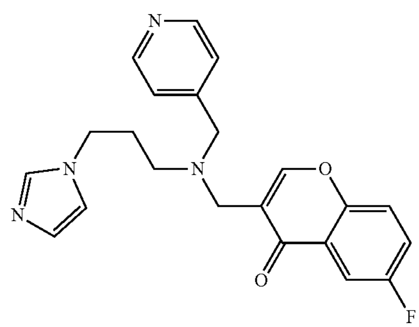 [SMILES: O=c1c(CN(CCCn2ccnc2)Cc2ccncc2)coc2ccc(F)cc12] | +++ | ++ |
| 30 | 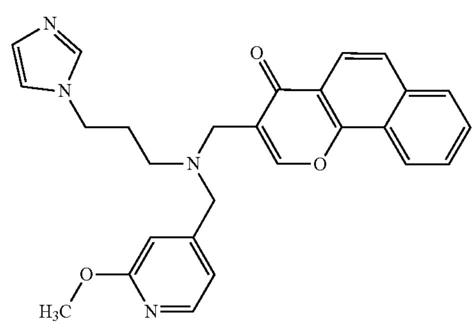 [SMILES: COc1cc(CN(CCCn2ccnc2)Cc2coc3c(ccc4ccccc43)c2=O)ccn1] | +++ | +++ |
| 31 | 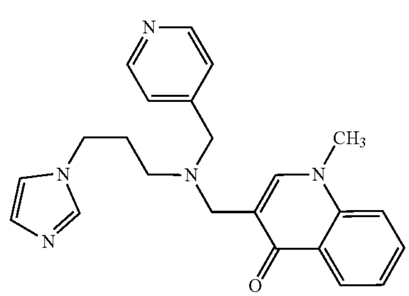 [SMILES: Cn1cc(CN(CCCn2ccnc2)Cc2ccncc2)c(=O)c2ccccc21] | + | + |

-continued

| Examples | Structure | THP1 Dual EC50 (μM) IRF | THP1 Dual EC50 (μM) NFkB |
|---|---|---|---|
| 32 | 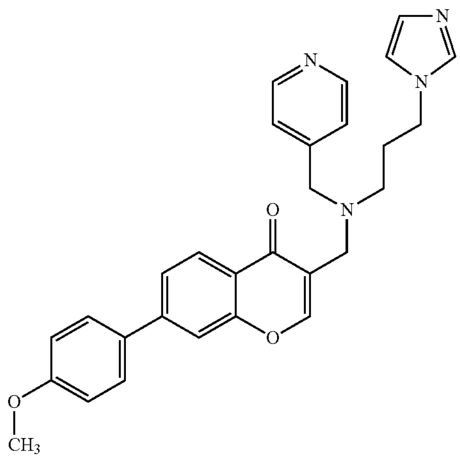 [SMILES: COc1ccc(-c2ccc3c(=O)c(CN(CCCn4ccnc4)Cc4ccncc4)coc3c2)cc1] | ++ | + |
| 33 | 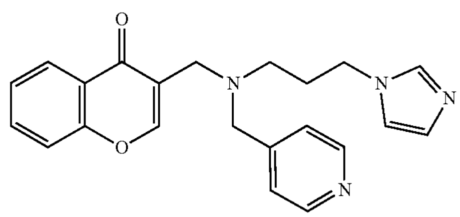 [SMILES: O=c1c(CN(CCCn2ccnc2)Cc2ccncc2)coc2ccccc12] | ++ | + |
| 34 | 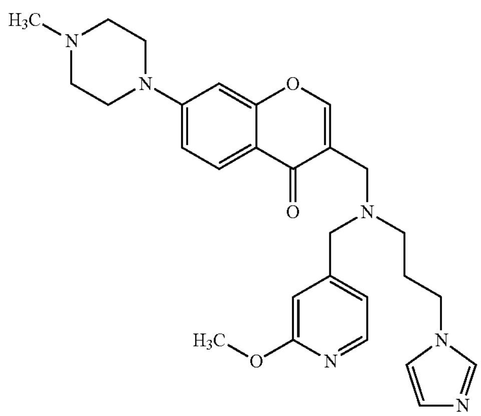 [SMILES: COc1cc(CN(CCCn2ccnc2)Cc2coc3cc(N4CCN(C)CC4)ccc3c2=O)ccn1] | + | ++ |
| 35 | 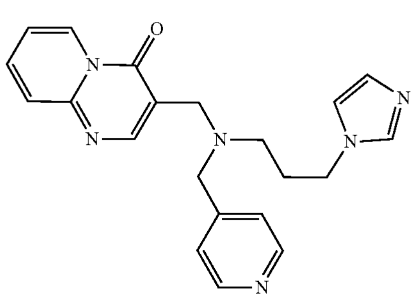 [SMILES: O=c1c(CN(CCCn2ccnc2)Cc2ccncc2)cnc2ccccn12] | + | + |

-continued

| Examples | Structure | THP1 Dual EC50 (μM) IRF | THP1 Dual EC50 (μM) NFkB |
|---|---|---|---|
| 36 | 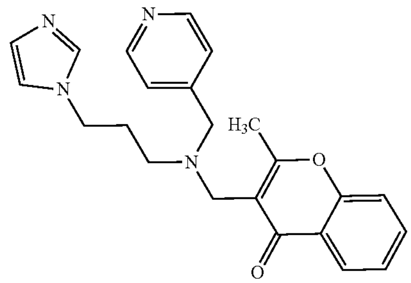 [SMILES: Cc1oc2ccccc2c(=O)c1CN(CCCn1ccnc1)Cc1ccncc1] | +++ | ++ |
| 37 | 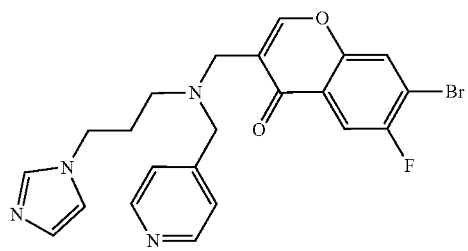 [SMILES: O=c1c(CN(CCCn2ccnc2)Cc2ccncc2)coc2cc(Br)c(F)cc12] | +++ | +++ |
| 38 | 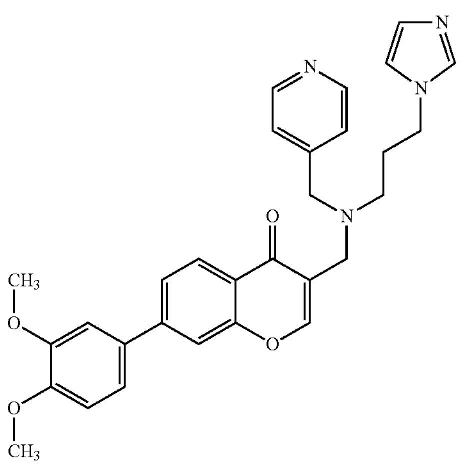 [SMILES: COc1ccc(-c2ccc3c(=O)c(CN(CCCn4ccnc4)Cc4ccncc4)coc3c2)cc1OC] | + | + |
| 39 | 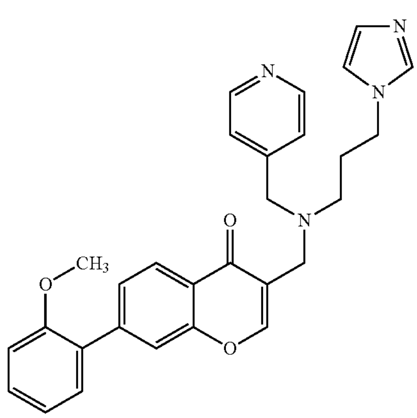 [SMILES: COc1ccccc1-c1ccc2c(=O)c(CN(CCCn3ccnc3)Cc3ccncc3)coc2c1] | +++ | ++ |

-continued

| Examples | Structure | THP1 Dual EC50 (μM) IRF | THP1 Dual EC50 (μM) NFkB |
|---|---|---|---|
| 40 | 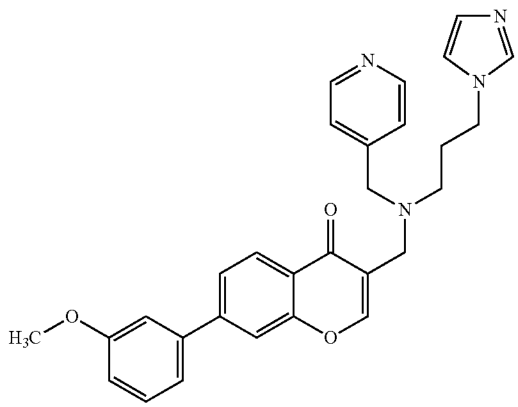 [SMILES: COc1cccc(-c2ccc3c(=O)c(CN(CCCn4ccnc4)Cc4ccncc4)coc3c2)c1] | +++ | +++ |
| 41 | 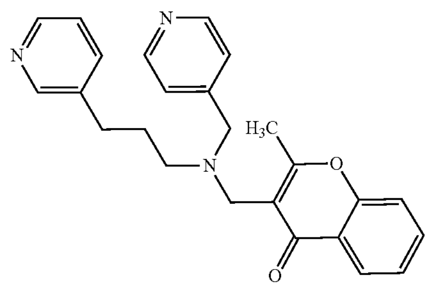 [SMILES: Cc1oc2ccccc2c(=O)c1CN(CCCc1cccnc1)Cc1ccncc1] | ++ | ++ |
| 42 | 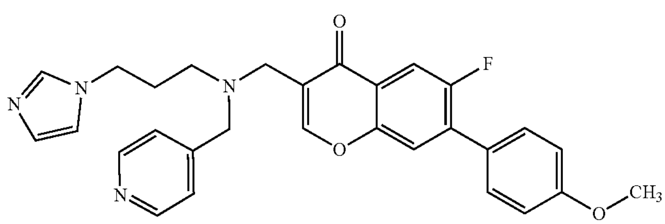 [SMILES: COc1ccc(-c2cc3occ(CN(CCCn4ccnc4)Cc4ccncc4)c(=O)c3cc2F)cc1] | +++ | +++ |
| 43 | 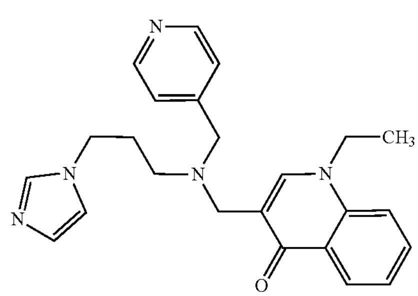 [SMILES: CCn1cc(CN(CCCn2ccnc2)Cc2ccncc2)c(=O)c2ccccc21] | + | + |
| 44 | 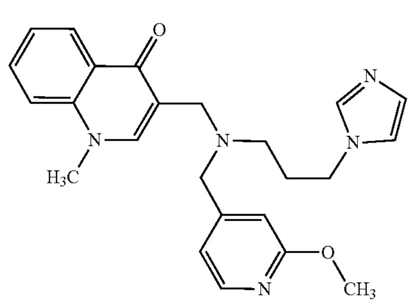 [SMILES: COc1cc(CN(CCCn2ccnc2)Cc2cn(C)c3ccccc3c2=O)ccn1] | ++ | + |

| Examples | Structure | THP1 Dual EC50 (μM) IRF | THP1 Dual EC50 (μM) NFkB |
|---|---|---|---|
| 45 | 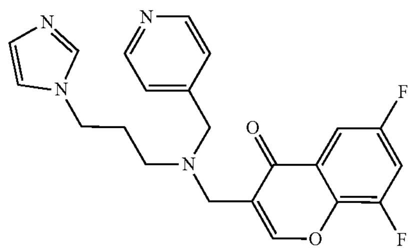 [SMILES: O=c1c(CN(CCCn2ccnc2)Cc2ccncc2)coc2c(F)cc(F)cc12] | ++ | + |
| 46 | 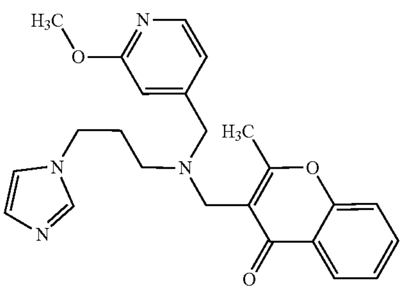 [SMILES: COc1cc(CN(CCCn2ccnc2)Cc2c(C)oc3ccccc3c2=O)ccn1] | +++ | + |
| 47 | 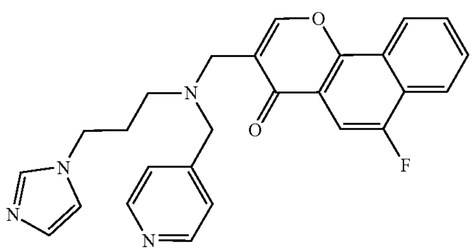 [SMILES: O=c1c(CN(CCCn2ccnc2)Cc2ccncc2)coc2c1cc(F)c1ccccc12] | +++ | +++ |
| 48 | 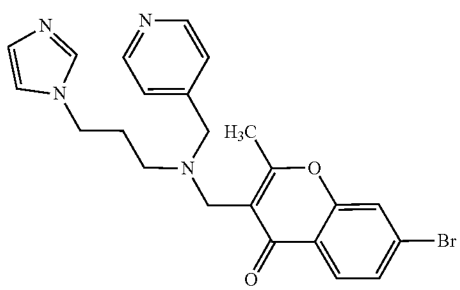 [SMILES: Cc1oc2cc(Br)ccc2c(=O)c1CN(CCCn1ccnc1)Cc1ccncc1] | +++ | +++ |
| 49 | 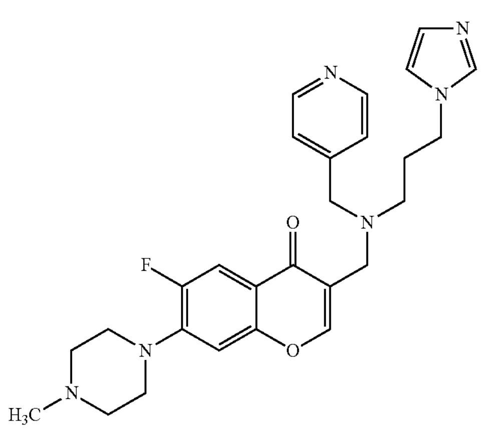 [SMILES: CN1CCN(c2cc3occ(CN(CCCn4ccnc4)Cc4ccncc4)c(=O)c3cc2F)CC1] | +++ | +++ |

-continued

| Examples | Structure | THP1 Dual EC50 (μM) IRF | THP1 Dual EC50 (μM) NFkB |
|---|---|---|---|
| 50 | 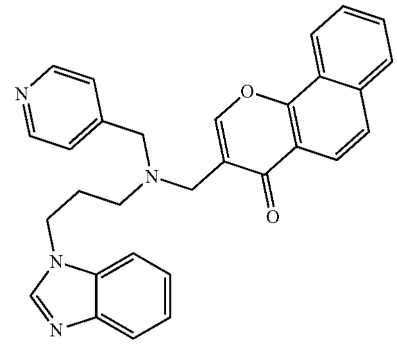 [SMILES: O=c1c(CN(CCCn2cnc3ccccc32)Cc2ccncc2)coc2c1ccc1ccccc12] | +++ | +++ |
| 51 | 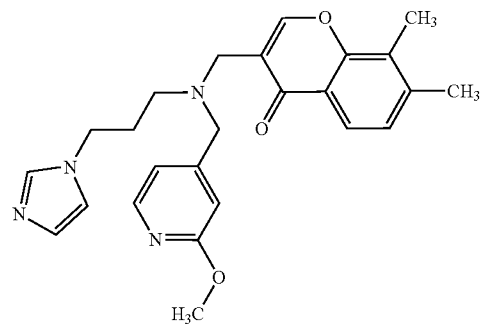 [SMILES: COc1cc(CN(CCCn2ccnc2)Cc2coc3c(C)c(C)ccc3c2=O)ccn1] | +++ | +++ |
| 52 | 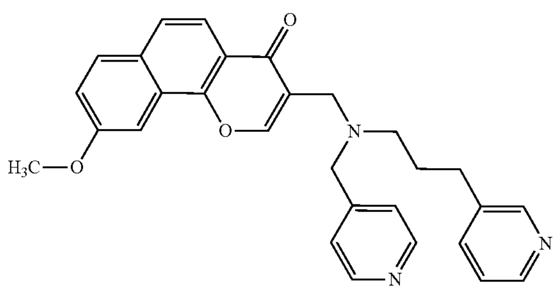 [SMILES: COc1ccc2ccc3c(=O)c(CN(CCCc4cccnc4)Cc4ccncc4)coc3c2c1] | +++ | +++ |
| 53 | 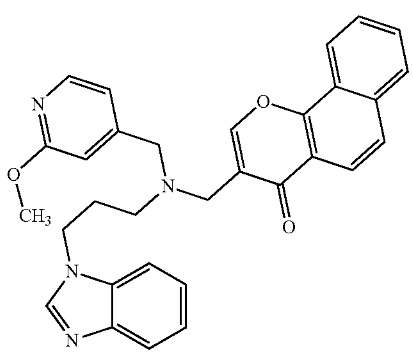 [SMILES: COc1cc(CN(CCCn2cnc3ccccc32)Cc2coc3c(ccc4ccccc43)c2=O)ccn1] | +++ | +++ |

| Examples | Structure | THP1 Dual EC50 (μM) IRF | THP1 Dual EC50 (μM) NFkB |
|---|---|---|---|
| 54 | 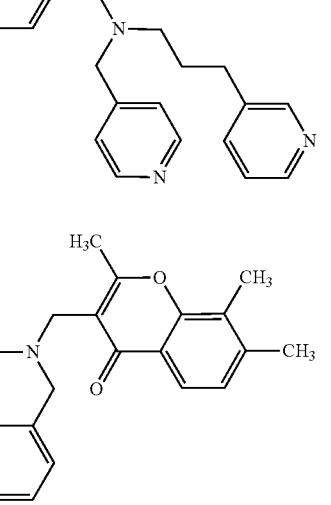 | +++ | +++ |
| 55 | 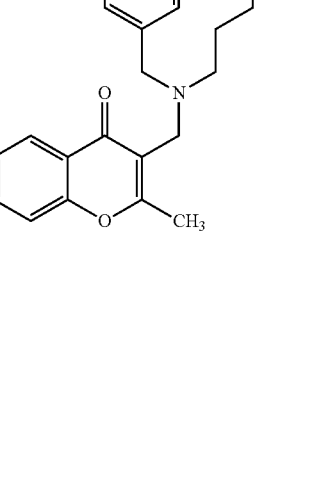 | +++ | +++ |
| 56 | 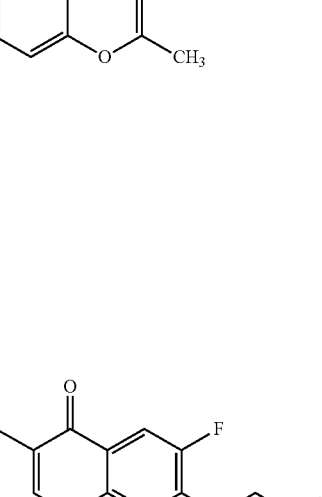 | +++ | +++ |
| 57 | 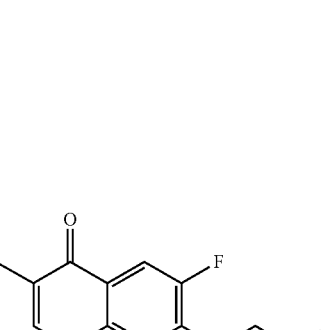 | + | + |

-continued
| Examples | Structure | THP1 Dual EC50 (µM) IRF | THP1 Dual EC50 (µM) NFkB |
|---|---|---|---|
| 58 | 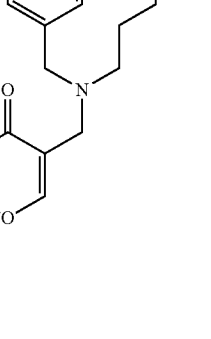 | +++ | +++ |
| 59 | 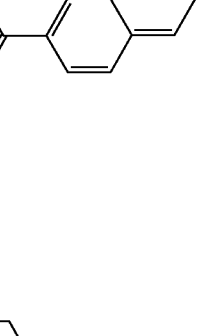 | +++ | +++ |
| 60 | 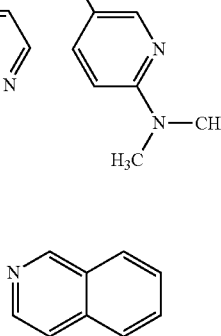 | + | + |
| 61 | 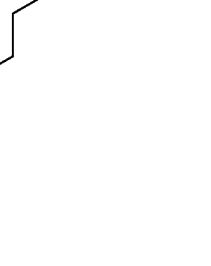 | + | + |

-continued

| Examples | Structure | THP1 Dual EC50 (μM) IRF | THP1 Dual EC50 (μM) NFkB |
|---|---|---|---|
| 62 | 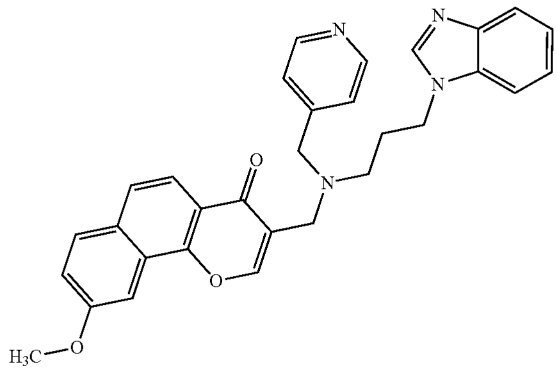 [SMILES: COc1ccc2ccc3c(=O)c(CN(CCCn4cnc5ccccc54)Cc4ccncc4)coc3c2c1] | +++ | +++ |
| 63 | 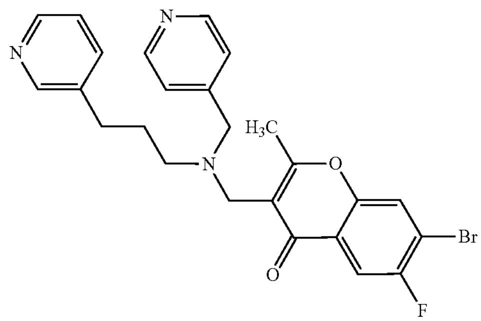 [SMILES: Cc1oc2cc(Br)c(F)cc2c(=O)c1CN(CCCc1cccnc1)Cc1ccncc1] | +++ | +++ |
| 64 | 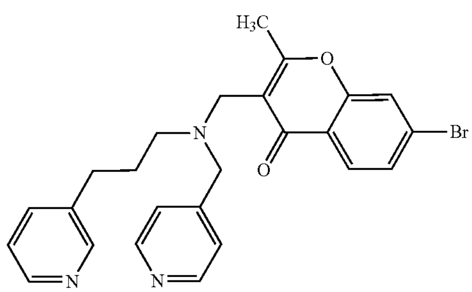 [SMILES: Cc1oc2cc(Br)ccc2c(=O)c1CN(CCCc1cccnc1)Cc1ccncc1] | +++ | +++ |
| 65 | 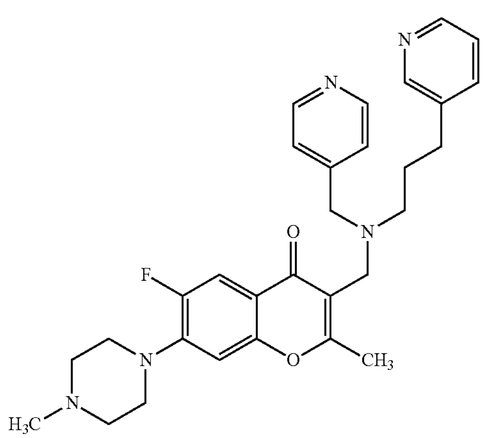 [SMILES: Cc1oc2cc(N3CCN(C)CC3)c(F)cc2c(=O)c1CN(CCCc1cccnc1)Cc1ccncc1] | +++ | +++ |

| Examples | Structure | THP1 Dual EC50 (μM) IRF | THP1 Dual EC50 (μM) NFkB |
|---|---|---|---|
| 66 | 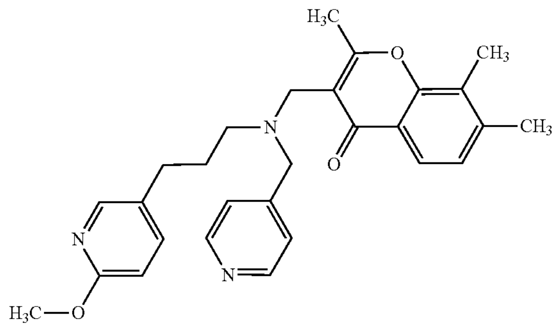 | +++ | +++ |
| 67 | 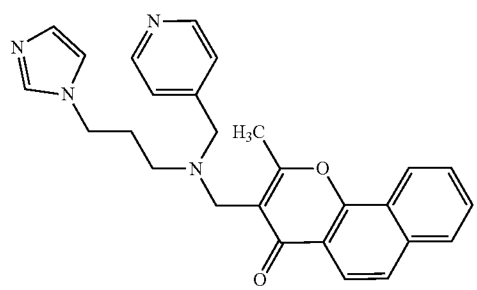 [SMILES: Cc1oc2c(ccc3ccccc32)c(=O)c1CN(CCCn1ccnc1)Cc1ccncc1] | +++ | +++ |
| 68 | 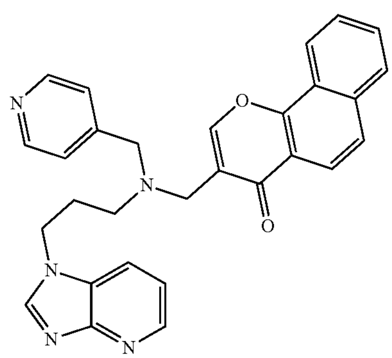 [SMILES: O=c1c(CN(CCCn2cnc3ncccc32)Cc2ccncc2)coc2c1ccc1ccccc12] | +++ | +++ |
| 69 | 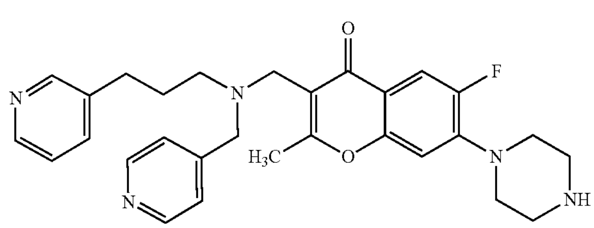 [SMILES: Cc1oc2cc(N3CCNCC3)c(F)cc2c(=O)c1CN(CCCc1cccnc1)Cc1ccncc1] | +++ | +++ |

-continued

| Examples | Structure | THP1 Dual EC50 (μM) IRF | THP1 Dual EC50 (μM) NFkB |
|---|---|---|---|
| 70 | 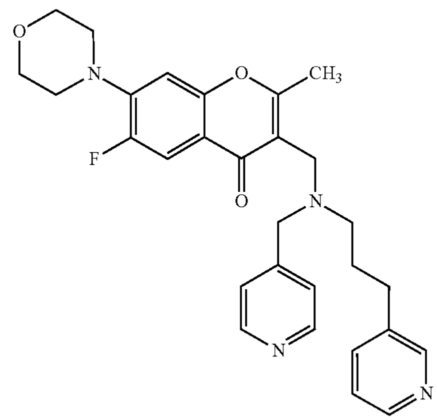 [SMILES: Cc1oc2cc(N3CCOCC3)c(F)cc2c(=O)c1CN(CCCc1cccnc1)Cc1ccncc1] | +++ | +++ |
| 71 | 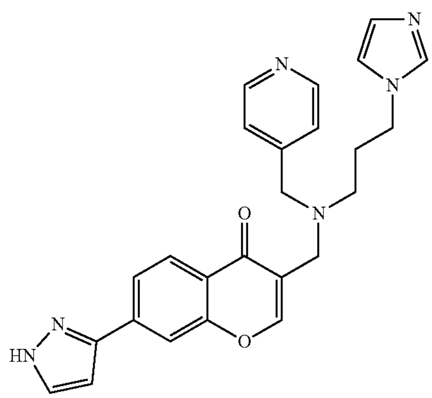 [SMILES: O=c1c(CN(CCCn2ccnc2)Cc2ccncc2)coc2cc(-c3cc[nH]n3)ccc12] | +++ | ++ |
| 72 | 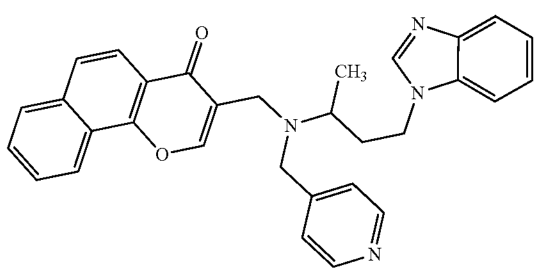 [SMILES: CC(CCn1cnc2ccccc21)N(Cc1ccncc1)Cc1coc2c(ccc3ccccc32)c1=O] | +++ | +++ |
| 73 | 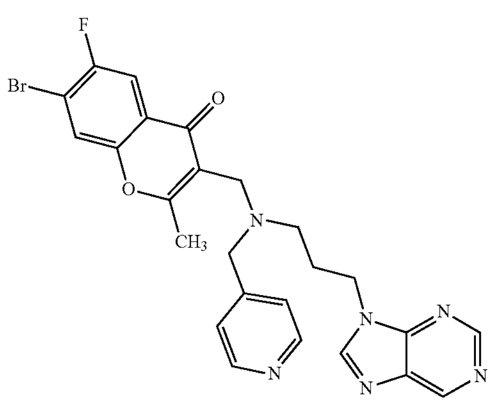 [SMILES: Cc1oc2cc(Br)c(F)cc2c(=O)c1CN(CCCn1cnc2cncnc21)Cc1ccncc1] | ++ | +++ |

-continued

| Examples | Structure | THP1 Dual EC50 (μM) IRF | THP1 Dual EC50 (μM) NFkB |
|---|---|---|---|
| 74 | 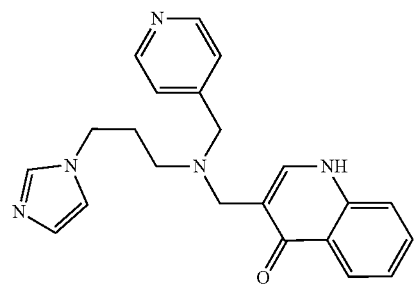 [SMILES: O=c1c(CN(CCCn2ccnc2)Cc2ccncc2)c[nH]c2ccccc12] | + | + |
| 75 | 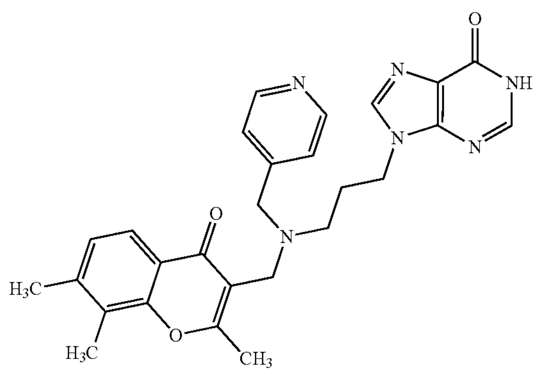 [SMILES: Cc1ccc2c(=O)c(CN(CCCn3cnc4c(=O)[nH]cnc43)Cc3ccncc3)c(C)oc2c1C] | +++ | ++ |
| 76 | 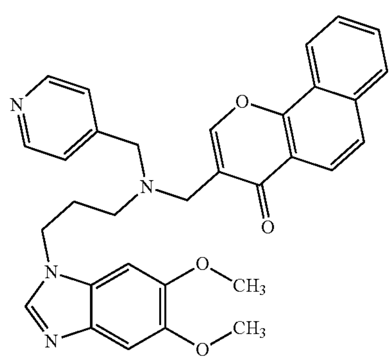 [SMILES: COc1cc2ncn(CCCN(Cc3ccncc3)Cc3coc4c(ccc5ccccc54)c3=O)c2cc1OC] | +++ | +++ |
| 77 | 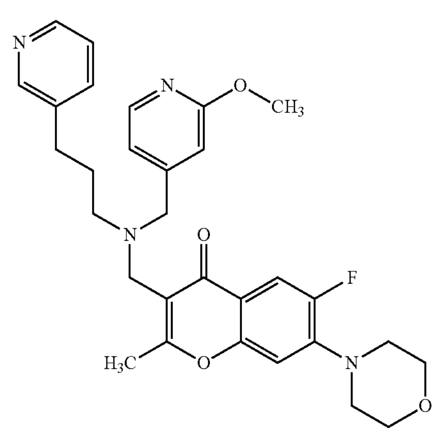 [SMILES: COc1cc(CN(CCCc2cccnc2)Cc2c(C)oc3cc(N4CCOCC4)c(F)cc3c2=O)ccn1] | +++ | +++ |

-continued

| Examples | Structure | THP1 Dual EC50 (μM) IRF | THP1 Dual EC50 (μM) NFkB |
|---|---|---|---|
| 78 | 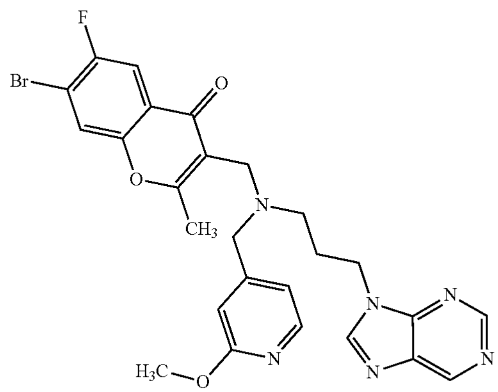 [SMILES: COc1cc(CN(CCCn2cnc3cncnc32)Cc2c(C)oc3cc(Br)c(F)cc3c2=O)ccn1] | +++ | +++ |
| 79 | 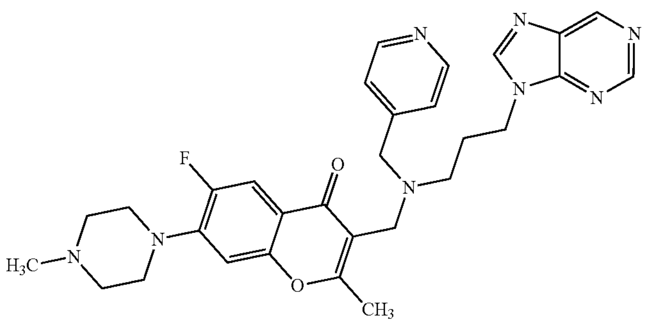 [SMILES: Cc1oc2cc(N3CCN(C)CC3)c(F)cc2c(=O)c1CN(CCCn1cnc2cncnc21)Cc1ccncc1] | +++ | +++ |
| 80 | 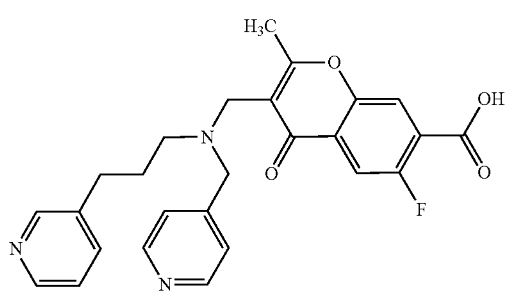 [SMILES: Cc1oc2cc(C(=O)O)c(F)cc2c(=O)c1CN(CCCc1cccnc1)Cc1ccncc1] | + | + |
| 81 | 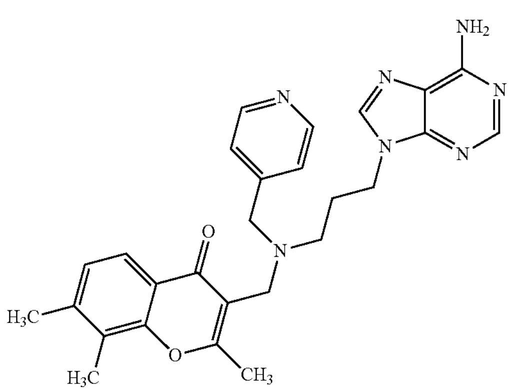 [SMILES: Cc1ccc2c(=O)c(CN(CCCn3cnc4c(N)ncnc43)Cc3ccncc3)c(C)oc2c1C] | + | ++ |

-continued

| Examples | Structure | THP1 Dual EC50 (μM) IRF | THP1 Dual EC50 (μM) NFkB |
|---|---|---|---|
| 82 | 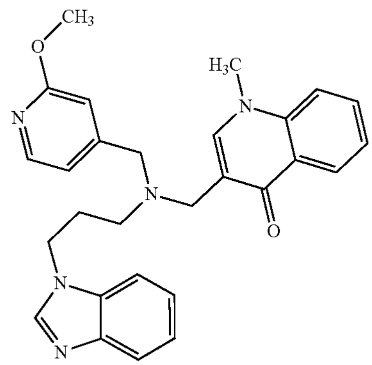 [SMILES: COc1cc(CN(CCCn2cnc3ccccc32)Cc2cn(C)c3ccccc3c2=O)ccn1] | +++ | +++ |
| 83 | 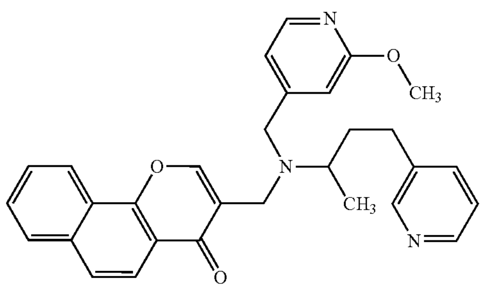 [SMILES: COc1cc(CN(Cc2coc3c(ccc4ccccc43)c2=O)C(C)CCc2cccnc2)ccn1] | +++ | +++ |
| 84 | 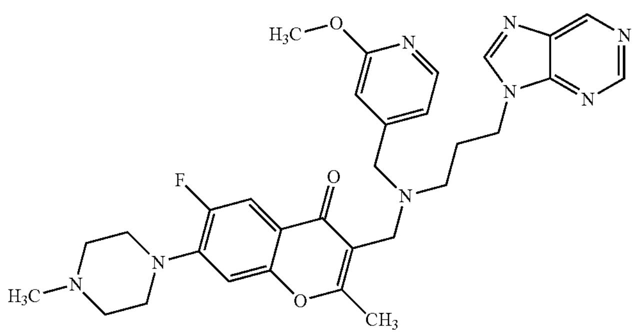 [SMILES: COc1cc(CN(CCCn2cnc3cncnc32)Cc2c(C)oc3cc(N4CCN(C)CC4)c(F)cc3c2=O)ccn1] | ++ | +++ |
| 85 | 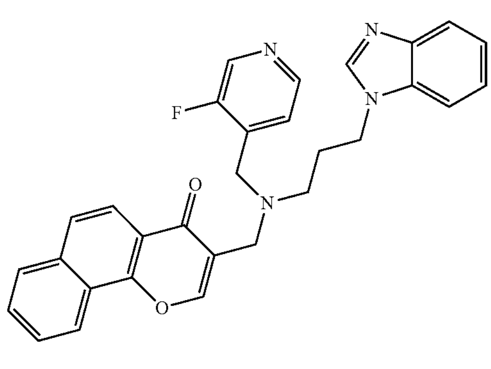 [SMILES: O=c1c(CN(CCCn2cnc3ccccc32)Cc2ccncc2F)coc2c1ccc1ccccc12] | + | + |

| Examples | Structure | THP1 Dual EC50 (μM) IRF | THP1 Dual EC50 (μM) NFkB |
|---|---|---|---|
| 86 | 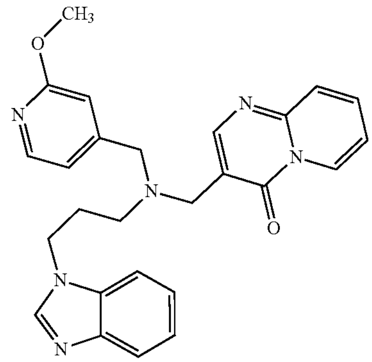 [SMILES: COc1cc(CN(CCCn2cnc3ccccc32)Cc2cnc3ccccn3c2=O)ccn1] | + | + |
| 87 | 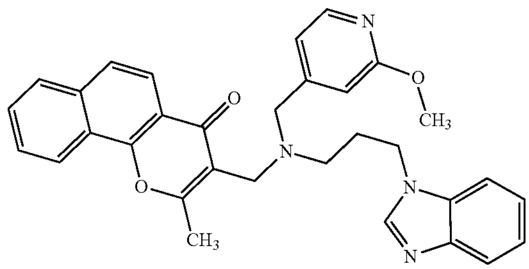 [SMILES: COc1cc(CN(CCCn2cnc3ccccc32)Cc2c(C)oc3c(ccc4ccccc43)c2=O)ccn1] | + | + |
| 88 | 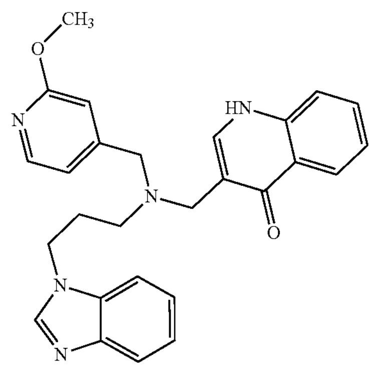 [SMILES: COc1cc(CN(CCCn2cnc3ccccc32)Cc2c[nH]c3ccccc3c2=O)ccn1] | + | + |
| 89 | 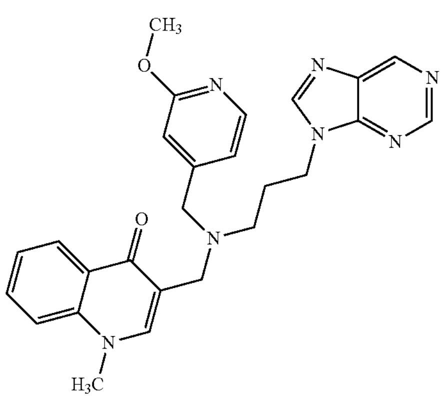 [SMILES: COc1cc(CN(CCCn2cnc3cncnc32)Cc2cn(C)c3ccccc3c2=O)ccn1] | +++ | +++ |

-continued
| Examples | Structure | THP1 Dual EC50 (μM) IRF | THP1 Dual EC50 (μM) NFkB |
|---|---|---|---|
| 90 | 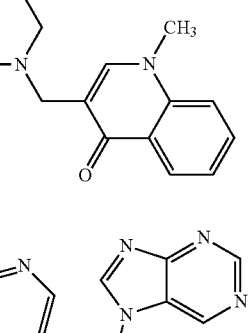 | +++ | ++ |
| 91 | 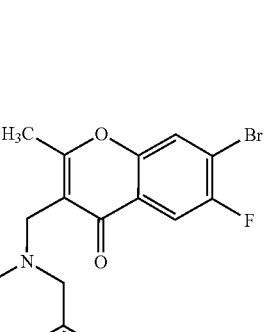 | + | + |
| 92 | 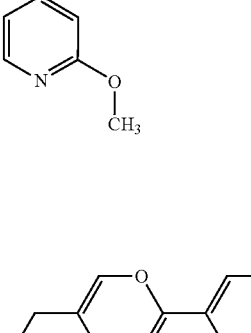 | + | + |
| 93 | 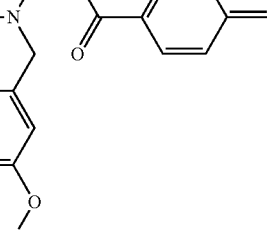 | + | + |

| Examples | Structure | THP1 Dual EC50 (μM) IRF | THP1 Dual EC50 (μM) NFkB |
|---|---|---|---|
| 94 | 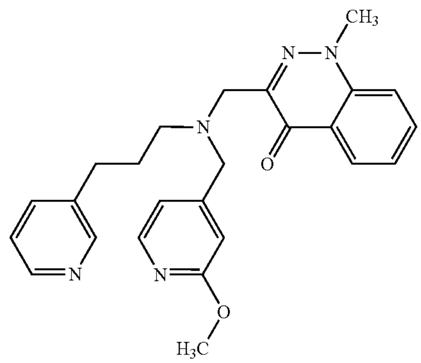 [SMILES: COc1cc(CN(CCCc2cccnc2)Cc2nn(C)c3ccccc3c2=O)ccn1] | +++ | + |
| 95 | 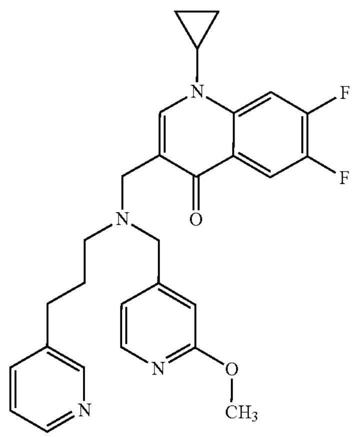 [SMILES: COc1cc(CN(CCCc2cccnc2)Cc2cn(C3CC3)c3cc(F)c(F)cc3c2=O)ccn1] | +++ | ++ |
| 96 | 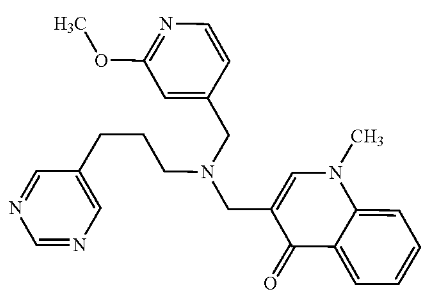 [SMILES: COc1cc(CN(CCCc2cncnc2)Cc2cn(C)c3ccccc3c2=O)ccn1] | +++ | +++ |
| 97 | 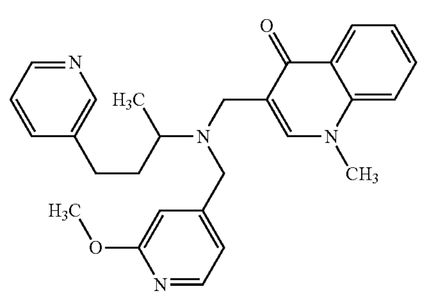 [SMILES: COc1cc(CN(Cc2cn(C)c3ccccc3c2=O)C(C)CCc2cccnc2)ccn1] | +++ | +++ |

-continued

| Examples | Structure | THP1 Dual EC50 (μM) IRF | THP1 Dual EC50 (μM) NFkB |
|---|---|---|---|
| 98 | 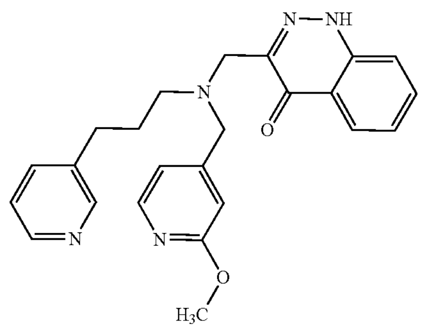 [SMILES: COc1cc(CN(CCCc2cccnc2)Cc2n[nH]c3ccccc3c2=O)ccn1] | ++ | + |
| 99 | 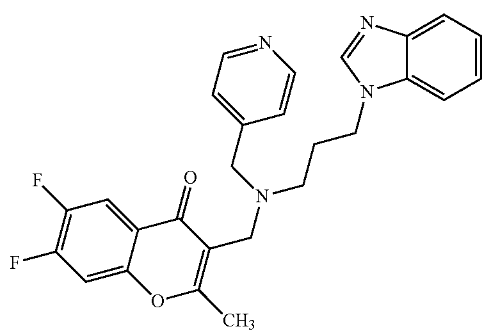 [SMILES: Cc1oc2cc(F)c(F)cc2c(=O)c1CN(CCCn1cnc2ccccc21)Cc1ccncc1] | +++ | +++ |
| 100 | 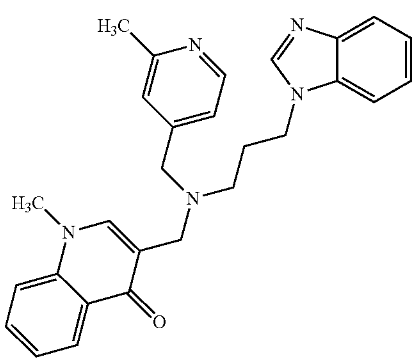 [SMILES: Cc1cc(CN(CCCn2cnc3ccccc32)Cc2cn(C)c3ccccc3c2=O)ccn1] | +++ | +++ |
| 101 | 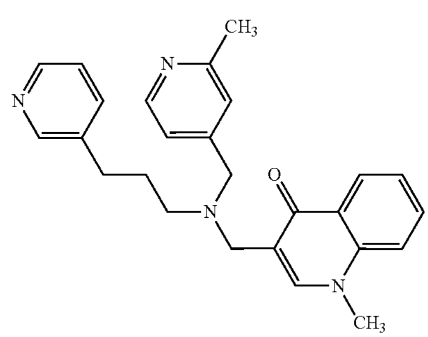 [SMILES: Cc1cc(CN(CCCc2cccnc2)Cc2cn(C)c3ccccc3c2=O)ccn1] | +++ | ++ |

-continued

| Examples | Structure | THP1 Dual EC50 (μM) IRF | THP1 Dual EC50 (μM) NFkB |
|---|---|---|---|
| 102 | 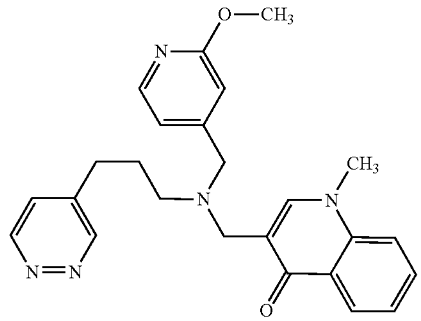 [SMILES: COc1cc(CN(CCCc2ccnnc2)Cc2cn(C)c3ccccc3c2=O)ccn1] | + | + |
| 103 | 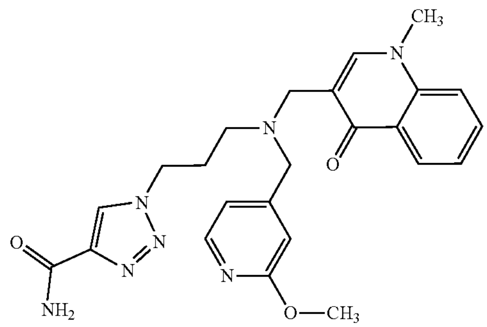 [SMILES: COc1cc(CN(CCCn2cc(C(N)=O)nn2)Cc2cn(C)c3ccccc3c2=O)ccn1] | + | + |

In particular, the present invention relates to the following further items.

1. A compound of formula (I)

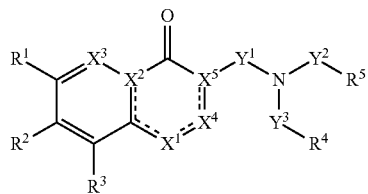

or a salt, stereoisomer, tautomer, or N-oxide thereof, wherein the dashed lines in the 6-membered ring that contains the =O substituent denote the presence of one or two additional bonds, so that one or two double bonds are formed, wherein, in case of two double bonds, between each double bond a single bond must be present;

and wherein $X^1$ is O, S, S(=O), S(=O)$_2$, N, or NR$^N$;

$X^2$ is C, CH, or N;

$X^3$ is CR$^A$, or N;

$X^4$ is CR$^A$, CR$^A$R$^B$, N, or NR$^N$;

$X^5$ is C, CH, or N;

$Y^1$ is S(=O)$_2$, or C$_1$-C$_2$-alkylene, which is unsubstituted or substituted with one or more, same or different substituents R$^Z$;

$Y^2$ is absent, S(=O)$_2$, S(=O)$_2$—C$_1$-C$_4$-alkylene, S(=O)$_2$-arylene, or C$_1$-C$_4$-alkylene, wherein the carbon atoms are in each case unsubstituted or substituted with one or more, same or different substituents R$^Z$;

$Y^3$ is absent, S(=O)$_2$, or C$_1$-alkylene, which is unsubstituted or substituted with one or more, same or different substituents R$^Z$;

$R^1$, $R^2$ and $R^3$ are independently H, OH, CN, halogen, C$_1$-C$_4$-alkyl, C$_1$-C$_4$-alkoxy, aryloxy, benzyloxy, C(=O)R$^E$, NR$^F$C(=O)R$^E$, or 5- or 6-membered saturated, partially or fully unsaturated, or aromatic carbocyclyl, carbocyclyl-C$_1$-C$_2$-alkyl, heterocyclyl, or heterocyclyl-C1-C$_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents R$^X$;

or $R^1$ and $R^2$ or $R^2$ and $R^3$ together with the carbon atoms to which they are bonded form a 5- or 6-membered saturated, partially or fully unsaturated, or aromatic carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents R$^X$;

$R^4$ is a 5- or 6-membered aromatic carbocyclic or heterocyclic ring, or a 9- or 10-membered aromatic carbobycyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^X$;

$R^5$ is a 5- or 6-membered saturated, partially or fully unsaturated, or aromatic carbocyclic or heterocyclic ring, or a 9- or 10-membered saturated, partially or fully unsaturated, or aromatic carbobycyclic or heterobicyclic ring, wherein the heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^Y$;

and wherein $R^N$ is H, $C_1$-$C_6$-alkyl or 3- to 6-membered carbocyclyl or heterocyclyl, wherein the aforementioned heterocyclic ring comprises one or more, same or different heteroatoms selected from O, N or S, wherein said N-atoms are independently oxidized or non-oxidized;

$R^A$ is H, halogen, CN, OH, $C_1$-$C_3$-alkyl, $C_1$-$C_3$-alkoxy, or 3- to 6-membered saturated, partially or fully unsaturated, or aromatic carbocyclyl, or heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^B$ is H, halogen, CN, OH, $C_1$-$C_3$-alkyl, or $C_1$-$C_3$-alkoxy; or $R^A$ and $R^B$ together with the carbon atom to which they are bonded form a 3- to 5-membered saturated, partially or fully unsaturated, or aromatic carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^C$ and $R^D$ are independently H, or $C_1$-$C_2$-alkyl; or $R^C$ and $R^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^E$ is H, $C_1$-$C_2$-alkyl, phenyl, benzyl, $OR^G$, or $NR^H R^I$;

$R^F$ is H, $C_1$-$C_2$-alkyl, $C_3$-$C_6$-cycloalkyl, phenyl, or benzyl;

$R^G$ is H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized; or $R^H$ and $R^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^X$ is halogen, CN, $C_1$-$C_2$-alkyl, or $C_1$-$C_2$-alkoxy;

$R^Y$ is halogen, CN, OH, $C_1$-$C_2$-alkyl, $C_3$-$C_6$-cycloalkyl, $C_1$-$C_2$-alkoxy, $NR^C R^D$, $S(=O)_2 NR^C R^D$, $C(=O)R^E$, or 5- or 6-membered saturated, partially or fully unsaturated, or aromatic carbocyclyl, carbocyclyl-$C_1$-$C_2$-alkyl, heterocyclyl, and heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$; or two $R^Y$ form =O;

$R^Z$ is halogen, CN, $C_1$-$C_3$-alkyl, or $C_3$-$C_6$-cycloalkyl; or two $R^Z$ together with the atom to which they are bonded form a 3- to 5-membered saturated carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

2. The compound according to item 1, wherein the compound is not:

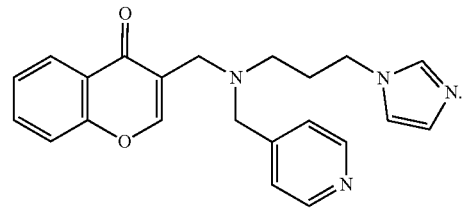 [SMILES: O=c1c(CN(CCCn2ccnc2)Cc2ccncc2)coc2ccccc12]

3. The compound according to item 1 or 2, wherein said compound is a compound according to formula (Ia*):

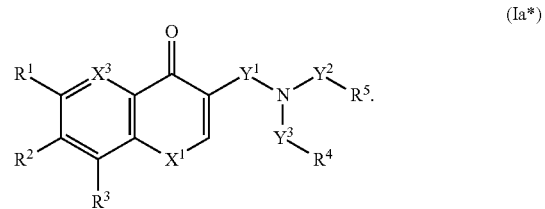

(Ia*)

4. The compound according to any one of items 1 to 3, wherein
X¹ is O; and
X³ is CH.

5. The compound according to any one of items 1 to 4, wherein
Y¹ is C₁-alkylene, which is unsubstituted or substituted with one or more, same or different substituents R$^Z$.

6. The compound according to any one of items 1 to 5, wherein
Y² is absent, or C₁-C₄-alkylene, preferably C₂- or C₃-alkylene, wherein the carbon atoms are in each case unsubstituted or substituted with one or more, same or different substituents R$^Z$.

7. The compound according to any one of items 1 to 6, wherein
Y³ is C₁-alkylene, which is unsubstituted or substituted with one or more, same or different substituents R$^Z$.

8. The compound according to any one of items 1 to 7, wherein
R¹ is H or halogen, preferably H or F.

9. The compound according to any one of items 1 to 8, wherein
R² and R³ are independently H, halogen, CN, OH, C₁-C₂-alkyl, C₁-C₂-alkoxy, benzyloxy, or 6-membered saturated heterocyclyl, wherein the aforementioned heterocyclic ring comprises one or more nitrogen atoms, wherein said N-atoms are independently oxidized or non-oxidized, and wherein each substitutable carbon or heteroatom in the aforementioned groups is independently unsubstituted or substituted with one or more, same or different substituents R$^X$;
or
R² and R³ together with the carbon atoms to which they are bonded form 6-membered aromatic carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents R$^X$.

10. The compound according to any one of items 1 to 8, wherein
R⁴ is pyridinyl, wherein each substitutable carbon or heteroatom in the cyclic ring is independently unsubstituted or substituted with one or more, same or different substituents R$^X$.

11. The compound according to any one of items 1 to 10, wherein
R⁵ is a 5- or 6-membered saturated, partially or fully unsaturated, or aromatic heterocyclic ring, or a 9- or 10-membered saturated, partially or fully unsaturated, or aromatic heterobicyclic ring, wherein the heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents R$^Y$.

12. A compound according to any one of items 1 to 11, wherein the compound of formula (I) is a compound selected from the group consisting of:
3-({[3-(1H-imidazol-1-yl)propyl](pyridin-4-ylmethyl)amino}methyl)-7,8-dimethyl-4H-chromen-4-one;
3-({[3-(1H-imidazol-1-yl)propyl](pyridin-4-ylmethyl)amino}methyl)-4H-benzo[h]chromen-4-one;
3-({[3-(1H-imidazol-1-yl)propyl](pyridin-4-ylmethyl)amino}methyl)-7-methoxy-4H-chromen-4-one;
7-bromo-3-({[3-(1H-imidazol-1-yl)propyl](pyridin-4ylmethyl)amino}methyl)-4H-chromen-4-one;
3-({[3-(1H-imidazol-1-yl)propyl](pyridin-4-ylmethyl)amino}methyl)-7-(4-methylpiperazin-1-yl)-4H-chromen-4-one;
7-(benzyloxy)-3-({[3-(1H-imidazol-1-yl)propyl](pyridin-4-ylmethyl)amino}methyl)-4H-chromen-4-one;
3-({[3-(1H-1,3-benzodiazol-1-yl)propyl](pyridin-4-ylmethyl)amino}methyl)-4H-chromen-4-one;
3-({[3-(pyridin-3-yl)propyl][(pyridin-4-yl)methyl]amino}methyl)-4H-chromen-4-one;
3-({[3-(1H-imidazol-1-yl)propyl](pyridin-4-ylmethyl)amino}methyl)-4H,7H,8H,9H,10H-cyclohexa[h]chromen-4-one;
3-({[(pyridin-4-yl)methyl][3-(pyridin-4-yl)propyl]amino}methyl)-4H-chromen-4-one;
3-({[3-(pyridin-3-yl)propyl](pyridin-4-ylmethyl)amino}methyl)-4H-benzo[h]chromen-4-one;
6-fluoro-3-({[3-(1H-imidazol-1-yl)propyl][(pyridin-4-yl)methyl]amino}methyl)-4H-chromen-4-one; and
3-({[3-(1H-imidazol-1-yl)propyl][(2-methoxypyridin-4-yl)methyl]amino}methyl)-4H-benzo[h]chromen-4-one.

13. A pharmaceutical composition comprising a pharmaceutically effective amount of the compound according to any one of items 1 to 12 and optionally a pharmaceutically acceptable carrier, diluent or excipient.

14. A compound according to any one of items 1 to 12 or a pharmaceutical composition according to item 13 for use in medicine.

15. A compound according to any one of items 1 to 12 or a pharmaceutical composition according to item 13 for use in the treatment of a disease selected from the group consisting of cancer, pre-cancerous syndromes, and infectious diseases; or for use in an immunogenic composition or as vaccine adjuvant.

16. A compound according to any one of items 1 to 12 or a pharmaceutical composition according to item 13 for use in the treatment of a disease selected from the group consisting of inflammatory diseases, allergic diseases, and autoimmune diseases.

The invention claimed is:
1. A compound of formula (I)

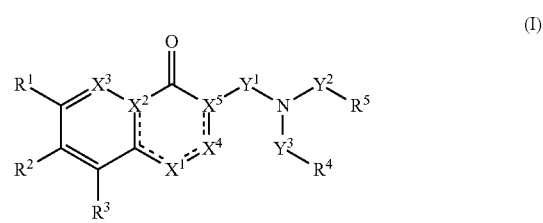

or a salt, stereoisomer, tautomer, or N-oxide thereof, wherein
the dashed lines in the 6-membered ring that contains the =O substituent denote the presence of one or two additional bonds, so that one or two double bonds are formed, wherein, in case of two double bonds, between each double bond a single bond must be present;
and wherein $X^1$ is O, S, S(=O), S(=O)$_2$, N, or NR$^N$;

$X^2$ is C, CH, or N;

$X^3$ is CR$^A$, or N;

$X^4$ is CR$^A$, CR$^A$R$^B$, N, or NR$^N$;

$X^5$ is C, CH, or N;

$Y^1$ is S(=O)$_2$, or $C_1$-$C_2$-alkylene, which is unsubstituted or substituted with one or more, same or different substituents R$^Z$;

$Y^2$ is absent or $C_3$-$C_4$ alkylene, wherein the carbon atoms are in each case unsubstituted or substituted with one or more, same or different substituents R$^Z$;

$Y^3$ is absent, S(=O)$_2$, or $C_1$-alkylene, which is unsubstituted or substituted with one or more, same or different substituents R$^{Z1}$;

$R^1$, $R^2$ and $R^3$ are independently H, OH, CN, halogen, $C_1$-$C_4$-alkyl, $C_1$-$C_4$-alkoxy, aryloxy, benzyloxy, C(=O)R$^E$, NR$^F$C(=O)R$^E$, or 5- or 6-membered saturated, partially or fully unsaturated, or aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents R$^X$;

or $R^1$ and $R^2$ or $R^2$ and $R^3$ together with the carbon atoms to which they are bonded form a 5- or 6-membered saturated, partially or fully unsaturated, or aromatic carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents R$^X$;

$R^4$ is pyridinyl, wherein each substitutable carbon or heteroatom in the cyclic ring is independently unsubstituted or substituted with one or more, same or different substituents R$^X$;

$R^5$ is a 5- or 6-membered saturated, partially or fully unsaturated, or aromatic carbocyclic or heterocyclic ring, or a 9- or 10-membered saturated, partially or fully unsaturated, or aromatic carbobicyclic or heterobicyclic ring, wherein the heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents R$^Y$;

and wherein

R$^N$ is H, $C_1$-$C_6$-alkyl or 3-to 6-membered carbocyclyl or heterocyclyl, wherein the aforementioned heterocyclic ring comprises one or more, same or different heteroatoms selected from O, N or S, wherein said N-atoms are independently oxidized or non-oxidized;

R$^A$ is H, halogen, CN, OH, $C_1$-$C_3$-alkyl, $C_1$-$C_3$-alkoxy, or 3-to 6-membered saturated, partially or fully unsaturated, or aromatic carbocyclyl, or heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents R$^X$;

R$^B$ is H, halogen, CN, OH, $C_1$-$C_3$-alkyl, or $C_1$-$C_3$-alkoxy; or

R$^A$ and R$^B$ together with the carbon atom to which they are bonded form a 3-to 5-membered saturated, partially or fully unsaturated, or aromatic carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents R$^X$;

R$^C$ and R$^D$ are independently H, or $C_1$-$C_2$-alkyl; or

R$^C$ and R$^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents R$^X$;

R$^E$ is H, $C_1$-$C_2$-alkyl, phenyl, benzyl, OR$^G$, or NR$^H$R$^I$;

R$^F$ is H, $C_1$-$C_2$-alkyl, $C_3$-$C_6$-cycloalkyl, phenyl, or benzyl;

R$^G$ is H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized;

R$^H$ and R$^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized; or R$^H$ and R$^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents R$^X$;

R$^X$ is halogen, CN, $C_1$-$C_2$-alkyl, or $C_1$-$C_2$-alkoxy;

R$^Y$ is halogen, CN, OH, $C_1$-$C_2$-alkyl, $C_3$-$C_6$-cycloalkyl, $C_1$-$C_2$-alkoxy, NR$^C$R$^D$, S(=O)$_2$NR$^C$R$^D$, C(=O)R$^E$, or 5- or 6-membered saturated, partially or fully unsaturated, or aromatic carbocyclyl, carbocyclyl-$C_1$-$C_2$-alkyl, heterocyclyl, and heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$; or two $R^Y$ form =O;

$R^Z$ is halogen, CN, $C_1$-$C_3$-alkyl, or $C_3$-$C_6$-cycloalkyl; or two RZ together with the atom to which they are bonded form a 3-to 5-membered saturated carbocyclic or heterocyclic ring, wherein the heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$; and wherein the compound is not

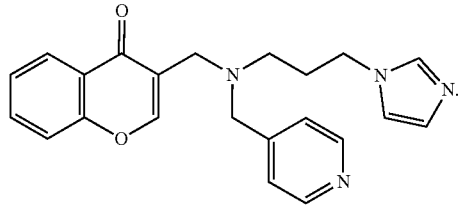 [SMILES: O=c1c(CN(CCCn2ccnc2)Cc2ccncc2)coc2ccccc12]

2. The compound according to claim 1, or a salt, stereoisomer, tautomer, or N-oxide thereof, wherein said compound is a compound according to formula (Ia*):

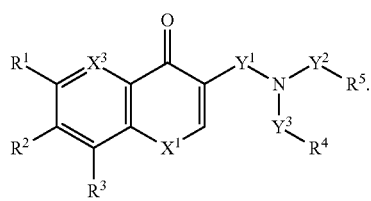

(Ia*)

3. The compound according to claim 1, or a salt, stereoisomer, tautomer, or N-oxide thereof, wherein
$X^1$ is O; and
$X^3$ is CH.

4. The compound according to claim 1, or a salt, stereoisomer, tautomer, or N-oxide thereof, wherein
$Y^1$ is $C_1$-alkylene, which is unsubstituted or substituted with one or more, same or different substituents $R^Z$.

5. The compound according to claim 1, or a salt, stereoisomer, tautomer, or N-oxide thereof, wherein
$Y^3$ is $C_1$-alkylene, which is unsubstituted or substituted with one or more, same or different substituents $R^Z$.

6. The compound according to claim 1, or a salt, stereoisomer, tautomer, or N-oxide thereof, wherein
$R^1$ is H or halogen.

7. The compound according to claim 1, wherein
$R^2$ and $R^3$ are independently H, halogen, CN, OH, $C_1$-$C_2$-alkyl, $C_1$-$C_2$-alkoxy, benzyloxy, or 6-membered saturated heterocyclyl, wherein the aforementioned heterocyclic ring comprises one or more nitrogen atoms, wherein said N-atoms are independently oxidized or non-oxidized, and wherein each substitutable carbon or heteroatom in the aforementioned groups is independently unsubstituted or substituted with one or more, same or different substituents $R^X$;

or $R^2$ and $R^3$ together with the carbon atoms to which they are bonded form 6-membered aromatic carbocyclic or heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^X$.

8. The compound according to claim 1, or a salt, stereoisomer, tautomer, or N-oxide thereof, wherein
$R^5$ is a 5- or 6-membered saturated, partially or fully unsaturated, or aromatic heterocyclic ring, or a 9- or 10-membered saturated, partially or fully unsaturated, or aromatic heterobicyclic ring, wherein the heterocyclic or heterobicyclic ring comprises one or more, same or different heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents $R^Y$.

9. A compound according to claim 1, wherein the compound of formula (I) is a compound selected from the group consisting of:

3-({[3-(1H-imidazol-1-yl)propyl](pyridin-4-ylmethyl) amino}methyl)-7,8-dimethyl-4H-chromen-4-one;

3-({[3-(1H-imidazol-1-yl)propyl](pyridin-4-ylmethyl) amino}methyl)-4H-benzo[h]chromen-4-one;

3-({[3-(1H-imidazol-1-yl)propyl](pyridin-4-ylmethyl) amino}methyl)-7-methoxy-4H-chromen-4-one;

7-bromo-3-({[3-(1H-imidazol-1-yl)propyl](pyridin-4yl-methyl)amino}methyl)-4H-chromen-4-one;

3-({[3-(1H-imidazol-1-yl)propyl](pyridin-4-ylmethyl) amino}methyl)-7-(4-methylpiperazin-1-yl) 4H-chromen-4-one;

7-(benzyloxy)-3-({[3-(1H-imidazol-1-yl)propyl](pyridin-4-ylmethyl)amino}methyl)-4H-chromen-4-one;

3-({[3-(1H-1,3-benzodiazol-1-yl)propyl](pyridin-4-ylmethyl)amino}methyl)-4H-chromen-4-one;

3-({[3-(pyridin-3-yl)propyl][(pyridin-4-yl)methyl] amino}methyl)-4H-chromen-4-one;

3-({[3-(1H-imidazol-1-yl)propyl](pyridin-4-ylmethyl) amino}methyl)-4H,7H,8H,9H,10H-cyclohexa [h]chromen-4-one;

3-({[(pyridin-4-yl)methyl][3-(pyridin-4-yl)propyl] amino}methyl)-4H-chromen-4-one;

3-({[3-(pyridin-3-yl)propyl](pyridin-4-ylmethyl) amino}methyl)-4H-benzo[h]chromen-4-one;

6-fluoro-3-({[3-(1H-imidazol-1-yl)propyl][(pyridin-4-yl) methyl]amino}methyl)-4H-chromen-4-one;

3-({[3-(1H-imidazol-1-yl)propyl][(2-methoxypyridin-4-yl)methyl]amino}methyl)-4H-benzo[h]chromen-4-one;

6-fluoro-3-({[3-(1H-imidazol-1-yl)propyl][(pyridin-4-yl) methyl]amino}methyl)-4H benzo[h]chromen-4-one;

7-bromo-3-({[3-(1H-imidazol-1-yl)propyl][(pyridin-4-yl)methyl]amino}methyl)-2-methyl-4H-chromen-4-one;

6-fluoro-3-({[3-(1H-imidazol-1-yl)propyl][(pyridin-4-yl)methyl]amino}methyl)-7-(4-methylpiperazin-1-yl)-4H-chromen-4-one;

3-({[3-(1H-1,3-benzodiazol-1-yl)propyl][(pyridin-4-yl)methyl]amino}methyl)-4H-benzo[h]chromen-4-one;

3-({[3-(1H-imidazol-1-yl)propyl][(2-methoxypyridin-4-yl)methyl]amino}methyl)-7,8-dimethyl-4H-chromen-4-one;

9-methoxy-3-({[3-(pyridin-3-yl)propyl][(pyridin-4-yl)methyl]amino}methyl)-4H-benzo[h]chromen-4-one;

3-({[3-(1H-1,3-benzodiazol-1-yl)propyl][(2-methoxypyridin-4-yl)methyl]amino}methyl)-4H-benzo[h]chromen-4-one;

6-fluoro-3-({[3-(pyridin-3-yl)propyl][(pyridin-4-yl)methyl]amino}methyl)-4H-benzo[h]chromen-4-one;

2,7,8-trimethyl-3-({[3-(pyridin-3-yl)propyl][(pyridin-4-yl)methyl]amino}methyl)-4H-chromen-4-one;

6-fluoro-7-(4-methylpiperazin-1-yl)-3-({[3-(pyridin-3-yl)propyl](pyridin-4-ylmethyl)amino}methyl)-4H-chromen-4-one;

3-({[3-(1H-1,3-benzodiazol-1-yl)propyl][(pyridin-4-yl)methyl]amino}methyl)-9-methoxy-4H-benzo[h]chromen-4-one;

7-bromo-6-fluoro-2-methyl-3-({[3-(pyridin-3-yl)propyl][(pyridin-4-yl)methyl]amino}methyl)-4H-chromen-4-one;

7-bromo-2-methyl-3-({[3-(pyridin-3-yl)propyl](pyridin-4-ylmethyl)amino}methyl)-4H-chromen-4-one;

6-fluoro-2-methyl-7-(4-methylpiperazin-1-yl)-3-({[3-(pyridin-3-yl)propyl][(pyridin-4-yl)methyl]amino}methyl)-4H-chromen-4-one;

3-{[(3-{1H-imidazo[4,5-b]pyridin-1-yl}propyl)(pyridin-4-ylmethyl)aminomethyl]-4H-benzo[h]chromen-4-one;

6-fluoro-2-methyl-7-(piperazin-1-yl)-3-({[3-(pyridin-3-yl)propyl][(pyridin-4-yl)methyl]amino}methyl)-4H-chromen-4-one;

6-fluoro-2-methyl-7-(morpholin-4-yl)-3-({[3-(pyridin-3-yl)propyl][(pyridin-4-yl)methyl]amino}methyl)-4H-chromen-4-one;

3-({[4-(1H-1,3-benzodiazol-1-yl)butan-2-yl](pyridin-4-ylmethyl)amino}methyl)-4H-benzo[h]chromen-4-one;

7-bromo-6-fluoro-2-methyl-3-({[3-(9H-purin-9-yl)propyl][(pyridin-4-yl)methyl]amino}methyl)-4H-chromen-4-one;

6-fluoro-3-({[(2-methoxypyridin-4-yl)methyl][3-(pyridin-3-yl)propyl]amino}methyl)-2-methyl-7-(morpholin-4-yl)-4H-chromen-4-one;

7-bromo-6-fluoro-3-({[(2-methoxypyridin-4-yl)methyl][3-(9H-purin-9-yl)propyl]amino}methyl)-2-methyl-4HI-chromen-4-one;

6-fluoro-2-methyl-7-(4-methylpiperazin-1-yl)-3-({[3-(9H-purin-9-yl)propyl][(pyridin-4-yl)methyl]amino}methyl)-4H-chromen-4-one;

3-({[3-(1H-1,3-benzodiazol-1-yl)propyl][(2-methoxypyridin-4-yl)methyl]amino}methyl)-1-methyl-1,4-dihydroquinolin-4-one;

3-({[(2-methoxypyridin-4-yl)methyl][4-(pyridin-3-yl)butan-2-yl]amino}methyl)-4H-benzo[h]chromen-4-one;

3-({[(2-methoxypyridin-4-yl)methyl][3-(9H-purin-9-yl)propyl]amino}methyl)-1-methyl-1,4-dihydroquinolin-4-one;

3-({[(2-methoxypyridin-4-yl)methyl][4-(pyridin-3-yl)butan-2-yl]amino}methyl)-1-methyl-1,4-dihydroquinolin-4-one;

3-({[3-(1H-1,3-benzodiazol-1-yl)propyl][(2-methylpyridin-4-yl)methyl]amino}methyl)-1-methyl-1,4-dihydroquinolin-4-one;

and 1-methyl-3-({[(2-methylpyridin-4-yl)methyl][3-(pyridin-3-yl)propyl]amino}methyl)-1,4-dihydroquinolin-4-one, or a salt, stereoisomer, tautomer, or N-oxide thereof.

10. A pharmaceutical composition comprising a pharmaceutically effective amount of the compound according to claim 1, or a salt, stereoisomer, tautomer, or N-oxide thereof, and optionally a pharmaceutically acceptable carrier, diluent or excipient.

11. The compound according to claim 1, or a salt, stereoisomer, tautomer, or N-oxide thereof, wherein
 $Y^2$ is $C_3$-alkylene, wherein the carbon atoms are in each case unsubstituted or substituted with one or more, same or different substituents $R^Z$.

* * * * *